(12) United States Patent
Daugan et al.

(10) Patent No.: US 9,061,998 B2
(45) Date of Patent: Jun. 23, 2015

(54) QUINOLINONE DERIVATIVES

(75) Inventors: Alain Claude-Marie Daugan, Les Ulis (FR); Olivier Mirguet, Les Ulis (FR); Yann Lamotte, Les Ulis (FR)

(73) Assignee: GlaxoSmithKline LLC, Wilmington, New Castle, DE (US)

( * ) Notice: Subject to any disclaimer, the term of this patent is extended or adjusted under 35 U.S.C. 154(b) by 10 days.

(21) Appl. No.: 14/003,423

(22) PCT Filed: Mar. 5, 2012

(86) PCT No.: PCT/EP2012/053731
§ 371 (c)(1),
(2), (4) Date: Sep. 5, 2013

(87) PCT Pub. No.: WO2012/119978
PCT Pub. Date: Sep. 13, 2012

(65) Prior Publication Data
US 2013/0345212 A1    Dec. 26, 2013

Related U.S. Application Data

(60) Provisional application No. 61/449,853, filed on Mar. 7, 2011.

(51) Int. Cl.
*C07D 215/22* (2006.01)
*C07D 215/36* (2006.01)
*C07D 401/04* (2006.01)
*C07D 401/10* (2006.01)
*C07D 401/14* (2006.01)
*C07D 409/14* (2006.01)
*C07D 413/04* (2006.01)
*C07D 413/14* (2006.01)
*C07D 417/04* (2006.01)
*C07D 417/10* (2006.01)
*C07D 417/14* (2006.01)
*C07D 215/48* (2006.01)
*C07D 401/12* (2006.01)
*C07D 309/14* (2006.01)

(52) U.S. Cl.
CPC ............ *C07D 215/22* (2013.01); *C07D 215/36* (2013.01); *C07D 401/04* (2013.01); *C07D 401/10* (2013.01); *C07D 401/14* (2013.01); *C07D 409/14* (2013.01); *C07D 413/04* (2013.01); *C07D 413/14* (2013.01); *C07D 417/04* (2013.01); *C07D 417/10* (2013.01); *C07D 417/14* (2013.01); *C07D 215/48* (2013.01); *C07D 401/12* (2013.01); *C07D 309/14* (2013.01)

(58) Field of Classification Search
None
See application file for complete search history.

(56) References Cited

FOREIGN PATENT DOCUMENTS

WO    2009076631 A1    6/2009
WO    2009100130 A1    8/2009

OTHER PUBLICATIONS

Jordan, V. C. Nature Reviews: Drug Discovery, 2, 2003, 205-213.*
Sharpless et al. The mighty mouse: genetically engineered mouse models in cancer drug development, Nature Reviews Drug Discovery | AOP, published online Aug. 18, 2006, pp. 1-14.*

* cited by examiner

*Primary Examiner* — Jeffrey S Lundgren
*Assistant Examiner* — William Lee
(74) *Attorney, Agent, or Firm* — Duke M. Fitch; John Lemanowicz; William R. Majarian

(57) ABSTRACT

The present invention relates to compounds of the formula (I),

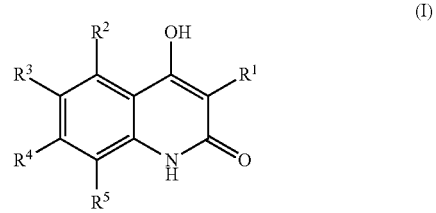

salts thereof, to pharmaceutical compositions containing them and their use in medicine. In particular, the invention relates to compounds as activators of AMPK.

13 Claims, No Drawings

US 9,061,998 B2

QUINOLINONE DERIVATIVES

CROSS-REFERENCE TO RELATED APPLICATIONS

This application is filed pursuant to 35 U.S.C. §371 as a United States National Phase Application of International Patent Application Serial No. PCT/EP2012/053731 filed Mar. 5, 2012, which claims priority from U.S. Provisional Application No. 61/449,853 filed on Mar. 7, 2011.

FIELD OF THE INVENTION

The present invention relates to a novel class of compounds which are activators of AMP-activated protein kinase (AMPK) (AMPK-activators), compositions comprising said compounds, methods of synthesis and uses for such compounds in treating various diseases mediated by AMPK, such as type 1 (Type I) diabetes, type 2 (Type II) diabetes, metabolic syndrome, atherosclerosis, dyslipidaemia, mitochondrial disorders, sarcopenia, obesity, hypertension, cerebral ischemia, cognitive defect, neurodegenerative diseases (including but not limited to Alzheimer's disease, Parkinson's disease, Huntington's disease), neurological and mitochondrial disorders (including but not limited to schizophrenia, Friedrich's Ataxia, amyotrophic lateral sclerosis, multiple sclerosis), neuroinflammation, inflammatory pain, neuropathic pain, epilepsy, cardiac ischemia, virus infection (HIV, cytomegalovirus and hepatitis C) or cancer.

BACKGROUND OF THE INVENTION

AMPK has been established as a sensor and regulator of cellular energy homeostasis (Hardie, D. G. and Hawley, S. A. AMP-activated protein kinase: the energy charge hypothesis revisited. Bioessays 23: 1112 (2001), Kemp, B. E. et. al. AMP-activated protein kinase, super metabolic regulator. Biochem. Soc. Transactions 31:162 (2003)). Allosteric activation of this kinase due to rising AMP levels occurs in states of cellular energy depletion. The resulting serine/threonine phosphorylation of target enzymes leads to an adaptation of cellular metabolism to the low energy state. The net effect of AMPK activation induced changes is inhibition of ATP consuming processes and activation of ATP generating pathways, and therefore regeneration of ATP stores. Examples of AMPK substrates include acetyl-CoA-carboxylase (ACC) and HMG-CoA-reductase (Carling, D. et. al. A common bicyclic protein kinase cascade inactivates the regulatory enzymes of fatty acid and cholesterol biosynthesis. FEBS Letters 223: 217 (1987)). Phosphorylation and therefore inhibition of ACC leads to a decrease in fatty acid synthesis (ATP-consuming) and at the same time to an increase in fatty acid oxidation (ATP-generating). Phosphorylation and resulting inhibition of HMG-CoA reductase leads to a decrease in cholesterol synthesis. Other substrates of AMPK include hormone sensitive lipase (Garton, A. J. et. al. Phosphorylation of bovine hormone-sensitive lipase by the AMP-activated protein kinase. A possible antilipolytic mechanism. Eur. J. Biochem. 179:249 (1989)), glycerol-3-phosphate acyltransferase (Muoio, D. M. et. al. AMP-activated kinase reciprocally regulates triacylglycerol synthesis and fatty acid oxidation in liver and muscle: evidence that sn-glycerol-3-phosphate acyltransferase is a novel target. Biochem. J. 338:783 (1999)), malonyl-CoA decarboxylase (Saha, A. K. et. al. Activation of malonyl-CoA decarboxylase in rat skeletal muscle by contraction and the AMP-activated protein kinase activator 5-aminoimidazole-4-carboxamide-1-.beta.-D-ribofuranoside. J. Biol. Chem. 275:24279 (2000)), some of which are potential drug targets for components of metabolic syndrome. Additional processes that are believed to be regulated through AMPK activation, but for which the exact AMPK substrates have not been identified, include stimulation of glucose transport in skeletal muscle and expressional regulation of key genes in fatty acid and glucose metabolism in liver (Hardie, D. G. and Hawley, S. A. AMP-activated protein kinase: the energy charge hypothesis revisited. Bioessays 23: 1112 (2001), Kemp, B. E. et. al. AMP-activated protein kinase, super metabolic regulator. Biochem. Soc. Transactions 31:162 (2003), Musi, N. and Goodyear, L. J. Targeting the AMP-activated protein kinase for the treatment of Type 2 diabetes. Current Drug Targets-Immune, Endocrine and Metabolic Disorders 2:119 (2002)). For example, decreased expression of glucose-6-phosphatase (Lochhead, P. A. et. al. 5-aminoimidazole-4-carboxamide riboside mimics the effects of insulin on the expression of the 2 key gluconeogenic genes PEPCK and glucose-6-phosphatase. Diabetes 49:896 (2000)), a key enzyme in hepatic glucose production, and SREBP-1c (Zhou, G. et. al. Role of AMP-activated protein kinase in mechanism of metformin action. The J. of Clin. Invest. 108: 1167 (2001)), a key lipogenic transcription factor, has been found following AMPK stimulation.

More recently an involvement of AMPK in the regulation of not only cellular but also whole body energy metabolism has become apparent. It was shown that the adipocyte-derived hormone leptin leads to a stimulation of AMPK and therefore to an increase in fatty acid oxidation in skeletal muscle (Minokoshi, Y. et. al. Leptin stimulates fatty-acid oxidation by activating AMP-activated protein kinase. Nature 415: 339 (2002)). Adiponectin, another adipocyte derived hormone leading to improved carbohydrate and lipid metabolism, has been demonstrated to stimulate AMPK in liver and skeletal muscle (Yamauchi, T. et. al. Adiponectin stimulates glucose utilization and fatty acid oxidation by activating AMP-activated protein kinase. Nature Medicine 8: 1288 (2002), Tomas, E. et. al. Enhanced muscle fat oxidation and glucose transport by ACRP30 globular domain: Acetyl-CoA carboxylase inhibition and AMP-activated protein kinase activation. PNAS 99: 16309 (2002)). The activation of AMPK in these circumstances seems to be independent of increasing cellular AMP levels but rather due to phosphorylation by one or more yet to be identified upstream kinases.

Based on the knowledge of the above-mentioned consequences of AMPK activation, certain beneficial effects could be expected from in vivo activation of AMPK. In liver, decreased expression of gluconeogenic enzymes could reduce hepatic glucose output and improve overall glucose homeostasis, and both direct inhibition and/or reduced expression of key enzymes in lipid metabolism could lead to decreased fatty acid and cholesterol synthesis and increased fatty acid oxidation. Stimulation of AMPK in skeletal muscle could increase glucose uptake and fatty acid oxidation with resulting improvement of glucose homeostasis and, due to a reduction in intra-myocyte triglyceride accumulation, to improved insulin action. Finally, the increase in energy expenditure could lead to a decrease in body weight. The combination of these effects in metabolic syndrome could be expected to reduce the risk for acquiring cardiovascular diseases.

Several studies in rodents support this hypothesis (Bergeron, R. et. al. Effect of 5-aminoimidazole-4-carboxamide-1 (beta)-D-ribofuranoside infusion on in vivo glucose metabolism in lean and obese Zucker rats. Diabetes 50:1076 (2001), Song, S. M. et. al. 5-Aminoimidazole-4-darboxamide ribonucleoside treatment improves glucose homeostasis in insulin-resistant diabeted (ob/ob) mice. Diabetologia 45:56 (2002), Halseth, A. E. et. al. Acute and chronic treatment of ob/ob and db/db mice with AICAR decreases blood glucose concentrations. Biochem. and Biophys. Res. Comm. 294:798 (2002), Buhl, E. S. et. al. Long-term AICAR administration reduces metabolic disturbances and lowers blood pressure in rats displaying feature of the insulin resistance syndrome. Diabetes 51: 2199 (2002)). Until recently most in vivo studies have relied on the AMPK activator AICAR, a cell permeable precursor of ZMP. ZMP acts as an intracellular AMP mimic, and, when accumulated to high enough levels, is able to stimulate AMPK activity (Corton, J. M. et. al. 5-Aminoimidazole-4-carboxamide ribonucleoside, a specific method for activating AMP-activated protein kinase in intact cells? Eur. J. Biochem. 229: 558 (1995)). However, ZMP also acts as an AMP mimic in the regulation of other enzymes, and is therefore not a specific AMPK activator (Musi, N. and Goodyear, L. J. Targeting the AMP-activated protein kinase for the treatment of Type 2 diabetes. Current Drug Targets-Immune, Endocrine and Metabolic Disorders 2:119 (2002)). Several in vivo studies have demonstrated beneficial effects of both acute and chronic AICAR administration in rodent models of obesity and Type 2 diabetes (Bergeron, R. et. al. Effect of 5-aminoimidazole-4-carboxamide-1(beta)-D-ribofuranoside infusion on in vivo glucose metabolism in lean and obese Zucker rats. Diabetes 50:1076 (2001), Song, S. M. et. al. 5-Aminoimidazole-4-darboxamide ribonucleoside treatment improves glucose homeostasis in insulin-resistant diabetic (ob/ob) mice. Diabetologia 45:56 (2002), Halseth, A. E. et. al. Acute and chronic treatment of ob/ob and db/db mice with AICAR decreases blood glucose concentrations. Biochem. and Biophys. Res. Comm. 294:798 (2002), Buhl, E. S. et. al. Long-term AICAR administration reduces metabolic disturbances and lowers blood pressure in rats displaying feature of the insulin resistance syndrome. Diabetes 51: 2199 (2002)). For example, 7 week AICAR administration in the obese Zucker (fa/fa) rat leads to a reduction in plasma triglycerides and free fatty acids, an increase in HDL cholesterol, and a normalization of glucose metabolism as assessed by an oral glucose tolerance test (Minokoshi, Y. et. al. Leptin stimulates fatty-acid oxidation by activating AMP-activated protein kinase. Nature 415: 339 (2002)). In both ob/ob and db/db mice, 8 day AICAR administration reduces blood glucose by 35% (Halseth, A. E. et. al. Acute and chronic treatment of ob/ob and db/db mice with AICAR decreases blood glucose concentrations. Biochem. and Biophys. Res. Comm. 294:798 (2002)). In addition to AICAR, more recently it was found that the diabetes drug metformin can activate AMPK in vivo at high concentrations (Zhou, G. et. al. Role of AMP-activated protein kinase in mechanism of metformin action. The J. of Clin. Invest. 108: 1167 (2001), Musi, N. et. al. Metformin increases AMP-activated protein kinase activity in skeletal muscle of subjects with Type 2 diabetes. Diabetes 51: 2074 (2002)), although it has to be determined to what extent its antidiabetic action relies on this activation. As with leptin and adiponectin, the stimulatory effect of metformin is indirect via a mild inhibition of mitochondrial respiratory chain complex 1 (Leverve X. M. et al. Mitochondrial metabolism and type-2 diabetes: a specific target of metformin. Diabetes Metab. 29: 6588 (2003)). In addition to pharmacologic intervention, several transgenic mouse models have been developed in the last years and initial results are becoming available. Expression of dominant negative AMPK in skeletal muscle of transgenic mice has demonstrated that the AICAR effect on stimulation of glucose transport is dependent on AMPK activation (Mu, J. et. al. A role for AMP-activated protein kinase in contraction and hypoxia-regulated glucose transport in skeletal muscle. Molecular Cell 7: 1085 (2001)), and therefore likely not caused by non-specific ZMP effects. Similar studies in other tissues will help to further define the consequences of AMPK activation. It is believed that pharmacologic activation of AMPK may have benefits in relation to metabolic syndrome with improved glucose and lipid metabolism and a reduction in body weight. To qualify a patient as having metabolic syndrome, three out of the five following criteria must be met: elevated blood pressure above 130/85 mmHg, fasting blood glucose above 110 mg/dl, abdominal obesity above 40" (men) or 35" (women) waist circumference, and blood lipid changes as defined by an increase in triglycerides above 150 mg/dl or decreased HDL cholesterol below 40 mg/dl (men) or 50 mg/dl (women). Therefore, the combined effects that may be achieved through activation of AMPK in a patient who qualifies as having metabolic syndrome would raise the interest of this target.

Lowering of blood pressure has been reported to be a consequence of AMPK activation (Buhl, E. S. et. al. Long-term AICAR administration reduces metabolic disturbances and lowers blood pressure in rats displaying feature of the insulin resistance syndrome. Diabetes 51: 2199 (2002)), therefore activation of AMPK might have beneficial effects in hypertension. Through combination of some or all of the above-mentioned effects stimulation of AMPK may to reduce the incidence of cardiovascular diseases (e.g. MI, stroke). Increased fatty acid synthesis is a characteristic of many tumor cells, therefore decreased synthesis of fatty acids through activation of AMPK could be useful as a cancer therapy (Huang X. et al. Important role of the LKB1-AMPK pathway in suppressing tumorigenesis in PTEN-deficient mice. Biochem J. 412: 211 (2008). AMPK can also be considered as a metabolic tumor suppressor and AMPK activators could be helpful in general cancer therapy (Luo Z. Et al. AMPK as a metabolic tumor suppressor: control of metabolism and cell growth. Future Oncol. 6: 457 (2010)). Pharmacological activation of the LKB1/AMPK/mTOR axis using known AMPK activators such as metformin, AICAR or A-769662 induce in most studies a dramatic suppression of cancer cell growth, demonstrating that the reinforcement of the tumor suppressive functions of LKB1/AMPK is a valuable therapeutic strategy for both solid tumors (such as breast or prostate cancer) and hematological cancers (such as acute myeloid leukemia or chronic myelogenous leukemia) (Green A. S. et al. LKB1/AMPK/mTOR signaling pathway in hematological malignancies: From metabolism to cancer cell biology. Cell Cycle 10: 2115 (2011). Micic D. et al. Metformin: Its emerging role in oncology. Hormones 10:5 (2011)). The connection of AMPK with several tumour suppressors suggests that therapeutic manipulation of this pathway using AMPK activators warrants further investigation in patients with cancer such as Peutz-Jeghers syndrome, a dominantly inherited cancer-predisposition syndrome in which, at least 80% of all reported cases are caused by mutations that inactivate the gene encoding LKB1 (chromosome 19p13.3), AMPK upstream kinase (Shackelford D. B.; Shaw R. J. The LKB1-AMPK pathway: metabolism and growth control in tumour suppression. Nature Rev. Cancer 2009, 9: 563 (2009). Carling D. LKB1: a sweet side to Peutz-Jeghers syndrome? TRENDS in Molecular Medicine 12: 144 (2006)).

Stimulation of AMPK has been shown to stimulate production of ketone bodies from astrocytes (Blazquez, C. et. al. The AMP-activated protein kinase is involved in the regulation of ketone body production by astrocytes. J. Neurochem. 73: 1674 (1999)), and might therefore be a strategy to treat ischemic events in the brain. Stimulation of AMPK has been shown to improve cognition and neurodegenerative diseases in a mice model (Dagon Y. et al. Nutritional status, cognition, and survival: a new role for leptin and AMP kinase. J. Biol. Chem. 280:42142 (2005)). Stimulation of AMPK has been shown to stimulate expression of uncoupling protein 3 (UCP3) in skeletal muscle (Zhou, M. et. al. UCP-3 expression in skeletal muscle: effects of exercise, hypoxia, and AMP-activated protein kinase. Am. J. Physiol. Endocrinol. Metab. 279: E622 (2000)) and might therefore be a way to prevent damage from reactive oxygen species. Endothelial NO synthase (eNOS) has been shown to be activated through AMPK mediated phosphorylation (Chen, Z.-P., et. al. AMP-activated protein kinase phosphorylation of endothelial NO synthase. FEBS Letters 443: 285 (1999)), therefore AMPK activation may be used to improve local circulatory systems. AMPK has also been described to directly affect PGC-1alpha activity through phosphorylation and then regulate mitochondria biogenesis (Jager S, et al. AMP-activated protein kinase (AMPK) action in skeletal muscle via direct phosphorylation of PGC-1alpha. Proc Natl Acad Sci 104:12017 (2007)). AMPK activation can be then a way to treat mitochondrial disorders (e.g. sarcopenia and some mitochondrial rare diseases). Recently, several reports describe beneficial effect of AMPK activation on virus infection. While virus infection is found to reduce AMPK activity in infected cells or tissues, AMPK activation is proposed as a anti-viral therapy (Mankouri J. et al., Enhanced hepatitis C virus genome replication and lipid accumulation mediated by inhibition of AMP-activated protein kinase, Proc Natl Acad Sci 107: 11549 (2010)).

The use of AMPK activators may represent a strategy to protect the heart and other solid organs against cardiac ischemia as it has been demonstrated with A-769662 (Kim A. S. et al. A small molecule AMPK activator protects the heart against ischemia-reperfusion injury. J. Mol. Cell. Cardiology 51: 24 (2011)) or metformin (Yin M. et al. Metformin improves cardiac function in a non-diabetic rat model of 2 post-MI heart failure Am J Physiol Heart Circ Physiol 301: H459 (2011)).

SUMMARY OF THE INVENTION

The present invention provides compounds of formula (I) or salts thereof:

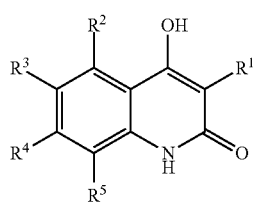

(I)

wherein:
A.
$R^1$ is a) a 5-membered heteroaryl optionally substituted with 1 or more groups selected from —$CH_3$, —$OCH_3$, —OH, —$CH_2OH$, —$CF_3$, —$OCF_3$, —CN, —$CO_2H$, —$CH_2CO_2H$, —$CONH_2$, —$NH_2$ and halogen;
b) O-phenyl optionally substituted with a group selected from methyl, methoxy, fluoro, and $CO_2H$;
c) selected from the group consisting of H, $CO_2H$, $CO_2Et$, and $NO_2$;
d) phenyl optionally substituted with a group selected from $CO_2H$, Cl, F, methyl, —CN, —$NMe_2$ and methoxy;
e) selected from the group consisting of 3-pyridinyl, 4 pyridinyl, and —$S(O)_n$-phenyl; or
f) selected from the group consisting of O-pyridin-2-yl, O-(4-methyl-pyridin-2-yl), O-(5-methoxy-pyridin-2-yl) and O-(5-methyl-pyridin-2-yl);
n=0 or 2;

$R^2$ is H;

$R^3$ is 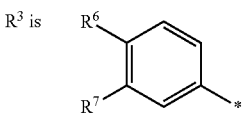

* designates point of attachment;

$R^4$ is Cl;
$R^5$ is H; and
$R^7$ is H and $R^6$ is selected from a group consisting of, NHMe, $NMe_2$, —NHC(O)OMe, —OMe, —OEt, Et, iPr, —$CH_2OH$, and —$CH_2CH_2OH$ or is a group selected from

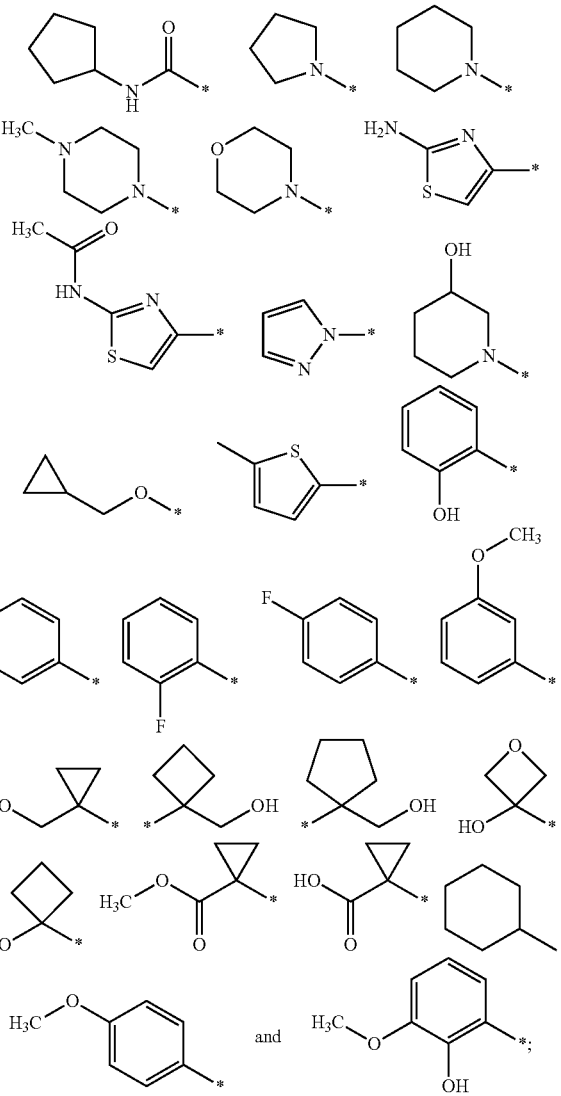

or $R^6$ and $R^7$ taken together form a group selected from

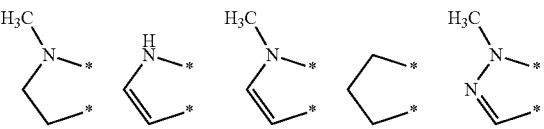

* designates point of attachment

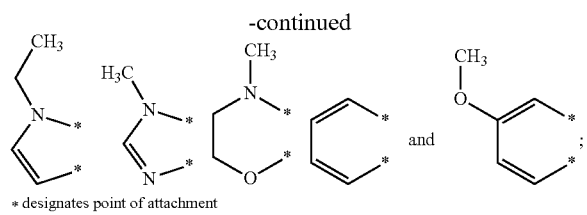

* designates point of attachment or

B. wherein:
i) R¹=3-methoxyphenyl, R⁴ is F and R³=4-(4-morpholino)phenyl;
ii) R¹=3-methylisoxazol-5-yl, and R³=3-dimethylaminophenyl; or
iii) R¹=3-methoxyphenyl, and R³=3-dimethylaminophenyl.

In a further aspect, the invention provides compounds of formula (A)

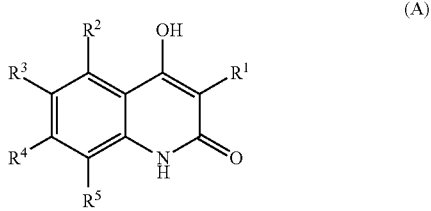

Wherein:
R¹ represents -(5 membered heteroaryl) optionally substituted by a group independently selected from —CH₃, —OCH₃, —OH, —CH₂OH, —CF₃, —OCF₃, —CN, —CO₂H, —CH₂CO₂H, —CONH₂, —NH₂ or halogen;
R² represents H;
R³ is

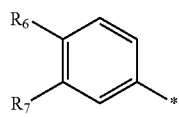

* designates point of attachment;

R⁴ represents chloro;
R⁵ represents H; and
R⁷ is H and R⁶ is selected from a group consisting of NHMe, NMe₂, —NHC(O)OMe, Et, iPr, or is a group selected from

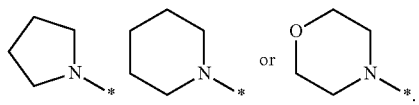

*designates point of attachment

In another aspect, the present invention provides pharmaceutical compositions comprising a compound of formula (I) or a pharmaceutically acceptable salt thereof.

In another aspect, the present invention provides methods of treating type 1 diabetes, type 2 diabetes, metabolic syndrome, atherosclerosis, dyslipidaemia, mitochondrial disorders, sarcopenia, obesity, hypertension, cerebral ischemia, cognitive defect, neurodegenerative diseases (including but not limited to Alzheimer's disease, Parkinson's disease, Huntington's disease), neurological and mitochondrial disorders (including but not limited to schizophrenia, Friedrich's Ataxia, amyotrophic lateral sclerosis, multiple sclerosis), neuroinflammation, inflammatory pain, neuropathic pain, epilepsy, cardiac ischemia, virus infection (HIV, cytomegalovirus or hepatitis C) or cancer comprising administration of a therapeutically effective amount of a compound of formula (I) or a pharmaceutically acceptable salt thereof to a subject in need thereof.

In another aspect, the present invention provides methods of treating type 1 diabetes, type 2 diabetes, metabolic syndrome, atherosclerosis, dyslipidaemia, mitochondrial disorders, sarcopenia, obesity, hypertension, cerebral ischemia, cognitive defect, Alzheimer's disease, Parkinson's disease, Huntington's disease, schizophrenia, Friedrich's Ataxia, amyotrophic lateral sclerosis, multiple sclerosis, neuroinflammation, inflammatory pain, neuropathic pain, epilepsy, virus infection (HIV, cytomegalovirus or hepatitis C) or cancer comprising administration of a therapeutically effective amount of a compound of formula (I) or a pharmaceutically acceptable salt thereof to a subject in need thereof.

In another aspect, the present invention provides methods of treating diabetes, metabolic syndrome, atherosclerosis, dyslipidaemia, obesity, hypertension, cerebral ischemia, cognitive defect and cancer comprising administration of a therapeutically effective amount of a compound of formula (I) or a pharmaceutically acceptable salt thereof to a subject in need thereof.

In another aspect, the present invention provides methods of treating type 2 diabetes, obesity or dyslipidaemia comprising administration of a therapeutically effective amount of a compound of formula (I) or a pharmaceutically acceptable salt thereof to a subject in need thereof.

In another aspect, the present invention provides methods of treating cancer comprising administration of a therapeutically effective amount of a compound of formula (I) or a pharmaceutically acceptable salt thereof to a subject in need thereof.

In another aspect, the invention provides a compound of formula (I) or a pharmaceutically acceptable salt thereof for use in human or veterinary medical therapy.

In another aspect, the invention provides a compound of formula (I) or a pharmaceutically acceptable salt thereof, for use in the treatment of type 1 diabetes, type 2 diabetes, metabolic syndrome, atherosclerosis, dyslipidaemia, mitochondrial disorders, sarcopenia, obesity, hypertension, cerebral ischemia, cognitive defect, neurodegenerative diseases (including but not limited to Alzheimer's disease, Parkinson's disease, Huntington's disease), neurological and mitochondrial disorders (including but not limited to schizophrenia, Friedrich's Ataxia, amyotrophic lateral sclerosis, multiple sclerosis), neuroinflammation, inflammatory pain, neuropathic pain, epilepsy, cardiac ischemia, virus infection (HIV, cytomegalovirus or hepatitis C) or cancer.

In another aspect, the invention provides a compound of formula (I) or a pharmaceutically acceptable salt thereof, for use in the treatment of type 1 diabetes, type 2 diabetes, metabolic syndrome, atherosclerosis, dyslipidaemia, mitochondrial disorders, sarcopenia, obesity, hypertension, cerebral ischemia, cognitive defect Alzheimer's disease, Parkinson's disease, Huntington's disease, schizophrenia, Friedrich's Ataxia, amyotrophic lateral sclerosis, multiple sclerosis, neuroinflammation, inflammatory pain, neuropathic pain, epilepsy, virus infection (HIV, cytomegalovirus or hepatitis C) or cancer.

In another aspect, the invention provides a compound of formula (I) or a pharmaceutically acceptable salt thereof, for use in the treatment of diabetes, metabolic syndrome, atherosclerosis, dyslipidaemia, obesity, hypertension, cerebral ischemia, cognitive defect or cancer.

In another aspect, the invention provides a compound of formula (I) or a pharmaceutically acceptable salt thereof, for use in the treatment of type 2 diabetes, obesity or dyslipidaemia.

In another aspect, the invention provides a compound of formula (I) or a pharmaceutically acceptable salt thereof, for use in the treatment of cancer.

In another aspect, the invention provides the use of a compound of formula (I) or a pharmaceutically acceptable salt thereof in the manufacture of a medicament for the treatment of type 1 diabetes, type 2 diabetes, metabolic syndrome, atherosclerosis, dyslipidaemia, mitochondrial disorders, sarcopenia, obesity, hypertension, cerebral ischemia, cognitive defect, neurodegenerative diseases (including but not limited to Alzheimer's disease, Parkinson's disease, Huntington's disease), neurological and mitochondrial disorders (including but not limited to schizophrenia, Friedrich's Ataxia, amyotrophic lateral sclerosis, multiple sclerosis), neuroinflammation, inflammatory pain, neuropathic pain, epilepsy, cardiac ischemia, virus infection (HIV, cytomegalovirus or hepatitis C) or cancer.

In another aspect, the invention provides the use of a compound of formula (I) or a pharmaceutically acceptable salt thereof in the manufacture of a medicament for the treatment of type 1 diabetes, type 2 diabetes, metabolic syndrome, atherosclerosis, dyslipidaemia, mitochondrial disorders, sarcopenia, obesity, hypertension, cerebral ischemia, cognitive defect Alzheimer's disease, Parkinson's disease, Huntington's disease, schizophrenia, Friedrich's Ataxia, amyotrophic lateral sclerosis, multiple sclerosis, neuroinflammation, inflammatory pain, neuropathic pain, epilepsy, virus infection (HIV, cytomegalovirus or hepatitis C) or cancer.

In another aspect, the invention provides the use of a compound of formula (I) or a pharmaceutically acceptable salt thereof in the manufacture of a medicament for the treatment of diabetes, metabolic syndrome, atherosclerosis, dyslipidaemia, obesity, hypertension, cerebral ischemia, cognitive defect or cancer.

In another aspect, the invention provides the use of a compound of formula (I) or a pharmaceutically acceptable salt thereof in the manufacture of a medicament for the treatment of type 2 diabetes, obesity or dyslipidaemia.

In another aspect, the invention provides the use of a compound of formula (I) or a pharmaceutically acceptable salt thereof in the manufacture of a medicament for the treatment of cancer.

DESCRIPTION OF THE EMBODIMENTS

All aspects and embodiments of the invention described herein are in respect of compounds of formula (I) unless otherwise specified.

In one aspect of the invention $R^1$ represents -(5 membered heteroaryl) optionally substituted by a group independently selected from —$CH_3$, —$OCH_3$, —OH, —$CH_2OH$, —$CF_3$, —$OCF_3$, —CN, —$CO_2H$, —$CH_2CO_2H$, —$CONH_2$, —$NH_2$ or halogen.

In another aspect of the invention $R^1$ represents isoxazoyl, pyrrolyl, pyrazolyl, 1,2,4-oxadiazolyl, 1,3,4-oxadiazolyl, 1H-1,2,4-triazolyl or 1H-1,2,3-triazolyl optionally substituted by a group independently selected from —$CH_3$, —$OCH_3$, —OH, —$CH_2OH$, —$CF_3$, —$OCF_3$, —CN, —$CO_2H$, —$CH_2CO_2H$, —$CONH_2$, —$NH_2$ and halogen.

In another aspect of the invention, $R^1$ represents a 5-membered heteroaryl containing at least 1 N heteroatom optionally substituted with 1 or more groups selected from methyl, chloro, bromo, $CO_2H$ and methoxy.

In another aspect of the invention $R^1$ represents isoxazoyl, pyrrolyl, pyrazolyl, 1,2,4-oxadiazolyl, 1,3,4-oxadiazolyl, 1H-1,2,4-triazolyl or 1H-1,2,3-triazolyl optionally substituted by a group independently selected from —$CH_3$, —$OCH_3$, —$CO_2H$— or halogen.

In another aspect of the invention $R^1$ represents a group selected from 3-methyl-5-isoxazoyl, 1-pyrazolyl, 3-methyl-1,2,5-oxadiazol-4-yl, 1H-1,2,4-triazol-1-yl, 3-carboxy-1-pyrrolyl, 1H-1,2,3-triazol-1-yl, 4-methyl-1-pyrazolyl, 4-carboxy-1-pyrazolyl, 1-methyl-4-pyrazolyl, 3-methyl-5-pyrazolyl, and 4-chloro-1-pyrazolyl.

In another aspect of the invention, $R^1$ represents -(5 membered heteroaryl) optionally substituted by a —$CH_3$ group.

In another aspect of the invention, $R^1$ represents

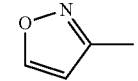

* designates point of attachment

In one aspect of the invention, $R^1$ represents O-phenyl optionally substituted with a group selected from methyl, methoxy, fluoro, ethoxy, and $CO_2H$.

In a further aspect of the invention, $R^1$ represents O-phenyl optionally substituted with methoxy.

In another aspect of the invention $R^3$ represents

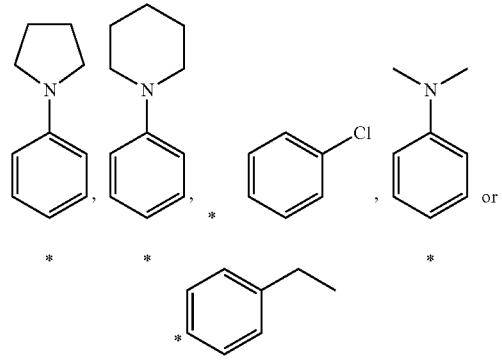

* designates point of attachment

In another aspect of the invention, $R^3$ represents

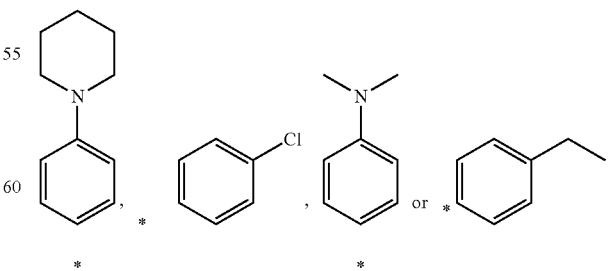

*designates point of attachment

In a further aspect of the invention, R³ represents

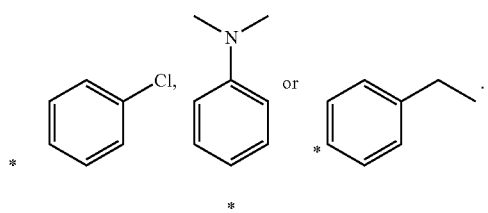

*designates point of attachment

In another aspect of the invention, R³ represents

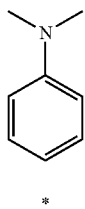

* designates point of attachment.

Each of the aspects of the invention are independent unless stated otherwise. Nevertheless the skilled person will understand that all the permutations of the aspects herein described are within the scope of the invention. Thus it is to be understood that the present invention covers all combinations of suitable, convenient and exemplified aspects described herein.

As used herein, the term "alkyl" refers to straight or branched hydrocarbon chains containing the specified number of carbon atoms. For example, —$C_{1-4}$alkyl refers to a straight or branched "alkyl" containing at least 1, and at most 4, carbon atoms. Examples of "alkyl" as used herein include, but are not limited to, methyl, ethyl, n-propyl, n-butyl, isobutyl, isopropyl and t-butyl.

As used herein, the term "—$C_{6-10}$aryl" refers to an aromatic carbocyclic moiety containing 6 to 10 carbon ring-atoms. The definition includes both monocyclic and bicyclic ring systems and bicyclic structures at least a portion of which is aromatic and the other part is saturated, partially or fully unsaturated. Examples of aryl groups as used herein include, but are not limited to, naphthyl, indanyl, indenyl, azulenyl, azulanyl, phenyl and naphthyl; and more specifically phenyl.

As used herein, the term "halogen" or "halo" refers to a fluorine (fluoro), chlorine (chloro), bromine (bromo) or iodine (iodo) atom.

As used herein, the term "-(5 membered heteroaryl)" refers to an aromatic cyclic group containing 5 ring-atoms 1, 2, 3 or 4 of which are hetero-atoms, at least 1 of which is N and the remaining 1, 2 or 3 are independently selected from nitrogen, oxygen and sulphur and the remaining ring-atoms are carbon. Examples of "-(5 membered heteroaryl)" include, but are not limited to isoxazolyl, pyrazolyl, oxadiazolyl, triazolyl, pyrrolyl, and thiazolyl, preferably isoxazolyl, pyrazolyl, 1H-1,2,3-triazolyl, 1H-1,2,4-triazolyl, thiazolyl, 1,2,5-oxadiazolyl, 1,3,4-oxadiazolyl and 1,2,4-oxadiazolyl.

As used herein, the term "substituted" refers to substitution with the named substituent or substituents, multiple degrees of substitution being allowed unless otherwise stated.

As used herein, the term "one or more group" refers to 1, 2 or 3 group, preferable 1 or 2 groups.

For the avoidance of doubt, the term "independently" means that where more than one substituent is selected from a number of possible substituents, those substituents may be the same or different.

Also included in the present invention are pharmaceutically acceptable salt complexes. In certain embodiments of the invention, pharmaceutically acceptable salts of the compounds according to formula I may be preferred over the respective free base or free acid because such salts impart greater stability or solubility to the molecule thereby facilitating formulation into a dosage form. Therefore, the present invention also covers the pharmaceutically acceptable salts of the compounds of formula (I).

Therefore, in one aspect of the invention there is provided a compound of formula (I) or a salt thereof wherein the salt is a pharmaceutically acceptable salt.

As used herein, the term "pharmaceutically acceptable", refers to salts, molecular entities and other ingredients of compositions that are generally physiologically tolerable and do not typically produce untoward reactions when administered to a subject (e.g. human). The term "pharmaceutically acceptable" also means approved by a regulatory agency of the Federal or a state government or listed in the U.S. Pharmacopoeia or other generally recognized pharmacopoeia for use in a subject, and more particularly in humans.

As used herein, the term "subject" refers to an animal, in particular a mammal and more particularly to a human or a domestic animal or an animal serving as a model for a disease (e.g., mouse, monkey, etc.). In one aspect, the subject is a human.

Salts of compounds of formula (I) which are suitable for use in medicine are those wherein the counterion is pharmaceutically acceptable. However, salts having non-pharmaceutically acceptable counterions are within the scope of the present invention, for example, for use as intermediates in the preparation of other compounds of formula (I) and their pharmaceutically acceptable salts.

Suitable pharmaceutically acceptable salts will be apparent to those skilled in the art and include for example base addition salts e.g. ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine or for example acid addition salts formed from acids which form non-toxic salts e.g. hydrochloride, hydrobromide, hydroiodide, sulphate, bisulphate, nitrate, phosphate, hydrogen phosphate, acetate, maleate, malate, fumarate, lactate, tartrate, citrate, formate, gluconate, succinate, piruvate, oxalate, oxaloacetate, trifluoroacetate, saccharate, benzoate, methansulphonate, ethanesulphonate, benzenesulphonate, p-toluensulphonate, methanesulphonic, ethanesulphonic, p-toluenesulphonic, and isethionate. For a review on suitable salts see Berge et al. J. Pharm. Sci., 1977, 66, 1-19. The invention includes within its scope all possible stoichiometric and non-stoichiometric forms of the salts of the compounds of formula (I).

Those skilled in the art of organic chemistry will appreciate that many organic compounds can form complexes with solvents in which they are reacted or from which they are precipitated or crystallized. These complexes are known as "solvates".

Solvates of the compounds of formula (I) and solvates of the salts of the compounds of formula (I) are included within the scope of the present invention.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Most preferably the solvent used is water and the solvate may also be referred to as a hydrate.

Solvates of compounds of formula (I) which are suitable for use in medicine are those wherein the solvent is pharmaceutically acceptable. However, solvates having non-pharmaceutically acceptable solvents are within the scope of the present invention, for example, for use as intermediates in the preparation of other compounds of formula (I) and their pharmaceutically acceptable salts.

In one aspect, the compounds of formula (I) may be in the form of pharmaceutically acceptable salts, solvates or solvates of salts. In a further aspect, the compounds of formula (I) may be in the form of pharmaceutically acceptable salts.

As used herein, the term "compounds of the invention" means the compounds according to formula (I) and pharmaceutically acceptable salts thereof. The term "a compound of the invention" means any one of the compounds of the invention as defined below.

Prodrugs of the compounds of formula (I) are included within the scope of the present invention.

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987 and in D. Fleishner, S. Ramon and H. Barba "Improved oral drug delivery: solubility limitations overcome by the use of prodrugs", Advanced Drug Delivery Reviews (1996) 19(2) 115-130. Prodrugs are any covalently bonded carriers that release a compound of structure (I) in vivo when such prodrug is administered to a patient. Prodrugs are generally prepared by modifying functional groups in a way such that the modification is cleaved in vivo yielding the parent compound. Prodrugs may include, for example, compounds of this invention wherein hydroxy or amine groups are bonded to any group that, when administered to a patient, cleaves to form the hydroxy or amine groups. Thus, representative examples of prodrugs include (but are not limited to) phosphonate, carbamate, acetate, formate and benzoate derivatives of hydroxy and amine functional groups of the compounds of formula (I).

Certain compounds of formula (I) may exist in stereoisomeric forms (e.g. they may contain one or more asymmetric carbon atoms). The individual stereoisomers (enantiomers and diastereomers) and mixtures or racemic mixtures thereof are included within the scope of the present invention.

Likewise, it is understood that compounds of formula (I) may exist in tautomeric forms other than that shown in the formula and these are also included within the scope of the present invention. In particular, compounds of formula (I) may exist in the following tautomeric forms.

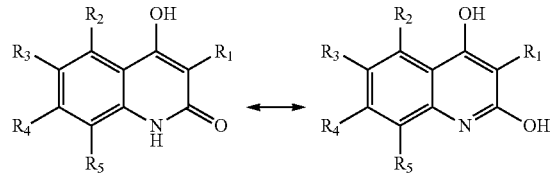
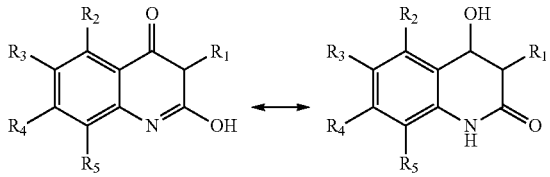

All possible tautomeric forms of the compounds of formula (I) are contemplated to be within the scope of the present invention.

It will be appreciated that racemic compounds of formula (I) may be optionally resolved into their individual enantiomers. Such resolutions may conveniently be accomplished by standard methods known in the art. For example, a racemic compound of formula (I) may be resolved by chiral preparative HPLC. An individual stereoisomer may also be prepared from a corresponding optically pure intermediate or by resolution, such as H.P.L.C. of the corresponding mixture using a suitable chiral support or by fractional crystallisation of the diastereoisomeric salts formed by reaction of the corresponding mixture with a suitable optically active acid or base, as appropriate.

In one aspect of the invention there is provided a compound of formula (I) selected from the group consisting of:

7-Chloro-4-hydroxy-6-(2'-hydroxy-3'-methoxy-[1,1'-biphenyl]-4-yl)-3-phenylquinolin-2(1H)-one 3-{7-Chloro-4-hydroxy-6-[2'-hydroxy-3'-(methyloxy)-4-biphenylyl]-2-oxo-1,2-dihydro-3-quinolinyl}benzoic acid 7-chloro-4-hydroxy-3-(3-methoxyphenyl)-6-(4-morpholinophenyl)quinolin-2(1H)-one 7-Chloro-4-hydroxy-6-[4-(4-morpholinyl)phenyl]-3-phenylquinolin-2(1H)-one 4-{7-Chloro-4-hydroxy-3-[3-(methyloxy)phenyl]-2-oxo-1,2-dihydro-6-quinolinyl}-N-cyclopentylbenzamide 7-Fluoro-4-hydroxy-3-(3-methoxyphenyl)-6-(4-morpholinophenyl)quinolin-2(1H)-one 3-[7-Chloro-4-hydroxy-6-(1-methyl-1H-indol-5-yl)-2-oxo-1,2-dihydro-3-quinolinyl]benzoic acid 7-Chloro-4-hydroxy-6-(1-methyl-1H-indol-5-yl)-3-[3-(methyloxy)phenyl]quinolin-2(1H)-one N-{4-[4-(7-Chloro-4-hydroxy-2-oxo-3-phenyl-1,2-dihydro-6-quinolinyl)phenyl]-1,3-thiazol-2-yl}acetamide 7-Chloro-4-hydroxy-6-(1-methyl-1H-indol-5-yl)-3-phenylquinolin-2(1H)-one 7-Chloro-4-hydroxy-3-(3-methylisoxazol-5-yl)-6-(4-(piperidin-1-yl)phenyl)quinolin-2(1H)-one 7-Chloro-6-(4-(dimethylamino)phenyl)-4-hydroxyquinolin-2(1H)-one 7-Chloro-4-hydroxy-3-(1-methyl-1H-pyrazol-4-yl)-6-(4-(piperidin-1-yl)phenyl)quinolin-2(1H)-one 7-Chloro-6-(4'-fluoro-[1,1'-biphenyl]-4-yl)-4-hydroxy-3-(3-methylisoxazol-5-yl)quinolin-2(1H)-one 7-Chloro-4-hydroxy-6-(3'-methoxy-[1,1'-biphenyl]-4-yl)-3-(3-methylisoxazol-5-yl)quinolin-2(1H)-one 7-Chloro-4-hydroxy-3-(3-methylisoxazol-5-yl)-6-(4-(5-methylthiophen-2-yl)phenyl)quinolin-2(1H)-one 7-Chloro-4-hydroxy-6-(4'-methoxy-[1,1'-biphenyl]-4-yl)-3-(3-methylisoxazol-5-yl)quinolin-2(1H)-one
7-Chloro-6-(2'-fluoro-[1,1'-biphenyl]-4-yl)-4-hydroxy-3-(3-methylisoxazol-5-yl)quinolin-2(1H)-one
3-(7-Chloro-6-(4-(dimethylamino)phenyl)-4-hydroxy-2-oxo-1,2-dihydroquinolin-3-yl)benzonitrile
7-Chloro-6-(4-(dimethylamino)phenyl)-3-(3-methyl-1,2,4-oxadiazol-5-yl)-2-oxo-1,2-dihydroquinolin-4-olate
7-Chloro-3,6-bis(4-(dimethylamino)phenyl)-2-oxo-1,2-dihydroquinolin-4-olate
7-Chloro-3-(4-cyanophenyl)-6-(4-(dimethylamino)phenyl)-2-oxo-1,2-dihydroquinolin-4-olate
7-Chloro-6-(4-(dimethylamino)phenyl)-3-(5-methyl-1,3,4-oxadiazol-2-yl)-2-oxo-1,2-dihydroquinolin-4-olate
7-Chloro-6-(4-(dimethylamino)phenyl)-3-(2-methylthiazol-5-yl)-2-oxo-1,2-dihydroquinolin-4-olate
7-Chloro-6-(4-(dimethylamino)phenyl)-3-(2,4-dimethylthiazol-5-yl)-2-oxo-1,2-dihydroquinolin-4-olate
7-Chloro-3-(5-methyl-1,3,4-oxadiazol-2-yl)-2-oxo-6-(4-(piperidin-1-yl)phenyl)-1,2-dihydroquinolin-4-olate
Ethyl 7-chloro-4-hydroxy-6-(1-methyl-1H-indol-5-yl)-2-oxo-1,2-dihydro-3-quinolinecarboxylate
Ethyl 7-chloro-4-hydroxy-6-[2'-hydroxy-3'-(methyloxy)-4-biphenylyl]-2-oxo-1,2-dihydro-3-quinoline carboxylate
7-Chloro-4-hydroxy-6-(1-methyl-1H-indol-5-yl)-3-nitro-quinolin-2(1H)-one
Ethyl 7-chloro-4-hydroxy-6-[4-(4-morpholinyl)phenyl]-2-oxo-1,2-dihydro-3-quinolinecarboxylate
7-Chloro-4-hydroxy-3-(3-methylisoxazol-5-yl)-6-(4-morpholino phenyl)quinolin-2(1H)-one
7-Chloro-4-hydroxy-3-(3-methoxyphenyl)-6-(4-(piperidin-1-yl)phenyl)quinolin-2(1H)-one
7-Chloro-4-hydroxy-3-(3-methoxyphenyl)-6-(1-methyl-1H-benzo[d]imidazol-6-yl)quinolin-2(1H)-one
7-Chloro-4-hydroxy-3-(3-methoxyphenyl)-6-(4-(pyrrolidin-1-yl)phenyl)quinolin-2(1H)-one
Methyl (4-(7-chloro-4-hydroxy-3-(3-methoxyphenyl)-2-oxo-1,2-dihydroquinolin-6-yl)phenyl)carbamate
7-Chloro-6-[4-(dimethylamino)phenyl]-4-hydroxy-3-[3-(methyloxy)phenyl]quinolin-2(1H)-one
7-Chloro-6-(2,3-dihydro-1H-inden-5-yl)-4-hydroxy-3-(3-methoxyphenyl)quinolin-2(1H)-one
7-Chloro-4-hydroxy-3-(3-methoxyphenyl)-6-(4-(4-methylpiperazin-1-yl)phenyl)quinolin-2(1H)-one
7-Chloro-6-(4-ethylphenyl)-4-hydroxy-3-(3-methoxyphenyl)quinolin-2(1H)-one
7-Chloro-6-[3-(dimethylamino)phenyl]-4-hydroxy-3-[3-(methyloxy)phenyl]-2(1H)-quinolinone
7-Chloro-6-(3-(dimethylamino)phenyl)-4-hydroxy-3-(3-methylisoxazol-5-yl)quinolin-2(1H)-one
7-Chloro-6-(4-(dimethylamino)phenyl)-4-hydroxy-3-(3-methylisoxazol-5-yl)quinolin-2(1H)-one
7-Chloro-6-(4-ethylphenyl)-4-hydroxy-3-(3-methylisoxazol-5-yl)quinolin-2(1H)-one
7-Chloro-4-hydroxy-6-(2'-hydroxy-3'-methoxy-[1,1'-biphenyl]-4-yl)-3-(3-methylisoxazol-5-yl)quinolin-2(1H)-one
7-Chloro-4-hydroxy-6-(4-morpholinophenyl)-3-phenoxyquinolin-2(1H)-one
7-Chloro-6-(4-(dimethylamino)phenyl)-4-hydroxy-3-phenylquinolin-2(1H)-one
6-(4-(1H-Pyrazol-1-yl)phenyl)-7-chloro-4-hydroxy-3-phenylquinolin-2(1H)-one
7-Chloro-4-hydroxy-6-(4-methoxyphenyl)-3-phenylquinolin-2(1H)-one
7-Chloro-6-(4-(dimethylamino)phenyl)-4-hydroxy-3-(1H-pyrazol-1-yl)quinolin-2(1H)-one
7-Chloro-4-hydroxy-6-(4-morpholinophenyl)-3-(1H-pyrazol-1-yl)quinolin-2(1H)-one
7-Chloro-6-(4-(dimethylamino)phenyl)-4-hydroxy-3-phenoxyquinolin-2(1H)-one
7-Chloro-4-hydroxy-3-phenyl-6-(4-(piperidin-1-yl)phenyl)quinolin-2(1H)-one
7-Chloro-4-hydroxy-6-(4-(2-hydroxyethyl)phenyl)-3-phenylquinolin-2(1H)-one
7-Chloro-4-hydroxy-6-(4-(3-hydroxypiperidin-1-yl)phenyl)-3-(3-methoxyphenyl)quinolin-2(1H)-one
7-Chloro-4-hydroxy-6-(2'-hydroxy-3'-methoxy-[1,1'-biphenyl]-4-yl)-3-(1H-pyrazol-1-yl)quinolin-2(1H)-one
7-Chloro-4-hydroxy-3-(3-methoxyphenyl)-6-(4-methyl-3,4-dihydro-2H-benzo[b][1,4]oxazin-7-yl)quinolin-2(1H)-one
7-Chloro-4-hydroxy-3-phenyl-6-(4-(pyrrolidin-1-yl)phenyl)quinolin-2(1H)-one
7-Chloro-4-hydroxy-6-(2'-hydroxy-3'-methoxy-[1,1'-biphenyl]-4-yl)-3-phenoxyquinolin-2(1H)-one
7-Chloro-4-hydroxy-6-(2'-hydroxy-3'-methoxy-[1,1'-biphenyl]-4-yl)quinolin-2(1H)-one
N-(4-(4-(7-Chloro-4-hydroxy-2-oxo-3-phenoxy-1,2-dihydroquinolin-6-yl)phenyl)thiazol-2-yl)acetamide
7-Chloro-6-(4-(dimethylamino)phenyl)-4-hydroxy-3-(o-tolyloxy)quinolin-2(1H)-one
7-Chloro-6-(4-(dimethylamino)phenyl)-4-hydroxy-3-(4-methoxyphenoxy)quinolin-2(1H)-one
7-Chloro-4-hydroxy-6-(4-(hydroxymethyl)phenyl)-3-phenylquinolin-2(1H)-one
7-Chloro-3-(3-fluorophenoxy)-4-hydroxy-6-(4-isopropylphenyl)quinolin-2(1H)-one
7-Chloro-6-(4-(dimethylamino)phenyl)-3-(3-fluorophenoxy)-4-hydroxyquinolin-2(1H)-one
7-Chloro-4-hydroxy-6-(4-(methylamino)phenyl)-3-phenylquinolin-2(1H)-one
7-Chloro-4-hydroxy-3-(1H-pyrazol-1-yl)-6-(4-(pyrrolidin-1-yl)phenyl)quinolin-2(1H)-one
7-Chloro-6-(4-ethoxyphenyl)-4-hydroxy-3-(1H-pyrazol-1-yl)quinolin-2(1H)-one
7-Chloro-4-hydroxy-3-phenoxy-6-(4-(pyrrolidin-1-yl)phenyl)quinolin-2(1H)-one
7-Chloro-6-(4-ethylphenyl)-4-hydroxy-3-phenoxyquinolin-2(1H)-one
7-Chloro-4-hydroxy-6-(4-isopropylphenyl)-3-phenoxyquinolin-2(1H)-one
7-Chloro-6-(4-(dimethylamino)phenyl)-4-hydroxy-3-(3-methoxyphenoxy)quinolin-2(1H)-one
7-Chloro-4-hydroxy-3-(3-methoxyphenoxy)-6-(4-(pyrrolidin-1-yl)phenyl)quinolin-2(1H)-one
7-Chloro-4-hydroxy-6-(4-isopropylphenyl)-3-(3-methoxyphenoxy)quinolin-2(1H)-one
7-Chloro-4-hydroxy-6-(1-methyl-1H-indol-5-yl)-3-(1H-pyrazol-1-yl)quinolin-2(1H)-one
7-Chloro-6-(4-(cyclopropylmethoxy)phenyl)-4-hydroxy-3-(1H-pyrazol-1-yl)quinolin-2(1H)-one
7-Chloro-4-hydroxy-6-(4-methyl-3,4-dihydro-2H-benzo[b][1,4]oxazin-7-yl)-3-(1H-pyrazol-1-yl)quinolin-2(1H)-one
7-Chloro-4-hydroxy-6-(1-methyl-1H-indazol-5-yl)-3-(1H-pyrazol-1-yl)quinolin-2(1H)-one
7-Chloro-4-hydroxy-6-(4-isopropylphenyl)-3-(3-methylisoxazol-5-yl)quinolin-2(1H)-one
7-Chloro-3-(3,5-dimethyl-1H-pyrazol-1-yl)-6-(4-(dimethylamino)phenyl)-4-hydroxyquinolin-2(1H)-one
7-Chloro-6-(4-(dimethylamino)phenyl)-4-hydroxy-3-(p-tolyloxy)quinolin-2(1H)-one 7-Chloro-6-(2,3-dihydro-1H-inden-5-yl)-4-hydroxy-3-(3-methylisoxazol-5-yl)quinolin-2(1H)-one
7-Chloro-6-(4-(dimethylamino)phenyl)-4-hydroxy-3-(4-methyl-1,2,5-oxadiazol-3-yl)quinolin-2(1H)-one
7-Chloro-6-(4-(dimethylamino)phenyl)-4-hydroxy-3-(pyridin-4-yl)quinolin-2(1H)-one
7-Chloro-6-(4-(dimethylamino)phenyl)-4-hydroxy-3-(pyridin-2-yloxy)quinolin-2(1H)-one
7-Chloro-6-(4-(dimethylamino)phenyl)-4-hydroxy-3-(1H-1,2,4-triazol-1-yl)quinolin-2(1H)-one
7-Chloro-6-(4-(dimethylamino)phenyl)-4-hydroxy-3-(2-methoxyphenoxy)quinolin-2(1H)-one
7-Chloro-6-(4-(dimethylamino)phenyl)-4-hydroxy-3-(1H-1,2,3-triazol-1-yl)quinolin-2(1H)-one
7-Chloro-6-(4-(dimethylamino)phenyl)-4-hydroxy-3-(4-methyl-1H-pyrazol-1-yl)quinolin-2(1H)-one
7-Chloro-6-(4-(dimethylamino)phenyl)-4-hydroxy-3-(m-tolyloxy)quinolin-2(1H)-one
7-Chloro-6-(4-(dimethylamino)phenyl)-4-hydroxy-3-(pyridin-3-yl)quinolin-2(1H)-one
3-((7-Chloro-6-(4-(dimethylamino)phenyl)-4-hydroxy-2-oxo-1,2-dihydroquinolin-3-yl)oxy)benzoic acid
1-(7-Chloro-6-(4-(dimethylamino)phenyl)-4-hydroxy-2-oxo-1,2-dihydroquinolin-3-yl)-1H-pyrazole-4-carboxylic acid
7-Chloro-6-(4-(dimethylamino)phenyl)-3-(4-fluorophenoxy)-4-hydroxyquinolin-2(1H)-one
7-Chloro-4-hydroxy-6-(2'-hydroxy-[1,1'-biphenyl]-4-yl)-3-(1H-pyrazol-1-yl)quinolin-2(1H)-one
7-Chloro-3-(1,3-dimethyl-1H-pyrazol-5-yl)-6-(4-(dimethylamino)phenyl)-4-hydroxyquinolin-2(1H)-one
7-Chloro-4-hydroxy-6-(4-(piperidin-1-yl)phenyl)-3-(1H-pyrazol-1-yl)quinolin-2(1H)-one
7-Chloro-6-(4-(dimethylamino)phenyl)-4-hydroxy-3-((4-methylpyridin-2-yl)oxy)quinolin-2(1H)-one
7-Chloro-4-hydroxy-6-(1-methyl-1H-indol-5-yl)-3-(3-methylisoxazol-5-yl)quinolin-2(1H)-one
7-Chloro-4-hydroxy-3-(3-methylisoxazol-5-yl)-6-(4-(pyrrolidin-1-yl)phenyl)quinolin-2(1H)-one
7-Chloro-4-hydroxy-6-(4-methoxyphenyl)-3-(3-methylisoxazol-5-yl)quinolin-2(1H)-one
7-Chloro-4-hydroxy-6-(1-methyl-1H-indol-5-yl)-3-(pyridin-3-yl)quinolin-2(1H)-one
1-(7-Chloro-4-hydroxy-2-oxo-6-(4-(pyrrolidin-1-yl)phenyl)-1,2-dihydroquinolin-3-yl)-1H-pyrazole-4-carboxylic acid
7-Chloro-4-hydroxy-3-(pyridin-3-yl)-6-(4-(pyrrolidin-1-yl)phenyl)quinolin-2(1H)-one
7-Chloro-4-hydroxy-3-(4-methyl-1,2,5-oxadiazol-3-yl)-6-(1-methyl-1H-indol-5-yl)quinolin-2(1H)-one
7-Chloro-4-hydroxy-3-(4-methyl-1,2,5-oxadiazol-3-yl)-6-(4-(pyrrolidin-1-yl)phenyl)quinolin-2(1H)-one
7-Chloro-4-hydroxy-3-(pyridin-4-yl)-6-(4-(pyrrolidin-1-yl)phenyl)quinolin-2(1H)-one
7-Chloro-4-hydroxy-6-(1-methyl-1H-indol-5-yl)-3-(4-methyl-1H-pyrazol-1-yl)quinolin-2(1H)-one
7-Chloro-4-hydroxy-6-(1-methyl-1H-indol-5-yl)-3-(pyridin-4-yl)quinolin-2(1H)-one
7-Chloro-4-hydroxy-6-(1-methyl-1H-indol-5-yl)-3-phenoxyquinolin-2(1H)-one
7-Chloro-4-hydroxy-3-(2-methoxyphenoxy)-6-(1-methyl-1H-indol-5-yl)quinolin-2(1H)-one
7-Chloro-4-hydroxy-6-(1-methyl-1H-indol-5-yl)-3-(p-tolyloxy)quinolin-2(1H)-one
7-Chloro-3-(3-fluorophenoxy)-4-hydroxy-6-(1-methyl-1H-indol-5-yl)quinolin-2(1H)-one
6-([1,1'-Biphenyl]-4-yl)-7-chloro-4-hydroxy-3-(3-methylisoxazol-5-yl)quinolin-2(1H)-one
7-Chloro-6-(4-cyclohexylphenyl)-4-hydroxy-3-(3-methylisoxazol-5-yl)quinolin-2(1H)-one
7-Chloro-6-(4-(dimethylamino)phenyl)-4-hydroxy-3-(5-methyl-1H-pyrazol-1-yl)quinolin-2(1H)-one
7-Chloro-4-hydroxy-3-(5-methyl-1H-pyrazol-1-yl)-6-(4-(pyrrolidin-1-yl)phenyl)quinolin-2(1H)-one
7-Chloro-4-hydroxy-3-(3-methylisoxazol-5-yl)-6-(naphthalen-2-yl)quinolin-2(1H)-one
7-Chloro-4-hydroxy-6-(4-(3-hydroxypiperidin-1-yl)phenyl)-3-(1H-pyrazol-1-yl)quinolin-2(1H)-one
7-Chloro-6-(4-(dimethylamino)phenyl)-4-hydroxy-3-(phenylthio)quinolin-2(1H)-one
7-Chloro-4-hydroxy-6-(4-morpholinophenyl)-3-(phenylthio)quinolin-2(1H)-one
7-Chloro-4-hydroxy-6-(4-(hydroxymethyl)phenyl)-3-(phenylthio)quinolin-2(1H)-one
7-Chloro-4-hydroxy-6-(6-methoxynaphthalen-2-yl)-3-(3-methylisoxazol-5-yl)quinolin-2(1H)-one
7-Chloro-4-hydroxy-6-(4-methoxyphenyl)-3-phenoxyquinolin-2(1H)-one
6-(4-(1H-Pyrazol-1-yl)phenyl)-7-chloro-4-hydroxy-3-(1H-pyrazol-1-yl)quinolin-2(1H)-one
7-Chloro-4-hydroxy-6-(1H-indol-5-yl)-3-(1H-pyrazol-1-yl)quinolin-2(1H)-one
7-Chloro-3-(1,3-dimethyl-1H-pyrazol-5-yl)-4-hydroxy-6-(1-methyl-1H-indol-5-yl)quinolin-2(1H)-one
7-Chloro-3-(4-chloro-1H-pyrazol-1-yl)-6-(4-(dimethylamino)phenyl)-4-hydroxyquinolin-2(1H)-one
7-Chloro-4-hydroxy-3-(3-methoxyphenoxy)-6-(1-methyl-1H-indol-5-yl)quinolin-2(1H)-one
7-Chloro-3-(1,3-dimethyl-1H-pyrazol-5-yl)-4-hydroxy-6-(4-(pyrrolidin-1-yl)phenyl)quinolin-2(1H)-one
7-Chloro-4-hydroxy-6-(1-methyl-1H-indol-5-yl)-3-(1H-1,2,4-triazol-1-yl)quinolin-2(1H)-one
7-Chloro-4-hydroxy-6-(1-methyl-1H-indol-5-yl)-3-(1-methyl-1H-pyrazol-4-yl)quinolin-2(1H)-one
7-Chloro-4-hydroxy-6-(1-methyl-1H-indol-5-yl)-3-(5-methylpyridin-2-yl)oxy)quinolin-2(1H)-one
7-Chloro-3-(4-chloro-1H-pyrazol-1-yl)-4-hydroxy-6-(1-methyl-1H-indol-5-yl)quinolin-2(1H)-one
7-Chloro-4-hydroxy-6-(4-(pyrrolidin-1-yl)phenyl)-3-(1H-1,2,4-triazol-1-yl)quinolin-2(1H)-one
7-Chloro-4-hydroxy-6-(4-(piperidin-1-yl)phenyl)-3-(1H-1,2,4-triazol-1-yl)quinolin-2(1H)-one
7-Chloro-6-(4-(dimethylamino)phenyl)-3-(3-fluorophenyl)-4-hydroxyquinolin-2(1H)-one
7-Chloro-4-hydroxy-6-(4-(methylamino)phenyl)-3-(3-methylisoxazol-5-yl)quinolin-2(1H)-one
7-Chloro-4-hydroxy-3-(4-methyl-1H-pyrazol-1-yl)-6-(4-(pyrrolidin-1-yl)phenyl)quinolin-2(1H)-one
7-Chloro-4-hydroxy-3-(4-methyl-1H-pyrazol-1-yl)-6-(4-(piperidin-1-yl)phenyl)quinolin-2(1H)-one
7-Chloro-4-hydroxy-6-(4-(1-(hydroxymethyl)cyclopropyl)phenyl)-3-(1H-pyrazol-1-yl)quinolin-2(1H)-one
7-Chloro-6-(1-ethyl-1H-indol-5-yl)-4-hydroxy-3-(1H-pyrazol-1-yl)quinolin-2(1H)-one
7-Chloro-4-hydroxy-3-(4-methyl-1,2,5-oxadiazol-3-yl)-6-(4-(piperidin-1-yl)phenyl)quinolin-2(1H)-one
7-Chloro-4-hydroxy-6-(4-(piperidin-1-yl)phenyl)-3-(pyridin-3-yl)quinolin-2(1H)-one
7-Chloro-4-hydroxy-6-(4-(1-(hydroxymethyl)cyclopropyl)phenyl)-3-(3-methylisoxazol-5-yl)quinolin-2(1H)-one
7-Chloro-6-(4-(dimethylamino)phenyl)-4-hydroxy-3-nitroquinolin-2(1H)-one 7-Chloro-6-(4-(dimethylamino)phenyl)-4-hydroxy-3-(phenylsulfonyl)quinolin-2(1H)-one
7-Chloro-4-hydroxy-6-(1-methyl-1H-indol-5-yl)-3-(phenylsulfonyl)quinolin-2(1H)-one
7-Chloro-6-(4-(dimethylamino)phenyl)-3-(4-fluorophenyl)-4-hydroxyquinolin-2(1H)-one
7-Chloro-6-(4-(dimethylamino)phenyl)-4-hydroxy-3-(o-tolyl)quinolin-2(1H)-one
7-Chloro-6-(4-(dimethylamino)phenyl)-4-hydroxy-3-(2-methoxyphenyl)quinolin-2(1H)-one
7-Chloro-3-(4-chlorophenyl)-6-(4-(dimethylamino)phenyl)-4-hydroxyquinolin-2(1H)-one
7-Chloro-3-(3-chlorophenyl)-6-(4-(dimethylamino)phenyl)-4-hydroxyquinolin-2(1H)-one
7-Chloro-3-(2-chlorophenyl)-6-(4-(dimethylamino)phenyl)-4-hydroxyquinolin-2(1H)-one
7-Chloro-6-(4-(dimethylamino)phenyl)-3-(2-fluoro phenyl)-4-hydroxyquinolin-2(1H)-one
7-Chloro-4-hydroxy-6-(1-methyl-1H-indol-6-yl)-3-(3-methylisoxazol-5-yl)quinolin-2(1H)-one
7-Chloro-4-hydroxy-6-(1-methylindolin-5-yl)-3-(3-methylisoxazol-5-yl)quinolin-2(1H)-one
7-Chloro-4-hydroxy-3-(4-methoxy-1H-pyrazol-1-yl)-6-(4-(piperidin-1-yl)phenyl)quinolin-2(1H)-one
7-Chloro-6-(4-(dimethylamino)phenyl)-4-hydroxy-3-(m-tolyl)quinolin-2(1H)-one
7-Chloro-6-(4-(dimethylamino)phenyl)-4-hydroxy-3-(p-tolyl)quinolin-2(1H)-one
7-Chloro-4-hydroxy-6-(4-(1-(hydroxymethyl)cyclopropyl) phenyl)-3-(2-methoxyphenoxy)quinolin-2(1H)-one
7-chloro-4-hydroxy-6-(4-(1-(hydroxymethyl)cyclopropyl) phenyl)-3-(4-methoxy-1H-pyrazol-1-yl)quinolin-2(1H)-one
7-Chloro-4-hydroxy-6-(4-(1-(hydroxymethyl)cyclopentyl) phenyl)-3-(3-methylisoxazol-5-yl)quinolin-2(1H)-one
7-Chloro-6-(4-(dimethylamino)phenyl)-4-hydroxy-3-(4-methoxyphenyl) quinolin-2(1H)-one
Methyl 1-(4-(7-chloro-4-hydroxy-3-(3-methylisoxazol-5-yl)-2-oxo-1,2-dihydroquinolin-6-yl)phenyl)cyclopropane carboxylate
7-Chloro-3-(3-chlorophenyl)-4-hydroxy-6-(1-methyl-1H-indol-5-yl)quinolin-2(1H)-one
7-Chloro-3-(3-chlorophenyl)-4-hydroxy-6-(4-(pyrrolidin-1-yl)phenyl)quinolin-2(1H)-one
7-Chloro-6-(4-(dimethylamino)phenyl)-4-hydroxy-3-(4-methoxy-1H-pyrazol-1-yl)quinolin-2(1H)-one
7-Chloro-4-hydroxy-6-(4-(1-(hydroxymethyl)cyclobutyl) phenyl)-3-(3-methylisoxazol-5-yl)quinolin-2(1H)-one
7-Chloro-6-(4-(1-hydroxycyclobutyl)phenyl)-3-(3-methylisoxazol-5-yl)-2-oxo-1,2-dihydroquinolin-4-olate
7-Chloro-6-(1-ethyl-1H-indol-5-yl)-3-(3-methylisoxazol-5-yl)-2-oxo-1,2-dihydroquinolin-4-olate
7-Chloro-6-(4-ethoxyphenyl)-3-(3-methylisoxazol-5-yl)-2-oxo-1,2-dihydroquinolin-4-olate
7-Chloro-6-(4-(3-hydroxyoxetan-3-yl)phenyl)-3-(3-methylisoxazol-5-yl)-2-oxo-1,2-dihydroquinolin-4-olate
7-Chloro-6-(4-(dimethylamino)phenyl)-4-hydroxy-3-(3-methyl-1H-pyrazol-1-yl)quinolin-2(1H)-one
7-Chloro-6-(4-(dimethylamino)phenyl)-4-hydroxy-3-((4-methoxypyridin-2-yl)oxy)quinolin-2(1H)-one
7-Chloro-4-hydroxy-3-(4-methoxyphenoxy)-6-(1-methyl-1H-indol-5-yl)quinolin-2(1H)-one
7-Chloro-6-(4-(dimethylamino)phenyl)-4-hydroxy-3-((5-methylpyridin-2-yl)oxy)quinolin-2(1H)-one
7-Chloro-6-(2'-fluoro-[1,1'-biphenyl]-4-yl)-4-hydroxy-3-(1H-pyrazol-1-yl)quinolin-2(1H)-one
7-Chloro-4-hydroxy-6-(4-(5-methylthiophen-2-yl)phenyl)-3-(1H-pyrazol-1-yl)quinolin-2(1H)-one
3-(4-Bromo-1H-pyrazol-1-yl)-7-chloro-6-(4-(dimethylamino)phenyl)-4-hydroxyquinolin-2(1H)-one
3-(4-Bromo-1H-pyrazol-1-yl)-7-chloro-4-hydroxy-6-(4-(piperidin-1-yl)phenyl)quinolin-2(1H)-one
6-[4-(2-Amino-1,3-thiazol-4-yl)phenyl]-7-chloro-4-hydroxy-3-phenylquinolin-2(1H)-one
6-[4-(2-Amino-1,3-thiazol-4-yl)phenyl]-7-chloro-4-hydroxy-3-[3-(methyloxy)phenyl]quinolin-2(1H)-one
6-(4-(2-Amino-1,3-thiazol-4-yl)phenyl)-7-chloro-4-hydroxy-3-(3-methylisoxazol-5-yl)quinolin-2(1H)-one
6-(4-(2-Amino-1,3-thiazol-4-yl)phenyl)-7-chloro-4-hydroxy-3-(3-methoxyphenyl)quinolin-2(1H)-one
6-(4-(2-Amino-1,3-thiazol-4-yl)phenyl)-7-chloro-4-hydroxy-3-(pyridin-3-yl)quinolin-2(1H)-one
6-[4-(2-Amino-1,3-thiazol-4-yl)phenyl]-7-chloro-4-hydroxy-3-(1H-pyrazol-1-yl)-2(1H)-quinolinone
6-(4-(2-Amino-1,3-thiazol-4-yl)phenyl)-7-chloro-4-hydroxy-3-(pyridin-4-yl)quinolin-2(1H)-one
6-(4-(2-Amino-1,3-thiazol-4-yl)phenyl)-7-chloro-4-hydroxy-3-(4-methyl-1H-pyrazol-1-yl)quinolin-2(1H)-one
6-(4-(2-Amino-1,3-thiazol-4-yl)phenyl)-7-chloro-4-hydroxy-3-(1H-1,2,3-triazol-1-yl)quinolin-2(1H)-one
7-Chloro-4-hydroxy-6-(1-methyl-1H-indol-5-yl)quinolin-2(1H)-one
7-Chloro-4-hydroxy-6-[4-(4-morpholinyl)phenyl]quinolin-2(1H)-one
7-chloro-4-hydroxy-6-[2'-hydroxy-3'-(methyloxy)-4-biphenylyl]-2-oxo-1,2-dihydro-3-quinolinecarboxylic acid
1-(4-(7-Chloro-3-(3-methylisoxazol-5-yl)-4-oxido-2-oxo-1,2-dihydroquinolin-6-yl)phenyl)cyclopropanecarboxylate,
1-(7-Chloro-4-oxido-2-oxo-6-(4-(piperidin-1-yl)phenyl)-1,2-dihydroquinolin-3-yl)-1H-pyrazole-4-carboxylate,
7-Chloro-3-(3-chlorophenyl)-4-hydroxy-6-(4-(piperidin-1-yl)phenyl) quinolin-2(1H)-one
or salts thereof.

In a further aspect of the invention there is provided a compound of formula (I) selected from the group consisting of Examples 1-196:
7-Chloro-4-hydroxy-6-(2'-hydroxy-3'-methoxy-[1,1'-biphenyl]-4-yl)-3-phenylquinolin-2(1H)-one
3-{7-Chloro-4-hydroxy-6-[2'-hydroxy-3'-(methyloxy)-4-biphenylyl]-2-oxo-1,2-dihydro-3-quinolinyl}benzoic acid
7-chloro-4-hydroxy-3-(3-methoxyphenyl)-6-(4-morpholinophenyl)quinolin-2(1H)-one
7-Chloro-4-hydroxy-6-[4-(4-morpholinyl)phenyl]-3-phenylquinolin-2(1H)-one
4-{7-Chloro-4-hydroxy-3-[3-(methyloxy)phenyl]-2-oxo-1,2-dihydro-6-quinolinyl}-N-cyclopentylbenzamide
7-Fluoro-4-hydroxy-3-(3-methoxyphenyl)-6-(4-morpholinophenyl)quinolin-2(1H)-one
3-[7-Chloro-4-hydroxy-6-(1-methyl-1H-indol-5-yl)-2-oxo-1,2-dihydro-3-quinolinyl]benzoic acid
7-Chloro-4-hydroxy-6-(1-methyl-1H-indol-5-yl)-3-[3-(methyloxy)phenyl]quinolin-2(1H)-one
N-{4-[4-(7-Chloro-4-hydroxy-2-oxo-3-phenyl-1,2-dihydro-6-quinolinyl)phenyl]-1,3-thiazol-2-yl}acetamide
7-Chloro-4-hydroxy-6-(1-methyl-1H-indol-5-yl)-3-phenylquinolin-2(1H)-one
7-Chloro-4-hydroxy-3-(3-methylisoxazol-5-yl)-6-(4-(piperidin-1-yl)phenyl)quinolin-2(1H)-one
7-Chloro-6-(4-(dimethylamino)phenyl)-4-hydroxyquinolin-2(1H)-one
7-Chloro-4-hydroxy-3-(1-methyl-1H-pyrazol-4-yl)-6-(4-(piperidin-1-yl)phenyl)quinolin-2(1H)-one 7-Chloro-6-(4'-fluoro-[1,1'-biphenyl]-4-yl)-4-hydroxy-3-(3-methylisoxazol-5-yl)quinolin-2(1H)-one
7-Chloro-4-hydroxy-6-(3'-methoxy-[1,1'-biphenyl]-4-yl)-3-(3-methylisoxazol-5-yl)quinolin-2(1H)-one
7-Chloro-4-hydroxy-3-(3-methylisoxazol-5-yl)-6-(4-(5-methylthiophen-2-yl)phenyl)quinolin-2(1H)-one
7-Chloro-4-hydroxy-6-(4'-methoxy-[1,1'-biphenyl]-4-yl)-3-(3-methylisoxazol-5-yl)quinolin-2(1H)-one
7-Chloro-6-(2'-fluoro-[1,1'-biphenyl]-4-yl)-4-hydroxy-3-(3-methylisoxazol-5-yl)quinolin-2(1H)-one
3-(7-Chloro-6-(4-(dimethylamino)phenyl)-4-hydroxy-2-oxo-1,2-dihydroquinolin-3-yl)benzonitrile
7-Chloro-6-(4-(dimethylamino)phenyl)-3-(3-methyl-1,2,4-oxadiazol-5-yl)-2-oxo-1,2-dihydroquinolin-4-olate, potassium salt
7-Chloro-3,6-bis(4-(dimethylamino)phenyl)-2-oxo-1,2-dihydroquinolin-4-olate, potassium salt
7-Chloro-3-(4-cyanophenyl)-6-(4-(dimethylamino)phenyl)-2-oxo-1,2-dihydroquinolin-4-olate, potassium salt
7-Chloro-6-(4-(dimethylamino)phenyl)-3-(5-methyl-1,3,4-oxadiazol-2-yl)-2-oxo-1,2-dihydroquinolin-4-olate, potassium salt
7-Chloro-6-(4-(dimethylamino)phenyl)-3-(2-methylthiazol-5-yl)-2-oxo-1,2-dihydroquinolin-4-olate, potassium salt
7-Chloro-6-(4-(dimethylamino)phenyl)-3-(2,4-dimethylthiazol-5-yl)-2-oxo-1,2-dihydroquinolin-4-olate, potassium salt
7-Chloro-3-(5-methyl-1,3,4-oxadiazol-2-yl)-2-oxo-6-(4-(piperidin-1-yl)phenyl)-1,2-dihydroquinolin-4-olate, potassium salt
Ethyl 7-chloro-4-hydroxy-6-(1-methyl-1H-indol-5-yl)-2-oxo-1,2-dihydro-3-quinolinecarboxylate
Ethyl 7-chloro-4-hydroxy-6-[2'-hydroxy-3'-(methyloxy)-4-biphenylyl]-2-oxo-1,2-dihydro-3-quinoline carboxylate
7-Chloro-4-hydroxy-6-(1-methyl-1H-indol-5-yl)-3-nitroquinolin-2(1H)-one
Ethyl 7-chloro-4-hydroxy-6-[4-(4-morpholinyl)phenyl]-2-oxo-1,2-dihydro-3-quinolinecarboxylate
7-Chloro-4-hydroxy-3-(3-methylisoxazol-5-yl)-6-(4-morpholino phenyl)quinolin-2(1H)-one
7-Chloro-4-hydroxy-3-(3-methoxyphenyl)-6-(4-(piperidin-1-yl)phenyl)quinolin-2(1H)-one
7-Chloro-4-hydroxy-3-(3-methoxyphenyl)-6-(1-methyl-1H-benzo[d]imidazol-6-yl)quinolin-2(1H)-one
7-Chloro-4-hydroxy-3-(3-methoxyphenyl)-6-(4-(pyrrolidin-1-yl)phenyl)quinolin-2(1H)-one
Methyl (4-(7-chloro-4-hydroxy-3-(3-methoxyphenyl)-2-oxo-1,2-dihydroquinolin-6-yl)phenyl)carbamate
7-Chloro-6-[4-(dimethylamino)phenyl]-4-hydroxy-3-[3-(methyloxy)phenyl]quinolin-2(1H)-one
7-Chloro-6-(2,3-dihydro-1H-inden-5-yl)-4-hydroxy-3-(3-methoxyphenyl)quinolin-2(1H)-one
7-Chloro-4-hydroxy-3-(3-methoxyphenyl)-6-(4-(4-methylpiperazin-1-yl)phenyl)quinolin-2(1H)-one
7-Chloro-6-(4-ethylphenyl)-4-hydroxy-3-(3-methoxyphenyl)quinolin-2(1H)-one
7-Chloro-6-[3-(dimethylamino)phenyl]-4-hydroxy-3-[3-(methyloxy)phenyl]-2(1H)-quinolinone
7-Chloro-6-(3-(dimethylamino)phenyl)-4-hydroxy-3-(3-methylisoxazol-5-yl)quinolin-2(1H)-one
7-Chloro-6-(4-(dimethylamino)phenyl)-4-hydroxy-3-(3-methylisoxazol-5-yl)quinolin-2(1H)-one
7-Chloro-6-(4-ethylphenyl)-4-hydroxy-3-(3-methylisoxazol-5-yl)quinolin-2(1H)-one
7-Chloro-4-hydroxy-6-(2'-hydroxy-3'-methoxy-[1,1'-biphenyl]-4-yl)-3-(3-methylisoxazol-5-yl)quinolin-2(1H)-one
7-Chloro-4-hydroxy-6-(4-morpholinophenyl)-3-phenoxyquinolin-2(1H)-one
7-Chloro-6-(4-(dimethylamino)phenyl)-4-hydroxy-3-phenylquinolin-2(1H)-one
6-(4-(1H-Pyrazol-1-yl)phenyl)-7-chloro-4-hydroxy-3-phenylquinolin-2(1H)-one
7-Chloro-4-hydroxy-6-(4-methoxyphenyl)-3-phenylquinolin-2(1H)-one
7-Chloro-6-(4-(dimethylamino)phenyl)-4-hydroxy-3-(1H-pyrazol-1-yl)quinolin-2(1H)-one
7-Chloro-4-hydroxy-6-(4-morpholinophenyl)-3-(1H-pyrazol-1-yl)quinolin-2(1H)-one
7-Chloro-6-(4-(dimethylamino)phenyl)-4-hydroxy-3-phenoxyquinolin-2(1H)-one
7-Chloro-4-hydroxy-3-phenyl-6-(4-(piperidin-1-yl)phenyl)quinolin-2(1H)-one
7-Chloro-4-hydroxy-6-(4-(2-hydroxyethyl)phenyl)-3-phenylquinolin-2(1H)-one
7-Chloro-4-hydroxy-6-(4-(3-hydroxypiperidin-1-yl)phenyl)-3-(3-methoxyphenyl)quinolin-2(1H)-one
7-Chloro-4-hydroxy-6-(2'-hydroxy-3'-methoxy-[1,1'-biphenyl]-4-yl)-3-(1H-pyrazol-1-yl)quinolin-2(1H)-one
7-Chloro-4-hydroxy-3-(3-methoxyphenyl)-6-(4-methyl-3,4-dihydro-2H-benzo[b][1,4]oxazin-7-yl)quinolin-2(1H)-one
7-Chloro-4-hydroxy-3-phenyl-6-(4-(pyrrolidin-1-yl)phenyl)quinolin-2(1H)-one
7-Chloro-4-hydroxy-6-(2'-hydroxy-3'-methoxy-[1,1'-biphenyl]-4-yl)-3-phenoxyquinolin-2(1H)-one
7-Chloro-4-hydroxy-6-(2'-hydroxy-3'-methoxy-[1,1'-biphenyl]-4-yl)quinolin-2(1H)-one
N-(4-(4-(7-Chloro-4-hydroxy-2-oxo-3-phenoxy-1,2-dihydroquinolin-6-yl)phenyl)thiazol-2-yl)acetamide
7-Chloro-6-(4-(dimethylamino)phenyl)-4-hydroxy-3-(o-tolyloxy)quinolin-2(1H)-one
7-Chloro-6-(4-(dimethylamino)phenyl)-4-hydroxy-3-(4-methoxyphenoxy)quinolin-2(1H)-one
7-Chloro-4-hydroxy-6-(4-(hydroxymethyl)phenyl)-3-phenylquinolin-2(1H)-one
7-Chloro-3-(3-fluorophenoxy)-4-hydroxy-6-(4-isopropylphenyl)quinolin-2(1H)-one
7-Chloro-6-(4-(dimethylamino)phenyl)-3-(3-fluorophenoxy)-4-hydroxyquinolin-2(1H)-one
7-Chloro-4-hydroxy-6-(4-(methylamino)phenyl)-3-phenylquinolin-2(1H)-one
7-Chloro-4-hydroxy-3-(1H-pyrazol-1-yl)-6-(4-(pyrrolidin-1-yl)phenyl)quinolin-2(1H)-one
7-Chloro-6-(4-ethoxyphenyl)-4-hydroxy-3-(1H-pyrazol-1-yl)quinolin-2(1H)-one
7-Chloro-4-hydroxy-3-phenoxy-6-(4-(pyrrolidin-1-yl)phenyl)quinolin-2(1H)-one
7-Chloro-6-(4-ethylphenyl)-4-hydroxy-3-phenoxyquinolin-2(1H)-one
7-Chloro-4-hydroxy-6-(4-isopropylphenyl)-3-phenoxyquinolin-2(1H)-one
7-Chloro-6-(4-(dimethylamino)phenyl)-4-hydroxy-3-(3-methoxyphenoxy)quinolin-2(1H)-one
7-Chloro-4-hydroxy-3-(3-methoxyphenoxy)-6-(4-(pyrrolidin-1-yl)phenyl)quinolin-2(1H)-one
7-Chloro-4-hydroxy-6-(4-isopropylphenyl)-3-(3-methoxyphenoxy)quinolin-2(1H)-one
7-Chloro-4-hydroxy-6-(1-methyl-1H-indol-5-yl)-3-(1H-pyrazol-1-yl)quinolin-2(1H)-one
7-Chloro-6-(4-(cyclopropylmethoxy)phenyl)-4-hydroxy-3-(1H-pyrazol-1-yl)quinolin-2(1H)-one 7-Chloro-4-hydroxy-6-(4-methyl-3,4-dihydro-2H-benzo[b]
[1,4]oxazin-7-yl)-3-(1H-pyrazol-1-yl)quinolin-2(1H)-
one
7-Chloro-4-hydroxy-6-(1-methyl-1H-indazol-5-yl)-3-(1H-
pyrazol-1-yl)quinolin-2(1H)-one
7-Chloro-4-hydroxy-6-(4-isopropylphenyl)-3-(3-methyl-
isoxazol-5-yl)quinolin-2(1H)-one
7-Chloro-3-(3,5-dimethyl-1H-pyrazol-1-yl)-6-(4-(dimethyl-
amino)phenyl)-4-hydroxyquinolin-2(1H)-one
7-Chloro-6-(4-(dimethylamino)phenyl)-4-hydroxy-3-(p-
tolyloxy)quinolin-2(1H)-one
7-Chloro-6-(2,3-dihydro-1H-inden-5-yl)-4-hydroxy-3-(3-
methylisoxazol-5-yl)quinolin-2(1H)-one
7-Chloro-6-(4-(dimethylamino)phenyl)-4-hydroxy-3-(4-
methyl-1,2,5-oxadiazol-3-yl)quinolin-2(1H)-one
7-Chloro-6-(4-(dimethylamino)phenyl)-4-hydroxy-3-(pyri-
din-4-yl)quinolin-2(1H)-one
7-Chloro-6-(4-(dimethylamino)phenyl)-4-hydroxy-3-(pyri-
din-2-yloxy)quinolin-2(1H)-one
7-Chloro-6-(4-(dimethylamino)phenyl)-4-hydroxy-3-(1H-1,
2,4-triazol-1-yl)quinolin-2(1H)-one
7-Chloro-6-(4-(dimethylamino)phenyl)-4-hydroxy-3-(2-
methoxyphenoxy)quinolin-2(1H)-one
7-Chloro-6-(4-(dimethylamino)phenyl)-4-hydroxy-3-(1H-1,
2,3-triazol-1-yl)quinolin-2(1H)-one
7-Chloro-6-(4-(dimethylamino)phenyl)-4-hydroxy-3-(4-
methyl-1H-pyrazol-1-yl)quinolin-2(1H)-one
7-Chloro-6-(4-(dimethylamino)phenyl)-4-hydroxy-3-(m-
tolyloxy)quinolin-2(1H)-one
7-Chloro-6-(4-(dimethylamino)phenyl)-4-hydroxy-3-(pyri-
din-3-yl)quinolin-2(1H)-one
3-((7-Chloro-6-(4-(dimethylamino)phenyl)-4-hydroxy-2-
oxo-1,2-dihydroquinolin-3-yl)oxy)benzoic acid
1-(7-Chloro-6-(4-(dimethylamino)phenyl)-4-hydroxy-2-
oxo-1,2-dihydroquinolin-3-yl)-1H-pyrazole-4-carboxylic
acid
7-Chloro-6-(4-(dimethylamino)phenyl)-3-(4-fluorophe-
noxy)-4-hydroxyquinolin-2(1H)-one
7-Chloro-4-hydroxy-6-(2'-hydroxy-[1,1'-biphenyl]-4-yl)-3-
(1H-pyrazol-1-yl)quinolin-2(1H)-one
7-Chloro-3-(1,3-dimethyl-1H-pyrazol-5-yl)-6-(4-(dimethyl-
amino)phenyl)-4-hydroxyquinolin-2(1H)-one
7-Chloro-4-hydroxy-6-(4-(piperidin-1-yl)phenyl)-3-(1H-
pyrazol-1-yl)quinolin-2(1H)-one
7-Chloro-6-(4-(dimethylamino)phenyl)-4-hydroxy-3-((4-
methylpyridin-2-yl)oxy)quinolin-2(1H)-one
7-Chloro-4-hydroxy-6-(1-methyl-1H-indol-5-yl)-3-(3-me-
thylisoxazol-5-yl)quinolin-2(1H)-one
7-Chloro-4-hydroxy-3-(3-methylisoxazol-5-yl)-6-(4-(pyrro-
lidin-1-yl)phenyl)quinolin-2(1H)-one
7-Chloro-4-hydroxy-6-(4-methoxyphenyl)-3-(3-methyl-
isoxazol-5-yl)quinolin-2(1H)-one
7-Chloro-4-hydroxy-6-(1-methyl-1H-indol-5-yl)-3-(pyri-
din-3-yl)quinolin-2(1H)-one
1-(7-Chloro-4-hydroxy-2-oxo-6-(4-(pyrrolidin-1-yl)phe-
nyl)-1,2-dihydroquinolin-3-yl)-1H-pyrazole-4-carboxylic
acid
7-Chloro-4-hydroxy-3-(pyridin-3-yl)-6-(4-(pyrrolidin-1-yl)
phenyl)quinolin-2(1H)-one
7-Chloro-4-hydroxy-3-(4-methyl-1,2,5-oxadiazol-3-yl)-6-
(1-methyl-1H-indol-5-yl)quinolin-2(1H)-one
7-Chloro-4-hydroxy-3-(4-methyl-1,2,5-oxadiazol-3-yl)-6-
(4-(pyrrolidin-1-yl)phenyl)quinolin-2(1H)-one
7-Chloro-4-hydroxy-3-(pyridin-4-yl)-6-(4-(pyrrolidin-1-yl)
phenyl)quinolin-2(1H)-one
7-Chloro-4-hydroxy-6-(1-methyl-1H-indol-5-yl)-3-(4-me-
thyl-1H-pyrazol-1-yl)quinolin-2(1H)-one
7-Chloro-4-hydroxy-6-(1-methyl-1H-indol-5-yl)-3-(pyri-
din-4-yl)quinolin-2(1H)-one
7-Chloro-4-hydroxy-6-(1-methyl-1H-indol-5-yl)-3-phenox-
yquinolin-2(1H)-one
7-Chloro-4-hydroxy-3-(2-methoxyphenoxy)-6-(1-methyl-
1H-indol-5-yl)quinolin-2(1H)-one
7-Chloro-4-hydroxy-6-(1-methyl-1H-indol-5-yl)-3-(p-toly-
loxy)quinolin-2(1H)-one
7-Chloro-3-(3-fluorophenoxy)-4-hydroxy-6-(1-methyl-1H-
indol-5-yl)quinolin-2(1H)-one
6-([1,1'-Biphenyl]-4-yl)-7-chloro-4-hydroxy-3-(3-methyl-
isoxazol-5-yl)quinolin-2(1H)-one
7-Chloro-6-(4-cyclohexylphenyl)-4-hydroxy-3-(3-methyl-
isoxazol-5-yl)quinolin-2(1H)-one
7-Chloro-6-(4-(dimethylamino)phenyl)-4-hydroxy-3-(5-
methyl-1H-pyrazol-1-yl)quinolin-2(1H)-one
7-Chloro-4-hydroxy-3-(5-methyl-1H-pyrazol-1-yl)-6-(4-
(pyrrolidin-1-yl)phenyl)quinolin-2(1H)-one
7-Chloro-4-hydroxy-3-(3-methylisoxazol-5-yl)-6-(naphtha-
len-2-yl)quinolin-2(1H)-one
7-Chloro-4-hydroxy-6-(4-(3-hydroxypiperidin-1-yl)phe-
nyl)-3-(1H-pyrazol-1-yl)quinolin-2(1H)-one
7-Chloro-6-(4-(dimethylamino)phenyl)-4-hydroxy-3-(phe-
nylthio)quinolin-2(1H)-one
7-Chloro-4-hydroxy-6-(4-morpholinophenyl)-3-(phe-
nylthio)quinolin-2(1H)-one
7-Chloro-4-hydroxy-6-(4-(hydroxymethyl)phenyl)-3-(phe-
nylthio)quinolin-2(1H)-one
7-Chloro-4-hydroxy-6-(6-methoxynaphthalen-2-yl)-3-(3-
methylisoxazol-5-yl)quinolin-2(1H)-one
7-Chloro-4-hydroxy-6-(4-methoxyphenyl)-3-phenox-
yquinolin-2(1H)-one
6-(4-(1H-Pyrazol-1-yl)phenyl)-7-chloro-4-hydroxy-3-(1H-
pyrazol-1-yl)quinolin-2(1H)-one
7-Chloro-4-hydroxy-6-(1H-indol-5-yl)-3-(1H-pyrazol-1-yl)
quinolin-2(1H)-one
7-Chloro-3-(1,3-dimethyl-1H-pyrazol-5-yl)-4-hydroxy-6-
(1-methyl-1H-indol-5-yl)quinolin-2(1H)-one
7-Chloro-3-(4-chloro-1H-pyrazol-1-yl)-6-(4-(dimethy-
lamino)phenyl)-4-hydroxyquinolin-2(1H)-one
7-Chloro-4-hydroxy-3-(3-methoxyphenoxy)-6-(1-methyl-
1H-indol-5-yl)quinolin-2(1H)-one
7-Chloro-3-(1,3-dimethyl-1H-pyrazol-5-yl)-4-hydroxy-6-
(4-(pyrrolidin-1-yl)phenyl)quinolin-2(1H)-one
7-Chloro-4-hydroxy-6-(1-methyl-1H-indol-5-yl)-3-(1H-1,2,
4-triazol-1-yl)quinolin-2(1H)-one
7-Chloro-4-hydroxy-6-(1-methyl-1H-indol-5-yl)-3-(1-me-
thyl-1H-pyrazol-4-yl)quinolin-2(1H)-one
7-Chloro-4-hydroxy-6-(1-methyl-1H-indol-5-yl)-3-(5-me-
thylpyridin-2-yl)oxy)quinolin-2(1H)-one
7-Chloro-3-(4-chloro-1H-pyrazol-1-yl)-4-hydroxy-6-(1-
methyl-1H-indol-5-yl)quinolin-2(1H)-one
7-Chloro-4-hydroxy-6-(4-(pyrrolidin-1-yl)phenyl)-3-(1H-1,
2,4-triazol-1-yl)quinolin-2(1H)-one
7-Chloro-4-hydroxy-6-(4-(piperidin-1-yl)phenyl)-3-(1H-1,
2,4-triazol-1-yl)quinolin-2(1H)-one
7-Chloro-6-(4-(dimethylamino)phenyl)-3-(3-fluorophenyl)-
4-hydroxyquinolin-2(1H)-one
7-Chloro-4-hydroxy-6-(4-(methylamino)phenyl)-3-(3-me-
thylisoxazol-5-yl)quinolin-2(1H)-one
7-Chloro-4-hydroxy-3-(4-methyl-1H-pyrazol-1-yl)-6-(4-
(pyrrolidin-1-yl)phenyl)quinolin-2(1H)-one
7-Chloro-4-hydroxy-3-(4-methyl-1H-pyrazol-1-yl)-6-(4-
(piperidin-1-yl)phenyl)quinolin-2(1H)-one
7-Chloro-4-hydroxy-6-(4-(1-(hydroxymethyl)cyclopropyl)
phenyl)-3-(1H-pyrazol-1-yl)quinolin-2(1H)-one 7-Chloro-6-(1-ethyl-1H-indol-5-yl)-4-hydroxy-3-(1H-pyrazol-1-yl)quinolin-2(1H)-one
7-Chloro-4-hydroxy-3-(4-methyl-1,2,5-oxadiazol-3-yl)-6-(4-(piperidin-1-yl)phenyl)quinolin-2(1H)-one
7-Chloro-4-hydroxy-6-(4-(piperidin-1-yl)phenyl)-3-(pyridin-3-yl)quinolin-2(1H)-one
7-Chloro-4-hydroxy-6-(4-(1-(hydroxymethyl)cyclopropyl)phenyl)-3-(3-methylisoxazol-5-yl)quinolin-2(1H)-one
7-Chloro-6-(4-(dimethylamino)phenyl)-4-hydroxy-3-nitroquinolin-2(1H)-one
7-Chloro-6-(4-(dimethylamino)phenyl)-4-hydroxy-3-(phenylsulfonyl)quinolin-2(1H)-one
7-Chloro-4-hydroxy-6-(1-methyl-1H-indol-5-yl)-3-(phenylsulfonyl)quinolin-2(1H)-one
7-Chloro-6-(4-(dimethylamino)phenyl)-3-(4-fluorophenyl)-4-hydroxyquinolin-2(1H)-one
7-Chloro-6-(4-(dimethylamino)phenyl)-4-hydroxy-3-(o-tolyl)quinolin-2(1H)-one
7-Chloro-6-(4-(dimethylamino)phenyl)-4-hydroxy-3-(2-methoxyphenyl)quinolin-2(1H)-one
7-Chloro-3-(4-chlorophenyl)-6-(4-(dimethylamino)phenyl)-4-hydroxyquinolin-2(1H)-one
7-Chloro-3-(3-chlorophenyl)-6-(4-(dimethylamino)phenyl)-4-hydroxyquinolin-2(1H)-one
7-Chloro-3-(2-chlorophenyl)-6-(4-(dimethylamino)phenyl)-4-hydroxyquinolin-2(1H)-one
7-Chloro-6-(4-(dimethylamino)phenyl)-3-(2-fluoro phenyl)-4-hydroxyquinolin-2(1H)-one
7-Chloro-4-hydroxy-6-(1-methyl-1H-indol-6-yl)-3-(3-methylisoxazol-5-yl)quinolin-2(1H)-one
7-Chloro-4-hydroxy-6-(1-methylindolin-5-yl)-3-(3-methylisoxazol-5-yl)quinolin-2(1H)-one
7-Chloro-4-hydroxy-3-(4-methoxy-1H-pyrazol-1-yl)-6-(4-(piperidin-1-yl)phenyl)quinolin-2(1H)-one
7-Chloro-6-(4-(dimethylamino)phenyl)-4-hydroxy-3-(m-tolyl)quinolin-2(1H)-one
7-Chloro-6-(4-(dimethylamino)phenyl)-4-hydroxy-3-(p-tolyl)quinolin-2(1H)-one
7-Chloro-4-hydroxy-6-(4-(1-(hydroxymethyl)cyclopropyl)phenyl)-3-(2-methoxyphenoxy)quinolin-2(1H)-one
7-chloro-4-hydroxy-6-(4-(1-(hydroxymethyl)cyclopropyl)phenyl)-3-(4-methoxy-1H-pyrazol-1-yl)quinolin-2(1H)-one
7-Chloro-4-hydroxy-6-(4-(1-(hydroxymethyl)cyclopentyl)phenyl)-3-(3-methylisoxazol-5-yl)quinolin-2(1H)-one
7-Chloro-6-(4-(dimethylamino)phenyl)-4-hydroxy-3-(4-methoxyphenyl)quinolin-2(1H)-one
Methyl 1-(4-(7-chloro-4-hydroxy-3-(3-methylisoxazol-5-yl)-2-oxo-1,2-dihydroquinolin-6-yl)phenyl)cyclopropane carboxylate
7-Chloro-3-(3-chlorophenyl)-4-hydroxy-6-(1-methyl-1H-indol-5-yl)quinolin-2(1H)-one
7-Chloro-3-(3-chlorophenyl)-4-hydroxy-6-(4-(pyrrolidin-1-yl)phenyl)quinolin-2(1H)-one
7-Chloro-6-(4-(dimethylamino)phenyl)-4-hydroxy-3-(4-methoxy-1H-pyrazol-1-yl)quinolin-2(1H)-one, potassium salt
7-Chloro-4-hydroxy-6-(4-(1-(hydroxymethyl)cyclobutyl)phenyl)-3-(3-methylisoxazol-5-yl)quinolin-2(1H)-one, potassium salt
7-Chloro-6-(4-(1-hydroxycyclobutyl)phenyl)-3-(3-methylisoxazol-5-yl)-2-oxo-1,2-dihydroquinolin-4-olate, potassium salt
7-Chloro-6-(1-ethyl-1H-indol-5-yl)-3-(3-methylisoxazol-5-yl)-2-oxo-1,2-dihydroquinolin-4-olate, potassium salt
7-Chloro-6-(4-ethoxyphenyl)-3-(3-methylisoxazol-5-yl)-2-oxo-1,2-dihydroquinolin-4-olate, potassium salt
7-Chloro-6-(4-(3-hydroxyoxetan-3-yl)phenyl)-3-(3-methylisoxazol-5-yl)-2-oxo-1,2-dihydroquinolin-4-olate, potassium salt
7-Chloro-6-(4-(dimethylamino)phenyl)-4-hydroxy-3-(3-methyl-1H-pyrazol-1-yl)quinolin-2(1H)-one
7-Chloro-6-(4-(dimethylamino)phenyl)-4-hydroxy-3-((4-methoxypyridin-2-yl)oxy)quinolin-2(1H)-one
7-Chloro-4-hydroxy-3-(4-methoxyphenoxy)-6-(1-methyl-1H-indol-5-yl)quinolin-2(1H)-one
7-Chloro-6-(4-(dimethylamino)phenyl)-4-hydroxy-3-((5-methylpyridin-2-yl)oxy)quinolin-2(1H)-one
7-Chloro-6-(2'-fluoro-[1,1'-biphenyl]-4-yl)-4-hydroxy-3-(1H-pyrazol-1-yl)quinolin-2(1H)-one
7-Chloro-4-hydroxy-6-(4-(5-methylthiophen-2-yl)phenyl)-3-(1H-pyrazol-1-yl)quinolin-2(1H)-one
3-(4-Bromo-1H-pyrazol-1-yl)-7-chloro-6-(4-(dimethylamino)phenyl)-4-hydroxyquinolin-2(1H)-one
3-(4-Bromo-1H-pyrazol-1-yl)-7-chloro-4-hydroxy-6-(4-(piperidin-1-yl)phenyl)quinolin-2(1H)-one
6-[4-(2-Amino-1,3-thiazol-4-yl)phenyl]-7-chloro-4-hydroxy-3-phenylquinolin-2(1H)-one hydrochloride
6-[4-(2-Amino-1,3-thiazol-4-yl)phenyl]-7-chloro-4-hydroxy-3-[3-(methyloxy)phenyl]quinolin-2(1H)-one
6-(4-(2-Amino-1,3-thiazol-4-yl)phenyl)-7-chloro-4-hydroxy-3-(3-methylisoxazol-5-yl)quinolin-2(1H)-one
6-(4-(2-Amino-1,3-thiazol-4-yl)phenyl)-7-chloro-4-hydroxy-3-(3-methoxyphenyl)quinolin-2(1H)-one
6-(4-(2-Amino-1,3-thiazol-4-yl)phenyl)-7-chloro-4-hydroxy-3-(pyridin-3-yl)quinolin-2(1H)-one
6-[4-(2-Amino-1,3-thiazol-4-yl)phenyl]-7-chloro-4-hydroxy-3-(1H-pyrazol-1-yl)-2(1H)-quinolinone hydrochloride
6-(4-(2-Amino-1,3-thiazol-4-yl)phenyl)-7-chloro-4-hydroxy-3-(pyridin-4-yl)quinolin-2(1H)-one
6-(4-(2-Amino-1,3-thiazol-4-yl)phenyl)-7-chloro-4-hydroxy-3-(4-methyl-1H-pyrazol-1-yl)quinolin-2(1H)-one
6-(4-(2-Amino-1,3-thiazol-4-yl)phenyl)-7-chloro-4-hydroxy-3-(1H-1,2,3-triazol-1-yl)quinolin-2(1H)-one
7-Chloro-4-hydroxy-6-(1-methyl-1H-indol-5-yl)quinolin-2(1H)-one
7-Chloro-4-hydroxy-6-[4-(4-morpholinyl)phenyl]quinolin-2(1H)-one
7-chloro-4-hydroxy-6-[2'-hydroxy-3'-(methyloxy)-4-biphenylyl]-2-oxo-1,2-dihydro-3-quinolinecarboxylic acid
1-(4-(7-Chloro-3-(3-methylisoxazol-5-yl)-4-oxido-2-oxo-1,2-dihydroquinolin-6-yl)phenyl)cyclopropanecarboxylate, bis potassium salt
1-(7-Chloro-4-oxido-2-oxo-6-(4-(piperidin-1-yl)phenyl)-1,2-dihydroquinolin-3-yl)-1H-pyrazole-4-carboxylate, bis potassium salt
7-Chloro-3-(3-chlorophenyl)-4-hydroxy-6-(4-(piperidin-1-yl)phenyl)quinolin-2(1H)-one In a still further aspect of the invention there is provided a compound of formula (I) selected from the group consisting of:
7-chloro-6-(4-(dimethylamino)phenyl)-4-hydroxy-3-(3-methylisoxazol-5-yl)quinolin-2(1H)-one;
7-chloro-6-(4-ethylphenyl)-4-hydroxy-3-(3-methylisoxazol-5-yl)quinolin-2(1H)-one;
7-chloro-4-hydroxy-3-(3-methylisoxazol-5-yl)-6-(4-morpholinophenyl)quinolin-2(1H)-one;
7-chloro-6-(4-(dimethylamino)phenyl)-4-hydroxy-3-(1H-pyrazol-1-yl)quinolin-2(1H)-one;
7-chloro-4-hydroxy-6-(4-morpholinophenyl)-3-(1H-pyrazol-1-yl)quinolin-2(1H)-one;
7-chloro-4-hydroxy-3-(1H-pyrazol-1-yl)-6-(4-(pyrrolidin-1-yl)phenyl)quinolin-2(1H)-one;

7-chloro-4-hydroxy-3-(pyridin-4-yl)-6-(4-(pyrrolidin-1-yl)phenyl)quinolin-2(1H)-one;
7-chloro-6-(4-(dimethylamino)phenyl)-4-hydroxy-3-(4-methyl-1,2,5-oxadiazol-3-yl)quinolin-2(1H)-one;
7-chloro-6-(4-(dimethylamino)phenyl)-4-hydroxy-3-(1H-1,2,4-triazol-1-yl)quinolin-2(1H)-one;
7-chloro-6-(4-(dimethylamino)phenyl)-4-hydroxy-3-(1H-1,2,3-triazol-1-yl)quinolin-2(1H)-one;
7-chloro-6-(4-(dimethylamino)phenyl)-4-hydroxy-3-(4-methyl-1H-pyrazol-1-yl)quinolin-2(1H)-one;
1-(7-chloro-6-(4-(dimethylamino)phenyl)-4-hydroxy-2-oxo-1,2-dihydroquinolin-3-yl)-1H-pyrazole-4-carboxylic acid;
7-chloro-4-hydroxy-6-(4-(piperidin-1-yl)phenyl)-3-(1H-pyrazol-1-yl)quinolin-2(1H)-one;
1-(7-chloro-4-hydroxy-2-oxo-6-(4-(pyrrolidin-1-yl)phenyl)-1,2-dihydroquinolin-3-yl)-1H-pyrazole-4-carboxylic acid;
3-(4-bromo-1H-pyrazol-1-yl)-7-chloro-6-(4-(dimethylamino)phenyl)-4-hydroxyquinolin-2(1H)-one;
3-(4-bromo-1H-pyrazol-1-yl)-7-chloro-4-hydroxy-6-(4-(piperidin-1-yl)phenyl)quinolin-2(1H)-one;
1-(7-chloro-4-hydroxy-2-oxo-6-(4-(piperidin-1-yl)phenyl)-1,2-dihydroquinolin-3-yl)-1H-pyrazole-4-carboxylic acid;
7-chloro-6-(4-(dimethylamino)phenyl)-4-hydroxy-3-(4-methoxy-1H-pyrazol-1-yl)quinolin-2(1H)-one;
7-chloro-6-(4-(dimethylamino)phenyl)-4-hydroxy-3-(3-methyl-1,2,4-oxadiazol-5-yl)quinolin-2(1H)-one;
7-chloro-6-(4-(dimethylamino)phenyl)-4-hydroxy-3-(5-methyl-1,3,4-oxadiazol-2-yl)quinolin-2(1H)-one;
7-chloro-3-(4-chloro-1H-pyrazol-1-yl)-4-hydroxy-6-(1-methyl-1H-indol-5-yl)quinolin-2(1H)-one;
7-chloro-4-hydroxy-6-(4-(pyrrolidin-1-yl)phenyl)-3-(1H-1,2,4-triazol-1-yl)quinolin-2(1H)-one;
7-chloro-4-hydroxy-3-(3-methylisoxazol-5-yl)-6-(4-(piperidin-1-yl)phenyl)quinolin-2(1H)-one;
7-chloro-4-hydroxy-6-(4-(piperidin-1-yl)phenyl)-3-(1H-1,2,4-triazol-1-yl)quinolin-2(1H)-one;
7-chloro-4-hydroxy-6-(4-(methylamino)phenyl)-3-(3-methylisoxazol-5-yl)quinolin-2(1H)-one;
7-chloro-4-hydroxy-3-(4-methyl-1H-pyrazol-1-yl)-6-(4-(pyrrolidin-1-yl)phenyl)quinolin-2(1H)-one;
7-chloro-4-hydroxy-3-(4-methyl-1H-pyrazol-1-yl)-6-(4-(piperidin-1-yl)phenyl)quinolin-2(1H)-one;
7-chloro-4-hydroxy-3-(1-methyl-1H-pyrazol-4-yl)-6-(4-(piperidin-1-yl)phenyl)quinolin-2(1H)-one;
7-chloro-4-hydroxy-3-(5-methyl-1,3,4-oxadiazol-2-yl)-6-(4-(piperidin-1-yl)phenyl)quinolin-2(1H)-one; and
7-chloro-6-(4-(dimethylamino)phenyl)-4-hydroxy-3-(2-methylthiazol-5-yl)quinolin-2(1H)-one;
or salts thereof.

In a further aspect of the invention there is provided a compound of formula (I) selected from the group consisting of:
7-chloro-6-(4-(dimethylamino)phenyl)-4-hydroxy-3-(3-methylisoxazol-5-yl)quinolin-2(1H)-one; and
7-chloro-4-hydroxy-6-(4-(piperidin-1-yl)phenyl)-3-(1H-pyrazol-1-yl)quinolin-2(1H)-one; or salts thereof.

In a still further aspect of the invention there is provided a compound of formula (I) selected from the group consisting of:
7-chloro-6-(4-(dimethylamino)phenyl)-4-hydroxy-3-(3-methylisoxazol-5-yl)quinolin-2(1H)-one;
7-chloro-6-(4-(dimethylamino)phenyl)-4-hydroxy-3-(3-methylisoxazol-5-yl)quinolin-2(1H)-one sodium salt;
7-chloro-6-(4-(dimethylamino)phenyl)-4-hydroxy-3-(3-methylisoxazol-5-yl)quinolin-2(1H)-one potassium salt;
7-Chloro-6-(4-(dimethylamino)phenyl)-3-(3-methylisoxazol-5-yl)-2-oxo-1,2-dihydroquinolin-4-olate, 2-amino-2-(hydroxymethyl)-1,3-propanediol salt;
7-Chloro-6-(4-(dimethylamino)phenyl)-3-(3-methylisoxazol-5-yl)-2-oxo-1,2-dihydroquinolin-4-olate, N-2-hydroxyethyl-N,N-dimethylmethanaminium salt; and
7-Chloro-6-(4-(dimethylamino)phenyl)-3-(3-methylisoxazol-5-yl)-2-oxo-1,2-dihydroquinolin-4-olate, hemi-1,2-ethanediamine salt.

Compounds of the invention have been found to activate AMPK and may therefore be useful in the treatment of type 1 diabetes, type 2 diabetes, metabolic syndrome, atherosclerosis, dyslipidaemia, mitochondrial disorders, sarcopenia, obesity, hypertension, cerebral ischemia, cognitive defect, Alzheimer's disease, Parkinson's disease, Huntington's disease, schizophrenia, Friedrich's Ataxia, amyotrophic lateral sclerosis, multiple sclerosis, neuroinflammation, inflammatory pain, neuropathic pain, epilepsy, virus infection (HIV, cytomegalovirus and hepatitis C) or cancer.

Compounds of the invention have been found to activate AMPK and may therefore be useful in the treatment of diabetes, metabolic syndrome, atherosclerosis, dyslipidaemia, obesity, hypertension, cerebral ischemia, cognitive defect and cancer.

Within the context of the present invention, the terms describing the indications used herein are classified in the Merck Manual of Diagnosis and Therapy, 17$^{th}$ Edition and/or the International Classification of Diseases 10$^{th}$ Edition (ICD-10). The various subtypes of the disorders mentioned herein are contemplated as part of the present invention.

In one aspect, the invention provides a compound of formula (I) or a pharmaceutically acceptable salt thereof for use in medical therapy.

In one aspect, the invention provides the use of a compound of formula (I) or a pharmaceutically acceptable salt thereof for the manufacture of a medicament for treating a disease or a condition mediated by AMPK activation.

In another aspect, the invention provides the use of a compound of formula (I) or a pharmaceutically acceptable salt thereof for the manufacture of a medicament for treating type 1 diabetes, type 2 diabetes, metabolic syndrome, atherosclerosis, dyslipidaemia, mitochondrial disorders, sarcopenia, obesity, hypertension, cerebral ischemia, cognitive defect, Alzheimer's disease, Parkinson's disease, Huntington's disease, schizophrenia, Friedrich's Ataxia, amyotrophic lateral sclerosis, multiple sclerosis, neuroinflammation, inflammatory pain, neuropathic pain, epilepsy, virus infection (HIV, cytomegalovirus and hepatitis C) or cancer.

In another aspect, the invention provides the use of a compound of formula (I) or a pharmaceutically acceptable salt thereof for the manufacture of a medicament for treating diabetes, metabolic syndrome, atherosclerosis, dyslipidaemia, obesity, hypertension, cerebral ischemia, cognitive defect or cancer.

In another aspect, the invention provides the use of a compound of formula (I) or a pharmaceutically acceptable salt thereof for the manufacture of a medicament for treating type 2 diabetes, obesity or dyslipidaemia.

In another aspect, the invention provides the use of a compound of formula (I) or a pharmaceutically acceptable salt thereof for the manufacture of a medicament for treating type 2 diabetes, dyslipidaemia and cancer.

In another aspect, the invention provides the use of a compound of formula (I) or a pharmaceutically acceptable salt thereof for the manufacture of a medicament for treating mitochondrial disorders or atherosclerosis.

In another aspect, the invention provides the use of a compound of formula (I) or a pharmaceutically acceptable salt thereof for the manufacture of a medicament for treating cancer.

In one aspect, the invention provides a compound of formula (I) or a pharmaceutically acceptable salt thereof for use in treating a disease or a condition mediated by AMPK activation.

In another aspect, the invention provides a compound of formula (I) or a pharmaceutically acceptable salt thereof for use in treating type 1 diabetes, type 2 diabetes, metabolic syndrome, atherosclerosis, dyslipidaemia, mitochondrial disorders, sarcopenia, obesity, hypertension, cerebral ischemia, cognitive defect, Alzheimer's disease, Parkinson's disease, Huntington's disease, schizophrenia, Friedrich's Ataxia, amyotrophic lateral sclerosis, multiple sclerosis, neuroinflammation, inflammatory pain, neuropathic pain, epilepsy, virus infection (HIV, cytomegalovirus and hepatitis C) or cancer.

In another aspect, the invention provides a compound of formula (I) or a pharmaceutically acceptable salt thereof for use in treating diabetes, metabolic syndrome, atherosclerosis, dyslipidaemia, obesity, hypertension, cerebral ischemia, cognitive defect or cancer.

In another aspect, the invention provides a compound of formula (I) or a pharmaceutically acceptable salt thereof for use in treating type 2 diabetes, obesity or dyslipidaemia.

In another aspect, the invention provides a compound of formula (I) or a pharmaceutically acceptable salt thereof for use in treating type 2 diabetes, dyslipidaemia or cancer.

In another aspect, the invention provides a compound of formula (I) or a pharmaceutically acceptable salt thereof for use in treating mitochondrial disorders or atherosclerosis.

In another aspect, the invention provides a compound of formula (I) or a pharmaceutically acceptable salt thereof for use in treating cancer.

In one aspect, the invention provides a method of treating a disease or a condition mediated by AMPK activation, which method comprises administering to a subject, for example a mammal, including human, a therapeutically effective amount of a compound of formula (I) or a pharmaceutically acceptable salt thereof.

In another aspect, the invention provides a method of treating type 1 diabetes, type 2 diabetes, metabolic syndrome, atherosclerosis, dyslipidaemia, mitochondrial disorders, sarcopenia, obesity, hypertension, cerebral ischemia, cognitive defect, Alzheimer's disease, Parkinson's disease, Huntington's disease, schizophrenia, Friedrich's Ataxia, amyotrophic lateral sclerosis, multiple sclerosis, neuroinflammation, inflammatory pain, neuropathic pain, epilepsy, virus infection (HIV, cytomegalovirus and hepatitis C) or cancer, which method comprises administering to a subject, for example a mammal, including human, a therapeutically effective amount of a compound of formula (I) or a pharmaceutically acceptable salt thereof.

In another aspect, the invention provides a method of treating diabetes, metabolic syndrome, atherosclerosis, dyslipidaemia, obesity, hypertension, cerebral ischemia, cognitive defect and cancer, which method comprises administering to a subject, for example a mammal, including human, a therapeutically effective amount of a compound of formula (I) or a pharmaceutically acceptable salt thereof.

In another aspect, the invention provides a method of treating type 2 diabetes, obesity or dyslipidaemia, which method comprises administering to a subject, for example a mammal, including human, a therapeutically effective amount of a compound of formula (I) or a pharmaceutically acceptable salt thereof.

In another aspect, the invention provides a method of treating type 2 diabetes, dyslipidaemia or cancer, which method comprises administering to a subject, for example a mammal, including human, a therapeutically effective amount of a compound of formula (I) or a pharmaceutically acceptable salt thereof.

In another aspect, the invention provides a method of treating mitochondrial disorders or atherosclerosis, which method comprises administering to a subject, for example a mammal, including human, a therapeutically effective amount of a compound of formula (I) or a pharmaceutically acceptable salt thereof.

In another aspect, the invention provides a method of treating cancer, which method comprises administering to a subject, for example a mammal, including human, a therapeutically effective amount of a compound of formula (I) or a pharmaceutically acceptable salt thereof.

It will be appreciated that reference to "treatment" and "therapy" includes acute treatment or prophylaxis as well as the alleviation of established symptoms and/or retardation of progression of the disease, and may include the suppression of symptom recurrence in an asymptomatic patient.

It will be appreciated that reference to "treatment" and "therapy" includes acute treatment as well as the alleviation of established symptoms and/or retardation of progression of the disease, and may include the suppression of symptom recurrence in an asymptomatic patient.

Pharmaceutical Compositions

While it is possible that, for use in the methods of the invention, a compound of formula (I) or a pharmaceutically acceptable salt thereof may be administered as the bulk substance, it is preferable to present the active ingredient in a pharmaceutical formulation, for example, wherein the agent is in admixture with at least one pharmaceutically acceptable carrier selected with regard to the intended route of administration and standard pharmaceutical practice.

Accordingly, the present invention also includes a pharmaceutical composition comprising a) a compound of formula (I) or a pharmaceutically acceptable salt thereof and b) one or more pharmaceutically acceptable carriers.

The term "pharmaceutically acceptable carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers or diluents are well known in the pharmaceutical art, and are described, for example, in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s) and/or coating agent(s).

The carrier, diluent and/or excipient must be "pharmaceutically acceptable" in the sense of being compatible with the other ingredients of the composition and not deleterious to the recipient thereof.

An "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use.

Examples of pharmaceutically acceptable diluent(s) useful in the compositions of the invention include, but are not limited to water, ethanol, propylene glycol and glycerine.

Examples of pharmaceutically acceptable binders for oral compositions useful herein include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable lubricants useful in the compositions of the invention include, but are not limited to, magnesium stearate, talc, polyethylene glycol, polymers of ethylene oxide, sodium lauryl sulfate, magnesium lauryl sulfate, sodium oleate, sodium stearyl fumarate, and colloidal silicon dioxide.

Examples of pharmaceutically acceptable suspending agents useful in the compositions of the invention include, but are not limited tosorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non aqueous vehicles (which may include edible oils), for example almond oil, oily esters such as glycerine, propylene glycol, or ethyl alcohol; preservatives, for example methyl or propyl p-hydroxybenzoate or sorbic acid.

Examples of pharmaceutically acceptable coating materials useful in the compositions of the invention include, but are not limited to, hydroxypropyl methylcellulose, ethyl cellulose, cellulose acetate phthalate, polyvinyl acetate phthalate, hydroxypropyl methylcellulose phthalate, polymers of metacrylic acid and its esters, and combinations thereof.

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

The present invention relates to a pharmaceutical composition for the treatment of type 2 diabetes, dyslipidaemia or cancer comprising a compound of formula (I) or a pharmaceutically acceptable salt thereof.

The present invention relates to a pharmaceutical composition for the treatment of type 2 diabetes, obesity or dyslipidaemia comprising a compound of formula (I) or a pharmaceutically acceptable salt thereof.

The present invention further relates to a pharmaceutical composition comprising a) 10 to 2000 mg of a compound of formula (I) or a pharmaceutically acceptable salt thereof, and b) 0.1 to 2 g of one or more pharmaceutically acceptable carriers.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The pharmaceutical compositions of the invention may be formulated for administration by any suitable route, and include those in a form adapted for oral, parenteral, transdermal, inhalation, sublingual, topical, implant, nasal, enterally (or other mucosally) administration to mammals including humans. The pharmaceutical compositions may be formulated in conventional manner using one or more pharmaceutically acceptable carriers or excipients. In one aspect, the pharmaceutical composition is formulated for oral administration The compositions may be in the form of tablets, capsules, powders, granules, lozenges, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

The compounds of the invention may also, for example, be formulated as suppositories containing conventional suppository bases e.g. cocoa butter or other glyceride for use in human or veterinary medicine or as pessaries e.g., containing conventional pessary bases.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

As indicated, the compound of the present invention can be administered intranasally or by inhalation and is conveniently delivered in the form of a dry powder inhaler or an aerosol spray presentation from a pressurized container, pump, spray or nebulizer with the use of a suitable propellant, e.g., a hydrofluoroalkane such as 1,1,1,2-tetrafluoroethane (HFA 134AT) or 1,1,1,2,3,3,3-heptafluoropropane (HFA 227EA), or a mixture thereof. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant e.g. sorbitan trioleate.

Capsules and cartridges (made, for example, from gelatin) for use in an inhaler or insufflator may be formulated to contain a powder mix of the compound and a suitable powder base such as lactose or starch.

Advantageously, agents such as a local anaesthetic, preservative and buffering agent can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compounds of the invention may be administered for immediate-, delayed-, modified-, sustained-, pulsed- or controlled-release applications.

In one aspect, oral compositions are slow, delayed or positioned release (e.g., enteric especially colonic release) tablets or capsules. This release profile can be achieved, for example, by use of a coating resistant to conditions within the stomach but releasing the contents in the colon or other portion of the GI tract wherein a lesion or inflammation site has been identified. Or a delayed release can be achieved by a coating that is simply slow to disintegrate. Or the two (delayed and positioned release) profiles can be combined in a single formulation by choice of one or more appropriate coatings and other excipients. Such formulations constitute a further feature of the present invention.

Suitable compositions for delayed or positioned release and/or enteric coated oral formulations include tablet formulations film coated with materials that are water resistant, pH sensitive, digested or emulsified by intestinal juices or sloughed off at a slow but regular rate when moistened. Suitable coating materials include, but are not limited to, hydroxypropyl methylcellulose, ethyl cellulose, cellulose acetate phthalate, polyvinyl acetate phthalate, hydroxypropyl methylcellulose phthalate, polymers of metacrylic acid and its esters, and combinations thereof. Plasticizers such as, but not limited to polyethylene glycol, dibutylphthalate, triacetin and castor oil may be used. A pigment may also be used to color the film. Suppositories are be prepared by using carriers like cocoa butter, suppository bases such as Suppocire C, and Suppocire NA50 (supplied by Gattefosse Deutschland GmbH, D-Weil am Rhein, Germany) and other Suppocire type excipients obtained by interesterification of hydrogenated palm oil and palm kernel oil ($C_8$-$C_{18}$ triglycerides), esterification of glycerol and specific fatty acids, or polyglycosylated glycerides, and whitepsol (hydrogenated plant oils derivatives with additives). Enemas are formulated by using the appropriate active compound according to the present invention and solvents or excipients for suspensions. Suspensions are produced by using micronized compounds, and appropriate vehicle containing suspension stabilizing agents, thickeners and emulsifiers like carboxymethylcellulose and salts thereof, polyacrylic acid and salts thereof, carboxyvinyl polymers and salts thereof, alginic acid and salts thereof, propylene glycol alginate, chitosan, hydroxypropylcellulose, hydroxypropylmethylcellulose, hydroxyethylcellulose, ethylcellulose, methylcellulose, polyvinyl alcohol, polyvinyl pyrrolidone, N-vinylacetamide polymer, polyvinyl methacrylate, polyethylene glycol, pluronic, gelatin, methyl vinyl ether-maleic anhydride copolymer, soluble starch, pullulan and a copolymer of methyl acrylate and 2-ethylhexyl acrylate lecithin, lecithin derivatives, propylene glycol fatty acid esters, glycerin fatty acid esters, sorbitan fatty acid esters, polyoxyethylene sorbitan fatty acid esters, polyethylene glycol fatty acid esters, polyoxyethylene hydrated caster oil, polyoxyethylene alkyl ethers, and pluronic and appropriate buffer system in pH range of 6.5 to 8. The use of preservatives, masking agents is suitable. The average diameter of micronized particles can be between 1 and 20 micrometers, or can be less than 1 micrometer. Compounds can also be incorporated in the formulation by using their water-soluble salt forms.

Alternatively, materials may be incorporated into the matrix of the tablet e.g. hydroxypropyl methylcellulose, ethyl cellulose or polymers of acrylic and metacrylic acid esters. These latter materials may also be applied to tablets by compression coating.

The compositions may contain from 0.1% by weight, preferably from 10-60% by weight, of the active ingredient, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

It will be recognised by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of a compound of the invention given per day for a defined number of days, can be ascertained by those skilled in the art using conventional course of treatment determination tests.

The compounds of formula (I) or pharmaceutically acceptable salt(s) thereof may also be used in combination with other therapeutic agents. The invention thus provides, in a further aspect, a combination comprising a) a compound of formula (I) or pharmaceutically acceptable salt thereof and b) one or more further therapeutically active agent(s).

The combinations referred to above may conveniently be presented for use in the form of a pharmaceutical composition and thus pharmaceutical compositions comprising a combination as defined above together with one or more pharmaceutically acceptable carriers thereof represent a further aspect of the invention.

Compounds of the invention may be administered in combination with other therapeutically active agents. Preferred therapeutic agents are selected from the list consisting of: insulin, bisguanidine, metformin, a DPP-IV inhibitor, sitagliptin, an inhibitor of cholesteryl ester transferase (CETP inhibitors), a HMG-CoA reductase inhibitor, a microsomal triglyceride transfer protein, a peroxisome proliferator-activated receptor activator (PPAR), a bile acid reuptake inhibitor, a cholesterol absorption inhibitor, a cholesterol synthesis inhibitor, a fibrate, niacin, an ion-exchange resin, an antioxidant, an inhibitor of AcylCoA: cholesterol acyltransferase (ACAT inhibitor), a cannabinoid 1 antagonist, a bile acid sequestrant, a corticosteroid, a vitamin D3 derivative, a retinoid, an immunomodulator, an anti androgen, a keratolytic agent, an anti-microbial, a platinum chemotherapeutic, an antimetabolite, hydroxyurea, a taxane, a mitotic disrupter, an anthracycline, dactinomycin, an alkylating agent and a cholinesterase inhibitor.

When the compound of formula (I) or pharmaceutically acceptable salt thereof is used in combination with a second therapeutically active agent the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The combinations referred to above may conveniently be presented for use in the form of a pharmaceutical formulation and thus pharmaceutical formulations comprising a combination as defined above together with at least one pharmaceutically acceptable carrier and/or excipient comprise a further aspect of the invention.

The individual components of such combinations may be administered either sequentially or simultaneously in separate or combined pharmaceutical formulations by any convenient route.

When administration is sequential, either the AMPK activator or the second therapeutically active agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

Methods of Preparation

Compounds of formula (I) and salts thereof may be prepared by the general methods outlined hereinafter or any method known in the art, said methods constituting a further aspect of the invention. $R^1$ to $R^7$ are as defined above unless otherwise specified. Throughout the specification, general formulae are designated by Roman numerals (I), (II), (III), (IV) etc.

In a general process, compounds of formula (I) may be prepared according to reaction Scheme 1 by reacting compounds of formula (II) (wherein OR is a leaving group such as methoxy) in the presence of a base such as potassium tert-butoxide or potassium hexamethyldisilazane or lithium hexamethyldisilazane or sodium hexamethyldisilazane in a suitable solvent such as THF or DMSO (suitably at −78° C. to 100° C.).

Scheme 1

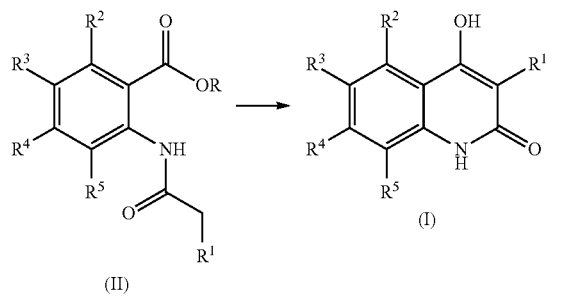

Compounds of formula (II) may be prepared according to Scheme 8.

Compounds of formula (I) may be alternatively prepared according to reaction Scheme 2 by reacting compounds of formula (X), with the appropriate $R^3$-boron derivative (III) in the presence of an inorganic base such as cesium carbonate or sodium carbonate and a catalyst such as $Pd(PPh_3)_4$ in a suitable solvent such as a 1,4-dioxane/water mixture (suitably at 80 to 130° C., under microwave irradiation or classical heating).

Scheme 2

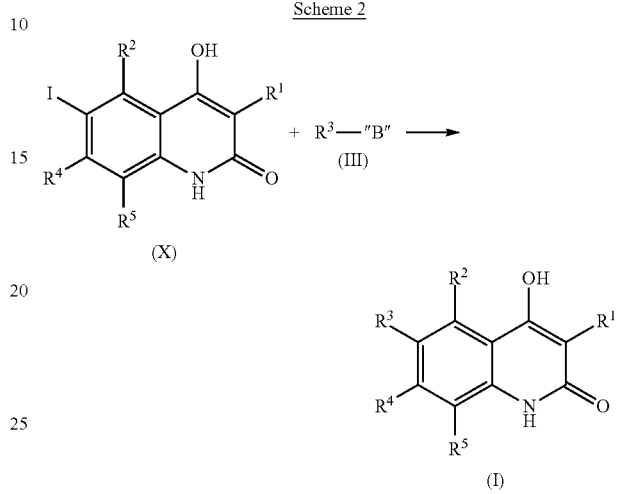

Compounds of formula (X) may be prepared according to Scheme 1, wherein $R^3$ is defined as iodine.

Compounds of formula (III) are commercially available or may be prepared by methods known in the literature or processes known to those skilled in the art or compounds of formula (IIIa) may be prepared according to Scheme 12.

Compounds of formula (I), wherein $R^1$ is hydrogen (formula (Ib)), may be prepared according to reaction Scheme 3 by reacting compounds of formula (I), wherein $R^1$ is $—CO_2C_2H_5$ (formula (Ic)), with NaOH in a suitable solvent such as ethanol (suitably at 80 to 160° C. under microwave irradiation) or with concentrated hydrochloric acid (suitably at 80° C.).

Scheme 3

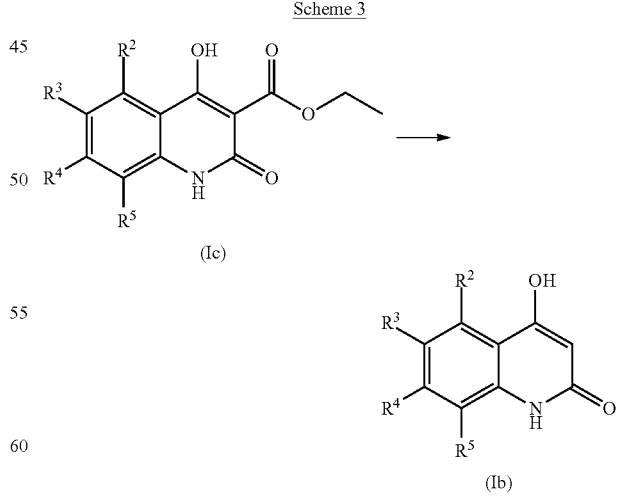

Compounds of formula (Ic) may be prepared according to Scheme 1 or Scheme 2.

Compounds of formula (I), wherein $R^3$ is [2-amino-1,3-thiazol-4-yl)phenyl] (formula (Id)), may be prepared according to reaction Scheme 4 by reacting compounds of formula (Ie) with HCl in a suitable solvent such as ethanol (suitably at reflux).

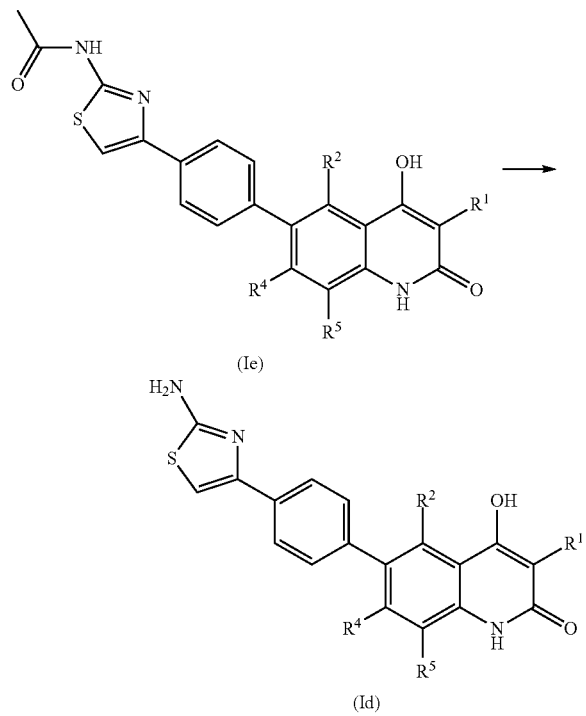

Compounds of formula (Ie) may be prepared according to Scheme 1 or Scheme 2.

Compounds of formula (I), wherein $R^1$ is a carboxylic acid (formula (If)), may be prepared according to reaction Scheme 5 by reacting compounds of formula (I), wherein $R^1$ is —$CO_2C_2H_5$ (formula (Ic)), with LiOH in a suitable solvent such as THF/water mixture (suitably at 50° C.).

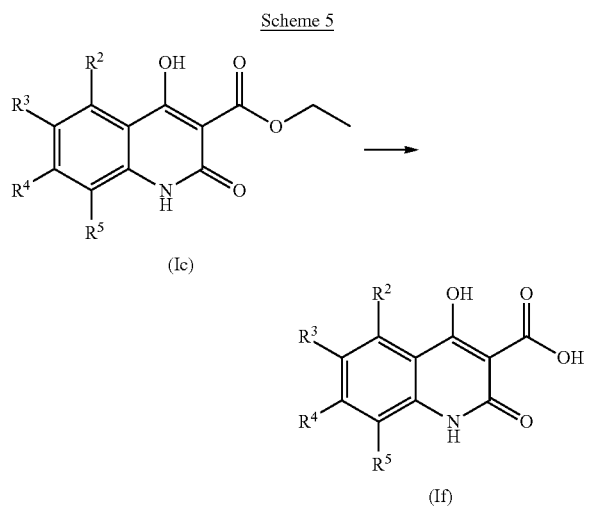

Compounds of formula (Ic) may be prepared according to Scheme 1 or Scheme 2.

Compounds of formula (I) may be prepared according to reaction Scheme 6 by reacting compounds of formula (IV) (wherein OR is a leaving group such as methoxy) with compounds of formula (V) (R': methyl or ethyl) in the presence of a base such as potassium hexamethyldisilazane in a suitable solvent such as THF (suitably at RT or 60° C.).

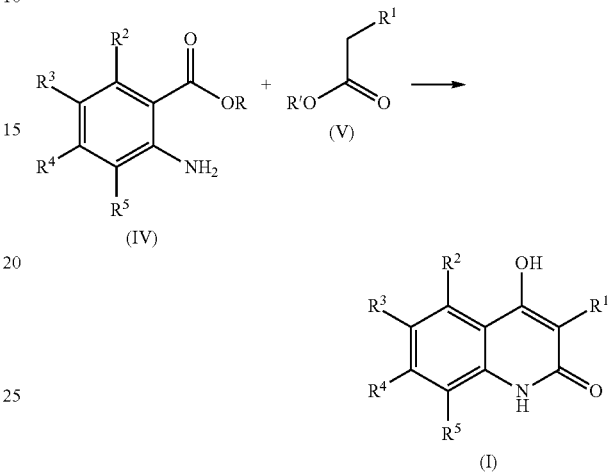

Compounds of formula (IV) may be prepared according to Scheme 9 or Scheme 10. Compounds of formula (V) are commercially available or may be prepared by methods known in the literature or processes known to those skilled in the art or may be prepared according to Scheme 13.

Compounds of formula (I), wherein $R^1$ is a nitro (formula (Ig)), may be prepared according to reaction Scheme 7 by reacting compounds of formula (I), wherein $R^1$ is hydrogen (formula (Ih)), with nitric acid (suitably at room temperature to 75° C.).

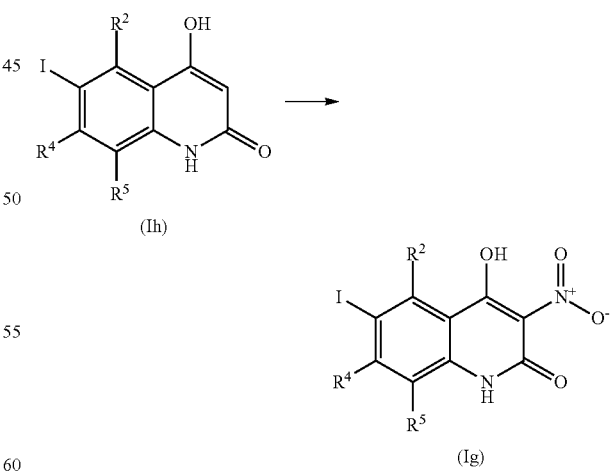

Compounds of formula (Ih) may be prepared according to Scheme 3, wherein $R^1$ is hydrogen and $R^3$ is iodine.

Compounds of formula (II) may be prepared according to reaction Scheme 8 by reacting compounds of formula (IV) (wherein OR is a leaving group such as methoxy) with acetic acid derivatives (VI) in the presence of a coupling reagent such as HATU and a base such as triethylamine in a suitable solvent such as DCM (suitably at room temperature) or with acetyl chloride derivatives (VII) in the presence of a base such as triethylamine or pyridine in a suitable solvent such as DCM (suitably at 0° C. to room temperature) or with acetic acid derivatives (VI) in the presence of thionyl chloride in suitable solvent such as toluene or with acetic acid derivatives (VI) in the presence of oxalyl chloride in suitable solvent such as DCM or with acetic acid derivatives (VI) in the presence of POCl$_3$ or with acetic anhydride (suitably at room temperature).

Scheme 8

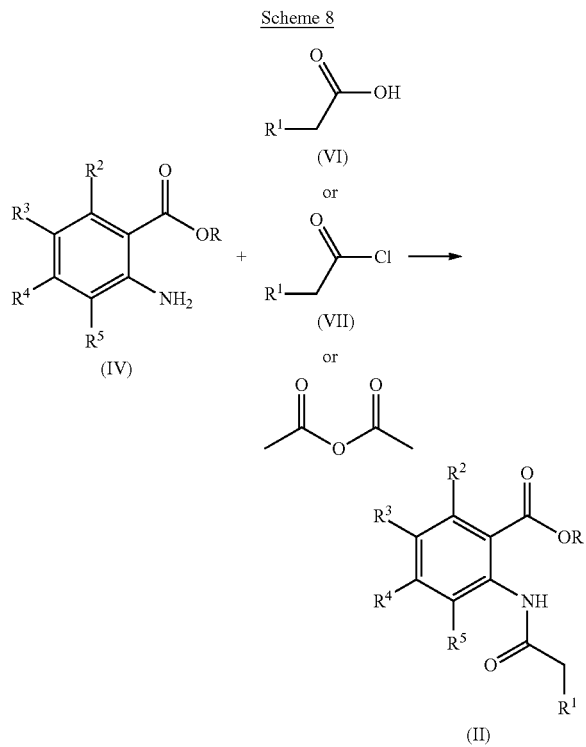

Compounds of formula (IV) may be prepared according to Scheme 9 or Scheme 10.

Compounds of formula (VI) or (VII) are commercially available or may be prepared by methods known in the literature or processes known to those skilled in the art.

Compounds of formula (IVa) may be prepared according to reaction Scheme 9 by reacting compounds of formula (IV), wherein R$^3$ is 4-bromo-phenyl (formula (IVb)), with the appropriate R$^6$-boron derivative (III) such as the appropriate boronic acid or appropriate borolane derivative in the presence of an inorganic base such as sodium carbonate or K$_3$PO$_4$ and a catalyst such as Pd(PPh$_3$)$_4$) or PdCl$_2$(dppf) in a suitable solvent such as 1,4-dioxane/water or THF/water mixture (suitably from 80 to 130° C.).

Scheme 9

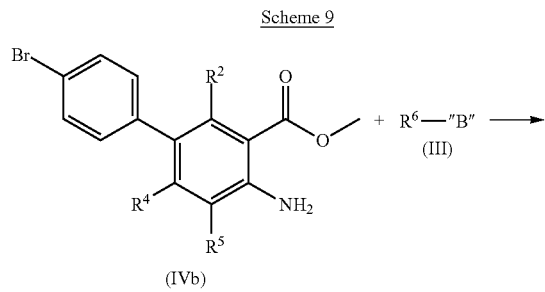

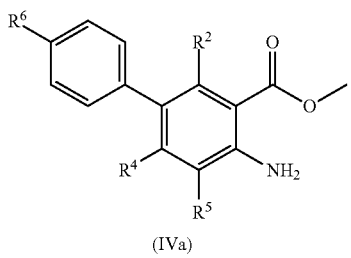

Compounds of formula (IVb) may be prepared according to Scheme 10.

Compounds of formula (III) are commercially available or may be prepared by methods known in the literature or processes known to those skilled in the art or may be prepared according to Scheme 12.

Compounds of formula (IV) may be prepared according to reaction Scheme 10 by reacting compounds of formula (IV), wherein R$^3$ is iodine (formula (IVc)), with the appropriate R$^3$-boron derivative (111) such as the appropriate boronic acid or borolane derivative in the presence of an inorganic base such as sodium carbonate or cesium carbonate and a catalyst such as Pd(PPh$_3$)$_4$ in a suitable solvent such as a 1,4-dioxane/water mixture (suitably at 70 to 100° C.).

Scheme 10

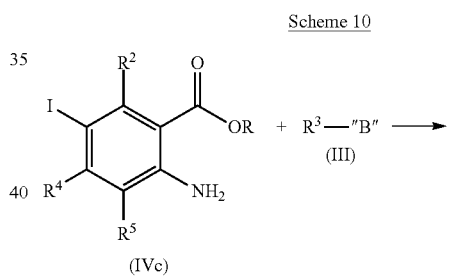

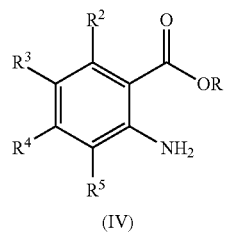

Compounds of formula (IVc) may be prepared according to Scheme 11.

Compounds of formula (III) are commercially available or may be prepared by methods known in the literature or processes known to those skilled in the art or compounds of formula (IIIa) may be prepared according to Scheme 12.

Compounds of formula (IV), wherein R$^3$ is iodine (formula (IVc) may be prepared according to reaction Scheme 11 by reacting compounds of formula (IV), wherein R$^3$ is hydrogen (formula (IVd)), with iodine in the presence of an inorganic salt such as silver sulfate in a suitable solvent such as ethanol (suitably at room temperature).

Scheme 11

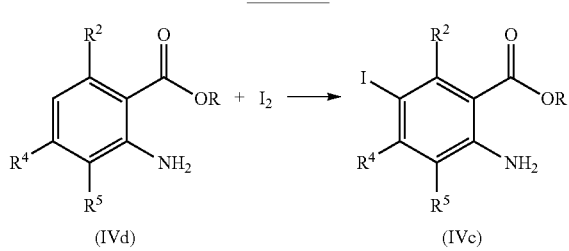

Compounds of formula (IVd) are commercially available or may be prepared by methods known in the literature or processes known to those skilled in the art.

Compounds of formula (IIIa) may be prepared according to reaction Scheme 12 by reacting compounds of formula (VIII) with 4,4,4',4',5,5,5',5'-octamethyl-2,2'-bi-1,3,2-dioxaborolane in the presence of an inorganic base such as potassium acetate and a catalyst (such as $PdCl_2dppf.DCM$) in a suitable solvent such as 1,4-dioxane (suitably at 100° C.).

Scheme 12

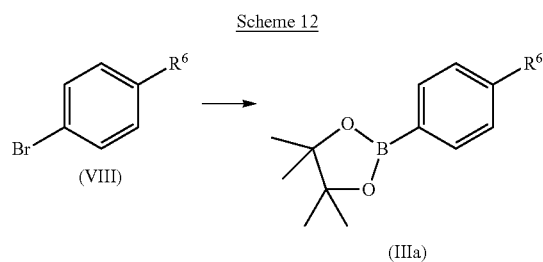

Compounds of formula (VIII) are commercially available or may be prepared by methods known in the literature or processes known to those skilled in the art.

Compounds of formula (V) may be prepared according to reaction Scheme 13 by reacting compounds of formula (IX) with ethyl 2-bromoacetate in the presence of an inorganic base such as potassium carbonate in a suitable solvent such as acetone (suitably at reflux) or in the presence of a base such as potassium tert-butoxide in a suitable solvent such as DMSO (suitably at RT).

Scheme 13

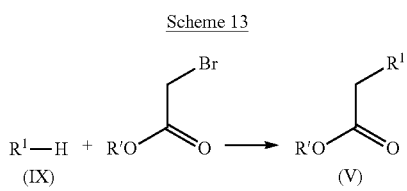

Compounds of formula (IX) are commercially available or may be prepared by methods known in the literature or processes known to those skilled in the art.

Further details for the preparation of compounds of formula (I) are found in the Examples section hereinafter.

The compounds of the invention may be prepared singly or as compound libraries comprising at least 2, for example 5 to 1,000 compounds, and more preferably 10 to 100 compounds. Libraries of compounds of the invention may be prepared by a combinatorial 'split and mix' approach or by multiple parallel synthesis using either solution phase or solid phase chemistry, by procedures known to those skilled in the art. Thus according to a further aspect there is provided a compound library comprising at least 2 compounds of the invention.

Those skilled in the art will appreciate that in the preparation of compounds of formula (I) and/or solvates thereof it may be necessary and/or desirable to protect one or more sensitive groups in the molecule or the appropriate intermediate to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl or aralkyl type protecting groups (e.g. benzyl, trityl, chlorotrityl).

The synthesis of the target compound is completed by removing any protecting groups, which are present in the penultimate intermediate using standard techniques, which are well-known to those skilled in the art. The final product is then purified, as necessary, using standard techniques such as silica gel chromatography, HPLC on silica gel, and the like or by recrystallization.

Various intermediate compounds used in the above-mentioned process, including but not limited to certain compounds of formulae (II) constitute a further aspect of the present invention.

Definitions

AcOH Acetic acid
DCM Dichloromethane
DMF N,N-dimethylformamide
DMSO d6 Deuterated dimethylsulfoxide
DMSO Dimethylsulfoxide
dppf Diphenylphosphinoferrocene
EtOAc Ethyl acetate
h Hours
HATU O-(7-Azabenzotriazol-1-yl)-N,N,N',N'-tetramethyluronium hexafluorophosphate
HRMS High resolution mass spectroscopy
Int. Intermediate
KHMDS Potassium hexamethyldisilazane
LC Liquid chromatography
LCMS Liquid chromatography mass spectroscopy
min. Minutes
mL Milliliter
NaHMDS Sodium hexamethyldisilazane
RT Room temperature
Rt Retention time
Sat. Saturated
SM Starting material
SPE Solid phase extraction
THF Tetrahydrofuran
TLC Thin-layer chromatography
Wt Weight Analytical Method LC-MS Methods:

(a) Analytical HPLC was conducted on a X-Terra MS C18 column (2.5 μm 30×3 mm id) at 40° C. eluting with 0.01M ammonium acetate in water (solvent A) and 100% acetonitrile (solvent B), using the following elution gradient 0 to 4 minutes. 0 to 100% B, 4 to 5 minutes 100% B at a flow rate of 1.1 mL/minute. The mass spectra (MS) were recorded on a Waters ZQ mass spectrometer using electrospray positive ionisation [ES+ to give (M+H)⁺ molecular ions] or electrospray negative ionisation [ES− to give (M−H)⁻ molecular ions] modes.

(b) Analytical HPLC was conducted on a X-Terra MS C18 column (3.5 μm 30×4.6 mm id) at 40° C. eluting with 0.01M ammonium acetate in water (solvent A) and 100% methanol (solvent B), using the following elution gradient 0 to 7.5 minutes, 10 to 100% B, 7.5 to 10 minutes 100% B, 10.5 to 12 min 10% B at a flow rate of 1.4 mL/minute. The mass spectra (MS) were recorded on a Waters ZQ mass spectrometer using electrospray positive ionisation [ES+ to give (M+H)⁺ molecular ions] or electrospray negative ionisation [ES− to give (M−H)⁻ molecular ions] modes.

(c) Analytical HPLC was conducted on a Acquity UPLC BEH C18 column (1.7 μm, 50×2.1 mm id) eluting with 0.1% v/v solution of formic acid in water (solvent A) and 0.1% v/v solution of formic acid in acetonitrile (solvent B), using the following elution gradient 0 to 1.5 minutes, 3% to 99.9% B, 1.5 to 1.9 minutes 99.9% B, 1.9 to 2 min 3% B at a flow rate of 1 mL/minute. The mass spectra (MS) were recorded on a Waters ZQ mass spectrometer using electrospray positive ionisation [ES+ to give (M+H)⁺ molecular ions] or electrospray negative ionisation [ES− to give (M−H)⁻ molecular ions] modes.

Analytical LC-HRMS

Analytical HPLC was conducted on a Waters XBridge column (2.5 μm 30×3 mm id) eluting with 0.01M ammonium acetate in water (solvent A) and 100% acetonitrile (solvent B) using the following elution gradient: 0 to 0.5 minutes, 5% B; 0.5 to 3.75 minutes, 5% B to 100% B; 3.75 to 4.5 minutes, 100% B; 4.5 to 5 minutes, 100% B to 5% B; 5 to 5.5 minutes, 5% B at a flowrate of 1.3 mL/min with a temperature of 40° C. The mass spectra (MS) were recorded on a Waters LCT mass spectrometer using electrospray positive ionisation [ES+ve to give (M+H)+ molecular ion] or electrospray negative ionisation [ES−ve to give (M−H)⁻ molecular ion] modes The following non-limiting Examples illustrate the present invention.

Intermediate 1: Ethyl 2-amino-4-fluorobenzoate

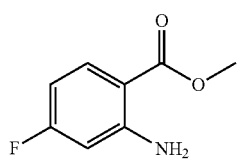

To a solution of 2-amino-4-fluorobenzoic acid (Aldrich, 2.22 g, 14.32 mmol) in methanol (20 mL) at 0° C. was added thionyl chloride (1.56 mL, 21.49 mmol). The reaction mixture was stirred at room temperature for 24 h. Additional thionyl chloride (10 mL) was added and the reaction mixture was stirred at room temperature for 24 h. Additional thionyl chloride (10 mL) was added and the reaction was stirred at room temperature for 48 h. The reaction mixture was evaporated to dryness and 200 mL of water was added. The precipitate was filtered and washed with water and to give the title compound methyl 2-amino-4-fluorobenzoate (1.350 g, 7.98 mmol, 55.7% yield) as a white solid. ¹H NMR: (DMSO-d6, 300 MHz) δ 7.76 (m, 1H), 6.90 (bs, 2H), 6.52 (m, 1H), 6.35 (m, 1H), 3.78 (s, 3H).

Intermediate 2: Methyl 2-amino-4-chloro-5-iodobenzoate

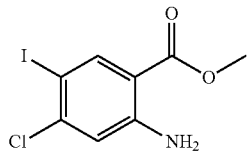

To a solution of methyl 2-amino-4-chlorobenzoate (Aldrich, 111 g, 600 mmol) and silver sulfate (187 g, 600 mmol) in ethanol (1000 mL) was added dropwise in 8 hours a solution of iodine (152 g, 600 mmol) in ethanol (2000 mL). The reaction mixture was stirred overnight then filtered through a celite plug. The filtrate was concentrated under reduced pressure and the residue was triturated in n-heptane. The resulting solid was filtered, washed with diisopropyl ether to give the title compound methyl 2-amino-4-chloro-5-iodobenzoate (103.76 g, 334 mmol, 55.6% yield) as a white powder. LCMS: (M+H)⁺=312; Rt=3.46 min.

Intermediate 3 was prepared by a method analogous to that described for Intermediate 2.

TABLE 1

| Intermediate | Structure | From | Physical data |
|---|---|---|---|
| 3<br>Ethyl 2-amino-4-fluoro-5-iodobenzoate | 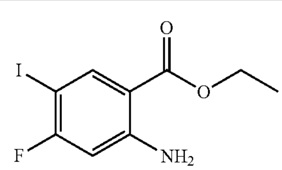 | ethyl 2-amino-4-fluorobenzoate (Intermediate 1) | LCMS: (M + H)⁺ = 310; Rt = 3.49 min. |

Intermediate 4: 1-Benzyl-1H-pyrazol-4-ol

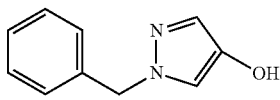 [SMILES: Oc1cnn(Cc2ccccc2)c1]

1-Benzyl-4-(4,4,5,5-tetramethyl-[1,3,2]dioxaborolan-2-yl)-1H-pyrazole (Aldrich, 700 mg, 2.46 mmol) was dissolved in THF (6 mL) and cooled to 0° C. NaOH 2.5 M (2 mL, 4.93 mmol) and $H_2O_2$ 30% solution in water (503 μl, 4.93 mmol) were added and the reaction mixture was stirred at room temperature for 45 min. Then the pH was adjusted to 2 by the addition of aqueous HCl 2 M and the mixture was extracted with dichloromethane. The organic layer was dried over $Na_2SO_4$, filtered, and concentrated under reduced pressure. The residue was purified by flash chromatography on silica gel using cyclohexane/EtOAc as eluant. The expected fractions were combined and evaporated under reduced pressure to give the title compound 1-benzyl-1H-pyrazol-4-ol (500 mg, quantitative yield). LCMS: $(M+H)^+=175$; Rt=0.61 min.

Intermediate 5: 4-(Methyloxy)-1-(phenylmethyl)-1H-pyrazole

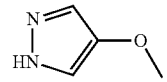

To a solution of 1-benzyl-1H-pyrazol-4-ol (Intermediate 4) (3.5 g, 20.1 mmol) and $Cs_2CO_3$ (8 g, 24.6 mmol) in DMF (100 mL) was added MeI (2 mL, 32 mmol). After stirring at room temperature for 2 h, the reaction mixture was diluted with EtOAc, washed with ice/brine. The aqueous was extracted with EtOAc, the combined organic solvents were removed under reduced pressure and the residue was purified by flash chromatography on silica gel (cyclohexane to cyclohexane/EtOAc 60:40 as eluant) to give the title compound 4-(methyloxy)-1-(phenylmethyl)-1H-pyrazole (2.5 g, 13.3 mmol, 63% yield) as a yellow oil. LCMS: $(M+H)^+=189$; Rt=0.81 min.

Intermediate 6: 4-Methoxy-1H-pyrazole

To a solution of 4-(methyloxy)-1-(phenylmethyl)-1H-pyrazole (Intermediate 5) (2.78 g, 15 mmol) in methanol (60 mL) was added HCl 1M (6.8 mL) and $Pd(OH)_2$ 20% Wt (2.78 g, 3.8 mmol). The vigorously stirred solution was evacuated and subsequently flushed with $N_2$ and then evacuated and flushed with $H_2$. The reaction mixture was stirred at room temperature for 36 h. The reaction mixture was filtered and the filtrate was concentrated in vacuo to give the title compound 4-methoxy-1H-pyrazole (1.65 g, quantitative yield). The crude product was used in the next step without further purification.

Intermediate 7: Ethyl 2-(3,5-dimethyl-1H-pyrazol-1-yl)acetate

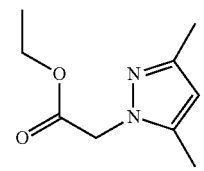

A mixture of 3,5-dimethyl-1H-pyrazole (Aldrich, 10 g, 104 mmol), $K_2CO_3$ (43.1 g, 312 mmol), and ethyl 2-bromoacetate (12.69 mL, 114 mmol) in acetone (100 mL) was refluxed overnight. The salts were removed by filtration and the filtrate was evaporated under reduced pressure. The residue was dissolved in diethyl ether and the organic phase was dried over anhydrous sodium sulfate, filtered and evaporated under reduced pressure. The oily residue was dissolved in hot hexane and the insoluble material was filtered and discarded. The filtrate was cooled at 0° C. and the precipitate obtained was filtered and dried to give the title compound ethyl 2-(3,5-dimethyl-1H-pyrazol-1-yl)acetate (8 g, 43.9 mmol, 42.2% yield) as a gum. $^1$H NMR: ($CDCl_3$-$d_6$, 300 MHz) δ 5.82 (s, 1H), 4.72 (s, 2H), 4.18 (q, 2H), 2.18 (s, 3H), 2.17 (s, 3H), 1.24 (t, J=7.1 Hz, 3H).

Intermediates 8 to 23 were prepared by methods analogous to that described for Intermediate 7. For Intermediate 23, potassium tBuOK/DMSO was used instead of $K_2CO_3$/acetone.

TABLE 2

| Intermediate | Structure | From | Physical data |
|---|---|---|---|
| 8<br>Ethyl 2-(3-fluorophenoxy)acetate | 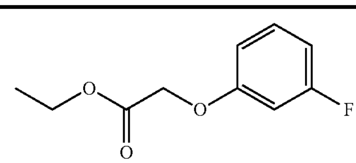 | 3-fluorophenol and (Aldrich) ethyl 2-bromoacetate (Aldrich) | LCMS: $(M + H)^+ = 199$;<br>Rt = 3.01 min. |
| 9<br>Ethyl 2-(3-methoxyphenoxy)acetate | 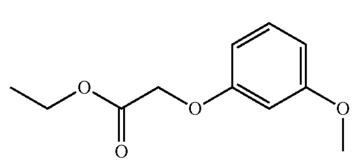 | 3-methoxyphenol and (Aldrich) ethyl 2-bromoacetate (Aldrich) | LCMS: $(M + H)^+ = 211$;<br>Rt = 2.93 min. |

TABLE 2-continued

| Intermediate | Structure | From | Physical data |
|---|---|---|---|
| 10<br>Ethyl 2-(p-tolyloxy) acetate | 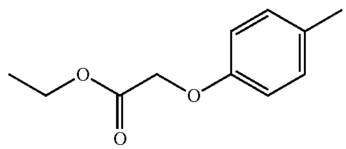 | p-cresol (Aldrich) and ethyl 2-bromoacetate (Aldrich) | LCMS: (M + H)$^+$ = 195; Rt = 3.14 min. |
| 11<br>Ethyl 2-(pyridin-2-yloxy) acetate | 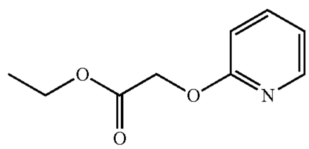 | pyridin-2-ol (Aldrich) and ethyl 2-bromoacetate (Aldrich) | LCMS: (M + H)$^+$ = 182; Rt = 1.41 min. |
| 12<br>Ethyl 2-(2-methoxyphenoxy) acetate | 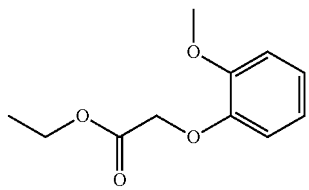 | 2-methoxyphenol (Aldrich) and ethyl 2-bromoacetate (Aldrich) | LCMS: (M + H)$^+$ = 211; Rt = 2.76 min. |
| 13<br>Ethyl 2-(m-tolyloxy)acetate | 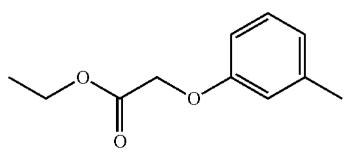 | m-cresol (Aldrich) and ethyl 2-bromoacetate (Aldrich) | LCMS: (M + H)$^+$ = 195; Rt = 3.13 min. |
| 14<br>Ethyl 2-(4-fluorophenoxy) acetate | 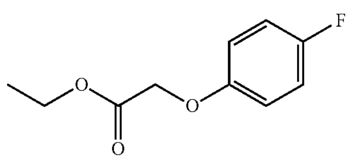 | 4-fluorophenol (Aldrich) and ethyl 2-bromoacetate (Aldrich) | LCMS: (M + H)$^+$ = 199; Rt = 2.95 min. |
| 15<br>Ethyl 2-((4-methylpyridin-2-yl) oxy) acetate | 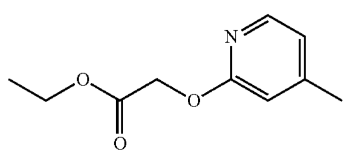 | 4-methylpyridin-2-ol (Aldrich) and ethyl 2-bromoacetate (Aldrich) | LCMS: (M + H)$^+$ = 196; Rt = 1.72 min. |
| 16<br>Ethyl 2-(4-methyl-1H-pyrazol-1-yl) acetate | 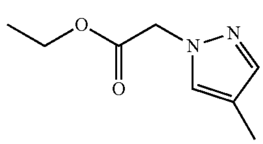 | 4-methyl-1H-pyrazole (Aldrich) and ethyl 2-bromoacetate (Aldrich) | $^1$H NMR: (CDCl$_3$-d6, 300 MHz) δ 7.38 (s, 1H), 7.26 (s, 1H), 4.87 (s, 2H), 4.23 (q, J = 7.1 Hz, 2H), 2.10 (s 3H), 1.29 (t, J = 7.1 Hz, 3H). |
| 17<br>tert-Butyl 3-(2-ethoxy-2-oxoethoxy) benzoate | 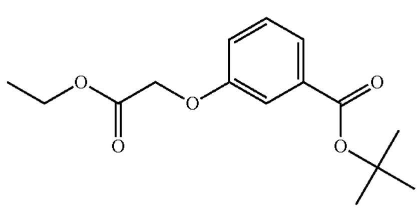 [SMILES: CCOC(=O)COc1cccc(C(=O)OC(C)(C)C)c1] | tert-butyl 3-hydroxybenzoate (Ukrorgsyntez Ltd) and ethyl 2-bromoacetate (Aldrich) | $^1$H NMR: (CDCl$_3$-d6, 300 MHz) δ 7.65, (m, 1H), 7.52 (s, 1H), 7.35 (m, 1H), 7.11 (m, 1H), 4.68 (s, 2H), 4.30 (q, J = 7.1 Hz, 2H), 1.60 (s, 9H), 1.32 (t, J = 7.1 Hz, 3H). |
| 18<br>Ethyl 1-(2-ethoxy-2-oxoethyl)-1H-pyrazole-4-carboxylate | 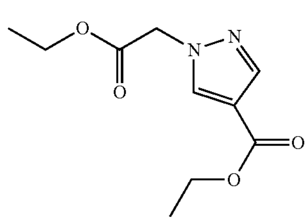 [SMILES: CCOC(=O)Cn1cc(C(=O)OCC)cn1] | ethyl 1H-pyrazole-4-carboxylate (Alfa-Aesar) and ethyl 2-bromoacetate (Aldrich) | LCMS: (M + H)$^+$ = 227; Rt = 2.37 min. |

TABLE 2-continued

| Intermediate | Structure | From | Physical data |
|---|---|---|---|
| 19 Ethyl 2-((4-methoxypyridin-2-yl)oxy) acetate | | 4-methoxypyridin-2-ol (Specs) and ethyl 2-bromoacetate (Aldrich) | LCMS: (M + H)$^+$ = 212; Rt = 1.78 min. |
| 20 Ethyl 2-((5-methylpyridin-2-yl)oxy) acetate | | 5-methylpyridin-2-ol (Aldrich) and ethyl 2-bromoacetate (Aldrich) | LCMS: (M + H)$^+$ = 196; Rt = 1.80 min. |
| 21 Ethyl 2-((3-methoxypyridin-2-yl)oxy)acetate | | 3-methoxypyridin-2-ol (Alinda chemical Ltd.) and ethyl 2-bromoacetate (Aldrich) | LCMS: (M + H)$^+$ = 212; Rt = 1.62 min. |
| 22 Ethyl 2-(4-bromo-1H-pyrazol-1-yl) acetate | | 4-bromo-1H-pyrazole (Aldrich) and ethyl 2-bromoacetate (Aldrich) | LCMS: (M + H)$^+$ = 233-235; Rt = 2.46 min. |
| 23 Ethyl 2-(4-methoxy 1H-pyrazol-1-yl) acetate | | 4-methoxy-1H-pyrazole (intermediate 9) and ethyl 2-bromoacetate (Aldrich) | $^1$H NMR: (CDCl$_3$-d6, 400 MHz) δ 7.32 (s, 1H), 7.16 (s, 1H), 4.82 (s, 2H), 4.26 (q, J = 7.1 Hz, 2H), 3.78 (s, 3H), 1.31 (t, J = 7.1 Hz, 3H). |

Intermediate 24: 2-(1,3-Dimethyl-1H-pyrazol-5-yl)acetyl chloride

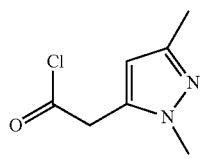

To a suspension 2-(1,3-dimethyl-1H-pyrazol-5-yl)acetic acid (Enamine, 0.370 g, 2.4 mmol) and DMF (3 μL, 0.039 mmol) in dichloromethane (5 mL) at 0° C. was added oxalyl chloride (244 μL, 2.88 mmol). The reaction mixture was stirred at room temperature for 16 h. The product was used in next step without further purification.

Intermediate 25 was prepared by methods analogous to that described for Intermediate 24.

TABLE 3

| Intermediate | Structure | From | Physical Data |
|---|---|---|---|
| 25 2-(pyridin-3-yl) acetylchloride, Hydrochloride | | 2-(pyridin-3-yl) acetic acid (Aldrich) | used in next step without further purification. |

Intermediate 26: 1-(4-Bromophenyl)piperidin-3-ol

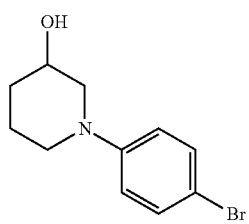 [SMILES: OC1CCCN(c2ccc(Br)cc2)C1]

A solution of 1-bromo-4-iodobenzene (Aldrich, 4 g, 14.14 mmol), piperidin-3-ol (Aldrich, 1.14 g, 11.31 mmol), copper (I) iodide (0.269 g, 1.41 mmol) and K$_3$PO$_4$ (6.00 g, 28.3 mmol) in N,N-dimethylformamide (50 mL) under N$_2$ were stirred at 100° C. for 48 h. The reaction mixture was poured into ice and extracted with ethyl acetate. The organic layer was washed successively with water and brine then dried over anhydrous Na$_2$SO$_4$, filtered through celite and concentrated under reduced pressure. The sample was purified on silica gel column chromatography using a cyclohexane to cyclohexane/ethyl acetate 70:30 as eluant. The appropriate fractions were combined and concentrated in vacuo and the residue was triturated with pentane. The resulting solid was filtered, washed with pentane and dried to give the title compound 1-(4-bromophenyl) piperidin-3-ol as a beige powder. LCMS: (M+H)$^+$=256-258; Rt=2.90 min.

Intermediate 27: 4'-Bromo-2-biphenylol

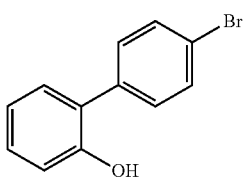 [SMILES: Oc1ccccc1-c1ccc(Br)cc1]

1-Bromo-4-iodobenzene (Aldrich, 2 g, 7.07 mmol), (2-hydroxyphenyl)boronic acid (Aldrich, 1.073 g, 7.78 mmol), Pd(Ph$_3$P)$_4$ (0.204 g, 0.177 mmol) were dissolved in 1,4-dioxane (30 mL) and water (10 mL), K$_3$PO$_4$ (2.251 g, 10.60 mmol) was added. The reaction mixture was stirred at 100° C. overnight. Solvents were removed under reduced pressure and DCM was added, mixture was washed with water, dried over anhydrous sodium sulfate. Then solvent was removed under reduced pressure to give the title product 4'-bromo-2-biphenylol (1.85 g, 6.54 mmol, 92% yield) as brown oil. LCMS: (M+H)$^+$=247-249; Rt=3.52 min.

Intermediate 28 was prepared by methods analogous to that described for Intermediate 27.

Intermediate 29: (1-(4-Bromophenyl)cyclopentyl)methanol

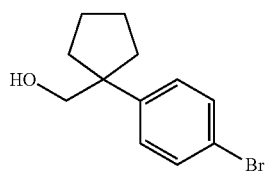 [SMILES: OCC1(c2ccc(Br)cc2)CCCC1]

To a solution of 1-(4-bromophenyl)cyclopentanecarboxylic acid (Enamine, 1 g, 3.72 mmol) in tetrahydrofuran (10 mL), at 0° C. was added slowly LiAlH$_4$ 1M/THF (7.43 mL, 7.43 mmol). The reaction mixture was stirred at room temperature for 1 h and quenched by water. The product was extracted with DCM and the organic layer was evaporated under reduced pressure. The product was purified on silica gel column chromatography using a cyclohexane to cyclohexane/EtOAc 70:30 as eluant. The appropriate fractions were combined and concentrated in vacuo to give the title product (1-(4-bromophenyl)cyclopentyl)methanol (832 mg, 3.26 mmol, 88% yield) as a colourless oil. $^1$H NMR: (DMSO-d6, 300 MHz) δ 7.40 (m, 2H), 7.25 (m, 2H), 4.65 (m, 1H), 3.38 (m, 2H), 1.95 (m, 2H), 1.65 (m, 6H).

TABLE 4

| Intermediate | Structure | From | Physical Data |
|---|---|---|---|
| 28<br>4'-Bromo-3-methoxy-[1,1'-biphenyl]-2-ol | | 1-bromo-4-iodobenzene (Aldrich) and (2-hydroxy-3-methoxyphenyl) boronic acid (Combi-Blocks) | $^1$H NMR: (DMSO-d6, 400 MHz) δ 7.50 (m, 4H), 6.92 (m, 3H), 3.95 (s, 3H) |

Intermediate 30 was prepared by methods analogous to that described for Intermediate 29.

TABLE 5

| Intermediate | Structure | From | Physical Data |
|---|---|---|---|
| 30<br>(1-(4-Bromophenyl)cyclobutyl)methanol | | 1-(4-bromophenyl) cyclobutane carboxylic acid (Combi-Blocks) | LCMS: (M + NH$_4$)$^+$ = 258-260; Rt = 3.19 min. |

Intermediate 31: N-{4-[4-(4,4,5,5-Tetramethyl-1,3,2-dioxaborolan-2-yl)phenyl]-1,3-thiazol-2-yl}acetamide

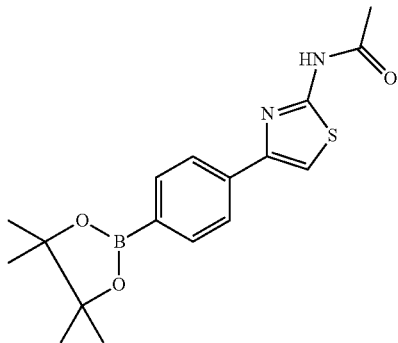 [SMILES: CC(=O)Nc1nc(-c2ccc(B3OC(C)(C)C(C)(C)O3)cc2)cs1]

A suspension of N-[4-(4-bromophenyl)-1,3-thiazol-2-yl]acetamide, (preparation described in *J. Am. Chem. Soc.* 1950, 72, 3722) (3.91 g, 13.16 mmol), 4,4,4',4',5,5,5',5'-octamethyl-2,2'-bi-1,3,2-dioxaborolane (4.01 g, 15.79 mmol), potassium acetate (3.87 g, 39.5 mmol) and [1,1'-Bis(diphenylphosphino)ferrocene]dichloropalladium(II), complex with dichloromethane (PdCl$_2$dppf.DCM) (0.537 g, 0.658 mmol) in 1,4-dioxane (30 mL) was stirred overnight at 100° C. After cooling, the reaction mixture was filtered and the filtrate was evaporated. The residue was then dissolved in dichloromethane and then washed with water and brine. The organic layer was dried over anhydrous sodium sulfate, filtered and concentrated in vacuo. The solid was then dissolved in a few drops of dichloromethane, precipitated with cyclohexane, filtered and dried to give the title compound N-{4-[4-(4,4,5,5-tetramethyl-1,3,2-dioxaborolan-2-yl)phenyl]-1,3-thiazol-2-yl}acetamide (2.37 g, 6.88 mmol, 52.3% yield) as a light brown solid. LCMS: (M+H)$^+$=345; Rt=3.50 min.

Intermediates 32 to 40 were prepared by methods analogous to that described for Intermediate 31.

TABLE 6

| Intermediate | Structure | From | Physical Data |
|---|---|---|---|
| 32<br>1-(4-(4,4,5,5-Tetramethyl-1,3,2-dioxaborolan-2-yl)phenyl)piperidin-3-ol | 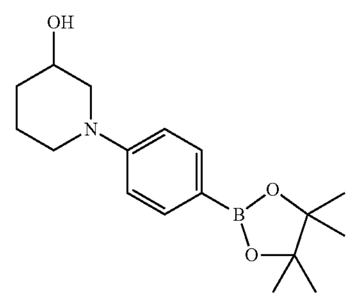 [SMILES: CC1(C)OB(c2ccc(N3CCCC(O)C3)cc2)OC1(C)C] | 1-(4-bromophenyl)piperidin-3-ol (Intermediate 26) | LCMS: (M + H)$^+$ = 304; Rt = 3.16 min. |
| 33<br>3-Methoxy-4'-(4,4,5,5-tetramethyl-1,3,2-dioxaborolan-2-yl)-[1,1'-biphenyl]-2-ol | 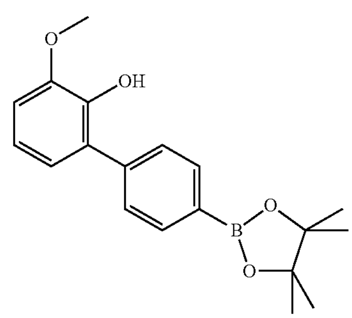 [SMILES: COc1cccc(-c2ccc(B3OC(C)(C)C(C)(C)O3)cc2)c1O] | 4'-bromo-3-methoxy-[1,1'-biphenyl]-2-ol (Intermediate 28) | $^1$H NMR: (CDCl$_3$-d6, 400 MHz) δ 7.88 (m, 2H), 7.63 (m, 2H), 6.92 (m, 3H), 5.86 (s, 1H), 3.95 (s, 3H), 1.36 (s, 12H). |
| 34<br>4'-(4,4,5,5-Tetramethyl-1,3,2-dioxaborolan-2-yl)-2-biphenylol | 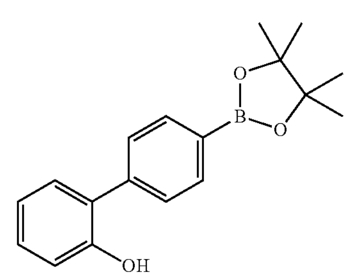 [SMILES: CC1(C)OB(c2ccc(-c3ccccc3O)cc2)OC1(C)C] | 4'-bromo-2-biphenylol (Intermediate 27) | LCMS: (M − H)$^+$ = 295; Rt = 3.77 min. |

TABLE 6-continued

| Intermediate | Structure | From | Physical Data |
|---|---|---|---|
| 35<br>(1-(4-(4,4,5,5-Tetramethyl-1,3,2-dioxaborolan-2-yl)phenyl) cyclopropyl) methanol | | (1-(4-bromophenyl) cyclopropyl) methanol (Combi-Blocks) | LCMS: $(M + NH_4)^+ = 292$; Rt = 3.20 min. |
| 36<br>(1-(4-(4,4,5,5-Tetramethyl-1,3,2-dioxaborolan-2-yl)phenyl)cyclopentyl) methanol | | (1-(4-bromophenyl) cyclopentyl) methanol (Intermediate 29) | LCMS: $(M + NH_4)^+ = 320$; Rt = 3.64 min. |
| 37<br>(1-(4-(4,4,5,5-Tetramethyl-1,3,2-dioxaborolan-2-yl)phenyl)cyclobutyl) methanol | | (1-(4-bromophenyl) cyclobutyl) methanol (Intermediate 30) | LCMS: $(M + NH_4)^+ = 306$; Rt = 3.49 min. |
| 38<br>2-(4-(4,4,5,5-tetramethyl-1,3,2-dioxaborolan-2-yl)phenyl)ethanol | | 2-(4-bromophenyl) ethanol (Acros Organics) | LCMS: $(M + NH_4)^+ = 306$; Rt = 3.49 min. |
| 39<br>1-(4-(4,4,5,5-tetramethyl-1,3,2-dioxaborolan-2-yl)phenyl)cyclobutanol | | 1-(4-bromophenyl) cyclobutanol (Biogene Organics) | LCMS: $(M + NH_4)^+ = 266$; Rt = 2.96 min. |
| 40<br>3-(4-(4,4,5,5-tetramethyl-1,3,2-dioxaborolan-2-yl)phenyl)oxetan-3-ol | | 3-(4-bromophenyl) oxetan-3-ol (Spirochem) | LCMS: $(M + NH_4)^+ = 294$; Rt = 2.80 min. |

Intermediate 41: Methyl 4-amino-4'-bromo-6-chloro-3-biphenylcarboxylate

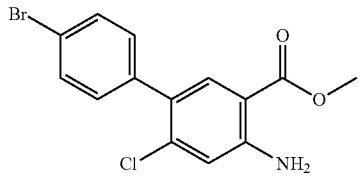

A suspension of methyl 2-amino-4-chloro-5-iodobenzoate (Intermediate 2) (8.2 g, 26.3 mmol), (4-bromophenyl)boronic acid (5.29 g, 26.3 mmol), tetrakis(triphenylphosphine) palladium (0.304 g, 0.263 mmol) and sodium carbonate (79 mL, 1M in water, 79 mmol) in 1,4-dioxane (300 mL) was stirred 3 days at 80° C. After cooling, the mixture was filtered through celite, the filtrate was then diluted with water and extracted twice with dichloromethane. The organic layer was dried over anhydrous sodium sulfate, filtered and concentrated in vacuo. The residue was triturated in diisopropylether, filtered and washed with acetonitrile then diisopropylether to give the title compound methyl 4-amino-4'-bromo-6-chloro-3-biphenylcarboxylate (2.5 g, 7.34 mmol, 27.9% yield) as an off-white powder. LCMS: $(M+H)^+$=340-342; Rt=4.09 min.

Intermediates 42 to 54 were prepared by methods analogous to that described for Intermediate 41. For Intermediate 47, cesium carbonate was used instead of sodium carbonate as base. For Intermediate 51, $K_3PO_4$ was used as base and $PdCl_2(dppf)$ as catalyst. For Intermediate 53, $K_3PO_4$ was used as base.

TABLE 7

| Intermediate | Structure | From | Physical Data |
|---|---|---|---|
| 42 Methyl 4-amino-6-chloro-4'-(4-morpholinyl)-3-biphenylcarboxylate | 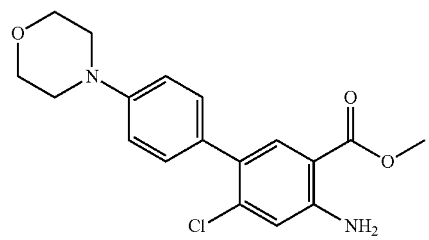 [SMILES: COC(=O)c1cc(-c2ccc(N3CCOCC3)cc2)c(Cl)cc1N] | methyl 2-amino-4-chloro-5-iodobenzoate (Intermediate 2) and [4-(4-morpholinyl)phenyl]boronic acid (Combi-Blocks) | LCMS: $(M + H)^+$ = 347; Rt = 3.51 min. |
| 43 Methyl 4-amino-6-chloro-4'-(cyclopentylamino)carbonyl]-3-biphenylcarboxylate | 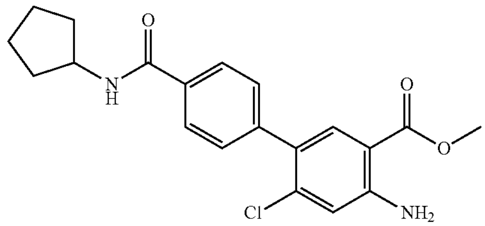 [SMILES: COC(=O)c1cc(-c2ccc(C(=O)NC3CCCC3)cc2)c(Cl)cc1N] | methyl 2-amino-4-chloro-5-iodobenzoate (Intermediate 2) and {4-[(cyclopentyl amino carbonyl)]phenyl}boronic acid (Combi-Blocks) | LCMS: $(M + H)^+$ = 373; Rt = 3.47 min. |
| 44 Ethyl 4-amino-6-fluoro-4'-morpholino-[1,1'-biphenyl]-3-carboxylate | 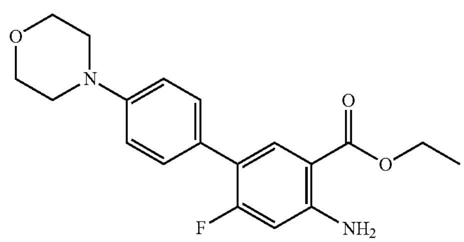 [SMILES: CCOC(=O)c1cc(-c2ccc(N3CCOCC3)cc2)c(F)cc1N] | ethyl 2-amino-4-fluoro-5-iodobenzoate (Intermediate 3) and 4-(4,4,5,5-Tetramethyl-1,3,2-dioxaborolan-2-yl)phenyl)morpholine (Combi-Blocks) | $^1$H NMR: (DMSO-d6, 300 MHz) δ 7.77 (m, 1H), 7.30 (m, 2H), 7 (m, 2H), 6.85 (s, 2H), 6.63 (m, 1H), 4.28 (q, J = 7.0 Hz, 2H), 3.75 (m, 4H), 3.13 (m, 4H), 1.3 (t, J = 7.0 Hz, 3H). |
| 45 Methyl 2-amino-4-chloro-5-(1-methyl-1H-indol-5-yl)benzoate | 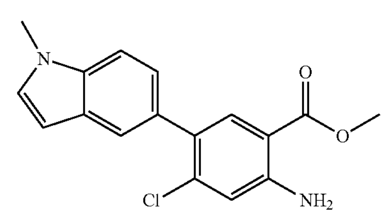 [SMILES: COC(=O)c1cc(-c2ccc3c(ccn3C)c2)c(Cl)cc1N] | methyl 2-amino-4-chloro-5-iodobenzoate (Intermediate 2) and (1-Methyl-1H-indol-5-yl) boronic acid (Combi-Blocks) | LCMS: $(M + H)^+$ = 315; Rt = 3.59 min. |

TABLE 7-continued

| Intermediate | Structure | From | Physical Data |
|---|---|---|---|
| 46 Methyl 4'-[2-(acetylamino)-1,3-thiazol-4-yl]-4-amino-6-chloro-3-biphenylcarboxylate | 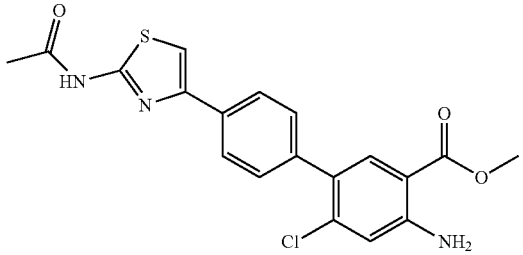 [SMILES: COC(=O)c1cc(-c2ccc(-c3csc(NC(C)=O)n3)cc2)c(Cl)cc1N] | methyl 2-amino-4-chloro-5-iodobenzoate (Intermediate 2) and N-{4-[4-(4,4,5,5-Tetramethyl-1,3,2-dioxaborolan-2-yl)phenyl]-1,3-thiazol-2-yl}acetamide, (Intermediate 31) | LCMS: $(M + H)^+$ = 402; Rt = 3.42 min. |
| 47 Methyl 4-amino-6-chloro-4'-(dimethylamino)-[1,1'-biphenyl]-3-carboxylate | 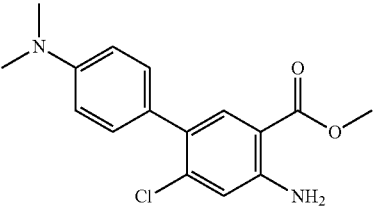 | methyl 2-amino-4-chloro-5-iodobenzoate (Intermediate 2) and (4-(dimethylamino)phenyl)boronic acid (Aldrich) | LCMS: $(M + H)^+$ = 305; Rt = 3.71 min. |
| 48 Methyl 4-amino-6-chloro-4'-(piperidin-1-yl)-[1,1'-biphenyl]-3-carboxylate | 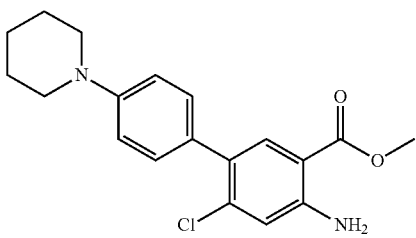 [SMILES: COC(=O)c1cc(-c2ccc(N3CCCCC3)cc2)c(Cl)cc1N] | methyl 2-amino-4-chloro-5-iodobenzoate (Intermediate 2) and (4-(piperidin-1-yl)phenyl) boronic acid hydrochloride (Combi-Blocks) | LCMS: $(M + H)^+$ = 345; Rt = 4.09 min. |
| 49 Methyl 4-amino-6-chloro-4''-methoxy-[1,1':4',1''-terphenyl]-3-carboxylate | 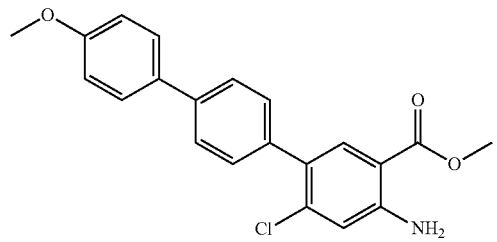 | methyl 4-amino-4'-bromo-6-chloro-3-biphenylcarboxylate (Intermediate 41) and 4-methoxyphenyl boronic acid (Aldrich) | LCMS: $(M + H)^+$ = 368; Rt = 1.36 min. |
| 50 Methyl 4-amino-6-chloro-3''-methoxy-[1,1':4',1''-terphenyl]-3-carboxylate | 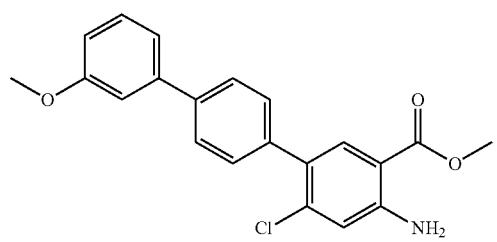 | methyl 4-amino-4'-bromo-6-chloro-3-biphenylcarboxylate (Intermediate 41) and 3-methoxyphenyl boronic acid (Aldrich) | LCMS: $(M + H)^+$ = 368; Rt = 1.37 min. |
| 51 Methyl 4-amino-6-chloro-4'-(5-methylthiophen-2-yl)-[1,1'-biphenyl]-3-carboxylate | 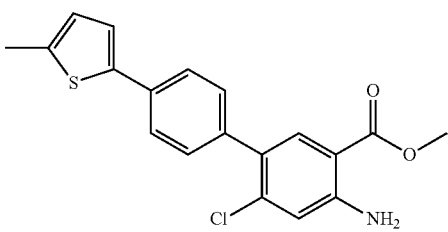 | methyl 4-amino-4'-bromo-6-chloro-3-biphenylcarboxylate (Intermediate 41) and 4,4,5,5-tetramethyl-2-(5-methylthiophen-2-yl)-1,3,2-dioxaborolane (Combi-Blocks) | LCMS: $(M + H)^+$ = 358; Rt = 1.46 min. |

TABLE 7-continued

| Intermediate | Structure | From | Physical Data |
|---|---|---|---|
| 52 Methyl 4-amino-6-chloro-4"-fluoro [1,1':4',1"-terphenyl]-3-carboxylate | | methyl 4-amino-4'-bromo-6-chloro-3-biphenylcarboxylate (Intermediate 41) and (4-fluorophenyl) boronic acid (Aldrich) | LCMS: (M + H)$^+$ = 356; Rt = 1.40 min. |
| 53 Methyl 4-amino-6-chloro-2'''-fluoro-[1,1':4',1"-terphenyl]-3-carboxylate | | methyl 4-amino-4'-bromo-6-chloro-3-biphenylcarboxylate (Intermediate 41) and (2-fluorophenyl) boronic acid (Aldrich) | LCMS: (M + H)$^+$ = 356; Rt = 1.38 min. |
| 54 Methyl 4-amino-6-chloro-2"-hydroxy-3"-(methyloxy)-1,1':4',1"-terphenyl-3-carboxylate | | methyl 4-amino-4'-bromo-6-chloro-3-biphenylcarboxylate (Intermediate 41) and 2-hydroxy-3-(methyloxy)phenyl] boronic acid (Combi-Blocks) | LCMS: (M + H)$^+$ = 384; Rt = 3.85 min. |

Intermediate 55: Methyl 4-chloro-2-{[3-(ethyloxy)-3-oxopropanoyl]amino}-5-iodobenzoate

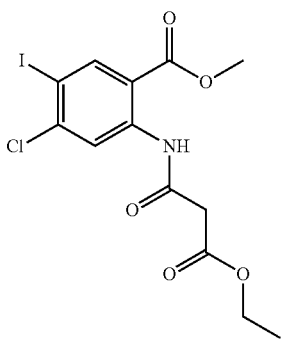 [SMILES: CCOC(=O)CC(=O)Nc1cc(Cl)c(I)cc1C(=O)OC]

To a solution of methyl 2-amino-4-chloro-5-iodobenzoate (Intermediate 2) (8 g, 25.7 mmol) and pyridine (2.18 mL, 27 mmol) in dichloromethane (200 mL) was added ethyl 3-chloro-3-oxopropanoate (Aldrich, 3.45 mL, 27 mmol) and the reaction mixture was stirred overnight at room temperature. The reaction mixture was evaporated to dryness, diluted with ethyl acetate, washed successively with water and brine. The organic layer was then dried over anhydrous sodium sulfate, filtered and concentrated in vacuo. The residue was triturated in pentane, filtered and dried to give the title compound methyl 4-chloro-2-{[3-(ethyloxy)-3-oxopropanoyl]amino}-5-iodobenzoate (8.24 g, 19.36 mmol, 75% yield) as beige solid. LCMS: (M+H)$^+$=426; Rt=3.78 min.

Intermediate 56: Methyl 4-acetamido-6-chloro-4'-(dimethylamino)-[1,1'-biphenyl]-3-carboxylate

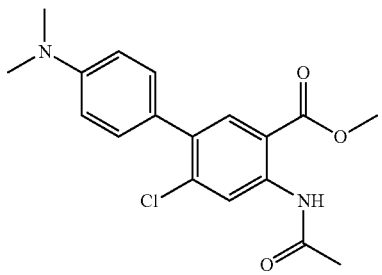

Methyl 4-amino-6-chloro-4'-(dimethylamino)-[1,1'-biphenyl]-3-carboxylate (Intermediate 47) (2 g, 6.56 mmol) was dissolved in acetic anhydride (Aldrich, 6.75 mL, 92 mmol) and the reaction mixture was stirred at room temperature overnight. The reaction mixture was poured into ice water and the resulting precipitate was isolated by filtration and dried. The solid was triturated with methanol, filtered and dried to give the title compound methyl 4-acetamido-6-chloro-4'-(dimethylamino)-[1,1'-biphenyl]-3-carboxylate (2.05 g, 5.91 mmol, 90% yield) as beige solid. LCMS: (M+H)$^+$=347; Rt=3.76 min.

Intermediate 57: Methyl 4-chloro-5-(1-methyl-1H-indol-5-yl)-2-({[3-(methyloxy)phenyl]acetyl}amino)benzoate

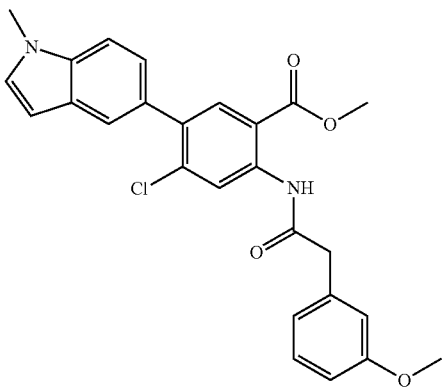 [SMILES: COC(=O)c1cc(-c2ccc3c(ccn3C)c2)c(Cl)cc1NC(=O)Cc1cccc(OC)c1]

To a suspension of methyl 2-amino-4-chloro-5-(1-methyl-1H-indol-5-yl)benzoate (Intermediate 45) (150 mg, 0.427 mmol) in dichloromethane (20 mL) at 0° C. was added triethylamine (0.131 mL, 0.940 mmol) and [3-(methyloxy)phenyl]acetyl chloride (Acros Organics, 79 mg, 0.427 mmol) was added dropwise. The reaction mixture was stirred from 0° C. to RT for 1 h before being quenched with 1N HCl. The organic layer was separated and washed successively with sat. NaHCO$_3$ and brine, dried over Na$_2$SO$_4$, filtered and concentrated under reduced pressure. The product was purified by chromatography using a cyclohexane to cyclohexane/EtOAc 80:20 as eluant. The appropriate fractions were combined and concentrated in vacuo to give the title compound methyl 4-chloro-5-(1-methyl-1H-indol-5-yl)-2-({[3-(methyloxy)phenyl]acetyl}amino)benzoate (150 mg, 0.324 mmol, 76% yield) as a white amorphous solid. LCMS: (M+H)$^+$= 463; Rt=4.23 min.

Intermediates 58 to 65 were prepared by methods analogous to that described for Intermediate 57. For Intermediates 58, 63 and 65, pyridine was used instead of triethylamine as base.

TABLE 8

| Intermediate | Formula | From | Physical data |
|---|---|---|---|
| 58 Methyl 6-chloro-2''-hydroxy-3''-methoxy-4-(2-phenylacetamido)-[1,1':4',1''-terphenyl]-3-carboxylate | | methyl 4-amino-6-chloro-2''-hydroxy-3''-(methyloxy)-1,1':4',1''-terphenyl-3-carboxylate (Intermediate 54) and phenacetyl chloride (Aldrich) | LCMS: (M + H)$^+$ = 502; Rt = 4.19 min. |
| 59 Methyl 4'-[2-(acetylamino)-1,3-thiazol-4-yl]-6-chloro-4-[(phenylacetyl)amino]-3-biphenylcarboxylate | | methyl 4'-[2-(acetylamino)-1,3-thiazol-4-yl]-4-amino-6-chloro-3-biphenylcarboxylate (Intermediate 46) and phenacetyl chloride (Aldrich) | LCMS: (M + H)$^+$ = 520; Rt = 3.95 min. |

TABLE 8-continued

| Intermediate | Formula | From | Physical data |
|---|---|---|---|
| 60 Methyl 4-chloro-5-(1-methyl-1H-indol-5-yl)-2-[(phenylacetyl)amino]benzoate | | methyl 2-amino-4-chloro-5-(1-methyl-1H-indol-5-yl)benzoate (Intermediate 45) and phenylacetyl chloride (Aldrich) | LCMS: $(M + H)^+$ = 433; Rt = 4.11 min. |
| 61 Methyl 6-chloro-4'-(4-morpholinyl)-4-[(phenylacetyl)amino]-3-biphenylcarboxylate | | methyl 4-amino-6-chloro-4'-(4-morpholinyl)-3-biphenylcarboxylate (Intermediate 42) and phenylacetyl chloride (Aldrich) | LCMS: $(M + H)^+$ = 465; Rt = 4.11 min. |
| 62 Methyl 4-chloro-5-iodo-2-(2-(pyridin-3-yl)acetamido)benzoate | | methyl 2-amino-4-chloro-5-iodobenzoate (Intermediate 2) and 2-(pyridin-3-yl) acetyl chloride hydrochloride (Intermediate 25) | LCMS: $(M + H)^+$ = 431; Rt = 3.34 min. |
| 63 Methyl 4-chloro-5-iodo-2-(2-phenylacetamido)benzoate | | methyl 2-amino-4-chloro-5-iodobenzoate (Intermediate 2) and phenylacetyl chloride (Aldrich) | LCMS: $(M + H)^+$ = 430; Rt = 4.01 min. |

TABLE 8-continued

| Intermediate | Formula | From | Physical data |
|---|---|---|---|
| 64<br>Methyl 4-chloro-2-(2-(1,3-dimethyl-1H-pyrazol-5-yl)acetamido)-5-iodobenzoate | (structure) | methyl 2-amino-4-chloro-5-iodobenzoate (Intermediate 2) and 2-(1,3-dimethyl-1H-pyrazol-5-yl)acetyl chloride (Intermediate 24) | LCMS: $(M + H)^+$ = 448; Rt = 3.42 min. |
| 65<br>Methyl 6-chloro-4-(2-(3-chlorophenyl)acetamido)-4'-(piperidin-1-yl)-[1,1'-biphenyl]-3-carboxylate | (structure) | methyl 4-amino-6-chloro-4'-(piperidin-1-yl)-[1,1'-biphenyl]-3-carboxylate (Intermediate 48) and 2-(3-chlorophenyl) acetyl chloride (UkrOrgSynthesis Ltd.) | LCMS: $(M + H)^+$ = 497; Rt = 4.66 min. |

Intermediate 66: Methyl 4-chloro-2-(2-(3-(methoxycarbonyl)phenyl)acetamido)-5-(1-methyl-1H-indol-5-yl)benzoate To a solution of methyl 2-amino-4-chloro-5-(1-methyl-1H-indol-5-yl)benzoate (Intermediate 45) (150 mg, 0.477 mmol) in dichloromethane (10 mL) was added {3-[(methyloxy) carbonyl]phenyl}acetic acid (Akos, 97 mg, 0.500 mmol), HATU (236 mg, 0.620 mmol) and triethylamine (0.073 mL, 0.524 mmol) and the reaction mixture was stirred at room temperature overnight. The mixture was washed with water and brine, the organic layer was dried over anhydrous sodium sulfate, filtered and concentrated in vacuo. Purification by flash chromatography using cyclohexane to cyclohexane/ethyl acetate 80:20 as eluant gave the title compound methyl 4-chloro-2-(2-(3-(methoxycarbonyl)phenyl)acetamido)-5-(1-methyl-1H-indol-5-yl)benzoate (205 mg, 0.418 mmol, 88% yield) as a white amorphous solid. LCMS: $(M+H)^+$=491; Rt=4.19 min.

Intermediates 67 to 89 were prepared by methods analogous to that described for Intermediate 66.

TABLE 9

| Intermediate | Formula | From | Physical data |
|---|---|---|---|
| 67<br>Methyl 6-chloro-4-({[3-(methyloxy)phenyl]acetyl}amino)-4'-(4-morpholinyl)-3-biphenylcarboxylate | 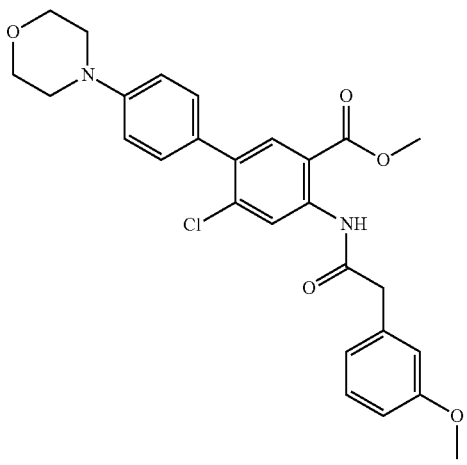 [SMILES: COC(=O)c1cc(-c2ccc(N3CCOCC3)cc2)c(Cl)cc1NC(=O)Cc1cccc(OC)c1] | methyl 4-amino-6-chloro-4'-(4-morpholinyl)-3-biphenylcarboxylate (Intermediate 42) and [3-(methyloxy)phenyl] acetic acid (Lancaster Synthesis Ltd.) | LCMS: $(M + H)^+ =$ 495; Rt = 4.01 min. |
| 68<br>Methyl 6-chloro-4'-[(cyclopentylamino)carbonyl]-4-({[3-(methyloxy)phenyl]acetyl} amino)-3-biphenylcarboxy | 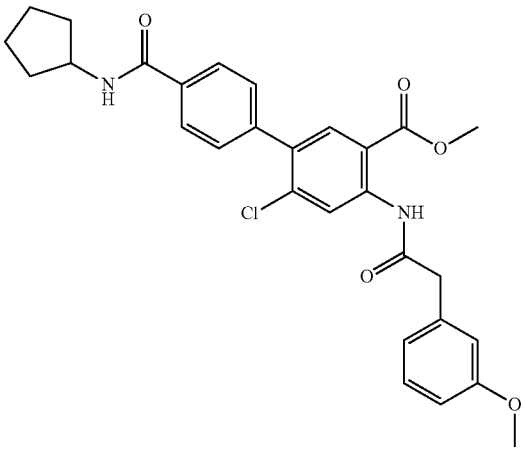 [SMILES: COC(=O)c1cc(-c2ccc(C(=O)NC3CCCC3)cc2)c(Cl)cc1NC(=O)Cc1cccc(OC)c1] | methyl 4-amino-6-chloro-4'-[(cyclopentylamino)carbonyl]-3-biphenylcarboxylate (Intermediate 43) and [3-(methyloxy)phenyl]acetic acid (Lancaster Synthesis Ltd.) | LCMS: $(M + H)^+ =$ 521; Rt = 3.90 min. |
| 69<br>Methyl 4'-[2-(acetylamino)-1,3-thiazol-4-yl]-6-chloro-4-({[3-(methyloxy)phenyl]acetyl}amino)-3-biphenylcarboxylate | 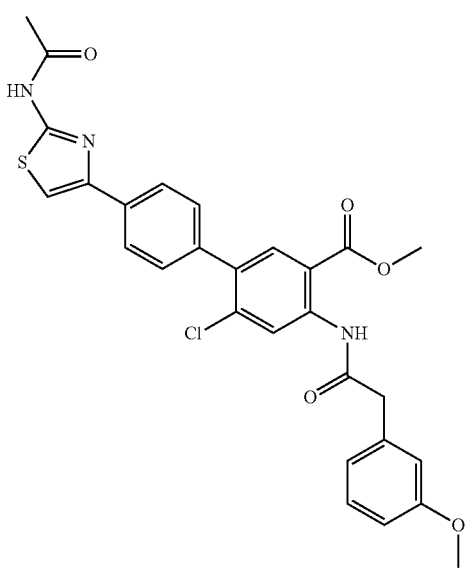 [SMILES: COC(=O)c1cc(-c2ccc(-c3csc(NC(C)=O)n3)cc2)c(Cl)cc1NC(=O)Cc1cccc(OC)c1] | methyl 4'-[2-(acetylamino)-1,3-thiazol-4-yl]-4-amino-6-chloro-3-biphenylcarboxylate (Intermediate 46) and [3-(methyloxy)phenyl]acetic acid (Lancaster Synthesis Ltd.) | LCMS: $(M + H)^+ =$ 550; Rt = 3.87 min. |

TABLE 9-continued

| Intermediate | Formula | From | Physical data |
|---|---|---|---|
| 70<br>Methyl 4-chloro-5-iodo-2-(2-(3-methylisoxazol-5-yl) acetamido) benzoate | | methyl 2-amino-4-chloro-5-iodobenzoate (Intermediate 2) and 2-(3-methyl isoxazol-5-yl)acetic acid (Aldrich) | LCMS: (M + H)⁺ = 435; Rt = 3.52 min. |
| 71<br>Ethyl 6-fluoro-4-(2-(3-methoxyphenyl) acetamido)-4'-morpholino-[1,1'-biphenyl]-3-carboxylate | | ethyl 4-amino-6-fluoro-4'-morpholino-[1,1'-biphenyl]-3-carboxylate (Intermediate 44) and [3-(methyloxy)phenyl]acetic acid (Lancaster Synthesis Ltd.) | LCMS: (M + H)⁺ = 493; Rt = 4.03 min. |
| 72<br>Methyl 4-chloro-5-iodo-2-(2-phenoxyacetamido) benzoate | | methyl 2-amino-4-chloro-5-iodobenzoate (Intermediate 2) and 2-phenoxyacetic acid (Aldrich) | LCMS: (M + H)⁺ = 446; Rt = 4.17 min. |
| 73<br>Methyl 4-chloro-5-iodo-2-(2-(4-methyl-1,2,5-oxadiazol-3-yl) acetamido) benzoate | | methyl 2-amino-4-chloro-5-iodobenzoate (Intermediate 2) and 2-(4-methyl-1,2,5-oxadiazol-3-yl)acetic acid (Chemical Block Ltd.) | LCMS: (M − H)⁺ = 434; Rt = 3.70 min. |

TABLE 9-continued

| Intermediate | Formula | From | Physical data |
|---|---|---|---|
| 74 Methyl 4-chloro-5-iodo-2-(2-(pyridin-4-yl)acetamido)benzoate | | methyl 2-amino-4-chloro-5-iodobenzoate (Intermediate 2) and 2-(pyridin-4-yl)acetic acid hydrochloride (Aldrich) | LCMS: $(M + H)^+$ = 431; Rt = 3.34 min. |
| 75 Methyl 2-(2-(1H-1,2,4-triazol-1-yl)acetamido)-4-chloro-5-iodobenzoate | | methyl 2-amino-4-chloro-5-iodobenzoate (Intermediate 2) and 2-(1H-1,2,4-triazol-1-yl)acetic acid (Chembridge) | LCMS: $(M + H)^+$ = 421; Rt = 2.96 min. |
| 76 Methyl 4-chloro-2-(2-(4-chloro-1H-pyrazol-1-yl)acetamido)-5-iodobenzoate | | methyl 2-amino-4-chloro-5-iodobenzoate (Intermediate 2) and -2-(4-chloro-1H-pyrazol-1-yl) acetic acid (Enamine) | LCMS: $(M + H)^+$ = 454; Rt = 3.65 min. |
| 77 Methyl 4-chloro-5-iodo-2-(2-(1-methyl-1H-pyrazol-4-yl)acetamido)benzoate | | methyl 2-amino-4-chloro-5-iodobenzoate (Intermediate 2) and 2-(1-methyl-1H-pyrazol-4-yl) acetic acid (Enamine) | LCMS: $(M + H)^+$ = 434; Rt = 3.24 min. |
| 78 Methyl 6-chloro-4-(2-(3-methylisoxazol-5-yl)acetamido)-4'-(piperidin-1-yl)-[1,1'-biphenyl]-3-arboxylate | | methyl 4-amino-6-chloro-4'-(piperidin-1-yl)-[1,1'-biphenyl]-3-carboxylate (Intermediate 48) and 2-(3-methylisoxazol-5-yl)acetic acid (Aldrich) | LCMS: $(M + H)^+$ = 468; Rt = 4.31 min. |

TABLE 9-continued

| Intermediate | Formula | From | Physical data |
|---|---|---|---|
| 79 Methyl 6-chloro-4-(2-(1-methyl-1H-pyrazol-4-yl)acetamido)-4'-(piperidin-1-yl)-[1,1'-biphenyl]-3-carboxylate | | methyl 4-amino-6-chloro-4'-(piperidin-1-yl)-[1,1'-biphenyl]-3-carboxylate (Intermediate 48) and 2-(1-methyl-1H-pyrazol-4-yl) acetic acid (Enamine) | LCMS: $(M + H)^+$ = 467; Rt = 3.96 min. |
| 80 Methyl 6-chloro-4''-fluoro-4-(2-(3-methylisoxazol-5-yl)acetamido)-[1,1':4',1''-terphenyl]-3-carboxylate | | methyl 4-amino-6-chloro-4''-fluoro-[1,1':4',1''-terphenyl]-3-carboxylate (Intermediate 52) and 2-(3-methylisoxazol-5-yl) acetic acid (Aldrich) | LCMS: $(M + H)^+$ = 479; Rt = 4.14 min. |
| 81 Methyl 6-chloro-4'-(dimethylamino)-4-(2-(3-methyl-1,2,4-oxadiazol-5-yl)acetamido)-[1,1'-biphenyl]-3-carboxylate | | methyl 4-amino-6-chloro-4'-(dimethylamino)-[1,1'-biphenyl]-3-carboxylate (Intermediate 47) and 2-(3-methyl-1,2,4-oxadiazol-5-yl)acetic acid (Otava) | LCMS: $(M + H)^+$ = 429; Rt = 3.75 min. |

TABLE 9-continued

| Intermediate | Formula | From | Physical data |
|---|---|---|---|
| 82 Methyl 6-chloro-4'-(dimethylamino)-4-(2-(5-methyl-1,3,4-oxadiazol-2-yl)acetamido)-[1,1'-biphenyl]-3-carboxylate | | methyl 4-amino-6-chloro-4'-(dimethylamino)-[1,1'-biphenyl]-3-carboxylate (Intermediate 47) and 2-(5-methyl-1,3,4-oxadiazol-2-yl)acetic acid (Otava) | LCMS: $(M + H)^+$ = 429; Rt = 3.49 min. |
| 83 Methyl 6-chloro-4'-(dimethylamino)-4-(2-(2-methylthiazol-5-yl)acetamido)-[1,1'-biphenyl]-3-carboxylate | | methyl 4-amino-6-chloro-4'-(dimethylamino)-[1,1'-biphenyl]-3-carboxylate (Intermediate 47) and 2-(2-methylthiazol-5-yl)acetic acid (Life Chemicals) | LCMS: $(M + H)^+$ = 444; Rt = 3.81 min. |
| 84 Methyl 6-chloro-4'-(dimethylamino)-4-(2-(2,4-dimethylthiazol-5-yl)acetamido)-[1,1'-biphenyl]-3-carboxylate | | methyl 4-amino-6-chloro-4'-(dimethylamino)-[1,1'-biphenyl]-3-carboxylate (Intermediate 47) and 2-(2,4-dimethylthiazol-5-yl)acetic acid (Chembridge) | LCMS: $(M + H)^+$ = 458; Rt = 3.91 min. |

TABLE 9-continued

| Intermediate | Formula | From | Physical data |
|---|---|---|---|
| 85<br>Methyl 6-chloro-4-(2-(5-methyl-1,3,4-oxadiazol-2-yl)acetamido)-4'-(piperidin-1-yl)-[1,1'-biphenyl]-3-carboxylate | | methyl 4-amino-6-chloro-4'-(piperidin-1-yl)-[1,1'-biphenyl]-3-carboxylate (Intermediate 48) and 2-(5-methyl-1,3,4-oxadiazol-2-yl)acetic acid (Otava) | LCMS: $(M + H)^+ =$ 469; Rt = 3.85 min. |
| 86<br>Methyl 6-chloro-4'-(dimethylamino)-4-(2-(4-(dimethylamino)phenyl)acetamido)-[1,1'-biphenyl]-3-carboxylate | | methyl 4-amino-6-chloro-4'-(dimethylamino)-[1,1'-biphenyl]-3-carboxylate (Intermediate 47) and 2-(4-(dimethylamino)phenyl) acetic acid (Aldrich) | LCMS: $(M + H)^+ =$ 466; Rt = 4.32 min. |
| 87<br>Methyl 6-chloro-4-(2-(4-cyanophenyl)acetamido)-4'-(dimethylamino)-[1,1'-biphenyl]-3-carboxylate | | methyl 4-amino-6-chloro-4'-(dimethylamino)-[1,1'-biphenyl]-3-carboxylate (Intermediate 47) and 2-(4-cyanophenyl) acetic acid (Aldrich) | LCMS: $(M + H)^+ =$ 448; Rt = 4.05 min. |

TABLE 9-continued

| Intermediate | Formula | From | Physical data |
|---|---|---|---|
| 88 Methyl 6-chloro-4-(2-(3-cyanophenyl)acetamido)-4'-(dimethylamino)-[1,1'-biphenyl]-3-carboxylate | | methyl 4-amino-6-chloro-4'-(dimethylamino)-[1,1'-biphenyl]-3-carboxylate (Intermediate 47) and 2-(3-cyanophenyl) acetic acid (Aldrich) | LCMS: (M + H)⁺ = 448; Rt = 4.06 min. |
| 89 Methyl 6-chloro-3''-methoxy-4-(2-(3-methylisoxazol-5-yl)acetamido)-[1,1':4',1''-terphenyl]-3-carboxylate | | methyl 4-amino-6-chloro-3''-methoxy-[1,1':4',1''-terphenyl]-3-carboxylate (Intermediate 50) and 2-(3-methylisoxazol-5-yl) acetic acid (Aldrich) | LCMS: (M + H)⁺ = 491; Rt = 1.38 min. |

Intermediate 90: Methyl 1-(2-((2-chloro-5-(methoxycarbonyl)-4'-(piperidin-1-yl)-[1,1'-biphenyl]-4-yl)amino)-2-oxoethyl)-1H-pyrazole-4-carboxylate

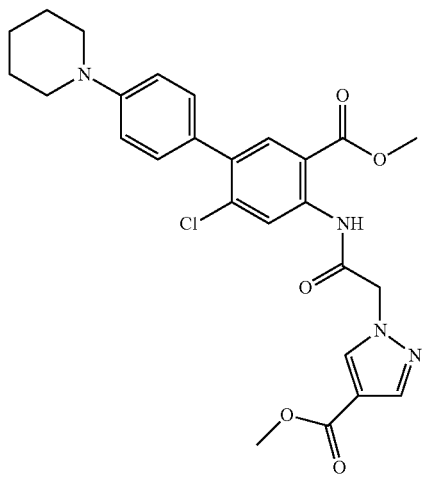 [SMILES: COC(=O)c1cnn(CC(=O)Nc2cc(Cl)c(-c3ccc(N4CCCCC4)cc3)cc2C(=O)OC)c1]

To a solution of 2-(4-(methoxycarbonyl)-1H-pyrazol-1-yl)acetic acid (ChemCollect GmbH, 401 mg, 2.175 mmol) in toluene (10 mL) was added thionyl chloride (0.317 mL, 4.35 mmol) and the reaction mixture was stirred at 90° C. for 2 h. The solvent was removed under reduced pressure and the residue was added to a solution of methyl 4-amino-6-chloro-4'-(piperidin-1-yl)-[1,1'-biphenyl]-3-carboxylate (Intermediate 48) (500 mg, 1.45 mmol) in dichloromethane (10 mL). The reaction mixture was stirred at room temperature overnight. Solvent was removed under reduced pressure and water was added. Precipitate was observed, solid was filtered and dried to give the title compound methyl 1-(2-((2-chloro-5-(methoxycarbonyl)-4'-(piperidin-1-yl)-[1,1'-biphenyl]-4-yl)amino)-2-oxoethyl)-1H-pyrazole-4-carboxylate (720 mg, 1.409 mmol, 97% yield) as a cream solid. LCMS: (M+H)⁺= 511; Rt=4.04 min.

Intermediate 91 was prepared by methods analogous to that described for Intermediate 90.

TABLE 10

| Intermediate | Structure | From | Physical data |
|---|---|---|---|
| 91<br>Methyl 4-chloro-5-iodo-2-({[3-(methyloxy) phenyl]acetyl}amino)benzoate | | methyl 2-amino-4-chloro-5-iodobenzoate (Intermediate 2) and [3-(methyloxy)phenyl] acetic acid (Aldrich) | LCMS: (M + H)+ = 460;<br>Rt = 3.99 min. |

Intermediate 92: Methyl 4-chloro-5-iodo-2-(2-(phenylsulfonyl)acetamido)benzoate

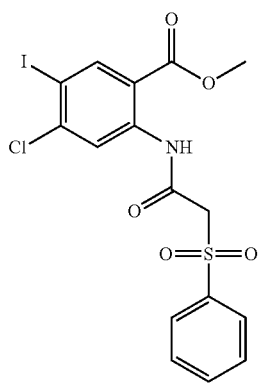 [SMILES: COC(=O)c1cc(I)c(Cl)cc1NC(=O)CS(=O)(=O)c1ccccc1]

To a solution of 2-(phenylsulfonyl) acetic acid (Lancaster Synthesis Ltd., 0.771 mg, 3.85 mmol) in dichloromethane (50 mL) was added oxalyl chloride (4.17 mL, 4.17 mmol) and few drops of DMF. The reaction mixture was stirred 2 hours at room temperature. To a solution of methyl 2-amino-4-chloro-5-iodobenzoate (Intermediate 2) (1 g, 3.21 mmol) and triethylamine (1.074 mL, 7.70 mmol) in dichloromethane (50 mL) at RT was added dropwise the acid chloride prepared above. The reaction mixture was stirred at room temperature overnight then quenched with aqueous solution of $NaHCO_3$. The organic layer was and washed with saturated $NaHCO_3$, water and brine. The organic layer was dried over anhydrous $Na_2SO_4$, filtered and concentrated in vacuo to give the title compound methyl 4-chloro-5-iodo-2-(2-(phenylsulfonyl)acetamido)benzoate (1.1 g, 2.228 mmol, 69.4% yield) as pale yellow powder. LCMS: (M+H)+=494; Rt=3.58 min.

Intermediate 93 to 94 were prepared by methods analogous to that described for Intermediate 92.

TABLE 11

| Intermediate | Structure | From | Physical data |
|---|---|---|---|
| 93<br>Methyl 6-chloro-2"-fluoro-4-(2-(3-methylisoxazol-5-yl)acetamido)-[1,1':4',1"-terphenyl]-3-carboxylate | | methyl 4-amino-6-chloro-2"-fluoro-[1,1':4',1"-terphenyl]-3-carboxylate (Intermediate 53) and 2-(3-methylisoxazol-5-yl) acetic acid (Aldrich) | LCMS: (M + H)+ = 479;<br>Rt = 1.40 min. |

TABLE 11-continued

| Intermediate | Structure | From | Physical data |
|---|---|---|---|
| 94 Methyl 6-chloro-2"-hydroxy-3"-(methyloxy)-4-[({3-[(methyloxy)carbonyl]phenyl}acetyl)amino]-1,1':4',1"-terphenyl-3-carboxylate | | methyl 4-amino-6-chloro-2"-hydroxy-3"-(methyloxy)-1,1':4',1"-terphenyl-3-carboxylate (Intermediate 54) and {3-[(methyloxy)carbonyl]phenyl}acetic acid (Akos) | LCMS: $(M + H)^+ = 560$; Rt = 4.10 min. |

Intermediate 95: Methyl 6-chloro-4"-methoxy-4-(2-(3-methylisoxazol-5-yl)acetamido)-[1,1':4',1"-terphenyl]-3-carboxylate

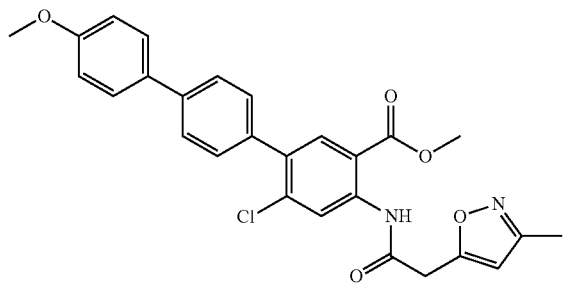

A stirred suspension of methyl 4-amino-6-chloro-4"-methoxy-[1,1':4',1"-terphenyl]-3-carboxylate (Intermediate 49) (520 mg, 1.41 mmol)) and 2-(3-methylisoxazol-5-yl) acetic acid (Aldrich, 219 mg, 1.56 mmol) in $POCl_3$ (6 mL) was heated at 80° C. for 2 h and then cooled to room temperature. The solution was concentrated under reduced pressure. The crude material was taken up with ethyl acetate and saturated $NaHCO_3$, the organic phase was washed with water and dried over $Na_2SO_4$ and the solvent removed under reduced pressure. The crude material was purified on silica gel column chromatography using cyclohexane to cyclohexane/ethyl acetate 75:25 as eluant to give the title compound methyl 6-chloro-4"-methoxy-4-(2-(3-methylisoxazol-5-yl)acetamido)-[1,1':4',1"-terphenyl]-3-carboxylate (210 mg, 0.43 mmol, 30.4%). LCMS: $(M+H)^+=491$; Rt=1.37 min.

Intermediate 96 was prepared by methods analogous to that described for Intermediate 95.

TABLE 12

| Intermediate | Structure | From | Physical data |
|---|---|---|---|
| 96 Methyl 6-chloro-4-(2-(3-methylisoxazol-5-yl)acetamido)-4'-(5-methylthiophen-2-yl)-[1,1'-biphenyl]-3-carboxylate | 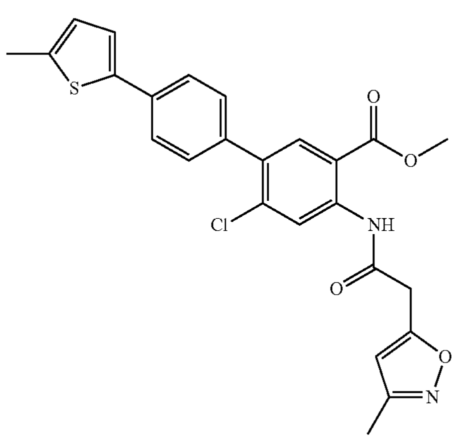 | methyl 4-amino-6-chloro-4'-(5-methylthiophen-2-yl)-[1,1'-biphenyl]-3-carboxylate (Intermediate 51) and 2-(3-methyl isoxazol-5-yl) acetic acid (Aldrich) | LCMS: $(M + H)^+ = 481$; Rt = 1.50 min. |

Intermediate 97: N-[4-(4-{7-Chloro-4-hydroxy-3-[3-(methyloxy)phenyl]-2-oxo-1,2-dihydro-6-quinolinyl}phenyl)-1,3-thiazol-2-yl]acetamide

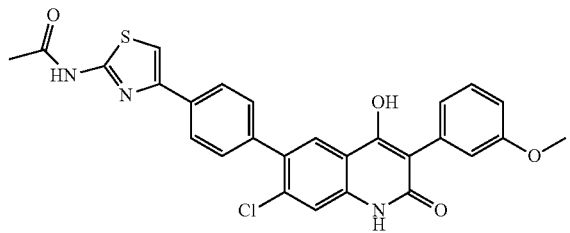 [SMILES: COc1cccc(-c2c(O)c3cc(-c4ccc(-c5csc(NC(C)=O)n5)cc4)c(Cl)cc3[nH]c2=O)c1]

To a solution of methyl 4'-[2-(acetylamino)-1,3-thiazol-4-yl]-6-chloro-4-({[3-(methyloxy) phenyl]acetyl}amino)-3-biphenylcarboxylate (Intermediate 69) (284 mg, 0.516 mmol) in tetrahydrofuran (5 mL) was added dropwise KHMDS 1M/THF (2.065 mL, 2.065 mmol) at 60° C. The reaction mixture was stirred 2 h after the end of addition. The reaction mixture was acidified with a 1N HCl, filtered and the resulting solid was recrystallized twice in methanol.

The solid was filtered and dried to give the title compound N-[4-(4-{7-chloro-4-hydroxy-3-[3-(methyloxy)phenyl]-2-oxo-1,2-dihydro-6-quinolinyl}phenyl)-1,3-thiazol-2-yl]acetamide (140 mg, 0.270 mmol, 52.3% yield) as a yellow solid. LCMS: (M+H)+=518; Rt=2.65 min.

Intermediates 98 to 110 were prepared by methods analogous to that described for Intermediate 97. For Intermediate 100, potassium tBuOK/DMSO was used instead of 1M KHMDS/THF. For Intermediate 101, 1M LiHMDS/THF was used instead of 1M KHMDS/THF.

TABLE 13

| Intermediate | Structure | From | Physical data |
|---|---|---|---|
| 98<br>7-Chloro-4-hydroxy-6-iodo-3-[3-(methyloxy)phenyl]quinolin-2(1H)-one | 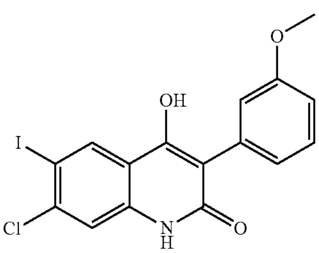 [SMILES: COc1cccc(-c2c(O)c3cc(I)c(Cl)cc3[nH]c2=O)c1] | methyl 4-chloro-5-iodo-2-({[3-(methyloxy)phenyl]acetyl}amino)benzoate (Intermediate 91) | LCMS: (M + H)+ = 428; Rt = 2.36 min. |
| 99<br>7-chloro-4-hydroxy-6-iodo-3-(3-methylisoxazol-5-yl)quinolin-2(1H)-one | 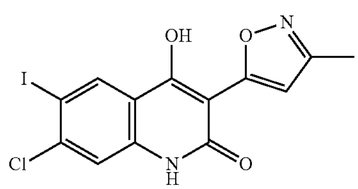 [SMILES: Cc1cc(-c2c(O)c3cc(I)c(Cl)cc3[nH]c2=O)on1] | methyl 4-chloro-5-iodo-2-(2-(3-methylisoxazol-5-yl)acetamido)benzoate (Intermediate 70) | LCMS: (M + H)+ = 403; Rt = 2.13 min. |
| 100<br>Ethyl 7-chloro-4-hydroxy-6-iodo-2-oxo-1,2-dihydro-3-quinolinecarboxylate | 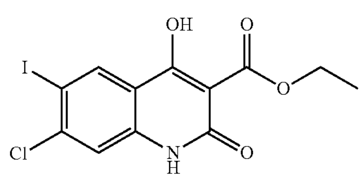 [SMILES: CCOC(=O)c1c(O)c2cc(I)c(Cl)cc2[nH]c1=O] | methyl 4-chloro-2-{[3-(ethyloxy)-3-oxopropanoyl]amino}-5-iodobenzoate (Intermediate 55) | LCMS: (M + H)+ = 394; Rt = 2.14 min. |
| 101<br>7-Chloro-4-hydroxy-6-iodo-3-phenoxyquinolin-2(1H)-one | 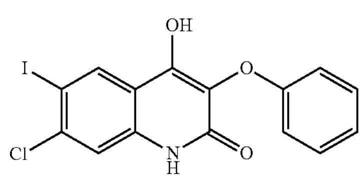 [SMILES: O=c1[nH]c2cc(Cl)c(I)cc2c(O)c1Oc1ccccc1] | methyl 4-chloro-5-iodo-2-(2-phenoxyacetamido)benzoate (Intermediate 72) | LCMS: (M + H)+ = 414; Rt = 2.26 min. |
| 102<br>7-Chloro-4-hydroxy-6-iodo-3-phenylquinolin-2(1H)-one | 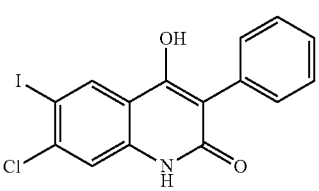 [SMILES: O=c1[nH]c2cc(Cl)c(I)cc2c(O)c1-c1ccccc1] | methyl 4-chloro-5-iodo-2-(2-phenylacetamido)benzoate (Intermediate 63) | LCMS: (M + H)+ = 398; Rt = 2.30 min. |

TABLE 13-continued

| Intermediate | Structure | From | Physical data |
|---|---|---|---|
| 103 7-Chloro-4-hydroxy-6-iodo-3-(4-methyl-1,2,5-oxadiazol-3-yl)quinolin-2(1H)-one | 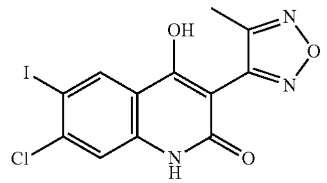 [SMILES: Cc1nonc1-c1c(O)c2cc(I)c(Cl)cc2[nH]c1=O] | methyl 4-chloro-5-iodo-2-(2-(4-methyl-1,2,5-oxadiazol-3-yl)acetamido)benzoate (Intermediate 73) | LCMS: $(M + H)^+$ = 404; Rt = 2.08 min. |
| 104 7-Chloro-4-hydroxy-6-iodo-3-(pyridin-4-yl) quinolin-2(1H)-one | 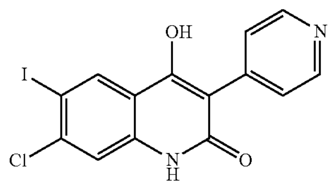 [SMILES: O=c1[nH]c2cc(Cl)c(I)cc2c(O)c1-c1ccncc1] | methyl 4-chloro-5-iodo-2-(2-(pyridin-4-yl)acetamido)benzoate (Intermediate 74) | LCMS: $(M + H)^+$ = 399; Rt = 2.17 min. |
| 105 7-Chloro-4-hydroxy-6-iodo-3-(1H-1,2,4-triazol-1-yl)quinolin-2(1H)-one | 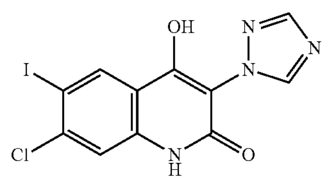 [SMILES: O=c1[nH]c2cc(Cl)c(I)cc2c(O)c1-n1cncn1] | methyl 2-(2-(1H-1,2,4-triazol-1-yl)acetamido)-4-choro-5-iodobenzoate (Intermediate 75) | LCMS: $(M + H)^+$ = 389; Rt = 1.91 min. |
| 106 7-Chloro-4-hydroxy-6-iodo-3-(pyridin-3-yl) quinolin-2(1H)-one | 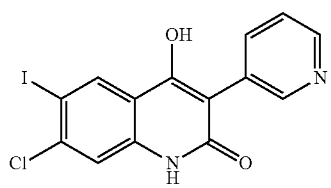 [SMILES: O=c1[nH]c2cc(Cl)c(I)cc2c(O)c1-c1cccnc1] | methyl 4-chloro-5-iodo-2-(2-(pyridin-3-yl)acetamido)benzoate (Intermediate 62) | LCMS: $(M + H)^+$ = 399; Rt = 2.02 min. |
| 107 7-Chloro-3-(1,3-dimethyl-1H-pyrazol-5-yl)-4-hydroxy-6-iodoquinolin-2(1H)-one | 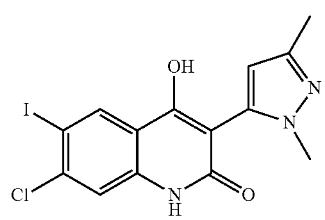 [SMILES: Cc1cc(-c2c(O)c3cc(I)c(Cl)cc3[nH]c2=O)n(C)n1] | methyl 4-chloro-2-(2-(1,3-dimethyl-1H-pyrazol-5-yl)acetamido)-5-iodobenzoate (Intermediate 64) | LCMS: $(M + H)^+$ = 416; Rt = 2.03 min. |
| 108 7-Chloro-3-(4-chloro-1H-pyrazol-1-yl)-4-hydroxy-6-iodoquinolin-2(1H)-one | 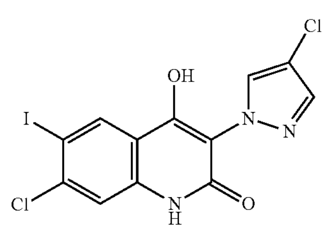 [SMILES: O=c1[nH]c2cc(Cl)c(I)cc2c(O)c1-n1cc(Cl)cn1] | methyl 4-chloro-2-(2-(4-chloro-1H-pyrazol-1-yl)acetamido)-5-iodobenzoate (Intermediate 76) | LCMS: $(M + H)^+$ = 422; Rt = 2.04 min. |
| 109 7-Chloro-4-hydroxy-6-iodo-3-(1-methyl-1H-pyrazol-4-yl) quinolin-2(1H)-one | 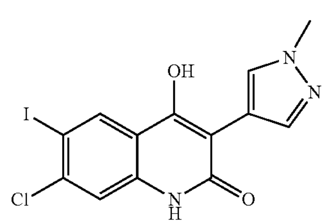 [SMILES: Cn1cc(-c2c(O)c3cc(I)c(Cl)cc3[nH]c2=O)cn1] | methyl 4-chloro-5-iodo-2-(2-(1-methyl-1H-pyrazol-4-yl)acetamido)benzoate (Intermediate 77) | LCMS: $(M + H)^+$ = 402; Rt = 2.03 min. |

TABLE 13-continued

| Intermediate | Structure | From | Physical data |
|---|---|---|---|
| 110<br>7-Chloro-4-hydroxy-6-iodo-3-(phenylsulfonyl)quinolin-2(1H)-one | 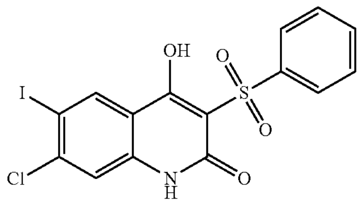 [SMILES: O=c1[nH]c2cc(Cl)c(I)cc2c(O)c1S(=O)(=O)c1ccccc1] | methyl 4-chloro-5-iodo-2-(2-(phenylsulfonyl)acetamido) benzoate (Intermediate 92) | LCMS: $(M + H)^+$ = 462; Rt = 2.25 min. |

Intermediate 111: 7-Chloro-4-hydroxy-6-iodo-3-(o-tolyloxy)quinolin-2(1H)-one

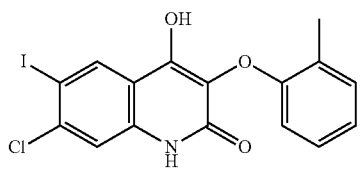 [SMILES: Cc1ccccc1Oc1c(O)c2cc(I)c(Cl)cc2[nH]c1=O]

Methyl 2-amino-4-chloro-5-iodobenzoate (Intermediate 2) (1 g, 3.21 mmol) and ethyl 2-(o-tolyloxy)acetate (Aldrich, 0.655 g, 3.37 mmol) were dissolved in THF (10 mL) and KHMDS 1M/THF (9.63 mL, 9.63 mmol) was added in one portion at room temperature under $N_2$. The reaction mixture was stirred at room temperature for 1 h before quenched with MeOH and concentrated under reduced pressure. The residue was dissolved in 1N NaOH then extracted with $Et_2O$. The aqueous extracts were acidified with 1N HCl and the resulting precipitate was collected by filtration then washed successively with water and diethyl ether to give 7-chloro-4-hydroxy-6-iodo-3-(o-tolyloxy)quinolin-2(1H)-one (1.03 g, 2.409 mmol, 75% yield) as white solid. LCMS: $(M+H)^+$ = 428; Rt=2.46 min.

Intermediates 112 to 141 were prepared by methods analogous to that described for Intermediate 111. For Intermediate 123, acetic acid was used instead of 1N HCl. Intermediate 137 was isolated as potassium salt.

TABLE 14

| Intermediate | Structure | From | Physical data |
|---|---|---|---|
| 112<br>7-Chloro-4-hydroxy-6-iodo-3-(1H-pyrazol-1-yl)quinolin-2(1H)-one | 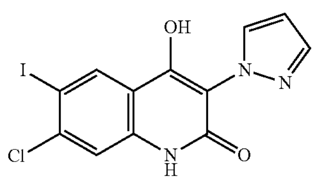 [SMILES: O=c1[nH]c2cc(Cl)c(I)cc2c(O)c1-n1cccn1] | methyl 2-amino-4-chloro-5-iodobenzoate (Intermediate 2) and ethyl 2-(1H-pyrazol-1-yl)acetate (Apollo Scientific Ltd.) | LCMS: $(M + H)^+$ = 388; Rt = 1.97 min. |
| 113<br>7-Chloro-4-hydroxy-6-iodo-3-(4-methoxyphenoxy)quinolin-2(1H)-one | 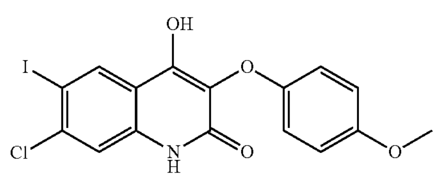 [SMILES: COc1ccc(Oc2c(O)c3cc(I)c(Cl)cc3[nH]c2=O)cc1] | methyl 2-amino-4-chloro-5-iodobenzoate (Intermediate 2) and ethyl 2-(4-methoxyphenoxy)acetate (UkrOrgSynthesis Ltd) | LCMS: $(M + H)^+$ = 444; Rt = 2.32 min. |
| 114<br>7-Chloro-3-(3-fluorophenoxy)-4-hydroxy-6-iodoquinolin-2(1H)-one | 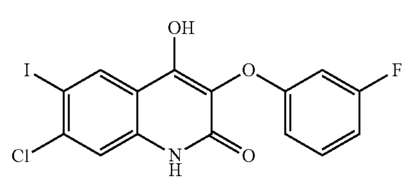 [SMILES: O=c1[nH]c2cc(Cl)c(I)cc2c(O)c1Oc1cccc(F)c1] | methyl 2-amino-4-chloro-5-iodobenzoate (Intermediate 2) and ethyl 2-(3-fluorophenoxy)acetate (Intermediate 8) | LCMS: $(M + H)^+$ = 432; Rt = 2.31 min. |
| 115<br>7-Chloro-4-hydroxy-6-iodo-3-(3-methoxyphenoxy)quinolin-2(1H)-one | 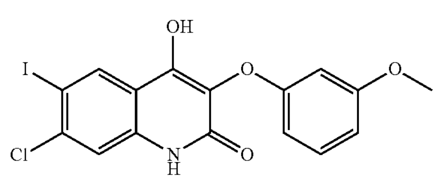 [SMILES: COc1cccc(Oc2c(O)c3cc(I)c(Cl)cc3[nH]c2=O)c1] | methyl 2-amino-4-chloro-5-iodobenzoate (Intermediate 2) and ethyl 2-(3-methoxyphenoxy)acetate (Intermediate 9) | LCMS: $(M + H)^+$ = 444; Rt = 2.32 min. |

TABLE 14-continued

| Intermediate | Structure | From | Physical data |
|---|---|---|---|
| 116<br>7-Chloro-3-(3,5-dimethyl-1H-pyrazol-1-yl)-4-hydroxy-6-iodoquinolin-2(1H)-one | | methyl 2-amino-4-chloro-5-iodobenzoate (Intermediate 2) and ethyl 2-(3,5-dimethyl-1H-pyrazol-1-yl)acetate (Intermediate 7) | LCMS: (M + H)⁺ = 416; Rt = 1.98 min. |
| 117<br>7-Chloro-4-hydroxy-6-iodo-3-(p-tolyloxy)quinolin-2(1H)-one | | methyl 2-amino-4-chloro-5-iodobenzoate (Intermediate 2) and ethyl 2-(p-tolyloxy) acetate (Intermediate 10) | LCMS: (M + H)⁺ = 428; Rt = 2.47 min. |
| 118<br>7-Chloro-4-hydroxy-6-iodo-3-(pyridin-2-yloxy)quinolin-2(1H)-one | | methyl 2-amino-4-chloro-5-iodobenzoate (Intermediate 2) and ethyl 2-(pyridin-2-yloxy)acetate (Intermediate 11) | LCMS: (M + H)⁺ = 415; Rt = 1.86 min. |
| 119<br>7-Chloro-4-hydroxy-6-iodo-3-(2-methoxyphenoxy)quinolin-2(1H)-one | | methyl 2-amino-4-chloro-5-iodobenzoate (Intermediate 2) and ethyl 2-(2-methoxyphenoxy)acetate (Intermediate 12) | LCMS: (M + H)⁺ = 444; Rt = 2.34 min. |
| 120<br>7-Chloro-4-hydroxy-6-iodo-3-(1H-1,2,3-triazol-1-yl)quinolin-2(1H)-one | | methyl 2-amino-4-chloro-5-iodobenzoate (Intermediate 2) and ethyl 2-(1H-1,2,3-triazol-1-yl) acetate (Aldrich) | LCMS: (M + H)⁺ = 389; Rt = 1.93 min. |
| 121<br>7-Chloro-4-hydroxy-6-iodo-3-(4-methyl-1H-pyrazol-1-yl)quinolin-2(1H)-one | | methyl 2-amino-4-chloro-5-iodobenzoate (Intermediate 2) and ethyl 2-(4-methyl-1H-pyrazol-1-yl)acetate (Intermediate 16) | LCMS: (M + H)⁺ = 402; Rt = 2.21 min. |
| 122<br>7-Chloro-4-hydroxy-6-iodo-3-(m-tolyloxy)quinolin-2(1H)-one | | methyl 2-amino-4-chloro-5-iodobenzoate (Intermediate 2) and ethyl 2-(m-tolyloxy)acetate (Intermediate 13) | LCMS: (M + H)⁺ = 428; Rt = 2.44 min. |
| 123<br>3-((7-Chloro-4-hydroxy-6-iodo-2-oxo-1,2-dihydroquinolin-3-yl)oxy)benzoic acid | | methyl 2-amino-4-chloro-5-iodobenzoate (Intermediate 2) and tert-butyl 3-(2-ethoxy-2-oxoethoxy)benzoate (Intermediate 17) | LCMS: (M + H)⁺ = 458; Rt = 1.89 min. |

TABLE 14-continued

| Intermediate | Structure | From | Physical data |
|---|---|---|---|
| 124<br>1-(7-Chloro-4-hydroxy-6-iodo-2-oxo-1,2-dihydroquinolin-3-yl)-1H-pyrazole-4-carboxylic acid | 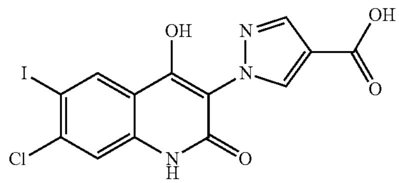 [SMILES: O=C(O)c1cnn(-c2c(O)c3cc(I)c(Cl)cc3[nH]c2=O)c1] | methyl 2-amino-4-chloro-5-iodobenzoate (Intermediate 2) and ethyl 1-(2-ethoxy-2-oxoethyl)-1H-pyrazole-4-carboxylate (Intermediate 18) | LCMS: $(M + H)^+$ = 432; Rt = 1.66 min. |
| 125<br>7-Chloro-3-(4-fluorophenoxy)-4-hydroxy-6-iodoquinolin-2(1H)-one | 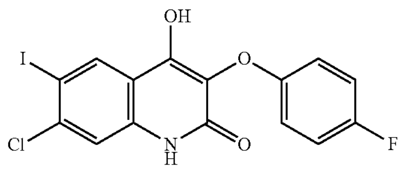 [SMILES: O=c1[nH]c2cc(Cl)c(I)cc2c(O)c1Oc1ccc(F)cc1] | methyl 2-amino-4-chloro-5-iodobenzoate (Intermediate 2) and ethyl 2-(4-fluorophenoxy) acetate (Intermediate 14) | LCMS: $(M + H)^+$ = 432; Rt = 2.32 min. |
| 126<br>7-Chloro-4-hydroxy-6-iodo-3-((4-methylpyridin-2-yl)oxy)quinolin-2(1H)-one | 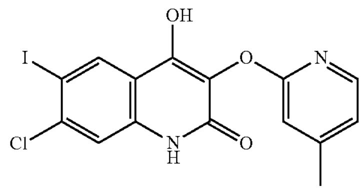 [SMILES: Cc1ccnc(Oc2c(O)c3cc(I)c(Cl)cc3[nH]c2=O)c1] | methyl 2-amino-4-chloro-5-iodobenzoate (Intermediate 2) and ethyl 2-((4-methylpyridin-2-yl)oxy)acetate (Intermediate 15) | LCMS: $(M + H)^+$ = 429; Rt = 1.88 min. |
| 127<br>7-Chloro-4-hydroxy-6-iodo-3-(5-methyl-1H-pyrazol-1-yl)quinolin-2(1H)-one | 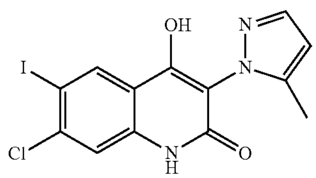 [SMILES: Cc1ccnn1-c1c(O)c2cc(I)c(Cl)cc2[nH]c1=O] | methyl 2-amino-4-chloro-5-iodobenzoate (Intermediate 2) and ethyl 2-(5-methyl-1 H-pyrazol-1-yl)acetate (Zelinsky Institute Inc.) | LCMS: $(M + H)^+$ = 402; Rt = 1.98 min. |
| 128<br>7-Chloro-3-(3-fluorophenyl)-4-hydroxy-6-iodoquinolin-2(1H)-one | 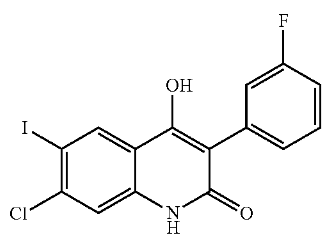 [SMILES: O=c1[nH]c2cc(Cl)c(I)cc2c(O)c1-c1cccc(F)c1] | methyl 2-amino-4-chloro-5-iodobenzoate (Intermediate 2) and methyl 3-fluoro-phenyl acetate (Acros organics) | LCMS: $(M + H)^+$ = 416; Rt = 1.02 min. |
| 129<br>7-Chloro-3-(4-fluorophenyl1H-hydroxy-6-iodoquinolin-2(1H)-one | | methyl 2-amino-4-chloro-5-iodobenzoate (Intermediate 2) and methyl 4-fluorophenyl acetate (Acros organics) | LCMS: $(M + H)^+$ = 416; Rt = 1.02 min. |
| 130<br>7-Chloro-4-hydroxy-6-iodo-3-(4-methoxyphenyl) quinolin-2(1H)-one | 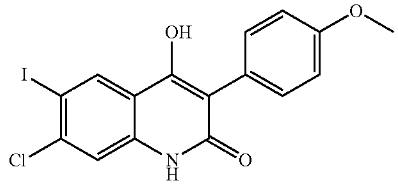 [SMILES: COc1ccc(-c2c(O)c3cc(I)c(Cl)cc3[nH]c2=O)cc1] | methyl 2-amino-4-chloro-5-iodobenzoate (Intermediate 2) and methyl 4-methoxyphenyl acetate (Aldrich) | LCMS: $(M + H)^+$ = 428; Rt = 1.03 min. |
| 131<br>7-Chloro-4-hydroxy-6-iodo-3-(p-tolyl)quinolin-2(1H)-one | 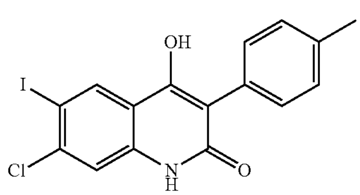 [SMILES: Cc1ccc(-c2c(O)c3cc(I)c(Cl)cc3[nH]c2=O)cc1] | methyl 2-amino-4-chloro-5-iodobenzoate (Intermediate 2) and methyl 4-methylphenyl acetate (Aldrich) | LCMS: $(M + H)^+$ = 412; Rt = 1.07 min. |

TABLE 14-continued

| Intermediate | Structure | From | Physical data |
|---|---|---|---|
| 132<br>7-Chloro-4-hydroxy-6-iodo-3-(2-methoxyphenyl)quinolin-2(1H)-one | 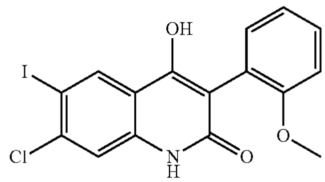 [SMILES: COc1ccccc1-c1c(O)c2cc(I)c(Cl)cc2[nH]c1=O] | methyl 2-amino-4-chloro-5-iodobenzoate (Intermediate 2) and methyl 2-methoxy phenylacetate (ABCR) | LCMS: $(M + H)^+ =$ 428; Rt = 0.97 min. |
| 133<br>7-Chloro-3-(2-fluorophenyl)-4-hydroxy-6-iodoquinolin-2(1H)-one | 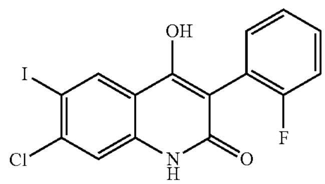 [SMILES: O=c1[nH]c2cc(Cl)c(I)cc2c(O)c1-c1ccccc1F] | methyl 2-amino-4-chloro-5-iodobenzoate (Intermediate 2) and methyl 2-fluorophenyl acetate (ABCR) | LCMS: $(M + H)^+ =$ 416; Rt = 0.95 min. |
| 134<br>7-Chloro-4-hydroxy-6-iodo-3-(o-tolyl)quinolin-2(1H)-one | 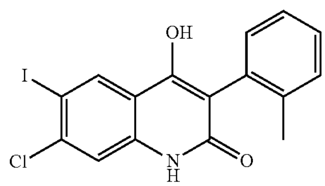 [SMILES: Cc1ccccc1-c1c(O)c2cc(I)c(Cl)cc2[nH]c1=O] | methyl 2-amino-4-chloro-5-iodobenzoate (Intermediate 2) and methyl 2-methylphenyl acetate (Aldrich) | LCMS: $(M + H)^+ =$ 412; Rt = 1.05 min. |
| 135<br>7-Chloro-3-(4-chlorophenyl)-4-hydroxy-3-iodoquinolin-2(1H)-one | 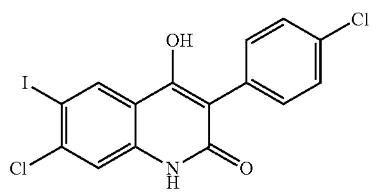 [SMILES: O=c1[nH]c2cc(Cl)c(I)cc2c(O)c1-c1ccc(Cl)cc1] | methyl 2-amino-4-chloro-5-iodobenzoate (Intermediate 2) and methyl 4-chlorophenyl acetate (Acros organics) | LCMS: $(M + H)^+ =$ 432; Rt = 1.08 min. |
| 136<br>7-Chloro-3-(3-chlorophenyl)-4-hydroxy-6-iodoquinolin-2(1H)-one | 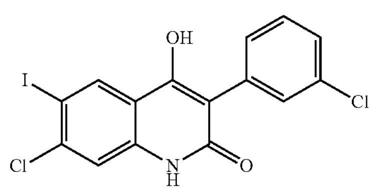 [SMILES: O=c1[nH]c2cc(Cl)c(I)cc2c(O)c1-c1cccc(Cl)c1] | methyl 2-amino-4-chloro-5-iodobenzoate (Intermediate 2) and methyl 3-chlorophenyl acetate (Acros organics) | LCMS: $(M + H)^+ =$ 432; Rt = 1.06 min. |
| 137<br>7-Chloro-3-(2-chlorophenyl)-6-iodo-2-oxo-1,2-dihydro quinolin-4-olate, potassium salt | 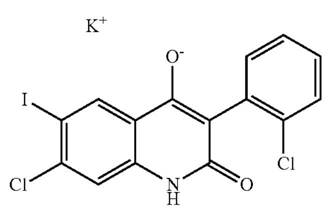 [SMILES: [K+] ; O=c1[nH]c2cc(Cl)c(I)cc2c([O-])c1-c1ccccc1Cl] | methyl 2-amino-4-chloro-5-iodobenzoate (Intermediate 2) and methyl 2-chlorophenyl acetate (Acros organics) | LCMS: $(M - H)^+ =$ 430; Rt = 1.02 min. |
| 138<br>7-Chloro-4-hydroxy-6-iodo-3-(4-methoxy-1H-pyrazol-1-yl)quinolin-2(1H)-one | 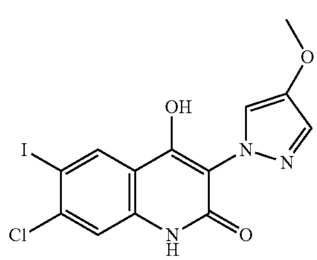 [SMILES: COc1cnn(-c2c(O)c3cc(I)c(Cl)cc3[nH]c2=O)c1] | methyl 2-amino-4-chloro-5-iodobenzoate (Intermediate 2) and ethyl 2-(4-methoxy-1H-pyrazol-1-yl)acetate (Intermediate 23) | LCMS: $(M - H)^+ =$ 416; Rt = 1.27 min. |

TABLE 14-continued

| Intermediate | Structure | From | Physical data |
|---|---|---|---|
| 139<br>7-Chloro-4-hydroxy-6-iodo-3-((5-methylpyridin-2-yl)oxy)quinolin-2(1H)-one | 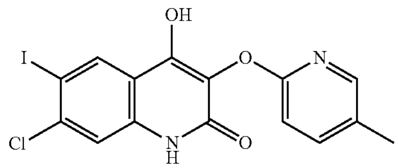 [SMILES: Cc1ccc(Oc2c(O)c3cc(I)c(Cl)cc3[nH]c2=O)nc1] | methyl 2-amino-4-chloro-5-iodobenzoate (Intermediate 2) and ethyl 2-((5-methylpyridin-2-yl)oxy)acetate (Intermediate 20) | LCMS: (M + H)⁺ = 429; Rt = 1.94 min. |
| 140<br>7-Chloro-4-hydroxy-6-iodo-3-(phenylthio)quinolin-2(1H)-one | 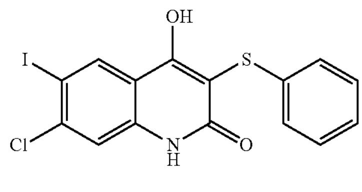 [SMILES: O=c1[nH]c2cc(Cl)c(I)cc2c(O)c1Sc1ccccc1] | methyl 2-amino-4-chloro-5-iodobenzoate (Intermediate 2) and ethyl 2-(phenylthio)acetate (Alfa-Aesar) | LCMS: (M + H)⁺ = 430; Rt = 0.72 min. |
| 141<br>7-Chloro-4-hydroxy-6-iodo-3-(m-tolyl)quinolin-2(1H)-one | 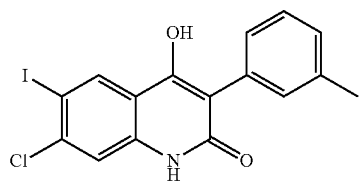 [SMILES: Cc1cccc(-c2c(O)c3cc(I)c(Cl)cc3[nH]c2=O)c1] | methyl 2-amino-4-chloro-5-iodobenzoate (Intermediate 2) and methyl 3-methylphenyl acetate (Acros organics) | LCMS: (M + H)⁺ = 412; Rt = 1.08 min. |

Intermediate 142:
7-Chloro-4-hydroxy-6-iodo-2(1H)-quinolinone

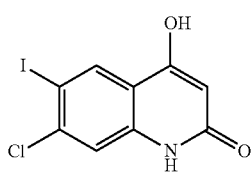 [SMILES: O=c1cc(O)c2cc(I)c(Cl)cc2[nH]1]

To a suspension of ethyl 7-chloro-4-hydroxy-6-iodo-2-oxo-1,2-dihydro-3-quinolinecarboxylate (Intermediate 100) (2 g, 5.08 mmol) in 1,4-dioxane (10 mL) was added concentrated hydrochloric acid (3 mL, 36.5 mmol) and the reaction mixture was stirred 72 h at 80° C. After cooling, the reaction mixture was evaporated and the resulting solid was filtered, washed with water and dried to give the title compound 7-chloro-4-hydroxy-6-iodo-2(1H)-quinolinone (700 mg, 2.177 mmol, 42.8% yield) as cream solid. LCMS: (M+H)⁺= 322; Rt=2.26 min.

Intermediate 143: 7-Chloro-4-hydroxy-6-iodo-3-nitro-2(1H)-quinolinone

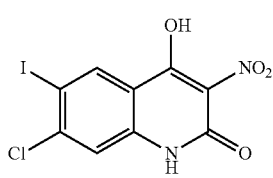 [SMILES: O=c1[nH]c2cc(Cl)c(I)cc2c(O)c1[N+](=O)[O-]]

7-Chloro-4-hydroxy-6-iodo-2(1H)-quinolinone (Intermediate 142) (300 mg, 0.933 mmol) was dissolved in nitric acid (1 mL, 22.38 mmol) and the reaction mixture was stirred 15 min at room temperature and heated 30 min at 75° C. After cooling, the reaction mixture was poured into ice water and the precipitate was filtered and dried to give the title compound 7-chloro-4-hydroxy-6-iodo-3-nitro-2(1H)-quinolinone (280 mg, 0.764 mmol, 82% yield) as yellow solid. LCMS: (M+H)⁺=367; Rt=2.06 min.

Intermediate 144: N-(4-(4-(7-Chloro-4-hydroxy-3-(3-methylisoxazol-5-yl)-2-oxo-1,2-dihydro quinolin-6-yl)phenyl)thiazol-2-yl)acetamide

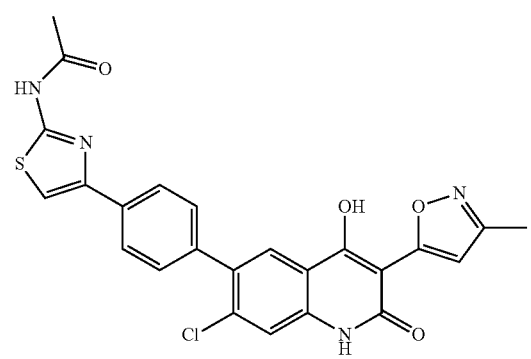 [SMILES: CC(=O)Nc1nc(-c2ccc(-c3cc4c(O)c(-c5cc(C)no5)c(=O)[nH]c4cc3Cl)cc2)cs1]

To a solution of 7-chloro-4-hydroxy-6-iodo-3-(3-methylisoxazol-5-yl)quinolin-2(1H)-one (Intermediate 99) (125 mg, 0.311 mmol) in 1,4-dioxane (4 mL) and water (2 mL) were added N-(4-(4-(4,4,5,5-tetramethyl-1,3,2-dioxaborolan-2-yl)phenyl)thiazol-2-yl)acetamide (Intermediate 31) (118 mg, 0.342 mmol), cesium carbonate (152 mg, 0.466 mmol) and tetrakis(triphenylphosphine)palladium (3.59 mg, 3.11 µmol). The reaction mixture was heated at 80° C. for 16 h. After cooling the reaction mixture was filtered, evaporated to dryness. The resulting residue was acidified with HCl 1N. The precipitate was filtered and dried to give the title compound N-(4-(4-(7-chloro-4-hydroxy-3-(3-methylisoxazol-5-yl)-2-oxo-1,2-dihydro quinolin-6-yl)phenyl)thiazol-2-yl)acetamide (130 mg, 0.264 mmol, 85% yield) as a grey solid. LCMS: (M+H)⁺=493; Rt=2.37 min.

Intermediate 145 was prepared by methods analogous to that described for Intermediate 144. For Intermediate 145, sodium carbonate was used instead of cesium carbonate as base.

TABLE 15

| Intermediate | Formula | From | Physical data |
|---|---|---|---|
| 145<br>N-(4-(4-(7-Chloro-4-hydroxy-2-oxo-3-(pyridin-3-yl)-1,2-dihydroquinolin-6-yl)phenyl)thiazol-2-yl)acetamide | 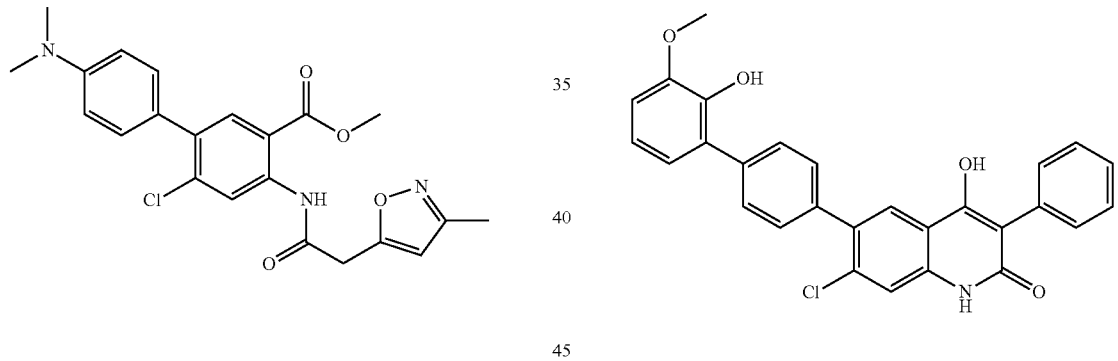 | 7-chloro-4-hydroxy-6-iodo-3-(pyridin-3-yl)quinolin-2(1H)-one (Intermediate 106) and N-(4-(4-(4,4,5,5-tetramethyl-1,3,2-dioxaborolan-2-yl)phenyl) thiazol-2-yl) acetamide Intermediate 31) | LCMS: $(M + H)^+$ = 489; Rt = 2.28 min. |

Intermediate 146: Methyl 6-chloro-4'-(dimethylamino)-4-(2-(3-methylisoxazol-5-yl)acetamido)-[1,1'-biphenyl]-3-carboxylate To a solution of methyl 4-amino-6-chloro-4'-(dimethylamino)-[1,1'-biphenyl]-3-carboxylate (Intermediate 47) (10.8 g, 35.4 mmol) in dichloromethane (525 mL) was added 2-(3-methylisoxazol-5-yl)acetic acid (Aldrich, 5 g, 35.4 mmol), HATU (17.52 g, 46.1 mmol) and triethylamine (11.85 mL, 85 mmol) and the reaction mixture was stirred at room temperature for 72 h. The mixture was washed with water. The organic layer was dried over anhydrous sodium sulfate, filtered and concentrated in vacuo. The residue was triturated with hot methanol, filtered and dried to give the title compound methyl 6-chloro-4'-(dimethylamino)-4-(2-(3-methylisoxazol-5-yl)acetamido)-[1,1'-biphenyl]-3-carboxylate (13.91 g, 32.5 mmol, 92% yield) as a beige solid. LCMS: $(M+H)^+$=428; Rt=3.86 min.

Example 1

7-chloro-4-hydroxy-6-(2'-hydroxy-3'-methoxy-[1,1'-biphenyl]-4-yl)-3-phenyl quinolin-2(1H)-one To a solution of methyl 6-chloro-2"-hydroxy-3"-methoxy-4-(2-phenylacetamido)-[1,1':4',1"-terphenyl]-3-carboxylate (Intermediate 58) (340 mg, 0.677 mmol) in tetrahydrofuran (100 mL) at 60° C. was added dropwise KHMDS 0.5M/THF (5.42 mL, 2.71 mmol). The reaction mixture was stirred for 2 h after the end of addition. After cooling, the reaction mixture was acidified with 1N HCl and extracted with dichloromethane. The organic layer was washed with brine then dried over anhydrous sodium sulfate, filtered and concentrated in vacuo. The residue was taken up in acetonitrile, filtered and was washed with acetonitrile and diisopropylether to give the title compound 7-chloro-4-hydroxy-6-[2'-hydroxy-3'-(methyloxy)-4-biphenylyl]-3-phenyl-2(1H)-quinolinone (175 mg, 0.372 mmol, 55% yield) as a light brown powder. LCMS: $(M+H)^+$=470; Rt=2.99 min. HRMS: calculated for $C_{28}H_{19}ClNO_4$ $(M-H)^+$: 468.1003. found: 468.0962.

Examples 2 to 19 were prepared by methods analogous to that described for Example 1.

TABLE 16

| Example | Structure | From | Physical data |
|---|---|---|---|
| 2<br>3-{7-Chloro-4-hydroxy-6-[2'-hydroxy-3'-(methyloxy)-4-biphenylyl]-2-oxo-1,2-dihydro-3-quinolinyl}benzoic acid | 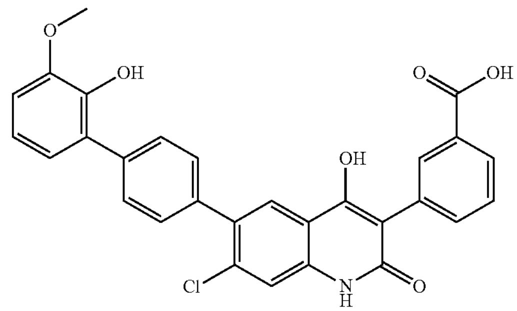 [SMILES: COc1cccc(-c2ccc(-c3cc4c(O)c(-c5cccc(C(=O)O)c5)c(=O)[nH]c4cc3Cl)cc2)c1O] | methyl 6-chloro-2''-hydroxy-3''-(methyloxy)-4-[({3-[(methyloxy)carbonyl]phenyl}acetyl)amino]-1,1':4',1''-terphenyl-3-carboxylate<br>(Intermediate 94) | LCMS: $(M + H)^+$ = 514; Rt = 2.63 min. HRMS: calculated for $C_{29}H_{19}ClNO_6$ $(M - H)^+$: 512.0901; found: 512.0848. |
| 3<br>7-chloro-4-hydroxy-3-(3-methoxyphenyl)-6-(4-morpholinophenyl)quinolin-2(1H)-one | 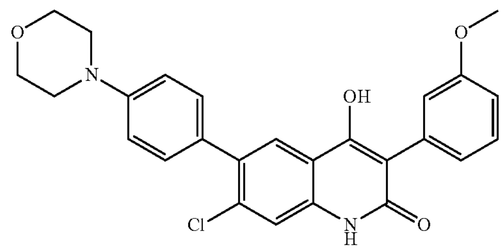 [SMILES: COc1cccc(-c2c(O)c3cc(-c4ccc(N5CCOCC5)cc4)c(Cl)cc3[nH]c2=O)c1] | methyl 6-chloro-4-({[3-(methyloxy)phenyl]acetyl}amino)-4'-(4-morpholinyl)-3-biphenylcarboxylate<br>(Intermediate 67) | LCMS: $(M + H)^+$ = 463; Rt = 2.65 min. HRMS: calculated for $C_{26}H_{24}ClN_2O_4$ $(M + H)^+$: 463.1425; found: 463.1442. |
| 4<br>7-Chloro-4-hydroxy-6-[4-(4-morpholinyl)phenyl]-3-phenylquinolin-2(1H)-one | 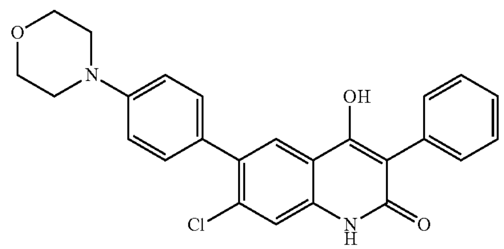 [SMILES: O=c1[nH]c2cc(Cl)c(-c3ccc(N4CCOCC4)cc3)cc2c(O)c1-c1ccccc1] | methyl 6-chloro-4'-(4-morpholinyl)-4-[(phenylacetyl)amino]-3-biphenylcarboxylate<br>(Intermediate 61) | LCMS: $(M + H)^+$ = 433; Rt = 2.62 min. HRMS: calculated for $C_{25}H_{22}ClN_2O_3$ $(M + H)^+$: 433.1319; found: 433.1312. |
| 5<br>4-{7-Chloro-4-hydroxy-3-[3-(methyloxy)phenyl]-2-oxo-1,2-dihydro-6-quinolinyl}-N-cyclopentylbenzamide | 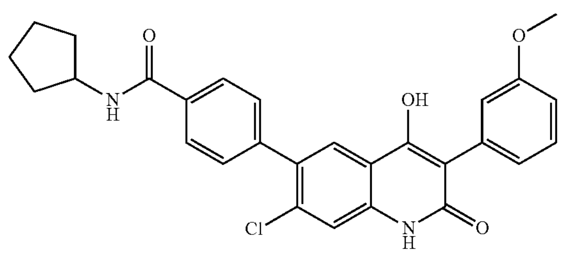 [SMILES: COc1cccc(-c2c(O)c3cc(-c4ccc(C(=O)NC5CCCC5)cc4)c(Cl)cc3[nH]c2=O)c1] | ethyl 6-fluoro-4-(2-(3-methoxyphenyl)acetamido)-4'-morpholino-[1,1'-biphenyl]-3-carboxylate<br>(Intermediate 68) | LCMS: $(M + H)^+$ = 489; Rt = 2.68 min. HRMS: calculated for $C_{28}H_{26}ClN_2O_4$ $(M + H)^+$: 489.1581; found: 489.1568. |
| 6<br>7-Fluoro-4-hydroxy-3-(3-methoxyphenyl)-6-(4-morpholinophenyl)quinolin-2(1H)-one | 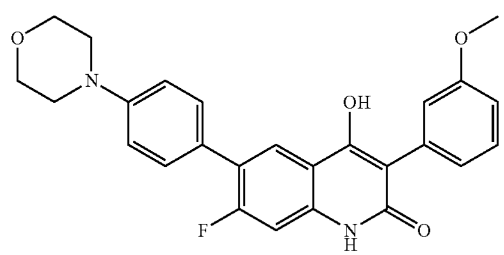 [SMILES: COc1cccc(-c2c(O)c3cc(-c4ccc(N5CCOCC5)cc4)c(F)cc3[nH]c2=O)c1] | methyl 6-fluoro-4-({[3-(methyloxy)phenyl]acetyl}amino)-4'-(4-morpholinyl)-3-biphenylcarboxylate<br>(Intermediate 71) | LCMS: $(M + H)^+$ = 447; Rt = 2.53 min. HRMS: calculated for $C_{26}H_{24}FN_2O_4$ $(M + H)^+$: 447.1720; found: 447.1714. |
| 7<br>3-[7-Chloro-4-hydroxy-6-(1-methyl-1H-indol-5-yl)-2-oxo-1,2-dihydro-3-quinolinyl]benzoic acid | 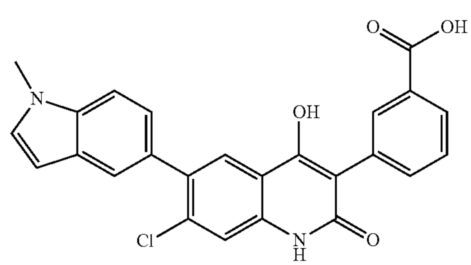 [SMILES: Cn1ccc2cc(-c3cc4c(O)c(-c5cccc(C(=O)O)c5)c(=O)[nH]c4cc3Cl)ccc21] | methyl 4-chloro-5-(1-methyl-1H-indol-5-yl)-2-[({3-[(methyloxy)carbonyl]phenyl}acetyl)amino]benzoate<br>(Intermediate 66) | LCMS: $(M + H)^+$ = 445; Rt = 2.31 min. HRMS: calculated for $C_{25}H_{18}ClN_2O_4$ $(M + H)^+$: 445.0955; found: 445.0980. |

TABLE 16-continued

| Example | Structure | From | Physical data |
|---|---|---|---|
| 8<br>7-Chloro-4-hydroxy-6-(1-methyl-1H-indol-5-yl)-3-[3-(methyloxy)phenyl]quinolin-2(1H)-one | 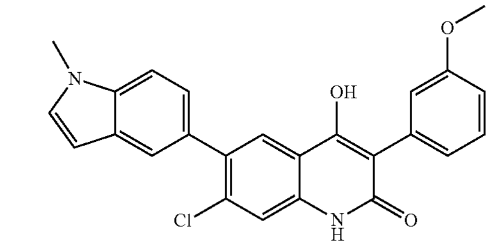 [SMILES: COc1cccc(-c2c(O)c3cc(-c4ccc5c(ccn5C)c4)c(Cl)cc3[nH]c2=O)c1] | methyl 4-chloro-5-(1-methyl-1H-indol-5-yl)-2-({[3-(methyloxy)phenyl]acetyl}amino)benzoate (Intermediate 57) | LCMS:<br>$(M + H)^+ =$ 431; Rt = 2.83 min.<br>HRMS: calculated for $C_{25}H_{20}ClN_2O_3$ $(M + H)^+$: 431.1162; found: 431.1171. |
| 9<br>N-{4-[4-(7-Chloro-4-hydroxy-2-oxo-3-phenyl-1,2-dihydro-6-quinolinyl)phenyl]-1,3-thiazol-2-yl}acetamide | 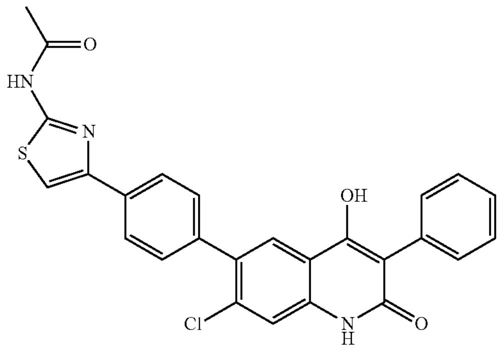 [SMILES: CC(=O)Nc1nc(-c2ccc(-c3cc4c(O)c(-c5ccccc5)c(=O)[nH]c4cc3Cl)cc2)cs1] | methyl 4'-[2-(acetylamino)-1,3-thiazol-4-yl]-6-chloro-4-[(phenylacetyl)amino]-3-biphenylcarboxylate (Intermediate 59) | LCMS:<br>$(M + H)^+ =$ 488; Rt = 2.63 min.<br>HRMS: calculated for $C_{26}H_{19}ClN_3O_3S$ $(M + H)^+$: 488.0836; found: 488.0834. |
| 10<br>7-Chloro-4-hydroxy-6-(1-methyl-1H-indol-5-yl)-3-phenylquinolin-2(1H)-one | 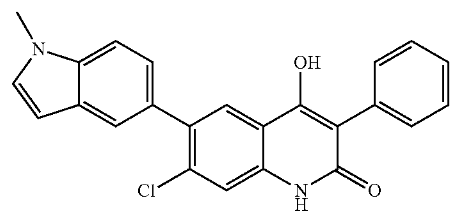 [SMILES: Cn1ccc2cc(-c3cc4c(O)c(-c5ccccc5)c(=O)[nH]c4cc3Cl)ccc21] | methyl 4-chloro-5-(1-methyl-1H-indol-5-yl)-2-[(phenylacetyl)amino]benzoate (Intermediate 60) | LCMS:<br>$(M + H)^+ =$ 401; Rt = 2.92 min.<br>HRMS: calculated for $C_{24}H_{18}ClN_2O_2$ $(M + H)^+$: 401.1057; found: 401.1056 |
| 11<br>7-Chloro-4-hydroxy-3-(3-methylisoxazol-5-yl)-6-(4-(piperidin-1-yl)phenyl)quinolin-2(1H)-one | 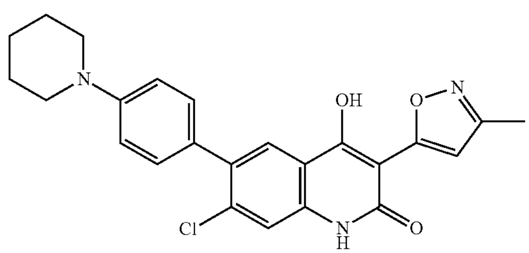 [SMILES: Cc1cc(-c2c(O)c3cc(-c4ccc(N5CCCCC5)cc4)c(Cl)cc3[nH]c2=O)on1] | methyl 6-chloro-4-(2-(3-methylisoxazol-5-yl)acetamido)-4'-(piperidin-1-yl)-[1,1'-biphenyl]-3-carboxylate (Intermediate 78) | LCMS:<br>$(M + H)^+ =$ 436; Rt = 2.69 min.<br>HRMS: calculated for $C_{24}H_{23}ClN_3O_3$ $(M + H)^+$: 436.1428; found: 436.1442. |
| 12<br>7-Chloro-6-(4-(dimethylamino)phenyl)-4-hydroxyquinolin-2(1H)-one | 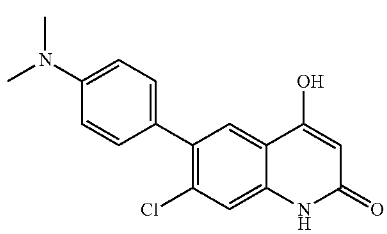 [SMILES: CN(C)c1ccc(-c2cc3c(O)cc(=O)[nH]c3cc2Cl)cc1] | methyl 4-acetamido-6-chloro-4'-(dimethylamino)-[1,1'-biphenyl]-3-carboxylate (Intermediate 56) | LCMS:<br>$(M + H)^+ =$ 315; Rt = 2.54 min.<br>HRMS: calculated for $C_{17}H_{16}ClN_2O_2$ $(M + H)^+$: 315.0900; found: 315.0909. |
| 13<br>7-Chloro-4-hydroxy-3-(1-methy-1H-pyrazol-4-yl)-6-(4-(piperidin-1-yl)phenyl)quinolin-2(1H)-one | 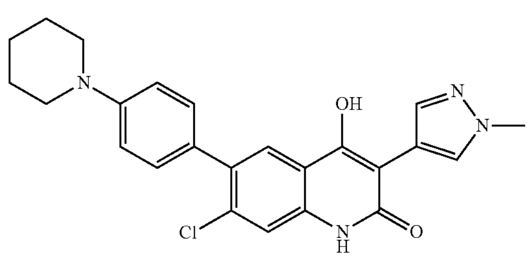 [SMILES: Cn1cc(-c2c(O)c3cc(-c4ccc(N5CCCCC5)cc4)c(Cl)cc3[nH]c2=O)cn1] | methyl 6-chloro-4-((2-(1-methyl-1H-pyrazol-4-yl)-2-oxoethyl)amino)-4'-(piperidin-1-yl)-[1,1'-biphenyl]-3-carboxylate (Intemediate 79) | LCMS:<br>$(M + H)^+ =$ 435; Rt = 2.70 min.<br>HRMS: calculated for $C_{24}H_{24}ClN_4O_2$ $(M + H)^+$: 435.1588; found: 435.1607. |

TABLE 16-continued

| Example | Structure | From | Physical data |
|---|---|---|---|
| 14<br>7-Chloro-6-(4'-fluoro-[1,1'-biphenyl]-4-yl)-4-hydroxy-3-(3-methylisoxazol-5-yl) quinolin-2(1H)-one | 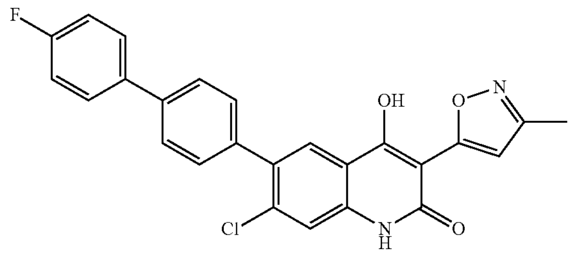 [SMILES: Cc1cc(-c2c(O)c3cc(-c4ccc(-c5ccc(F)cc5)cc4)c(Cl)cc3[nH]c2=O)on1] | methyl 6-chloro-4''-fluoro-4-((2-(3-methylisoxazol-5-yl)-2-oxoethyl)amino)-[1,1':4',1''-terphenyl]-3-carboxylate (Intemediate 80) | LCMS: $(M + H)^+$ = 447; Rt = 2.86 min.<br>HRMS calculated for $C_{25}H_{17}ClFN_2O_3$ $(M + H)^+$: 447.0912; found: 447.0909. |
| 15<br>7-Chloro-4-hydroxy-6-(3'-methoxy-[1,1'-biphenyl]-4-yl)-3-(3-methylisoxazol-5-yl) quinolin-2(1H)-one | 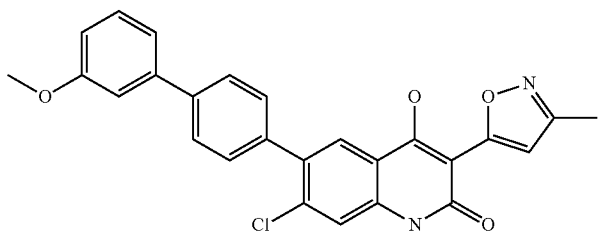 | methyl 4-chloro-5-[4-(3-methoxyphenyl)phenyl]-2-[2-(3-methyl-1,2-oxazol-5-yl)acetamido]benzoate (Intermediate 89) | LCMS: $(M + H)^+$ = 459; Rt = 2.69 min.<br>HRMS calculated for $C_{26}H_{20}ClN_2O_4$ $(M + H)^+$: 459.1111; found: 459.1085. |
| 16<br>7-Chloro-4-hydroxy-3-(3-methylisoxazol-5-yl)-6-(4-(5-methylthiophen-2-yl)phenyl)quinolin-2(1H)-one | 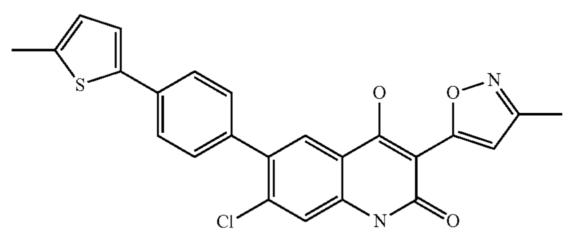 | methyl 6-chloro-4-(2-(3-methylisoxazol-5-yl)acetamido)-4'-(5-methylthiophen-2-yl)-[1,1'-biphenyl]-3-carboxylate (Intermediate 96) | LCMS: $(M + H)^+$ = 449; Rt = 2.87 min.<br>HRMS calculated for $C_{24}H_{18}ClN_2O_3S$ $(M + H)^+$: 449.0727; found: 449.0693. |
| 17<br>7-Chloro-4-hydroxy-6-(4'-methoxy-[1,1'-biphenyl]-4-yl)-3-(3-methylisoxazol-5-yl) quinolin-2(1H)-one | 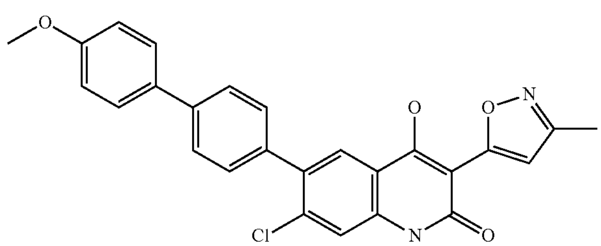 | methyl 6-chloro-4''-methoxy-4-(2-(3-methylisoxazol-5-yl)acetamido)-[1,1':4',1''-terphenyl]-3-carboxylate (Intermediate 95) | LCMS: $(M + H)^+$ = 459; Rt = 2.73 min.<br>HRMS calculated for $C_{26}H_{20}ClN_2O_4$ $(M + H)^+$: 459.1111; found: 459.1145. |
| 18<br>7-Chloro-6-(2'-fluoro-[1,1'-biphenyl]-4-yl)-4-hydroxy-3-(3-methylisoxazol-5-yl) quinolin-2(1H)-one | 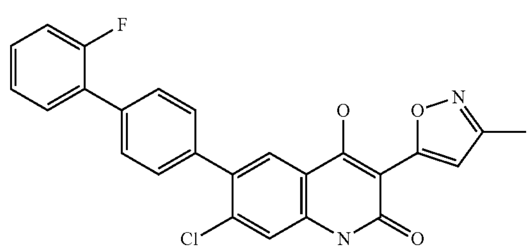 [SMILES: Cc1cc(-c2c(O)c3cc(-c4ccc(-c5ccccc5F)cc4)c(Cl)cc3[nH]c2=O)on1] | methyl 6-chloro-2''-fluoro-4-(2-(3-methylisoxazol-5-yl)acetamido)-[1,1':4',1''-terphenyl]-3-carboxylate (Intermediate 93) | LCMS: $(M + H)^+$ = 447; Rt = 2.77 min.<br>HRMS calculated for $C_{25}H_{17}ClFN_2O_3$ $(M + H)^+$: 447.0912; found: 447.0888. |
| 19<br>3-(7-Chloro-6-(4-(dimethylamino)phenyl)-4-hydroxy-2-oxo-1,2-dihydroquinolin-3-yl)benzonitrile | 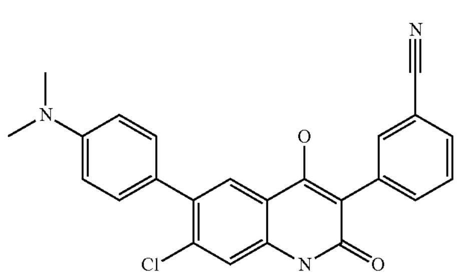 [SMILES: CN(C)c1ccc(-c2cc3c(O)c(-c4cccc(C#N)c4)c(=O)[nH]c3cc2Cl)cc1] | methyl 6-chloro-4-(2-(3-cyanophenyl)acetamido)-4'-(dimethylamino)-[1,1'-biphenyl]-3-carboxylate (Intermediate 88) | LCMS: $(M + H)^+$ = 416; Rt = 2.58 min.<br>HRMS calculated for $C_{24}H_{19}ClN_3O_2$ $(M + H)^+$: 416.1166; found: 416.1175. |

Example 20

7-Chloro-6-(4-(dimethylamino)phenyl)-3-(3-methyl-1,2,4-oxadiazol-5-yl)-2-oxo-1,2-dihydroquinolin-4-olate, potassium salt

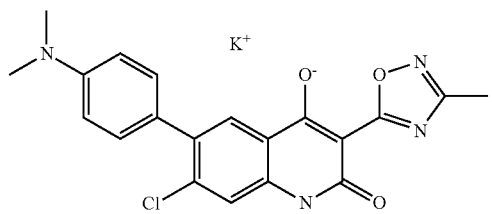

To a solution of methyl 6-chloro-4'-(dimethylamino)-4-(2-(3-methyl-1,2,4-oxadiazol-5-yl)acetamido)-[1,1'-biphenyl]-3-carboxylate (Intermediate 81) (290 mg, 0.676 mmol) in tetrahydrofuran (5 mL) at 60° C. was added dropwise KHMDS 1M/THF (1.758 mL, 1.758 mmol). The reaction mixture was stirred for 1 h after the end of addition. After cooling, the precipitate was filtered, washed with THF and dried. The crude salt was recrystallized in EtOH/water mixture. The solid filtered and dried to give the title compound 7-chloro-6-(4-(dimethylamino)phenyl)-3-(3-methyl-1,2,4-oxadiazol-5-yl)-2-oxo-1,2-dihydroquinolin-4-olate, potassium salt (225 mg, 0.517 mmol, 77% yield) as white solid. LCMS: $(M+H)^+=397$; Rt=2.43 min. HRMS: calculated for $C_{20}H_{17}ClN_4O_3$ $(M+H)^+$: 397.1067. found: 397.1075.

Examples 21 to 26 were prepared by methods analogous to that described for Example 20.

TABLE 17

| # | Name | Structure | Intermediate | LCMS/HRMS |
|---|------|-----------|--------------|-----------|
| 21 | 7-Chloro-3,6-bis(4-dimethylamino)phenyl)-2-oxo-1,2-dihydroquinolin-4-olate, potassium salt | (structure) | methyl 6-chloro-4'-(dimethylamino)-4-(2-(4-(dimethylamino)phenyl)acetamido)-[1,1'-biphenyl]-3-carboxylate (Intermediate 86) | LCMS: $(M+H)^+=434$; Rt=3.19 min. HRMS: calculated for $C_{25}H_{25}ClN_3O_2$ $(M+H)^+$: 434.1635; found: 434.1612. |
| 22 | 7-Chloro-3-(4-cyanophenyl)-6-(4-(dimethylamino)phenyl)-2-oxo-1,2-dihydroquinolin-4-olate, potassium salt | (structure) | methyl 6-chloro-4-(2-(4-cyanophenyl)acetamido)-4'-(dimethylamino)-[1,1'-biphenyl]-3-carboxylate (Intermediate 87) | LCMS: $(M+H)^+=416$; Rt=2.58 min. HRMS: calculated for $C_{24}H_{19}ClN_3O_2$ $(M+H)^+$: 416.1166; found: 416.1171. |
| 23 | 7-Chloro-6-(4-(dimethylamino)phenyl)-3-(5-methyl-1,3,4-oxadiazol-2-yl)-2-oxo-1,2-dihydroquinolin-4-olate, potassium salt | (structure) | methyl 6-chloro-4'-(dimethylamino)-4-(2-(5-methyl-1,3,4-oxadiazol-2-yl)acetamido)-[1,1'-biphenyl]-3-carboxylate (Intermediate 82) | LCMS: $(M+H)^+=397$; Rt=2.31 min. HRMS: calculated for $C_{20}H_{18}ClN_4O_3$ $(M+H)^+$: 397.1067; found: 397.1088. |
| 24 | 7-Chloro-6-(4-(dimethylamino)phenyl)-3-(2-methylthiazol-5-yl)-2-oxo-1,2-dihydroquinolin-4-olate, potassium salt | (structure) | methyl 6-chloro-4'-(dimethylamino)-4-(2-(2-methylthiazol-5-yl)acetamido)-[1,1'-biphenyl]-3-carboxylate (Intermediate 83) | LCMS: $(M+H)^+=412$; Rt=2.48 min. HRMS: calculated for $C_{21}H_{19}ClN_3O_2S$ $(M+H)^+$: 412.0887; found: 412.0889. |

TABLE 17-continued

| | | | | |
|---|---|---|---|---|
| 25<br>7-Chloro-6-(4-(dimethylamino)phenyl)-3-(2,4-dimethylthiazol-5-yl)-2-oxo-1,2-dihydroquinolin-4-olate, potassium salt | | | methyl 6-chloro-4'-(dimethylamino)-4-(2-(2,4-dimethylthiazol-5-yl)acetamido)-[1,1'-biphenyl]-3-carboxylate (Intermediate 84) | LCMS: $(M+H)^+ = 426$; Rt = 2.42 min. HRMS: calculated for $C_{22}H_{21}ClN_3O_2S$ $(M+H)^+$: 426.1043; found: 426.1058. |
| 26<br>7-Chloro-3-(5-methyl-1,3,4-oxadiazol-2-yl)-2-oxo-6-(4-(piperidin-1-yl)phenyl)-1,2-dihydroquinolin-4-olate, potassium salt | | | methyl 6-chloro-4-(2-(5-methyl-1,3,4-oxadiazol-2-yl)acetamido)-4'-(piperidin-1-yl)-[1,1'-biphenyl]-3-carboxylate (Intermediate 85) | LCMS: $(M+H)^+ = 437$; Rt = 2.61 min. HRMS: calculated for $C_{23}H_{22}ClN_4O_3$ $(M+H)^+$: 437.1380; found: 437.1389. |

Example 27

Ethyl 7-chloro-4-hydroxy-6-(1-methyl-1H-indol-5-yl)-2-oxo-1,2-dihydro-3-quinolinecarboxylate

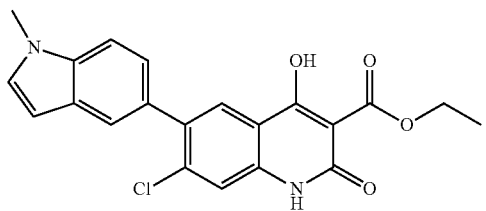 [SMILES: CCOC(=O)c1c(O)c2cc(-c3ccc4c(ccn4C)c3)c(Cl)cc2[nH]c1=O]

To a solution of ethyl 7-chloro-4-hydroxy-6-iodo-2-oxo-1,2-dihydro-3-quinolinecarboxylate (Intermediate 100) (300 mg, 0.762 mmol) in 1,4-dioxane (7 mL) and water (3.5 mL) were added (1-methyl-1H-indol-5-yl)boronic acid (Combi-Blocks, 140 mg, 0.800 mmol), cesium carbonate (373 mg, 1.143 mmol) and tetrakis(triphenylphosphine)palladium (8.81 mg, 7.62 µmol). The reaction vessel was sealed and heated to 120° C. for 20 min in a microwave. After cooling, the mixture was filtered, evaporated to dryness and the resulting residue was acidified with 1N HCl. The precipitate was filtered and dried to give ethyl 7-chloro-4-hydroxy-6-(1-methyl-1H-indol-5-yl)-2-oxo-1,2-dihydro-3-quinolinecarboxylate (198 mg, 0.499 mmol, 65.5% yield) as off-white solid. LCMS: $(M+H)^+=397$; Rt=2.79 min. HRMS: calculated for $C_{21}H_{18}ClN_2O_4$ $(M+H)^+$: 397.0955. found: 397.0927.

Examples 28 to 168 were prepared by methods analogous to that described for Example 27 (starting from boronic acid or borolane analogue). For Examples 32, 33, 34, 35, 36, 37, 38, 39, 40, 46, 47, 48, 49, 50, 52, 53, 54, 55, 56, 63, 66, 67, 68, 75, 76, 77, 78, 91, 93, 95, 96, 97, 98, 103, 104, 105, 117, 118, 120, 126, 127, 128, 129, 131, 132, 133, 135, 136, 137, 140, 141, 142, 143, 146, 148, 149, 157, 158, 162, 163, 164 and 166, sodium carbonate was used instead of cesium carbonate as base.

TABLE 18

| Example | Structure | From | Physical data |
|---|---|---|---|
| 28<br>Ethyl 7-chloro-4-hydroxy-6-[2'-hydroxy-3'-(methyloxy)-4-biphenylyl]-2-oxo-1,2-dihydro-3-quinoline carboxylate | 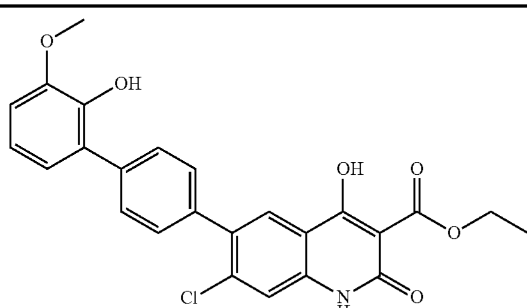 | ethyl 7-chloro-4-hydroxy-6-iodo-2-oxo-1,2-dihydro-3-quinolinecarboxylate (Intermediate 100) and 3-methoxy-4'-(4,4,5,5-tetramethyl-1,3,2-dioxaborolan-2-yl)-[1,1'-biphenyl]-2-ol (Intermediate 33) | LCMS: $(M+H)^+ = 466$; Rt = 2.85 min. HRMS: calculated for $C_{25}H_{21}ClNO_6$ $(M+H)^+$: 466.1057; found: 466.1053. |

TABLE 18-continued

| Example | Structure | From | Physical data |
|---|---|---|---|
| 29<br>7-Chloro-4-hydroxy-6-(1-methyl-1H-indol-5-yl)-3-nitroquinolin-2(1H)-one | | 7-chloro-4-hydroxy-6-iodo-3-nitro-2(1H)-quinolinone (Intermediate 143) and (1-Methyl-1H-indol-5-yl) boronic acid (Combi-Blocks) | LCMS: (M + H)$^+$ = 370; Rt = 2.55 min. HRMS: calculated for C$_{18}$H$_{13}$ClN$_3$O$_4$ (M + H)$^+$: 370.0594; found: 370.0605. |
| 30<br>Ethyl 7-chloro-4-hydroxy-6-[4-(4-morpholinyl)phenyl]-2-oxo-1,2-dihydro-3-quinolinecarboxylate | | ethyl 7-chloro-4-hydroxy-6-iodo-2-oxo-1,2-dihydro-3-quinoline carboxylate (Intermediate 100) and 4-[4-(4,4,5,5-tetramethyl-1,3,2-dioxaborolan-2-yl) phenyl]morpholine (Combi-Blocks) | LCMS: (M + H)$^+$ = 429; Rt = 2.48 min. HRMS: calculated for C$_{22}$H$_{22}$ClN$_2$O$_5$ (M + H)$^+$: 429.1217; found: 429.1218. |
| 31<br>7-Chloro-4-hydroxy-3-(3-methylisoxazol-5-yl)-6-(4-morpholino phenyl) quinolin-2(1H)-one | | 7-chloro-4-hydroxy-6-iodo-3-(3-methylisoxazol-5-yl) quinolin-2(1H)-one (Intermediate 99) and 4-(4-(4,4,5,5-tetramethyl-1,3,2-dioxaborolan-2-yl) phenyl)morpholine (Combi-Blocks) | LCMS: (M + H)$^+$ = 438; Rt = 2.24 min. HRMS: calculated for C$_{23}$H$_{21}$ClN$_3$O$_4$ (M + H)$^+$: 438.1220; found: 438.1201. |
| 32<br>7-Chloro-4-hydroxy-3-(3-methoxyphenyl)-6-(4-(piperidin-1-yl) phenyl)quinolin-2(1H)-one | | 7-chloro-4-hydroxy-6-iodo-3-[3-(methyloxy)phenyl] quinolin-2(1H)-one (Intermediate 98) and [4-(1-piperidinyl)phenyl] boronic acid, hydrochloride (Combi-Blocks) | LCMS: (M + H)$^+$ = 461; Rt = 3.31 min. HRMS: calculated for C$_{27}$H$_{24}$ClN$_2$O$_3$ (M − H)$^+$: 459.1476; found: 459.1433. |
| 33<br>7-Chloro-4-hydroxy-3-(3-methoxyphenyl)-6-(1-methyl-1H-benzo[d]imidazol-6-yl) quinolin-2(1H)-one | | 7-chloro-4-hydroxy-6-iodo-3-[3-(methyloxy)phenyl] quinolin-2(1H)-one (Intermediate 98) and (1-Methyl-1H-benzimidazol-6-yl) boronic acid (Combi-Blocks) | LCMS: (M + H)$^+$ = 432; Rt = 2.21 min. HRMS: calculated for C$_{24}$H$_{17}$ClN$_3$O$_3$ (M − H)$^+$: 430.0959; found: 430.0956. |
| 34<br>7-Chloro-4-hydroxy-3-(3-methoxyphenyl)-6-(4-(pyrrolidin-1-yl) phenyl)quinolin-2(1H)-one | | 7-chloro-4-hydroxy-6-iodo-3-[3-(methyloxy)phenyl] quinolin-2(1H)-one (Intermediate 98) and [4-(1-pyrrolidinyl)phenyl] boronic acid, hydrochloride (Combi-Blocks) | LCMS: (M + H)$^+$ = 447; Rt = 3.25 min. HRMS: calculated for C$_{26}$H$_{22}$ClN$_2$O$_3$ (M − H)$^+$: 445.1319; found: 445.1325. |

TABLE 18-continued

| Example | Structure | From | Physical data |
|---|---|---|---|
| 35<br>Methyl (4-(7-chloro-4-hydroxy-3-(3-methoxyphenyl)-2-oxo-1,2-dihydroquinolin-6-yl)phenyl)carbamate | | 7-chloro-4-hydroxy-6-iodo-3-[3-(methyloxy)phenyl]quinolin-2(1H)-one (Intermediate 98) and (4-{[(methyloxy)carbonyl]amino}phenyl)boronic acid (Combi-Blocks) | LCMS: (M + H)$^+$ = 451; Rt = 2.50 min. HRMS: calculated for C$_{24}$H$_{18}$ClN$_2$O$_5$ (M − H)$^+$: 449.0904; found: 449.0905. |
| 36<br>7-Chloro-6-[4-(dimethylamino)phenyl]-4-hydroxy-3-[3-(methyloxy)phenyl]quinolin-2(1H)-one | | 7-chloro-4-hydroxy-6-iodo-3-[3-(methyloxy)phenyl]quinolin-2(1H)-one (Intermediate 98) and [4-(dimethylamino)phenyl]boronic acid (Aldrich) | LCMS: (M + H)$^+$ = 421 Rt = 2.97 min. HRMS: calculated for C$_{24}$H$_{22}$ClN$_2$O$_3$ (M + H)$^+$: 421.1319; found: 421.1308. |
| 37<br>7-Chloro-6-(2,3-dihydro-1H-inden-5-yl)-4-hydroxy-3-(3-methoxyphenyl)quinolin-2(1H)-one | | 7-chloro-4-hydroxy-6-iodo-3-[3-(methyloxy)phenyl]quinolin-2(1H)-one (Intermediate 98) and (2,3-dihydro-1H-inden-5-yl)boronic acid (UkrOrgSynthesis Ltd.) | LCMS: (M + H)$^+$ = 418 Rt = 3.23 min. HRMS: calculated for C$_{25}$H$_{21}$ClNO$_3$ (M + H)$^+$: 418.1210; found: 418.1192. |
| 38<br>7-Chloro-4-hydroxy-3-(3-methoxyphenyl)-6-(4-(4-methylpiperazin-1-yl)phenyl)quinolin-2(1H)-one | | 7-chloro-4-hydroxy-6-iodo-3-[3-(methyloxy)phenyl]quinolin-2(1H)-one (Intermediate 98) and 1-methyl-4-[4-(4,4,5,5-tetramethyl-1,3,2-dioxaborolan-2-yl)phenyl]piperazine (Combi-Blocks) | LCMS: (M + H)$^+$ = 476; Rt = 2.20 min. HRMS: calculated for C$_{27}$H$_{25}$ClN$_3$O$_3$ (M − H)$^+$: 474.1584; found: 474.1566. |
| 39<br>7-Chloro-6-(4-ethylphenyl)-4-hydroxy-3-(3-methoxyphenyl)quinolin-2(1H)-one | | 7-chloro-4-hydroxy-6-iodo-3-[3-(methyloxy)phenyl]quinolin-2(1H)-one (Intermediate 98) and (4-ethylphenyl)boronic acid (Aldrich) | LCMS: (M + H)$^+$ = 406; Rt = 3.14 min. HRMS: calculated for C$_{24}$H$_{21}$ClNO$_3$ (M + H)$^+$: 406.1210; found: 406.1198. |
| 40<br>7-Chloro-6-[3-(dimethylamino)phenyl]-4-hydroxy-3-[3-(methyloxy)phenyl]-2(1H)-quinolinone | | 7-chloro-4-hydroxy-6-iodo-3-[3-(methyloxy)phenyl]quinolin-2(1H)-one (Intermediate 98) and [3-(dimethylamino)phenyl]boronic acid (Aldrich) | LCMS: (M + H)$^+$ = 421; Rt = 2.84 min. HRMS: calculated for C$_{24}$H$_{22}$ClN$_2$O$_3$ (M + H)$^+$: 421.1319; found: 421.1284. |

TABLE 18-continued

| Example | Structure | From | Physical data |
|---|---|---|---|
| 41<br>7-Chloro-6-(3-(dimethylamino)phenyl)-4-hydroxy-3-(3-methylisoxazol-5-yl)quinolin-2(1H)-one | 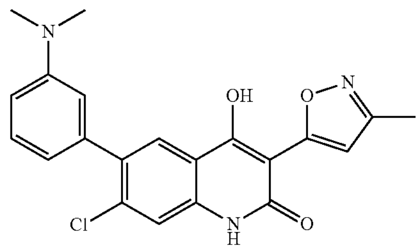 [SMILES: Cc1cc(-c2c(O)c3cc(-c4cccc(N(C)C)c4)c(Cl)cc3[nH]c2=O)on1] | 7-chloro-4-hydroxy-6-iodo-3-(3-methylisoxazol-5-yl)quinolin-2(1H)-one (Intermediate 99) and [3-(dimethylamino) phenyl] boronic acid (Aldrich) | LCMS: $(M + H)^+ =$ 396; Rt = 2.39 min. HRMS: calculated for $C_{21}H_{19}ClN_3O_3$ $(M + H)^+$: 396.1115; found: 396.1104. |
| 42<br>7-Chloro-6-(4-(dimethylamino)phenyl)-4-hydroxy-3-(3-methylisoxazol-5-yl)quinolin-2(1H)-one | 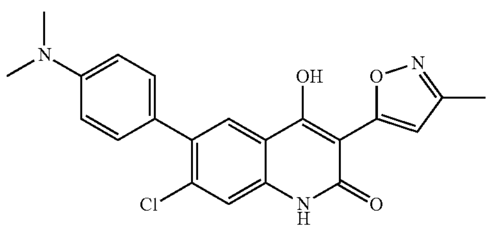 | 7-chloro-4-hydroxy-6-iodo-3-(3-methylisoxazol-5-yl)quinolin-2(1H)-one (Intermediate 99) and [4-(dimethylamino) phenyl]boronic acid (Aldrich) | LCMS: $(M + H)^+ =$ 396; Rt = 2.48 min. HRMS: calculated for $C_{21}H_{19}ClN_3O_3$ $(M + H)^+$: 396.1115; found: 396.1108. |
| 43<br>7-Chloro-6-(4-ethylphenyl)-4-hydroxy-3-(3-methylisoxazol-5-yl) quinolin-2(1H)-one | 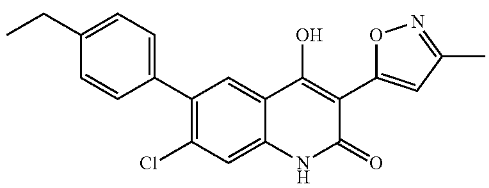 [SMILES: CCc1ccc(-c2cc3c(O)c(-c4cc(C)no4)c(=O)[nH]c3cc2Cl)cc1] | 7-chloro-4-hydroxy-6-iodo-3-(3-methylisoxazol-5-yl)quinolin-2(1H)-one (Intermediate 99) and (4-ethylphenyl)boronic acid (Aldrich) | LCMS: $(M + H)^+ =$ 381; Rt = 2.61 min. HRMS: calculated for $C_{21}H_{18}ClN_2O_3$ $(M + H)^+$: 381.1006; found: 381.1003. |
| 44<br>7-Chloro-4-hydroxy-6-(2'-hydroxy-3'-methoxy-[1,1'-biphenyl]-4-yl)-3-(3-methylisoxazol-5-yl) quinolin-2(1H)-one | 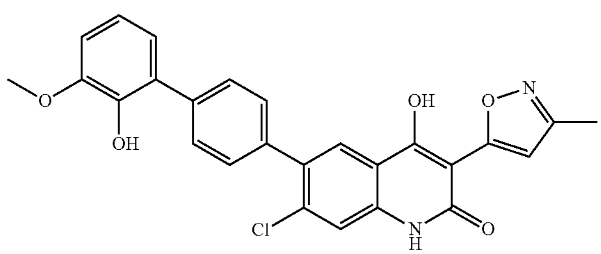 | 7-chloro-4-hydroxy-6-iodo-3-(3-methylisoxazol-5-yl)quinolin-2(1H)-one (Intermediate 99) and 3-methoxy-4'-(4,4,5,5-tetramethyl-1,3,2-dioxaborolan-2-yl)-[1,1'-biphenyl]-2-ol (Intermediate 33) | LCMS: $(M + H)^+ =$ 475; Rt = 2.64 min. HRMS: calculated for $C_{26}H_{20}ClN_2O_5$ $(M + H)^+$: 475.1060; found: 475.1054. |
| 45<br>7-Chloro-4-hydroxy-6-(4-morpholinophenyl)-3-phenoxyquinolin-2(1H)-one | 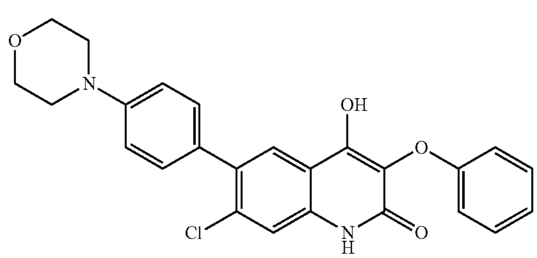 [SMILES: O=c1[nH]c2cc(Cl)c(-c3ccc(N4CCOCC4)cc3)cc2c(O)c1Oc1ccccc1] | 7-chloro-4-hydroxy-6-iodo-3-phenoxyquinolin-2(1H)-one (Intermediate 101) and (4-morpholino phenyl)boronic acid (Combi-Blocks) | LCMS: $(M + H)^+ =$ 449; Rt = 2.41 min. HRMS: calculated for $C_{25}H_{22}ClN_2O_4$ $(M + H)^+$: 449.1268; found: 449.1273. |
| 46<br>7-Chloro-6-(4-(dimethylamino)phenyl)-4-hydroxy-3-phenylquinolin-2(1H)-one | 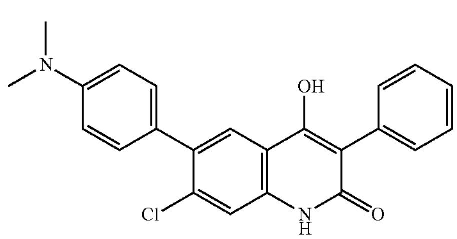 [SMILES: CN(C)c1ccc(-c2cc3c(O)c(-c4ccccc4)c(=O)[nH]c3cc2Cl)cc1] | 7-chloro-4-hydroxy-6-iodo-3-phenylquinolin-2(1H)-one (Intermediate 102) and [4-(dimethylamino) phenyl]boronic acid (Aldrich) | LCMS: $(M + H)^+ =$ 391; Rt = 2.87 min. HRMS: calculated for $C_{23}H_{20}ClN_2O_2$ $(M + H)^+$: 391.1213; found: 391.1208. |

TABLE 18-continued

| Example | Structure | From | Physical data |
|---|---|---|---|
| 47<br>6-(4-(1H-Pyrazol-1-yl)phenyl)-7-chloro-4-hydroxy-3-phenyl quinolin-2(1H)-one | | 7-chloro-4-hydroxy-6-iodo-3-phenylquinolin-2(1H)-one (Intermediate 102) and (4-(1H-pyrazol-1-yl)phenyl)boronic acid (Combi-Blocks) | LCMS: $(M + H)^+ =$ 414; Rt = 2.61 min. HRMS: calculated for $C_{24}H_{17}ClN_3O_2$ $(M + H)^+$: 414.1009; found; 414.1003. |
| 48<br>7-Chloro-4-hydroxy-6-(4-methoxyphenyl)-3-phenylquinolin-2(1H)-one | | 7-chloro-4-hydroxy-6-iodo-3-phenylquinolin-2(1H)-one (Intermediate 102) and (4-methoxyphenyl) boronic acid (Aldrich) | LCMS: $(M + H)^+ =$ 378; Rt = 2.65 min. HRMS: calculated for $C_{22}H_{17}ClNO_3$ $(M + H)^+$: 378.0897; found: 378.0862. |
| 49<br>7-Chloro-6-(4-(dimethylamino)phenyl)-4-hydroxy-3-(1H-pyrazol-1-yl)quinolin-2(1H)-one | | 7-chloro-4-hydroxy-6-iodo-3-(1H-pyrazol-1-yl)quinolin-2(1H)-one (Intermediate 112) and (4-(dimethylamino)phenyl)boronic acid (Aldrich) | LCMS: $(M + H)^+ =$ 381; Rt = 2.43 min. HRMS: calculated for $C_{20}H_{16}ClN_4O_2$ $(M - H)^+$: 379.0962; found: 379.0974. |
| 50<br>7-Chloro-4-hydroxy-6-(4-morpholinophenyl)-3-(1H-pyrazol-1-yl)quinolin-2(1H)-one | | 7-chloro-4-hydroxy-6-iodo-3-(1H-pyrazol-1-yl)quinolin-2(1H)-one (Intermediate 112) and (4-morpholinophenyl) boronic acid (Combi-Blocks) | LCMS: $(M + H)^+ =$ 423; Rt = 2.16 min. HRMS: calculated for $C_{22}H_{18}ClN_4O_3$ $(M - H)^+$: 421.1068; found: 421.1050. |
| 51<br>7-Chloro-6-(4-(dimethylamino)phenyl)-4-hydroxy-3-phenoxyquinolin-2(1H)-one | | 7-chloro-4-hydroxy-6-iodo-3-phenoxyquinolin-2(1H)-one (Intermediate 101) and (4-(dimethylamino)phenyl) boronic acid (Aldrich) | LCMS: $(M + H)^+ =$ 407; Rt = 2.71 min. HRMS: calculated for $C_{23}H_{20}ClN_2O_3$ $(M + H)^+$: 407.1162; found: 407.1162 |
| 52<br>7-Chloro-4-hydroxy-3-phenyl-6-(4-(piperidin-1-yl)phenyl)quinolin-2(1H)-one | | 7-chloro-4-hydroxy-6-iodo-3-phenylquinolin-2(1H)-one (Intermediate 102) and (4-(piperidin-1-yl)phenyl) boronic acid hydrochloride (Combi-Blocks) | LCMS: $(M + H)^+ =$ 431; Rt = 3.23 min. HRMS: calculated for $C_{26}H_{24}ClN_2O_2$ $(M + H)^+$: 431.1526; found: 431.1539. |

TABLE 18-continued

| Example | Structure | From | Physical data |
|---|---|---|---|
| 53<br>7-Chloro-4-hydroxy-6-(4-(2-hydroxyethyl)phenyl)-3-phenyl quinolin-2(1H)-one | | 7-chloro-4-hydroxy-6-iodo-3-phenylquinolin-2(1H)-one (Intermediate 102) and 2-(4-(4,4,5,5-tetramethyl-1,3,2-dioxaborolan-2-yl)phenyl)ethanol (Intermediate 38) | LCMS: $(M + H)^+ =$ 392; Rt = 2.25 min. HRMS: calculated for $C_{23}H_{19}ClNO_3$ $(M + H)^+$: 392.1053; found: 392.1060. |
| 54<br>7-Chloro-4-hydroxy-6-(4-(3-hydroxy piperidin-1-yl)phenyl)-3-(3-methoxyphenyl)quinolin-2(1H)-one | | 7-chloro-4-hydroxy-6-iodo-3-[3-(methyloxy)phenyl]quinolin-2(1H)-one (Intermediate 98) and 1-(4-(4,4,5,5-tetramethyl-1,3,2-dioxaborolan-2-yl)phenyl)piperidin-3-ol (Intermediate 32) | LCMS: $(M + H)^+ =$ 477; Rt = 2.44 min. HRMS: calculated for $C_{27}H_{24}ClN_2O_4$ $(M - H)^+$: 475.1425; found: 475.1402. |
| 55<br>7-Chloro-4-hydroxy-6-(2-hydroxy-3'-methoxy-[1,1'-biphenyl]-4-yl)-3-(1H-pyrazol-1-yl) quinolin-2(1H)-one | | 7-chloro-4-hydroxy-6-iodo-3-(1H-pyrazol-1-yl)quinolin-2(1H)-one (Intermediate 112) and 3-methoxy-4'-(4,4,5,5-tetramethyl-1,3,2-dioxaborolan-2-yl)-[1,1'-biphenyl]-2-ol (Intermediate 33) | LCMS: $(M + H)^+ =$ 460; Rt = 2.56 min. HRMS: calculated for $C_{25}H_{17}ClN_3O_4$ $(M - H)^+$: 458.0908; found: 458.0891. |
| 56<br>7-Chloro-4-hydroxy-3-(3-methoxyphenyl)-6-(4-methyl-3,4-dihydro-2H-benzo[b][1,4]oxazin-7-yl) quinolin-2(1H)-one | | 7-chloro-4-hydroxy-6-iodo-3-[3-(methyloxy)phenyl]quinolin-2(1H)-one (Intermediate 98) and 4-methyl-7-(4,4,5,5-tetramethyl-1,3,2-dioxaborolan-2-yl)-3,4-dihydro-2H-1,4-benzoxazine (Maybridge) | LCMS: $(M + H)^+ =$ 449; Rt = 2.74 min. HRMS: calculated for $C_{25}H_{20}ClN_2O_4$ $(M - H)^+$: 447.1112; found: 447.1073. |
| 57<br>7-Chloro-4-hydroxy-3-phenyl-6-(4-(pyrrolidin-1-yl)phenyl)quinolin-2(1H)-one | | 7-chloro-4-hydroxy-6-iodo-3-phenylquinolin-2(1H)-one (Intermediate 102) and 1-(4-(4,4,5,5-tetramethyl-1,3,2-dioxaborolan-2-yl)phenyl)pyrrolidine (Combi-Blocks) | LCMS: $(M + H)^+ =$ 417; Rt = 3.28 min. HRMS: calculated for $C_{25}H_{22}ClN_2O_2$ $(M + H)^+$: 417.1370; found: 417.1359. |

TABLE 18-continued

| Example | Structure | From | Physical data |
|---|---|---|---|
| 58<br>7-Chloro-4-hydroxy-6-(2'-hydroxy-3'-methoxy-[1,1'-biphenyl]-4-yl)-3-phenoxyquinolin-2(1H)-one | | 7-chloro-4-hydroxy-6-iodo-3-phenoxyquinolin-2(1H)-one (Intermediate 101) and 3-methoxy-4'-(4,4,5,5-tetramethyl-1,3,2-dioxaborolan-2-yl)-[1,1'-biphenyl]-2-ol (Intermediate 33) | LCMS: $(M + H)^+ =$ 486; Rt = 2.96 min. HRMS: calculated for $C_{28}H_{21}ClNO_5$ $(M + H)^+$: 486.1108; found: 486.1068. |
| 59<br>7-Chloro-4-hydroxy-6-(2'-hydroxy-3'-methoxy-[1,1'-biphenyl]-4-yl)quinolin-2(1H)-one | | 7-chloro-4-hydroxy-6-iodoquinolin-2(1H)-one (Intermediate 142) and 3-methoxy-4'-(4,4,5,5-tetramethyl-1,3,2-dioxaborolan-2-yl)-[1,1'-biphenyl]-2-ol (Intermediate 33) | LCMS: $(M + H)^+ =$ 394; Rt = 2.71 min. HRMS: calculated for $C_{22}H_{17}ClNO_4$ $(M + H)^+$: 394.0846; found: 394.0835. |
| 60<br>N-(4-(4-(7-Chloro-4-hydroxy-2-oxo-3-phenoxy-1,2-dihydroquinolin-6-yl)phenyl)thiazol-2-yl)acetamide | | 7-chloro-4-hydroxy-6-iodo-3-phenoxyquinolin-2(1H)-one (Intermediate 101) and N-(4-(4-(4,4,5,5-tetramethyl-1,3,2-dioxaborolan-2-yl)phenyl)thiazol-2-yl)acetamide (Intermediate 31) | LCMS: $(M + H)^+ =$ 504; Rt = 2.49 min. HRMS: calculated for $C_{26}H_{19}ClN_3O_4S$ $(M + H)^+$: 504.0785; found: 504.0762. |
| 61<br>7-Chloro-6-(4-(dimethylamino)phenyl)-4-hydroxy-3-(o-tolyloxy)quinolin-2(1H)-one | | 7-chloro-4-hydroxy-6-iodo-3-(o-tolyloxy)quinolin-2(1H)-one (Intermediate 111) and (4-(dimethylamino)phenyl)boronic acid (Aldrich) | LCMS: $(M + H)^+ =$ 421; Rt = 2.95 min. HRMS: calculated for $C_{24}H_{22}ClN_2O_3$ $(M + H)^+$: 421.1319; found: 421.1332. |
| 62<br>7-Chloro-6-(4-(dimethylamino)phenyl)-4-hydroxy-3-(4-methoxyphenoxy)quinolin-2(1H)-one | | 7-chloro-4-hydroxy-6-iodo-3-(4-methoxyphenoxy)quinolin-2(1H)-one (Intermediate 113) and (4-(dimethylamino)phenyl)boronic acid (Aldrich) | LCMS: $(M + H)^+ =$ 437; Rt = 2.75 min. HRMS: calculated for $C_{24}H_{22}ClN_2O_4$ $(M + H)^+$: 437.1268; found: 437.1241. |

TABLE 18-continued

| Example | Structure | From | Physical data |
|---|---|---|---|
| 63<br>7-Chloro-4-hydroxy-6-(4-(hydroxymethyl)phenyl)-3-phenyl quinolin-2(1H)-one | | 7-chloro-4-hydroxy-6-iodo-3-phenylquinolin-2(1H)-one (Intermediate 102) and (4-(hydroxymethyl)phenyl)boronic acid (Lancaster Synthesis) | LCMS: $(M + H)^+$ = 378; Rt = 2.06 min. HRMS: calculated for $C_{22}H_{17}ClNO_3$ $(M + H)^+$: 378.0897; found: 378.0921. |
| 64<br>7-Chloro-3-(3-fluorophenoxy)-4-hydroxy-6-(4-isopropylphenyl)quinolin 2(1H)-one | | 7-chloro-3-(3-fluorophenoxy)-4-hydroxy-6-iodoquinolin-2(1H)-one (Intermediate 114) and and (4-isopropylphenyl)boronic acid (Lancaster Synthesis) | LCMS: $(M + H)^+$ = 424; Rt = 3.04 min. HRMS: calculated for $C_{24}H_{20}ClFNO_3$ $(M + H)^+$: 424.1116; found: 424.1093. |
| 65<br>7-Chloro-6-(4-(dimethylamino)phenyl)-3-(3-fluorophenoxy)-4-hydroxyquinolin-2(1H)-one | | 7-chloro-3-(3-fluorophenoxy)-4-hydroxy-6-iodoquinolin-2(1H)-one (Intermediate 114) and and(4-(dimethylamino)phenyl)boronic acid (Aldrich) | LCMS: $(M + H)^+$ = 425; Rt = 2.68 min. HRMS: calculated for $C_{23}H_{19}ClFN_2O_3$ $(M + H)^+$: 425.1068; found: 425.1033. |
| 66<br>7-Chloro-4-hydroxy-6-(4-(methylamino)phenyl)-3-phenyl quinolin-2(1H)-one | | 7-chloro-4-hydroxy-6-iodo-3-phenylquinolin-2(1H)-one (Intermediate 102) and N-methyl-4-(4,4,5,5-tetramethyl-1,3,2-dioxaborolan-2-yl)aniline (Boron Molecular) | LCMS: $(M + H)^+$ = 377; Rt = 2.57 min. HRMS: calculated for $C_{22}H_{18}ClN_2O_2$ $(M + H)^+$: 377.1057; found: 377.1053. |
| 67<br>7-Chloro-4-hydroxy-3-(1H-pyrazol-1-yl)-6-(4-(pyrrolidin-1-yl)phenyl)quinolin-2(1H)-one | | 7-chloro-4-hydroxy-6-iodo-3-(1H-pyrazol-1-yl)quinolin-2(1H)-one (Intermediate 112) and 1-(4-(4,4,5,5-tetramethyl-1,3,2-dioxaborolan-2-yl)phenyl)pyrrolidine (Combi-Blocks) | LCMS: $(M + H)^+$ = 407; Rt = 2.75 min. HRMS: calculated for $C_{22}H_{20}ClN_4O_2$ $(M + H)^+$: 407.1275; found: 407.1259. |
| 68<br>7-Chloro-6-(4-ethoxyphenyl)-4-hydroxy-3-(1H-pyrazol-1-yl)quinolin-2(1H)-one | | 7-chloro-4-hydroxy-6-iodo-3-(1H-pyrazol-1-yl)quinolin-2(1H)-one (Intermediate 112) and (4-ethoxyphenyl)boronic acid (Aldrich) | LCMS: $(M + H)^+$ = 382; Rt = 2.47 min. HRMS: calculated for $C_{20}H_{17}ClN_3O_3$ $(M + H)^+$: 382.0958; found: 382.0962. |

TABLE 18-continued

| Example | Structure | From | Physical data |
|---|---|---|---|
| 69<br>7-Chloro-4-hydroxy-3-phenoxy-6-(4-(pyrrolidin-1-yl)phenyl)quinolin-2(1H)-one | 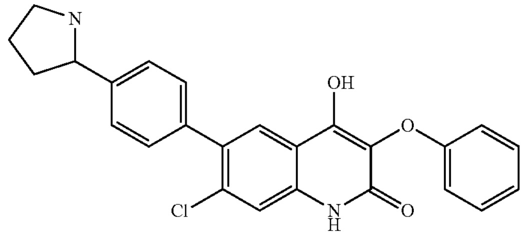 [SMILES: O=c1[nH]c2cc(Cl)c(-c3ccc(C4CCCN4)cc3)cc2c(O)c1Oc1ccccc1] | 7-chloro-4-hydroxy-6-iodo-3-phenoxyquinolin-2(1H)-one (Intermediate 101) and 1-(4-(4,4,5,5-tetramethyl-1,3,2-dioxaborolan-2-yl)phenyl) pyrrolidine (Combi-Blocks) | LCMS: $(M + H)^+$ = 433; Rt = 3.05 min. HRMS: calculated for $C_{25}H_{22}ClN_2O_3$ $(M + H)^+$: 433.1319; found: 433.1302. |
| 70<br>7-Chloro-6-(4-ethylphenyl)-4-hydroxy-3-phenoxyquinolin-2(1H)-one | 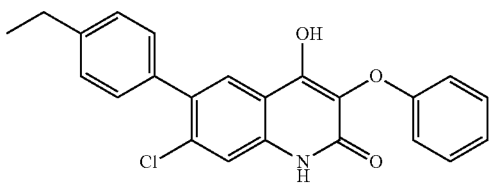 [SMILES: CCc1ccc(-c2cc3c(O)c(Oc4ccccc4)c(=O)[nH]c3cc2Cl)cc1] | 7-chloro-4-hydroxy-6-iodo-3-phenoxyquinolin-2(1H)-one (Intermediate 101) and (4-ethylphenyl) boronic acid (Aldrich) | LCMS: $(M + H)^+$ = 392; Rt = 2.93 min. HRMS: calculated for $C_{23}H_{19}ClNO_3$ $(M + H)^+$: 392.1053; found: 392.1058. |
| 71<br>7-Chloro-4-hydroxy-6-(4-isopropylphenyl)-3-phenoxyquinolin-2(1H)-one | 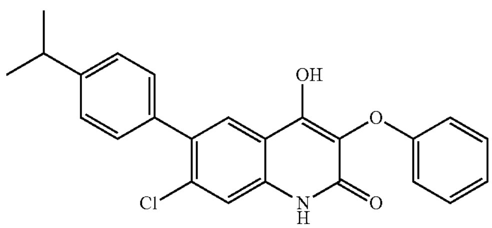 | 7-chloro-4-hydroxy-6-iodo-3-phenoxyquinolin-2(1H)-one (Intermediate 101) and (4-isopropylphenyl)boronic acid (Lancaster Synthesis) | LCMS: $(M + H)^+$ = 406; Rt = 3.07 min. HRMS: calculated for $C_{24}H_{21}ClNO_3$ $(M + H)^+$: 406.1210; found: 406.1186. |
| 72<br>7-Chloro-6-(4-(dimethylamino)phenyl)-4-hydroxy-3-(3-methoxyphenoxy)quinolin-2(1H)-one | 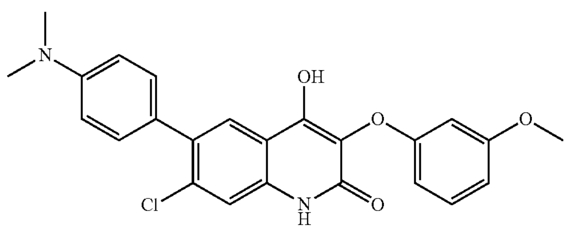 | 7-chloro-4-hydroxy-6-iodo-3-(3-methoxyphenoxy)quinolin-2(1H)-one (Intermediate 115) and (4-(dimethylamino)phenyl)boronic acid (Aldrich) | LCMS: $(M + H)^+$ = 437; Rt = 2.74 min. HRMS: calculated for $C_{24}H_{22}ClN_2O_4$ $(M + H)^+$: 437.1268; found: 437.1276. |
| 73<br>7-Chloro-4-hydroxy-3-(3-methoxyphenoxy)-6-(4-(pyrrolidin-1-yl)phenyl)quinolin-2(1H)-one | 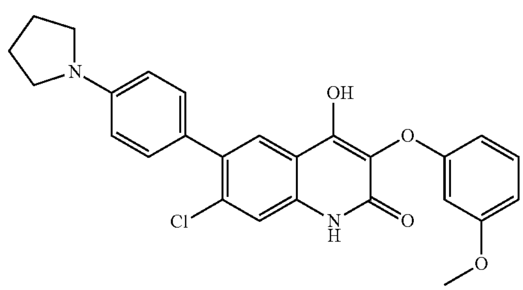 [SMILES: COc1cccc(Oc2c(O)c3cc(-c4ccc(N5CCCC5)cc4)c(Cl)cc3[nH]c2=O)c1] | 7-chloro-4-hydroxy-6-iodo-3-(3-methoxyphenoxy)quinolin-2(1H)-one (Intermediate 115) and 1-(4-(4,4,5,5-tetramethyl-1,3,2-dioxaborolan-2-yl)phenyl)pyrrolidine (Combi-Blocks) | LCMS: $(M + H)^+$ = 463; Rt = 3.06 min. HRMS: calculated for $C_{26}H_{24}ClN_2O_4$ $(M + H)^+$: 463.1425; found: 463.1434. |
| 74<br>7-Chloro-4-hydroxy-6-(4-isopropylphenyl)-3-(3-methoxyphenoxy)quinolin-2(1H)-one | 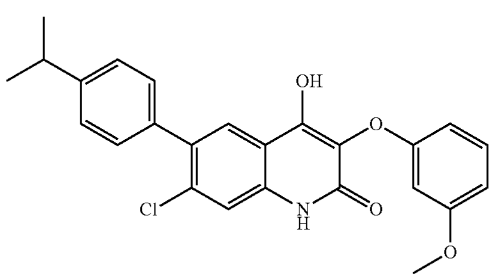 [SMILES: COc1cccc(Oc2c(O)c3cc(-c4ccc(C(C)C)cc4)c(Cl)cc3[nH]c2=O)c1] | 7-chloro-4-hydroxy-6-iodo-3-(3-methoxyphenoxy)quinolin-2(1H)-one (Intermediate 115) and (4-isopropylphenyl) boronic acid (Lancaster Synthesis) | LCMS: $(M + H)^+$ = 436; Rt = 3.05 min. HRMS: calculated for $C_{25}H_{23}ClNO_4$ $(M + H)^+$: 436.1316; found: 436.1354. |

TABLE 18-continued

| Example | Structure | From | Physical data |
|---|---|---|---|
| 75 7-Chloro-4-hydroxy-6-(1-methyl-1H-indol-5-yl)-3-(1H-pyrazol-1-yl) quinolin-2(1H)-one | 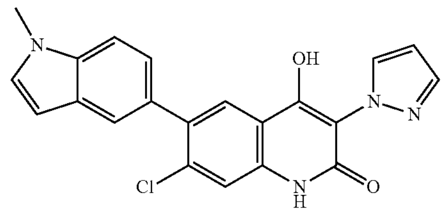 [SMILES: Cn1ccc2cc(-c3cc4c(O)c(-n5cccn5)c(=O)[nH]c4cc3Cl)ccc21] | 7-chloro-4-hydroxy-6-iodo-3-(1H-pyrazol-1-yl) quinolin-2(1H)-one (Intermediate 112) and (1-methyl-1H-indol-5-yl) boronic acid (Combi-Blocks) | LCMS: $(M + H)^+ =$ 391; Rt = 2.42 min. HRMS: calculated for $C_{21}H_{16}ClN_4O_2$ 391.0962; found: 391.0984. |
| 76 7-Chloro-6-(4-(cyclopropylmethoxy)phenyl)-4-hydroxy-3-(1H-pyrazol-1-yl) quinolin-2(1H)-one | 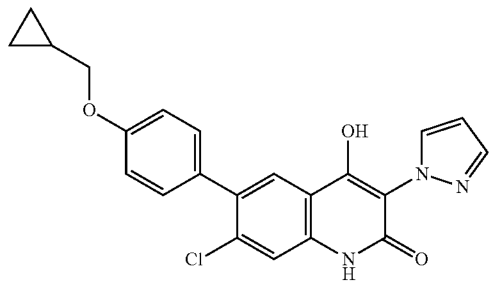 [SMILES: O=c1[nH]c2cc(Cl)c(-c3ccc(OCC4CC4)cc3)cc2c(O)c1-n1cccn1] | 7-chloro-4-hydroxy-6-iodo-3-(1H-pyrazol-1-yl) quinolin-2(1H)-one (Intermediate 112) and (4-(cyclopropylmethoxy)phenyl)boronic acid (Apollo Scientific) | LCMS: $(M + H)^+ =$ 408; Rt = 2.65 min. HRMS: calculated for $C_{22}H_{19}ClN_3O_3$ $(M + H)^+$: 408.1115; found: 408.1096. |
| 77 7-Chloro-4-hydroxy-6-(4-methyl-3,4-dihydro-2H-benzo[b][1,4]oxazin-7-yl)-3-(1H-pyrazol-1-yl)quinolin-2(1H)-one | 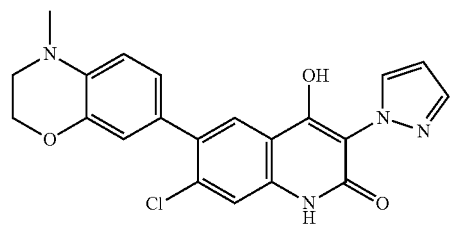 [SMILES: CN1CCOc2cc(-c3cc4c(O)c(-n5cccn5)c(=O)[nH]c4cc3Cl)ccc21] | 7-chloro-4-hydroxy-6-iodo-3-(1H-pyrazol-1-yl) quinolin-2(1H)-one (Intermediate 112) and 4-methyl-7-(4,4,5,5-tetramethyl-1,3,2-dioxaborolan-2-yl)-3,4-dihydro-2H-benzo[b][1.4]oxazine (Maybridge) | LCMS: $(M + H)^+ =$ 409; Rt = 2.30 min. HRMS: calculated for $C_{21}H_{18}ClN_4O_3$ $(M + H)^+$: 409.1067; found: 409.1042. |
| 78 7-Chloro-4-hydroxy-6-(1-methyl-1H-indazol-5-yl)-3-(1H-pyrazol-1-yl)quinolin-2(1H)-one | 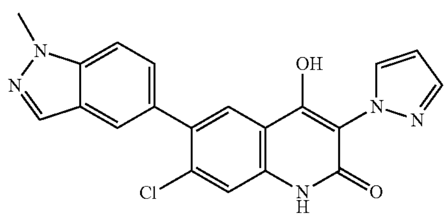 [SMILES: Cn1ncc2cc(-c3cc4c(O)c(-n5cccn5)c(=O)[nH]c4cc3Cl)ccc21] | 7-chloro-4-hydroxy-6-iodo-3-(1H-pyrazol-1-yl) quinolin-2(1H)-one (Intermediate 112) and (1-methyl-1H-indazol-5-yl)boronic acid (Combi-Blocks) | LCMS: $(M + H)^+ =$ 392; Rt = 2.07 min. HRMS: calculated for $C_{20}H_{15}ClN_5O_2$ $(M + H)^+$: 392.0914; found: 392.0882. |
| 79 7-Chloro-4-hydroxy-6-(4-isopropylphenyl)-3-(3-methylisoxazol-5-yl) quinolin-2(1H)-one | 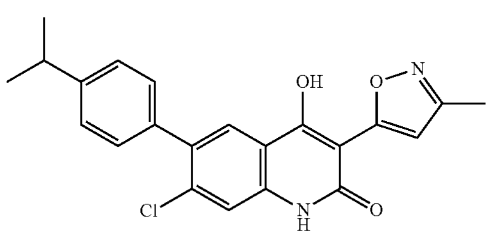 [SMILES: Cc1cc(-c2c(O)c3cc(-c4ccc(C(C)C)cc4)c(Cl)cc3[nH]c2=O)on1] | 7-chloro-4-hydroxy-6-iodo-3-(3-methylisoxazol-5-yl)quinolin-2(1H)-one (Intermediate 99) and (4-isopropylphenyl) boronic acid (Lancaster Synthesis) | LCMS: $(M + H)^+ =$ 395; Rt = 2.76 min. HRMS: calculated for $C_{22}H_{20}ClN_2O_3$ $(M + H)^+$: 395.1162; found; 395.1144. |
| 80 7-Chloro-3-(3,5-dimethyl-1H-pyrazol-1-yl)-6-(4-(dimethylamino)phenyl)-4-hydroxyquinolin-2(1H)-one | 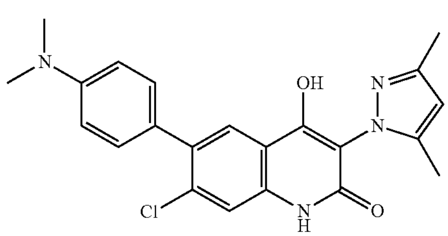 [SMILES: Cc1cc(C)n(-c2c(O)c3cc(-c4ccc(N(C)C)cc4)c(Cl)cc3[nH]c2=O)n1] | 7-chloro-3-(3,5-dimethyl-1H-pyrazol-1-yl)-4-hydroxy-6-iodoquinolin-2(1H)-one (Intermediate 116) and (4-(dimethylamino)phenyl) boronic acid (Aldrich) | LCMS: $(M + H)^+ =$ 409; Rt = 2.35 min. HRMS: calculated for $C_{22}H_{22}ClN_4O_2$ $(M + H)^+$: 409.1431; found: 409.1458. |

TABLE 18-continued

| Example | Structure | From | Physical data |
|---|---|---|---|
| 81<br>7-Chloro-6-(4-(dimethylamino)phenyl)-4-hydroxy-3-(p-tolyloxy)quinolin-2(1H)-one | | 7-chloro-4-hydroxy-6-iodo-3-(p-tolyloxy)quinolin-2(1H)-one (Intermediate 117) and (4-(dimethylamino)phenyl)boronic acid (Aldrich) | LCMS: $(M + H)^+ =$ 421; Rt = 2.86 min. HRMS: calculated for $C_{24}H_{22}ClN_2O_3$ $(M + H)^+$: 421.1319; found: 421.1311. |
| 82<br>7-Chloro-6-(2,3-dihydro-1H-inden-5-yl)-4-hydroxy-3-(3-methylisoxazol-5-yl) quinolin-2(1H)-one | | 7-chloro-4-hydroxy-6-iodo-3-(3-methylisoxazol-5-yl)quinolin-2(1H)-one (Intermediate 99) and (2,3-dihydro-1H-inden-5-yl)boronic acid (UkrOrgSynthesis Ltd.) | LCMS: $(M + H)^+ =$ 393; Rt = 2.65 min. HRMS: calculated for $C_{22}H_{18}ClN_2O_3$ $(M + H)^+$: 393.1006; found: 393.1002. |
| 83<br>7-Chloro-6-(4-(dimethylamino)phenyl)-4-hydroxy-3-(4-methyl-1,2,5-oxadiazol-3-yl)quinolin-2(1H)-one | | 7-chloro-4-hydroxy-6-iodo-3-(4-methyl-1,2,5-oxadiazol-3-yl)quinolin-2(1H)-one (Intermediate 103) and (4-(dimethylamino) phenyl) boronic acid (Aldrich) | LCMS: $(M + H)^+ =$ 397; Rt = 2.43 min. HRMS: calculated for $C_{20}H_{18}ClN_4O_3$ $(M + H)^+$: 397.1067; found: 397.1077. |
| 84<br>7-Chloro-6-(4-(dimethylamino)phenyl)-4-hydroxy-3-(pyridin-4-yl)quinolin-2(1H)-one | | 7-chloro-4-hydroxy-6-iodo-3-(pyridin-4-yl)quinolin-2(1H)-one (Intermediate 104) and (4-(dimethylamino)phenyl)boronic acid (Aldrich) | LCMS: $(M + H)^+ =$ 392; Rt = 2.49 min. HRMS: calculated for $C_{22}H_{19}ClN_3O_2$ $(M + H)^+$: 392.1166; found: 392.1162. |
| 85<br>7-Chloro-6-(4-(dimethylamino)phenyl)-4-hydroxy-3-(pyridin-2-yloxy) quinolin-2(1H)-one | | 7-chloro-4-hydroxy-6-iodo-3-(pyridin-2-yloxy) quinolin-2(1H)-one (Intermediate 118) and (4-(dimethylamino)phenyl)boronic acid (Aldrich) | LCMS: $(M + H)^+ =$ 408: Rt = 2.21 min. HRMS: calculated for $C_{22}H_{19}ClN_3O_3$ $(M + H)^+$: 408.1115; found: 408.1125. |
| 86<br>7-Chloro-6-(4-(dimethylamino)phenyl)-4-hydroxy-3-(1H-1,2,4-triazo-1-yl) quinolin-2(1H)-one | | 7-chloro-4-hydroxy-6-iodo-3-(1H-1,2,4-triazol-1-yl)quinolin-2(1H)-one (Intermediate 105) and (4-(dimethylamino)phenyl)boronic acid (Aldrich) | LCMS: $(M + H)^+ =$ 382; Rt = 2.27 min. HRMS: calculated for $C_{19}H_{17}ClN_5O_2$ $(M + H)^+$: 382.1071; found: 382.1054. |
| 87<br>7-Chloro-6-(4-(dimethylamino)phenyl)-4-hydroxy-3-(2-methoxyphenoxy) quinolin-2(1H)-one | | 7-chloro-4-hydroxy-6-iodo-3-(2-methoxyphenoxy) quinolin-2(1H)-one (Intermediate 119) and (4-(dimethylamino)phenyl)boronic acid (Aldrich) | LCMS: $(M + H)^+ =$ 437; Rt = 2.77 min. HRMS: calculated for $C_{24}H_{22}ClN_2O_4$ $(M + H)^+$: 437.1268: found: 437.1275. |

TABLE 18-continued

| Example | Structure | From | Physical data |
| --- | --- | --- | --- |
| 88<br>7-Chloro-6-(4-(dimethylamino)phenyl)-4-hydroxy-3-(1H-1,2,3-triazol-1-yl) quinolin-2(1H)-one | | 7-chloro-4-hydroxy-6-iodo-3-(1H-1,2,3-triazol-1-yl)quinolin-2(1H)-one (Intermediate 120) and (4-(dimethylamino)phenyl)boronic acid (Aldrich) | LCMS: $(M + H)^+ =$ 382; Rt = 2.31 min. HRMS: calculated for $C_{19}H_{17}ClN_5O_2$ $(M + H)^+$: 382.1071; found: 382.1101. |
| 89<br>7-Chloro-6-(4-(dimethylamino)phenyl)-4-hydroxy-3-(4-methyl-1H-pyrazol-1-yl)quinolin-2(1H)-one | | 7-chloro-4-hydroxy-6-iodo-3-(4-methyl-1H-pyrazol-1-yl)quinolin-2(1H)-one (Intermediate 121) and (4-(dimethylamino)phenyl)boronic acid (Aldrich) | LCMS: $(M + H)^+ =$ 395; Rt = 2.76 min. HRMS: calculated for $C_{21}H_{20}ClN_4O_2$ $(M + H)^+$: 395.1275; found: 395.1294. |
| 90<br>7-Chloro-6-(4-(dimethylamino)phenyl)-4-hydroxy-3-(m-tolyloxy)quinolin-2(1H)-one | | 7-chloro-4-hydroxy-6-iodo-3-(m-tolyloxy)quinolin-2(1H)-one (Intermediate 122) and (4-(dimethylamino)phenyl)boronic acid (Aldrich) | LCMS: $(M + H)^+ =$ 421; Rt = 2.89 min. HRMS: calculated for $C_{24}H_{22}ClN_2O_3$ $(M + H)^+$: 421.1319; found: 421.1305. |
| 91<br>7-Chloro-6-(4-(dimethylamino)phenyl)-4-hydroxy-3-(pyridin-3-yl)quinolin-2(1H)-one | | 7-chloro-4-hydroxy-6-iodo-3-(pyridin-3-yl)quinolin-2(1H)-one (Intermediate 106) and (4-(dimethylamino)phenyl)boronic acid (Aldrich) | LCMS: $(M + H)^+ =$ 392; Rt = 2.38 min. HRMS: calculated for $C_{22}H_{19}ClN_3O_2$ $(M + H)^+$: 392.1166; found: 392.1157. |
| 92<br>3-((7-Chloro-6-(4-(dimethylamino)phenyl)-4-hydroxy-2-oxo-1,2-dihydro quinolin-3-yl)oxy) benzoic acid | | 3-((7-chloro-4-hydroxy-6-iodo-2-oxo-1,2-dihydro quinolin-3-yl)oxy)benzoic acid (Intermediate 123) and (4-(dimethylamino)phenyl)boronic acid (Aldrich) | LCMS: $(M + H)^+ =$ 451; Rt = 2.27 min. HRMS: calculated for $C_{24}H_{20}ClN_2O_5$ $(M + H)^+$: 451.1060; found: 451.1038. |
| 93<br>1-(7-Chloro-6-(4-(dimethylamino)phenyl)-4-hydroxy-2-oxo 1,2-dihydro quinolin-3-yl)-1H-pyrazole-4-carboxylic acid | | 1-(7-chloro-4-hydroxy-6-iodo-2-oxo-1,2-dihydroquinolin-3-yl)-1H-pyrazole-4-carboxylic acid (Intermediate 124) and (4-(dimethylamino)phenyl)boronic acid (Aldrich) | LCMS: $(M + H)^+ =$ 425; Rt = 2 09 min. HRMS: calculated for $C_{21}H_{18}ClN_4O_4$ $(M + H)^+$: 425.1017; found: 425.0993. |

TABLE 18-continued

| Example | Structure | From | Physical data |
|---|---|---|---|
| 94<br>7-Chloro-6-(4-(dimethylamino)phenyl)-3-(4-fluorophenoxy)-4-hydroxyquinolin-2(1H)-one | | 7-chloro-3-(4-fluorophenoxy)-4-hydroxy-6-iodoquinolin-2(1H)-one (Intermediate 125) and (4-(dimethylamino)phenyl)boronic acid (Aldrich) | LCMS: $(M + H)^+ =$ 425; Rt = 2.70 min. HRMS: calculated for $C_{23}H_{19}ClFN_2O_3$ $(M + H)^+$: 425.1068; found: 425.1031. |
| 95<br>7-Chloro-4-hydroxy-6-(2'-hydroxy-[1,1'-biphenyl]-4-yl)-3-(1H-pyrazol-1-yl)quinolin-2(1H)-one | | 7-chloro-4-hydroxy-6-iodo-3-(1H-pyrazol-1-yl)quinolin-2(1H)-one (Intermediate 112) and 4'-(4,4,5,5-tetramethyl-1,3,2-dioxaborolan-2-yl)-[1,1'-biphenyl]-2-ol (Intermediate 34) | LCMS: $(M + H)^+ =$ 430; Rt = 2.50 min. HRMS: calculated for $C_{24}H_{17}ClN_3O_3$ $(M + H)^+$: 430.0958; found: 430.0934. |
| 96<br>7-Chloro-3-(1,3-dimethyl-1H-pyrazol-5-yl)-6-(4-(dimethylamino)phenyl)-4-hydroxyquinolin-2(1H)-one | | 7-chloro-3-(1,3-dimethyl-1H-pyrazol-5-yl)-4-hydroxy-6-iodoquinolin-2(1H)-one (Intermediate 107) and (4-(dimethylamino)phenyl)boronic acid (Aldrich) | LCMS: $(M + H)^+ =$ 409; Rt = 2.38 min. HRMS: calculated for $C_{22}H_{22}ClN_4O_2$ $(M + H)^+$: 409.1431; found: 409.1461. |
| 97<br>7-Chloro-4-hydroxy-6-(4-(piperidin-1-yl)phenyl)-3-(1H-pyrazol-1-yl)quinolin-2(1H)-one | | 7-chloro-4-hydroxy-6-iodo-3-(1H-pyrazol-1-yl)quinolin-2(1H)-one (Intermediate 112) and (4-(piperidin-1-yl)phenyl)boronic acid hydrochloride (Combi-Blocks) | LCMS: $(M + H)^+ =$ 421; Rt = 2.67 min. HRMS: calculated for $C_{23}H_{22}ClN_4O_2$ $(M + H)^+$: 421.1431; found: 421.1439. |
| 98<br>7-Chloro-6-(4-(dimethylamino)phenyl)-4-hydroxy-3-((4-methylpyridin-2-yl)oxy)quinolin-2(H)-one | | 7-chloro-4-hydroxy-6-iodo-3-((4-methylpyridin-2-yl)oxy)quinolin-2(1H)-one (Intermediate 126) and (4-(dimethylamino)phenyl)boronic acid (Aldrich) | LCMS: $(M + H)^+ =$ 422; Rt = 2.23 min. HRMS: calculated for $C_{23}H_{21}ClN_3O_3$ $(M + H)^+$: 422.1271; found: 422.1272. |
| 99<br>7-Chloro-4-hydroxy-6-(1-methy-1H-indol-5-yl)-3-(3-methyl isoxazol-5-yl)quinolin-2(1H)-one | | 7-chloro-4-hydroxy-6-iodo-3-(3-methylisoxazol-5-yl)quinolin-2(1H)-one (Intermediate 99) and (1-methyl-1H-indol-5-yl)boronic acid (Combi-Blocks) | LCMS: $(M + H)^+ =$ 406; Rt = 2.40 min. HRMS: calculated for $C_{22}H_{17}ClN_3O_3$ $(M + H)^+$: 406.0958; found: 406.0960. |

TABLE 18-continued

| Example | Structure | From | Physical data |
| --- | --- | --- | --- |
| 100<br>7-Chloro-4-hydroxy-3-(3-methylisoxazol-5-yl)-6-(4-(pyrrolidin-1-yl)phenyl)quinolin-2(1H)-one | | 7-chloro-4-hydroxy-6-iodo-3-(3-methylisoxazol-5-yl)quinolin-2(1H)-one (Intermediate 99) and 1-(4-(4,4,5,5-tetramethyl-1,3,2-dioxaborolan-2-yl)phenyl) pyrrolidine (Combi-Blocks) | LCMS: $(M + H)^+ =$ 422; Rt = 2.70 min. HRMS: calculated for $C_{23}H_{21}ClN_3O_3$ $(M + H)^+$: 422.1271; found: 422.1264. |
| 101<br>7-Chloro-4-hydroxy-6-(4-methoxyphenyl)-3-(3-methylisoxazol-5-yl)quinolin-2(1H)-one | | 7-chloro-4-hydroxy-6-iodo-3-(3-methylisoxazol-5-yl)quinolin-2(1H)-one (Intermediate 99) and (4-methoxy phenyl) boronic acid (Aldrich) | LCMS: $(M + H)^+ =$ 383; Rt = 2.32 min. HRMS: calculated for $C_{20}H_{16}ClN_2O_4$ $(M + H)^+$: 383.0798; found: 383.0796. |
| 102<br>7-Chloro-4-hydroxy-6-(1-methyl-1H-indol-5-yl)-3-(pyridin-3-yl)quinolin-2(1H)-one | | 7-chloro-4-hydroxy-6-iodo-3-(pyridin-3-yl)quinolin-2(1H)-one (Intermediate 106) and (1-methyl-1H-indol-5-yl) boronic acid (Combi-Blocks) | LCMS: $(M + H)^+ =$ 402; Rt = 2.36 min. HRMS: calculated for $C_{23}H_{17}ClN_3O_2$ $(M + H)^+$: 402.1009; found: 402.1032. |
| 103<br>1-(7-Chloro-4-hydroxy-2-oxo-6-(4-(pyrrolidin-1-yl)phenyl)-1,2-dihydroquinolin-3-yl)-1H-pyrazole-4-carboxylic acid | | 1-(7-chloro-4-hydroxy-6-iodo-2-oxo-1,2-dihydro quinolin-3-yl)-1H-pyrazole-4-carboxylic acid (Intermediate 124) and 1-(4-(4,4,5,5-tetramethyl-1,3,2-dioxaborolan-2-yl) phenyl)pyrrolidine (Combi-Blocks) | LCMS: $(M + H)^+ =$ 451; Rt = 2.38 min. HRMS: calculated for $C_{23}H_{20}ClN_4O_4$ $(M + H)^+$: 451.1173; found: 451.1162. |
| 104<br>7-Chloro-4-hydroxy-3-(pyridin-3-yl)-6-(4-(pyrrolidin-1-yl)phenyl)quinolin-2(1H)-one | | 7-chloro-4-hydroxy-6-iodo-3-(pyridin-3-yl)quinolin-2(1H)-one (Intermediate 106) and 1-(4-(4,4,5,5-tetramethyl-1,3,2-dioxaborolan-2-yl)phenyl)pyrrolidine (Combi-Blocks) | LCMS: $(M + H)^+ =$ 418; Rt = 2.69 min. HRMS: calculated for $C_{24}H_{21}ClN_3O_2$ $(M + H)^+$: 418.1322; found: 418.1361. |
| 105<br>7-Chloro-4-hydroxy-3-(4-methyl-1,2,5-oxadiazol-3-yl)-6-(1-methyl-1H-indol-5-yl)quinolin-2(1H)-one | | 7-chloro-4-hydroxy-6-iodo-3-(4-methyl-1,2,5-oxadiazol-3-yl)quinolin-2(1H)-one (Intermediate 103) and (1-methyl-1H-indol-5-yl)boronic acid (Combi-Blocks) | LCMS: $(M + H)^+ =$ 407; Rt = 2.42 min. HRMS: calculated for $C_{21}H_{16}ClN_4O_3$ $(M + H)^+$: 407.0911; found: 407.0925. |

TABLE 18-continued

| Example | Structure | From | Physical data |
|---|---|---|---|
| 106 7-Chloro-4-hydroxy-3-(4-methyl-1,2,5-oxadiazol-3-yl)-6-(4-(pyrrolidin-1-yl)phenyl)quinolin-2(1H)-one | 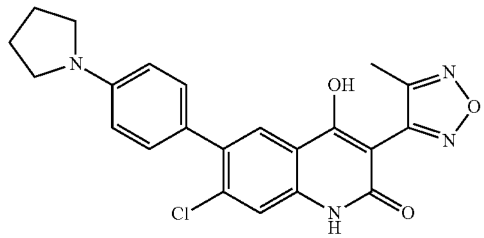 [SMILES: Cc1nonc1-c1c(O)c2cc(-c3ccc(N4CCCC4)cc3)c(Cl)cc2[nH]c1=O] | 7-chloro-4-hydroxy-6-iodo-3-(4-methyl-1,2,5-oxadiazol-3-yl)quinolin-2(1H)-one (Intermediate 103) and 1-(4-(4,4,5,5-tetramethyl-1,3,2-dioxaborolan-2-yl)phenyl)pyrrolidine (Combi-Blocks) | LCMS: $(M + H)^+ =$ 423; Rt = 2.69 min. HRMS: calculated for $C_{22}H_{20}ClN_4O_3$ $(M + H)^+$: 423.1224; found: 423.1211. |
| 107 7-Chloro-4-hydroxy-3-(pyridin-4-yl)-6-(4-(pyrrolidin-1-yl)phenyl)quinolin-2(1H)-one | 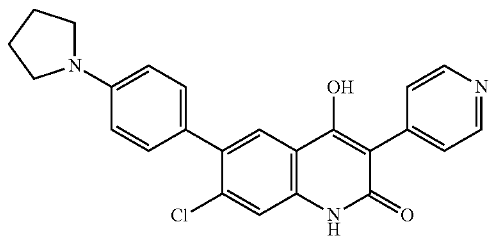 [SMILES: O=c1[nH]c2cc(Cl)c(-c3ccc(N4CCCC4)cc3)cc2c(O)c1-c1ccncc1] | 7-chloro-4-hydroxy-6-iodo-3-(pyridin-4-yl)quinolin-2(1H)-one (Intermediate 104) and 1-(4-(4,4,5,5-tetramethyl-1,3,2-dioxaborolan-2-yl)phenyl)pyrrolidine (Combi-Blocks) | LCMS: $(M + H)^+ =$ 418; Rt = 2.78 min. HRMS: calculated for $C_{24}H_{21}ClN_3O_2$ $(M + H)^+$: 418.1322; found: 418.1352. |
| 108 7-Chloro-4-hydroxy-6-(1-methyl-1H-indol-5-yl)-3-(4-methyl-1H-pyrazol-1-yl)quinolin-2(1H)-one | 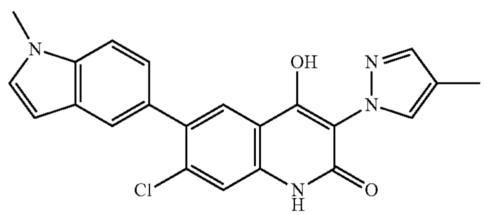 [SMILES: Cc1cnn(-c2c(O)c3cc(-c4ccc5c(ccn5C)c4)c(Cl)cc3[nH]c2=O)c1] | 7-chloro-4-hydroxy-6-iodo-3-(4-methyl-1H-pyrazol-1-yl)quinolin-2(1H)-one (Intermediate 121) and (1-methyl-1H-indol-5-yl)boronic acid (Combi-Blocks) | LCMS: $(M + H)^+ =$ 405; Rt = 2.66 min. HRMS: calculated for $C_{22}H_{18}ClN_4O_3$ $(M + H)^+$: 405.1118; found: 405.1145. |
| 109 7-Chloro-4 hydroxy-6-(1-methyl-1H-indol-5-yl)-3-(pyridin-4-yl)quinolin-2(1H)-one | 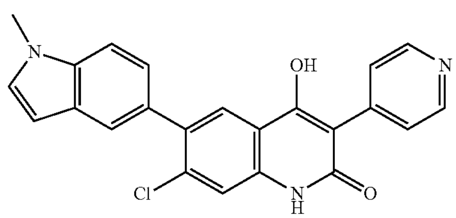 [SMILES: Cn1ccc2cc(-c3cc4c(O)c(-c5ccncc5)c(=O)[nH]c4cc3Cl)ccc21] | 7-chloro-4-hydroxy-6-iodo-3-(pyridin-4-yl)quinolin-2(1H)-one (Intermediate 104) and (1-methyl-1H-indol-5-yl)boronic acid (Combi-Blocks) | LCMS: $(M + H)^+ =$ 402; Rt = 2.47 min. HRMS: calculated for $C_{23}H_{17}ClN_3O_2$ $(M + H)^+$: 402.1009; found: 402.1018. |
| 110 7-Chloro-4-hydroxy-6-(1-methyl-1H-indol-5-yl)-3-phenoxyquinolin-2(1H)-one | 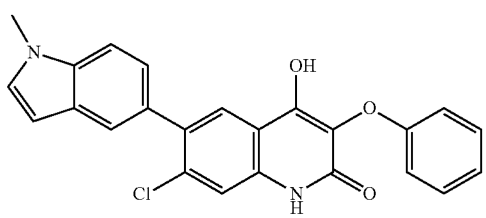 [SMILES: Cn1ccc2cc(-c3cc4c(O)c(Oc5ccccc5)c(=O)[nH]c4cc3Cl)ccc21] | 7-chloro-4-hydroxy-6-iodo-3-phenoxyquinolin-2(1H)-one (Intermediate 101) and (1-methyl-1H-indol-5-yl)boronic acid (Combi-Blocks) | LCMS: $(M + H)^+ =$ 417; Rt = 2.66 min. HRMS: calculated for $C_{24}H_{18}ClN_2O_3$ $(M + H)^+$: 417.1006; found: 417.1020. |
| 111 7-Chloro-4-hydroxy-3-(2-methoxyphenoxy)-6-(1-methyl-1H-indol-5-yl)quinolin-2(1H)-one | 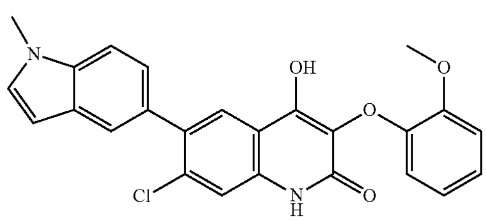 [SMILES: COc1ccccc1Oc1c(O)c2cc(-c3ccc4c(ccn4C)c3)c(Cl)cc2[nH]c1=O] | 7-chloro-4-hydroxy-6-iodo-3-(2-methoxyphenoxy)quinolin-2(1H)-one (Intermediate 119) and (1-methyl-1H-indol-5-yl)boronic acid (Combi-Blocks) | LCMS: $(M + H)^+ =$ 447; Rt = 2.71 min. HRMS: calculated for $C_{25}H_{20}ClN_2O_4$ $(M + H)^+$: 447.1111; found: 447.1150. |
| 112 7-Chloro-4-hydroxy-6-(1-methyl-1H-indol-5-yl)-3-(p-tolyloxy)quinolin-2(1H)-one | 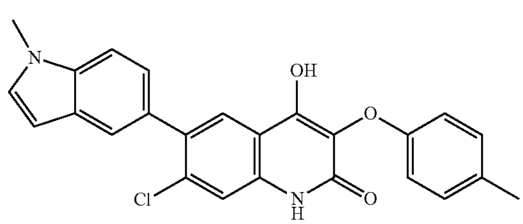 [SMILES: Cc1ccc(Oc2c(O)c3cc(-c4ccc5c(ccn5C)c4)c(Cl)cc3[nH]c2=O)cc1] | 7-chloro-4-hydroxy-6-iodo-3-(p-tolyloxy)quinolin-2(1H)-one (Intermediate 117) and (1-methyl-1H-indol-5-yl)boronic acid (Combi-Blocks) | LCMS: $(M + H)^+ =$ 431; Rt = 2.82 min. HRMS: calculated for $C_{25}H_{20}ClN_3O_3$ $(M + H)^+$: 431.1162; found: 431.1203. |

TABLE 18-continued

| Example | Structure | From | Physical data |
|---|---|---|---|
| 113<br>7-Chloro-3-(3-fluorophenoxy)-4-hydroxy-6-(1-methyl-1H-indol-5-yl)quinolin-2(1H)-one | | 7-chloro-3-(3-fluorophenoxy)-4-hydroxy-6-iodoquinolin-2(1H)-one (Intermediate 114) and (1-methyl-1H-indol-5-yl)boronic acid (Combi-Blocks) | LCMS: $(M + H)^+ =$ 435; Rt = 2.66 min. HRMS: calculated for $C_{24}H_{17}ClFN_2O_3$ $(M + H)^+$: 435.0912; found: 435.0928. |
| 114<br>6-([1,1'-Biphenyl]-4-yl)-7-chloro-4-hydroxy-3-(3-methylisoxazol-5-yl)quinolin-2(1H)-one | | 7-chloro-4-hydroxy-6-iodo-3-(3-methylisoxazol-5-yl)quinolin-2(1H)-one (Intermediate 99) and [1,1'-biphenyl]-4-yl boronic acid (Lancaster Synthesis) | LCMS $(M + H)^+ =$ 429; Rt = 2.82 min. HRMS: calculated for $C_{25}H_{18}ClN_2O_3$ $(M + H)^+$: 429.1006; found: 429.1040. |
| 115<br>7-Chloro-6-(4-cyclohexylphenyl)-4-hydroxy-3-(3-methylisoxazol-5-yl) quinolin-2(1H)-one | | 7-chloro-4-hydroxy-6-iodo-3-(3-methylisoxazol-5-yl)quinolin-2(1H)-one (Intermediate 99) and (4-cyclohexyl phenyl) boronic acid (Apollo Scientific) | LCMS: $(M + H)^+ =$ 435; Rt = 3.11 min. HRMS: calculated for $C_{25}H_{24}ClN_2O_3$ $(M + H)^+$: 435.1475; found: 435.1479. |
| 116<br>7-Chloro-6-(4-(dimethylamino) phenyl)-4-hydroxy-3-(5-methyl-1H-pyrazol-1-yl)quinolin-2(1H)-one | | 7-chloro-4-hydroxy-6-iodo-3-(5-methyl-1H-pyrazol-1-yl)quinolin-2(1H)-one (Intermediate 127) and (4-(dimethylamino)phenyl) boronic acid (Aldrich) | LCMS: $(M + H)^+ =$ 395; Rt = 2.31 min HRMS: calculated for $C_{21}H_{20}ClN_4O_2$ $(M + H)^+$: 395.1275; found: 395.1305. |
| 117<br>7-Chloro-4-hydroxy-3-(5-methyl-1H-pyrazol-1-yl)-6-(4-(pyrrolidin-1-yl)phenyl)quinolin-2(1H)-one | | 7-chloro-4-hydroxy-6-iodo-3-(5-methyl-1H-pyrazol-1-yl)quinolin-2(1H)-one (Intermediate 127) and 1-(4-(4,4,5,5-tetramethyl-1,3,2-dioxaborolan-2-yl) phenyl)pyrrolidine (Combi-Blocks) | LCMS: $(M + H)^+ =$ 421; Rt = 2.58 min. HRMS: calculated for $C_{23}H_{22}ClN_4O_2$ $(M + H)^+$: 421.1431; found; 421.1436 |
| 118<br>7-Chloro-4-hydroxy-3-(3-methylisoxazol-5-yl)-6-(naphthalen-2-yl) quinolin-2(1H)-one | | 7-chloro-4-hydroxy-6-iodo-3-(3-methylisoxazol-5-yl)quinolin-2(1H)-one (Intermediate 99) and naphthalen-2-yl boronic acid (Lancaster Synthesis) | LCMS: $(M + H)^+ =$ 403; Rt = 2.64 min. HRMS: calculated for $C_{23}H_{16}ClN_2O_3$ $(M + H)^+$: 403.0849; found: 403.0872. |

TABLE 18-continued

| Example | Structure | From | Physical data |
|---|---|---|---|
| 119<br>7-Chloro-4-hydroxy-6-(4-(3-hydroxy piperidin-1-yl)phenyl)-3-(1H-pyrazol-1-yl) quinolin-2(1H)-one | | 7-chloro-4-hydroxy-6-iodo-3-(1H-pyrazol-1-yl)quinolin-2(1H)-one (Intermediate 112) and 1-(4-(4,4,5,5-tetramethyl-1,3,2-dioxaborolan-2-yl)phenyl)piperidin-3-ol (Intermediate 32) | LCMS: $(M + H)^+$ = 437; Rt = 2.06 min. HRMS: calculated for $C_{23}H_{22}ClN_4O_3$ $(M + H)^+$: 437.1380; found: 437.1378. |
| 120<br>7-Chloro-6-(4-(dimethylamino)phenyl)-4-hydroxy-3-(phenylthio)quinolin-2(1H)-one | | 7-Chloro-4-hydroxy-6-iodo-3-(phenylthio)quinolin-2(1H)-one (Intermediate 140) and (4-(dimethylamino)phenyl)boronic acid (Aldrich) | LCMS: $(M + H)^+$ = 423; Rt = 2.56 min. HRMS: calculated for $C_{23}H_{20}ClN_2O_2S$ $(M + H)^+$: 423.0934; found: 423.0923. |
| 121<br>7-chloro-4-hydroxy-6-(4-morpholinophenyl)-3-(phenylthio)quinolin-2(1H)-one | | 7-chloro-4-hydroxy-6-iodo-3-(phenylthio)quinolin-2(1H)-one (Intermediate 140) and 4-morpholinophenyl boronic acid (Combi-Blocks) | LCMS: $(M + H)^+$ = 465; Rt = 2.35 min. HRMS: calculated for $C_{25}H_{22}ClN_2O_3S$ $(M + H)^+$: 465.1039; found: 465.1018. |
| 122<br>7-chloro-4-hydroxy-6-(4-(hydroxymethyl)phenyl)-3-(phenylthio)quinolin-2(1H)-one | | 7-chloro-4-hydroxy-6-iodo-3-(phenylthio)quinolin-2(1H)-one (Intermediate 140) and (4-(hydroxymethyl)phenyl)boronic acid (Lancaster Synthesis) | LCMS $(M + H)^+$ = 410; Rt = 2.06 min. HRMS: calculated for $C_{22}H_{17}ClNO_3S$ $(M + H)^+$: 410.0618; found: 410.0613. |
| 123<br>7-Chloro-4-hydroxy-6-(6-methoxy naphthalen-2-yl)-3-(3-methylisoxazol-5-yl) quinolin-2(1H)-one | | 7-chloro-4-hydroxy-6-iodo-3-(3-methylisoxazol-5-yl)quinolin-2(1H)-one (Intermediate 99) and (6-methoxy naphthalen-2-yl)boronic acid (Aldrich) | LCMS: $(M + H)^+$ = 433; Rt = 2.62 min HRMS: calculated for $C_{24}H_{18}ClN_2O_4$ $(M + H)^+$: 433.0955; found: 433.0987. |
| 124<br>7-Chloro-4-hydroxy-6-(4-methoxyphenyl)-3-phenoxyquinolin-2(1H)-one | | 7-chloro-4-hydroxy-6-iodo-3-phenoxyquinolin-2(1H)-one (Intermediate 101) and (4-methoxyphenyl)boronic acid (Aldrich) | LCMS $(M + H)^+$ = 394; Rt = 2.53 min. HRMS: calculated for $C_{22}H_{17}ClNO_4$ $(M + H)^+$: 394.0846: found 394.0873. |

TABLE 18-continued

| Example | Structure | From | Physical data |
|---|---|---|---|
| 125 6-(4-(1H-Pyrazol-1-yl)phenyl)-7-chloro-4-hydroxy-3-(1H-pyrazol-1-yl)quinolin-2(1H)-one | | 7-chloro-4-hydroxy-6-iodo-3-(1H-pyrazol-1-yl)quinolin-2(1H)-one (Intermediate 112) and (4-(1H-pyrazol-1-yl)phenyl)boronic acid (Combi-blocks) | LCMS: $(M + H)^+ =$ 404; Rt = 2.21 min. HRMS: calculated for $C_{21}H_{15}ClN_5O_2$ $(M + H)^+$: 404.0914; found; 404.0895. |
| 126 7-Chloro-4-hydroxy-6-(1H-indol-5-yl)-3-(1H-pyrazol-1-yl)quinolin-2(1H)-one | | 7-chloro-4-hydroxy-6-iodo-3-(1H-pyrazol-1-yl)quinolin-2(1H)-one (Intermediate 112) and (1H-indol-5-yl)boronic acid (Combi-blocks) | LCMS: $(M + H)^+ =$ 377; Rt = 2.12 min. HRMS: calculated for $C_{20}H_{14}ClN_4O_2$ $(M + H)^+$: 377.0805; found; 377.0797. |
| 127 7-Chloro-3-(1,3-dimethyl-1H-pyrazol-5-yl)-4-hydroxy-6-(1-methyl-1H-indol-5-yl)quinolin-2(1H)-one | | 7-chloro-3-(1,3-dimethyl-1H-pyrazol-5-yl)-4-hydroxy-6-iodoquinolin-2(1H)-one (Intermediate 107) and(1-methyl-1H-indol-5-yl)boronic acid (Combi-Blocks) | LCMS: $(M + H)^+ =$ 419; Rt = 2.35 min. HRMS: calculated for $C_{23}H_{20}ClN_4O_2$ $(M + H)^+$: 419.1275; found: 419.1316. |
| 128 7-Chloro-3-(4-chloro-1H-pyrazol-1-yl)-6-(4-(dimethylamino)phenyl)-4-hydroxyquinolin-2(1H)-one | | 7-chloro-3-(4-chloro-1H-pyrazol-1-yl)-4-hydroxy-6-iodoquinolin-2(1H)-one (Intermediate 108) and (4-(dimethylamino)phenyl)boronic acid (Aldrich) | LCMS: $(M + H)^+ =$ 415; Rt = 2.44 min. HRMS: calculated for $C_{20}H_{17}Cl_2N_4O_2$ $(M + H)^+$: 415.0728; found; 415.0757. |
| 129 7-Chloro-4-hydroxy-3-(3-methoxyphenoxy)-6-(1-methyl-1H-indol-5-yl)quinolin-2(1H)-one | | 7-chloro-4-hydroxy-6-iodo-3-(3-methoxyphenoxy)quinolin-2(1H)-one (Intermediate 115) and (1-methyl-1H-indol-5-yl)boronic acid (Combi-Blocks) | LCMS: $(M + H)^+ =$ 447; Rt = 2.68 min. HRMS: calculated for $C_{25}H_{20}ClN_2O_4$ $(M + H)^+$: 447.1111; found: 447.1146. |
| 130 7-Chloro-3-(1,3-dimethyl-1H-pyrazol-5-yl)-4-hydroxy-6-(4-(pyrrolidin-1-yl)phenyl)quinolin-2(1H)-one | | 7-chloro-3-(1,3-dimethyl-1H-pyrazol-5-yl)-4-hydroxy-6-iodoquinolin-2(1H)-one (Intermediate 107) and 1-(4-(4,4,5,5-tetramethyl-1,3,2-dioxaborolan-2-yl)phenyl) pyrrolidine (Combi-blocks) | LCMS $(M + H)^+ =$ 435; Rt = 2.65 min. HRMS: calculated for $C_{24}H_{24}ClN_4O_2$ $(M + H)^+$: 435.1588. found: 435.1591. |
| 131 7-Chloro-4-hydroxy-6-(1-methyl-1H-indol-5-yl)-3-(1H-1,2,4-triazol-1-yl)quinolin-2(1H)-one | | 7-chloro-4-hydroxy-6-iodo-3-(1H-1,2,4-triazol-1-yl)quinolin-2(1H)-one (Intermediate 105) and (1-methyl-1H-indol-5-yl)boronic acid (Combi-blocks) | LCMS $(M + H)^+ =$ 392; Rt = 2.27 min. HRMS: calculated for $C_{20}H_{15}ClN_5O_2$ $(M + H)^+$: 392.0914; found: 392.0926. |

TABLE 18-continued

| Example | Structure | From | Physical data |
| --- | --- | --- | --- |
| 132<br>7-Chloro-4-hydroxy-6-(1-methyl-1H-indol-5-yl)-3-(1-methyl-1H-pyrazol-4-yl)quinolin-2(1H)-one | | 7-chloro-4-hydroxy-6-iodo-3-(1-methyl-1H-pyrazol-4-yl) quinolin-2(1H)-one (Intermediate 109) and (1-methyl-1H-indol-5-yl) boronic acid (Combi-Blocks) | LCMS: $(M + H)^+ =$ 405; Rt = 2.41 min. HRMS: calculated for $C_{22}H_{18}ClN_4O_2$ $(M + H)^+$: 405.1118; found: 405.1152. |
| 133<br>7-Chloro-4-hydroxy-6-(1-methyl-1H-indol-5-yl)-3-((5-methyl pyridin-2-yl) oxy) quinolin-2(1H)-one | | 7-chloro-4-hydroxy-6-iodo-3-((5-methylpyridin-2-yl)oxy)quinolin-2(1H)-one (Intermediate 139) and (1-methyl-1H-indol-5-yl)boronic acid (Combi-Blocks) | LCMS: $(M + H)^+ =$ 432; Rt = 2.25 min. HRMS: calculated for $C_{24}H_{19}ClN_3O_3$ $(M + H)^+$: 432.1115; found: 432.1100. |
| 134<br>7-Chloro-3-(4-chloro-1H-pyrazol-1-yl)-4-hydroxy-6-(1-methyl-1H-indol-5-yl)quinolin-2(1H)-one | | 7-chloro-3-(4-chloro-1H-pyrazol-1-yl)-4-hydroxy-6-iodoquinolin-2(1H)-one (Intermediate 108) and (1-methyl-1H-indol-5-yl) boronic acid (Combi-Blocks) | LCMS: $(M + H)^+ =$ 425; Rt = 2.55 min. HRMS: calculated for $C_{21}H_{15}Cl_2N_4O_2$ $(M + H)^+$: 425.0572; found: 425.0596. |
| 135<br>7-Chloro-4-hydroxy-6-(4-(pyrrolidin-1-yl)phenyl)-3-(1H-1,2,4-triazol-1-yl)quinolin-2(1H)-one | | 7-chloro-4-hydroxy-6-iodo-3-(1H-1,2,4-triazol-1-yl)quinolin-2(1H)-one (Intermediate 105) and (4-(pyrrolidin-1-yl) phenyl)boronic acid (Combi Blocks) | LCMS: $(M + H)^+ =$ 408; Rt = 2.65 min. HRMS: calculated for $C_{21}H_{19}ClN_5O_2$ $(M + H)^+$: 408.1227; found: 408.1256. |
| 136<br>7-Chloro-4-hydroxy-6-(4-(piperidin-1-yl)phenyl)-3-(1H-1,2,4-triazol-1-yl)quinolin-2(1H)-one | | 7-chloro-4-hydroxy-6-iodo-3-(1H-1,2,4-triazol-1-yl)quinolin-2(1H)-one (Intermediate 105) and 1-(4-(4,4,5,5-tetramethyl-1,3,2-dioxaborolan-2-yl) phenyl)piperidine (Boropharm) | LCMS: $(M + H)^+ =$ 422; Rt = 2.56 min. HRMS: calculated for $C_{22}H_{21}ClN_5O_2$ $(M + H)^+$: 422.1384; found: 422.1389. |
| 137<br>7-Chloro-6-(4-(dimethylamino)phenyl)-3-(3-fluorophenyl)-4-hydroxyquinolin-2(1H)-one | | 7-chloro-3-(3-fluorophenyl)-4-hydroxy-6-iodoquinolin-2(1H)-one (Intermediate 128) and [4-(dimethylamino) phenyl]boronic acid (Aldrich) | LCMS: $(M + H)^+ =$ 409; Rt = 2.68 min. HRMS: calculated for $C_{23}H_{19}ClFN_2O_2$ $(M + H)^+$: 409.1119; found: 409.1093. |

TABLE 18-continued

| Example | Structure | From | Physical data |
|---|---|---|---|
| 138<br>7-Chloro-4-hydroxy-6-(4-(methylamino)phenyl)-3-(3-methylisoxazol-5-yl) quinolin-2(1H)-one | | 7-chloro-4-hydroxy-6-iodo-3-(3-methylisoxazol-5-yl)quinolin-2(1H)-one (Intermediate 99) and N-methyl-4-(4,4,5,5-tetramethyl-1,3,2-dioxaborolan-2-yl) aniline (Boron Molecular) | LCMS: $(M + H)^+ =$ 382; Rt = 2.16 min. HRMS: calculated for $C_{20}H_{17}ClN_3O_3$ $(M + H)^+$: 382.0958; found; 382.0966. |
| 139<br>7-Chloro-4-hydroxy-3-(4-methyl-1H-pyrazol-1-yl)-6-(4-(pyrrolidin-1-yl)phenyl)quinolin-2(1H)-one | | 7-chloro-4-hydroxy-6-iodo-3-(4-methyl-1H-pyrazol-1-yl)quinolin-2(1H)-one (Intermediate 121) and 1-(4-(4,4,5,5-tetramethyl-1,3,2-dioxaborolan-2-yl) phenyl)pyrrolidine (Combi-blocks) | LCMS: $(M + H)^+ =$ 421; Rt = 3.10 min. HRMS: calculated for $C_{23}H_{22}ClN_4O_2$ $(M + H)^+$: 421.1431; found: 421.1399. |
| 140<br>7-Chloro-4-hydroxy-3-(4-methyl-1H-pyrazol-1-yl)-6-(4-(piperidin-1-yl)phenyl)quinolin-2(1H)-one | | 7-chloro-4-hydroxy-6-iodo-3-(4-methyl-1H-pyrazol-1-yl)quinolin-2(1H)-one (Intermediate 121) and 1-(4-(4,4,5,5-tetramethyl-1,3,2-dioxaborolan-2-yl) phenyl)piperidine (Boropharm) | LCMS: $(M + H)^+ =$ 435; Rt= 3.05 min. HRMS: calculated for $C_{24}H_{24}ClN_4O_2$ $(M + H)^+$: 435.1588; found: 435.1617. |
| 141<br>7-Chloro-4-hydroxy-6-(4-(1-(hydroxymethyl)cyclopropyl)phenyl)-3-(1H-pyrazol-1-yl)quinolin-2(1H)-one | | 7-chloro-4-hydroxy-6-iodo-3-(1H-pyrazol-1-yl) quinolin-2(1H)-one (Intermediate 112) and (1-(4-(4,4,5,5-tetra methyl-1,3,2-dioxa borolan-2-yl)phenyl) cyclopropyl)methanol (Intermediate 35) | LCMS: $(M + H)^+ =$ 408; Rt = 2.14 min. HRMS: calculated for $C_{22}H_{19}ClN_3O_3$ $(M + H)^+$: 408.1115; found: 408.1098. |
| 142<br>7-Chloro-6-(1-ethy-1H-indol-5-yl)-4-hydroxy-3-(1H-pyrazol-1-yl)quinolin-2(1H)-one | | 7-chloro-4-hydroxy-6-iodo-3-(1H-pyrazol-1-yl) quinolin-2(1H)-one (Intermediate 112) and 1-ethyl-5-(4,4,5,5-tetramethyl-1,3,2-dioxaborolan-2-yl)-1H-indole (Milestone Pharmtech) | LCMS: $(M + H)^+ =$ 405; Rt = 2.55 min. HRMS: calculated for $C_{22}H_{18}ClN_4O_2$ $(M + H)^+$: 405.1118; found; 405.1113. |
| 143<br>7-Chloro-4-hydroxy-3-(4-methyl-1,2,5-oxadiazol-3-yl)-6-(4-(piperidin-1-yl)phenyl)quinolin-2(1H)-one | | 7-chloro-4-hydroxy-6-iodo-3-(4-methyl-1,2,5-oxadiazol-3-yl)quinolin-2(1H)-one (Intermediate 103) and (4-(piperidin-1-yl)phenyl) boronic acid hydrochloride (Combi-Blocks) | LCMS: $(M + H)^+ =$ 437; Rt = 2.72 min. HRMS: calculated for $C_{23}H_{22}ClN_4O_3$ $(M + H)^+$: 437.1380; found: 437.1411. |

TABLE 18-continued

| Example | Structure | From | Physical data |
|---|---|---|---|
| 144<br>7-Chloro-4-hydroxy-6-(4-(piperidin-1-yl)phenyl)-3-(pyridin-3-yl)quinolin-2(1H)-one | | 7-chloro-4-hydroxy-6-iodo-3-(pyridin-3-yl)quinolin-2(1H)-one (Intermediate 106) and (4-(piperidin-1-yl)phenyl) boronic acid hydrochloride (Combi-Blocks) | LCMS: $(M + H)^+ =$ 432; Rt = 2.65 min. HRMS: calculated for $C_{25}H_{23}ClN_3O_2$ $(M + H)^+$: 432.1479; found: 432.1489. |
| 145<br>7-Chloro-4-hydroxy-6-(4-(1-(hydroxymethyl)cyclopropyl)phenyl)-3-(3-methylisoxazol-5-yl)quinolin-2(1H)-one | | 7-chloro-4-hydroxy-6-iodo-3-(3-methylisoxazol-5-yl)quinolin-2(1H)-one (Intermediate 99) and (1-(4-(4,4,5,5-tetramethyl-1,3,2-dioxaborolan-2-yl)phenyl)cyclopropyl)methanol (Intermediate 35) | LCMS: $(M + H)^+ =$ 423; Rt = 2.21 min. HRMS: calculated for $C_{23}H_{20}ClN_2O_4$ $(M + H)^+$: 423.1111; found: 423.1121. |
| 146<br>7-Chloro-6-(4-(dimethylamino)phenyl)-4-hydroxy-3-nitroquinolin-2(1H)-one | | 7-chloro-4-hydroxy-6-iodo-3-nitroquinolin-2(1H)-one (Intermediate 143) and (4-(dimethylamino)phenyl) boronic acid (Aldrich) | LCMS: $(M + H)^+ =$ 360; Rt = 2.43 min. HRMS: calculated for $C_{17}H_{15}ClN_3O_4$ $(M + H)^+$: 360.0751; found: 360.0764. |
| 147<br>7-Chloro-6-(4-(dimethylamino)phenyl)-4-hydroxy-3-(phenylsulfonyl)quinolin-2(1H)-one | | 7-chloro-4-hydroxy-6-iodo-3-(phenylsulfonyl)quinolin-2(1H)-one (Intermediate 110) and (4-(dimethylamino)phenyl)boronic acid (Aldrich) | LCMS: $(M + H)^+ =$ 455; Rt = 2.54 min. HRMS: calculated for $C_{23}H_{20}ClN_2O_4S$ $(M + H)^+$: 455.0832; found: 455.0817. |
| 148<br>7-Chloro-4-hydroxy-6-(1-methyl-1H-indol-5-yl)-3-(phenylsulfonyl)quinolin-2(1H)-one | | 7-chloro-4-hydroxy-6-iodo-3-(phenylsulfonyl)quinolin-2(1H)-one (Intermediate 110) and (1-methyl-1H-indol-5-yl) boronic acid (Combi-Blocks) | LCMS: $(M + H)^+ =$ 465; Rt = 2.53 min. HRMS: calculated for $C_{24}H_{18}ClN_2O_4S$ $(M + H)^+$: 465.0676; found: 465.0637. |
| 149<br>7-Chloro-6-(4-(dimethylamino)phenyl)-3-(4-fluorophenyl)-4-hydroxyquinolin-2(1H)-one | | 7-chloro-3-(4-fluorophenyl)-4-hydroxy-6-iodoquinolin-2(1H)-one (Intermediate 129) and (4-(dimethylamino)phenyl)boronic acid (Aldrich) | LCMS: $(M + H)^+ =$ 409; Rt = 2.76 min. HRMS: calculated for $C_{23}H_{19}ClFN_2O_2$ $(M + H)^+$: 409.1119; found: 409.1104. |

TABLE 18-continued

| Example | Structure | From | Physical data |
|---------|-----------|------|---------------|
| 150<br>7-Chloro-6-(4-(dimethylamino)phenyl)-4-hydroxy-3-(o-tolyl)quinolin-2(1H)-one | | 7-chloro-4-hydroxy-6-iodo-3-(o-tolyl)quinolin-2(1H)-one (Intermediate 134) and (4-(dimethylamino)phenyl) boronic acid (Aldrich) | LCMS: $(M + H)^+$ = 405; Rt = 3.00 min. HRMS: calculated for $C_{24}H_{22}ClN_2O_2$ $(M + H)^+$: 405.1370; found: 405.1365. |
| 151<br>7-Chloro-6-(4-(dimethylamino)phenyl)-4-hydroxy-3-(2-methoxyphenyl)quinolin-2(1H)-one | | 7-chloro-4-hydroxy-6-iodo-3-(2-methoxyphenyl)quinolin-2(1H)-one (Intermediate 132) and (4-(dimethylamino)phenyl) boronic acid (Aldrich) | LCMS: $(M + H)^+$ = 421; Rt = 2.94 min. HRMS: calculated for $C_{24}H_{22}ClN_2O_3$ $(M + H)^+$: 421.1319; found: 421.1310. |
| 152<br>7-Chloro-3-(4-chlorophenyl)-6-(4-(dimethylamino)phenyl)-4-hydroxy quinolin-2(1H)-one | | 7-chloro-3-(4-chlorophenyl)-4-hydroxy-6-iodoquinolin-2(1H)-one (Intermediate 135) and (4-(dimethylamino)phenyl)boronic acid (Aldrich) | LCMS: $(M + H)^+$ = 425; Rt = 2.83 min. HRMS: calculated for $C_{23}H_{19}Cl_2N_2O_2$ $(M + H)^+$: 425.0823; found: 425.0864. |
| 153<br>7-Chloro-3-(3-chlorophenyl)-6-(4-(dimethylamino)phenyl)-4-hydroxy quinolin-2(1H)-one | | 7-chloro-3-(3-chlorophenyl)-4-hydroxy-6-iodoquinolin-2(1H)-one (Intermediate 136) and (4-(dimethylamino)phenyl)boronic acid (Aldrich) | LCMS: $(M + H)^+$ = 425; Rt = 2.81 min. HRMS: calculated for $C_{23}H_{19}Cl_2N_2O_2$ $(M + H)^+$: 425.0823; found: 425.0785. |
| 154<br>7-Chloro-3-(2-chlorophenyl)-6-(4-(dimethylamino)phenyl)-4-hydroxy quinolin-2(1H)-one | | 7-chloro-3-(2-chlorophenyl)-6-iodo-2-oxo-1,2-dihydro quinolin-4-olate, potassium salt (Intermediate 137) and (4-(dimethylamino)phenyl)boronic acid (Aldrich) | LCMS: $(M + H)^+$ = 425; Rt = 2.69 min. HRMS: calculated for $C_{23}H_{19}Cl_2N_2O_2$ $(M + H)^+$: 425.0823; found: 425.0808. |
| 155<br>7-Chloro-6-(4-(dimethylamino)phenyl)-3-(2-fluorophenyl)-4-hydroxy quinolin-2(1H)-one | | 7-Chloro-3-(2-fluorophenyl)-4-hydroxy-6-iodoquinolin-2(1H)-one (Intermediate 133) and (4-(dimethylamino)phenyl)boronic acid (Aldrich) | LCMS: $(M + H)^+$ = 409; Rt = 2.57 min. HRMS: calculated for $C_{23}H_{19}ClFN_2O_2$ $(M + H)^+$: 409.1119; found: 409.1132. |

TABLE 18-continued

| Example | Structure | From | Physical data |
|---|---|---|---|
| 156<br>7-Chloro-4-hydroxy-6-(1-methyl-1H-indol-6-yl)-3-(3-methyl isoxazol-5-yl)quinolin-2(1H)-one | | 7-chloro-4-hydroxy-6-iodo-3-(3-methylisoxazol-5-yl)quinolin-2(1H)-one (Intermediate 99) and 1-methyl-6-(4,4,5,5-tetramethyl-1,3,2-dioxaborolan-2-yl)-1H-indole (Maybridge) | LCMS: $(M + H)^+ =$ 406; Rt = 2.48 min. HRMS: calculated for $C_{22}H_{17}ClN_3O_3$ $(M + H)^+$: 406.0958; found: 406.0935. |
| 157<br>7-Chloro-4-hydroxy-6-(1-methylindolin-5-yl)-3-(3-methylisoxazol-5-yl)quinolin-2(1H)-one | | 7-chloro-4-hydroxy-6-iodo-3-(3-methylisoxazol-5-yl)quinolin-2(1H)-one (Intermediate 99) and 1-methyl-5-(4,4,5,5-tetramethyl-1,3,2-dioxaborolan-2-yl) indoline (Maybridge) | LCMS: $(M + H)^+ =$ 408; Rt = 2.38 min. HRMS: calculated for $C_{22}H_{19}ClN_3O_3$ $(M + H)^+$: 408.1115; found: 408.1121. |
| 158<br>7-Chloro-4-hydroxy-3-(4-methoxy-1H-pyrazol-1-yl)-6-(4-(piperidin-1-yl)phenyl)quinolin-2(1H)-one | | 7-chloro-4-hydroxy-6-iodo-3-(4-methoxy-1H-pyrazol-1-yl)quinolin-2(1H)-one (Intermediate 138) and 1-(4-(4,4,5,5-tetramethyl-1,3,2-dioxaborolan-2-yl) phenyl)piperidine (Boropharm) | LCMS: $(M + H)^+ =$ 451; Rt = 2.73 min. HRMS: calculated for $C_{24}H_{24}ClN_4O_3$ $(M + H)^+$: 451.1537; found: 451.1523. |
| 159<br>7-Chloro-6-(4-(dimethylamino) phenyl)-4-hydroxy-3-(m-tolyl)quinolin-2(1H)-one | | 7-chloro-4-hydroxy-6-iodo-3-(m-tolyl)quinolin-2(1H)-one (Intermediate 141) and [4-(dimethylamino)phenyl] boronic acid (Aldrich) | LCMS: $(M + H)^+ =$ 405; Rt = 3.00 min. HRMS: calculated for $C_{24}H_{22}ClN_2O_2$ $(M + H)^+$: 405.1370; found: 405.1334. |
| 160<br>7-Chloro-6-(4-(dimethylamino) phenyl)-4-hydroxy-3-(p-tolyl)quinolin-2(1H)-one | | 7-chloro-4-hydroxy-6-iodo-3-(p-tolyl)quinolin-2(1H)-one (Intermediate 131) and [4-(dimethylamino)phenyl] boronic acid (Aldrich) | LCMS: $(M + H)^+ =$ 405; Rt = 3.04 min. HRMS: calculated for $C_{24}H_{22}ClN_2O_2$ $(M + H)^+$: 405.1370; found: 405.1350. |
| 161<br>7-Chloro-4-hydroxy-6-(4-(1-(hydroxymethyl) cyclopropyl)phenyl)-3-(2-methoxyphenoxy) quinolin-2(1H)-one | | 7-chloro-4-hydroxy-6-iodo-3-(2-methoxyphenoxy) quinolin-2(1H)-one (Intermediate 119) and (1-(4-(4,4,5,5-tetramethyl-1,3,2-dioxaborolan-2-yl) phenyl)cyclopropyl) methanol (Intermediate 35) | LCMS: $(M + H)^+ =$ 464; Rt = 2.40 min. HRMS calculated for $C_{26}H_{23}ClNO_5$ $(M + H)^+$: 464.1265; found: 464.1259. |

TABLE 18-continued

| Example | Structure | From | Physical data |
|---|---|---|---|
| 162<br>7-chloro-4-hydroxy-6-(4-(1-(hydroxymethyl)cyclopropyl)phenyl)-3-(4-methoxy-1H-pyrazol-1-yl)quinolin-2(1H)-one | | 7-chloro-4-hydroxy-6-iodo-3-(4-methoxy-1H-pyrazol-1-yl)quinolin-2(1H)-one (Intermediate 138) and (1-(4-(4,4,5,5-tetramethyl-1,3,2-dioxaborolan-2-yl)phenyl)cyclopropyl)methanol (Intermediate 35) | LCMS: $(M + H)^+ =$ 438; Rt = 2.16 min. HRMS calculated for $C_{23}H_{21}ClN_3O_4$ $(M + H)^+$: 438.1220; found: 438.1229. |
| 163<br>7-Chloro-4-hydroxy-6-(4-(1-(hydroxymethyl)cyclopentyl)phenyl)-3-(3-methylisoxazol-5-yl) quinolin-2(1H)-one | | 7-chloro-4-hydroxy-6-iodo-3-(3-methylisoxazol-5-yl)quinolin-2(1H)-one (Intermediate 99) and (1-(4-(4,4,5,5-tetramethyl-1,3,2-dioxaborolan-2-yl)phenyl)cyclopentyl)methanol (Intermediate 36) | LCMS: $(M + H)^+ =$ 451; Rt = 2.50 min. HRMS: calculated for $C_{25}H_{24}ClN_2O_4$ $(M + H)^+$: 451.1425; found: 451.1412. |
| 164<br>7-Chloro-6-(4-(dimethylamino)phenyl)-4-hydroxy-3-(4-methoxyphenyl)quinolin-2(1H)-one | | 7-chloro-4-hydroxy-6-iodo-3-(4-methoxyphenyl)quinolin-2(1H)-one (Intermediate 130) and [4-(dimethylamino)phenyl] boronic acid (Aldrich) | LCMS: $(M + H)^+ =$ 421; Rt = 2.92 min. HRMS: calculated for $C_{24}H_{22}ClN_2O_3$ $(M + H)^+$: 421.1319; found: 421.1306. |
| 165<br>Methyl 1-(4-(7-chloro-4-hydroxy-3-(3-methylisoxazol-5-yl)-2-oxo-1,2-dihydroquinolin-6-yl)phenyl)cyclopropane carboxylate | | 7-chloro-4-hydroxy-6-iodo-3-(3-methylisoxazol-5-yl)quinolin-2(1H)-one (Intermediate 99) and (4-(1-(methoxycarbonyl)cyclopropyl)phenyl)boronic acid (Combi-Blocks) | LCMS: $(M + H)^+ =$ 451; Rt = 2.51 min. HRMS: calculated for $C_{24}H_{20}ClN_2O_5$ $(M + H)^+$: 451.1060; found: 451.1079. |
| 166<br>7-Chloro-3-(3-chlorophenyl)-4-hydroxy-6-(1-methyl-1H-indol-5-yl) quinolin-2(1H)-one | | 7-chloro-3-(3-chlorophenyl)-4-hydroxy-6-iodoquinolin-2(1H)-one (Intermediate 136) and 1-methyl-5-(4,4,5,5-tetramethyl-1,3,2-dioxaborolan-2-yl)-1H-indole (Combi-Blocks) | LCMS: $(M + H)^+ =$ 435; Rt = 2.78 min. HRMS: calculated for $C_{24}H_{17}Cl_2N_2O_2$ $(M + H)^+$: 435.0667; found: 435.0661. |
| 167<br>7-Chloro-3-(3-chlorophenyl)-4-hydroxy-6-(4-(pyrrolidin-1-yl)phenyl) quinolin-2(1H)-one | | 7-chloro-3-(3-chlorophenyl)-4-hydroxy-6-iodoquinolin-2(1H)-one (Intermediate 136) and 1-(4-(4,4,5,5-tetramethyl-1,3,2-dioxaborolan-2-yl)phenyl)pyrrolidine (Combi-blocks) | LCMS: $(M + H)^+ =$ 451; Rt = 3.14 min. HRMS: calculated for $C_{25}H_{21}Cl_2N_2O_2$ $(M + H)^+$: 451.0980; found: 451.0981. |

Example 168

7-Chloro-6-(4-(dimethylamino)phenyl)-4-hydroxy-3-(4-methoxy-1H-pyrazol-1-yl)quinolin-2(1H)-one, potassium salt

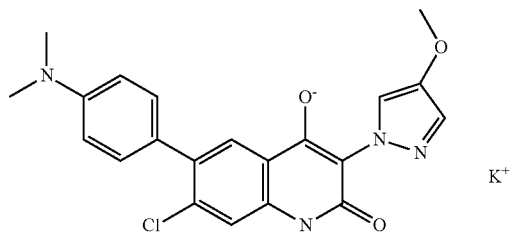 [SMILES: COc1cnn(-c2c([O-])c3cc(-c4ccc(N(C)C)cc4)c(Cl)cc3[nH]c2=O)c1 ; [K+]]

To a solution 7-chloro-4-hydroxy-6-iodo-3-(4-methoxy-1H-pyrazol-1-yl)quinolin-2(1H)-one (Intermediate 138) (250 mg, 0.599 mmol) in 1,4-dioxane (10 mL) and water (5 mL) were added (4-(dimethylamino)phenyl)boronic acid (Aldrich, 128 mg, 0.778 mmol), Pd(Ph$_3$P)$_4$ (6.92 mg, 5.99 µmol), Na$_2$CO$_3$ (190 mg, 1.796 mmol). The reaction vessel was sealed and heated at 140° C. for 40 min. After cooling, the reaction mixture was filtered and the solvent was removed under reduced pressure. The resulting material was taken up in water then acidified with 1N HCl. The solid was filtered then tritured in hot acetonitrile. The solid was filtered and dry under reduced pressure. The resulting solid was suspended in water (10 mL) and potassium hydroxide (101 mg, 1.796 mmol) was added. The reaction was stirred at 50° C. overnight. The solvent was removed under reduced pressure and the solid was tritured in hot ethanol, filtered, washed with water and dried under reduced pressure to give the title compound 7-chloro-6-(4-(dimethylamino)phenyl)-4-hydroxy-3-(4-methoxy-1H-pyrazol-1-yl) quinolin-2(1H)-one, potassium salt (131 mg, 0.277 mmol, 46.2% yield) as a white solid. LCMS: (M+H)$^+$=411; Rt=2.46 min. HRMS: calculated for C$_{21}$H$_{20}$ClN$_4$O$_3$ (M+H)$^+$: 411.1224. found: 411.1234.

Examples 169 to 173 were prepared by a method analogous to that described for Example 168.

TABLE 19

| # | Name | Structure | Description | LCMS/HRMS |
|---|------|-----------|-------------|-----------|
| 169 | 7-Chloro-4-hydroxy-6-(4-(1-(hydroxymethyl)cyclobutyl)phenyl)-3-(3-methylisoxazol-5-yl) quinolin-2(1H)-one, potassium salt | | 7-chloro-4-hydroxy-6-iodo-3-(3-methylisoxazol-5-yl)quinolin-2(1H)-one (Intermediate 99) and (1-(4-(4,4,5,5-tetramethyl-1,3,2-dioxaborolan-2-yl)phenyl)cyclobutyl)methanol (Intermediate 37) | LCMS: (M + H)$^+$ = 437; Rt = 2.39 min. HRMS: calculated for C$_{24}$H$_{22}$ClN$_2$O$_4$ (M + H)$^+$: 437.1268; found: 437.1274. |
| 170 | 7-Chloro-6-(4-(1-hydroxycyclobutyl)phenyl)-3-(3-methyl isoxazol-5-yl)-2-oxo-1,2-dihydroquinolin-4-olate, potassium salt | | 7-chloro-4-hydroxy-6-iodo-3-(3-methylisoxazol-5-yl)quinolin-2(1H)-one (Intermediate 99) and 1-(4-(4,4,5,5-tetramethyl-1,3,2-dioxaborolan-2-yl)phenyl)cyclobutanol (Intermediate 39) | LCMS: (M + H)$^+$ = 423; Rt = 2.24 min. HRMS: calculated for C$_{23}$H$_{20}$ClN$_2$O$_4$ (M + H)$^+$: 423.1111; found: 423.1112. |
| 171 | 7-Chloro-6-(1-ethyl-1H-indol-5-yl)-3-(3-methylisoxazol-5-yl)-2-oxo-1,2-dihydroquinolin-4-olate, potassium salt | | 7-chloro-4-hydroxy-6-iodo-3-(3-methylisoxazol-5-yl) quinolin-2(1H)-one (Intermediate 99) and 1-ethyl-5-(4,4,5,5-tetramethyl-1,3,2-dioxaborolan-2-yl)-1H-indole (Milestone Pharmtech) | LCMS: (M + H)$^+$ = 420; Rt = 2.51 min. HRMS: calculated for C$_{23}$H$_{19}$ClN$_3$O$_3$ (M + H)$^+$: 420.1115; found: 420.1076. |
| 172 | 7-Chloro-6-(4-ethoxyphenyl)-3-(3-methylisoxazol-5-yl)-2-oxo-1,2-dihydroquinolin-4-olate, potassium salt | | 7-chloro-4-hydroxy-6-iodo-3-(3-methylisoxazol-5-yl) quinolin-2(1H)-one (Intermediate 99) and (4-ethoxyphenyl)boronic acid (Aldrich) | LCMS: (M + H)$^+$ = 397; Rt = 2.48 min. HRMS: calculated for C$_{21}$H$_{18}$ClN$_2$O$_4$ (M + H)$^+$: 397.0955; found: 397.0954. |

TABLE 19-continued

| | | | |
|---|---|---|---|
| 173<br>7-Chloro-6-(4-(3-hydroxyoxetan-3-yl)phenyl)-3-(3-methyl isoxazol-5-yl)-2-oxo-1,2-dihydroquinolin-4-olate, potassium salt | (structure) | 7-chloro-4-hydroxy-6-iodo-3-(3-methylisoxazol-5-yl)quinolin-2(1H)-one (Intermediate 99) and 3-(4-(4,4,5,5-tetramethyl-1,3,2-dioxaborolan-2-yl)phenyl)oxetan-3-ol (Intermediate 40) | LCMS: (M + H)$^+$ = 425; Rt = 1.85 min. HRMS: calculated for $C_{22}H_{18}ClN_2O_5$ (M + H)$^+$: 425.0904; found: 425.0912. |

Example 174

7-Chloro-6-(4-(dimethylamino)phenyl)-4-hydroxy-3-(3-methyl-1H-pyrazol-1-yl)quinolin-2(1H)-one

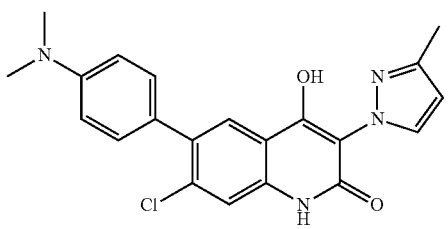 [SMILES: Cc1ccn(-c2c(O)c3cc(-c4ccc(N(C)C)cc4)c(Cl)cc3[nH]c2=O)n1]

To a solution of methyl 4-amino-6-chloro-4'-(dimethylamino)-[1,1'-biphenyl]-3-carboxylate, (Intermediate 47) (416 mg, 1.365 mmol) and ethyl 2-(3-methyl-1H-pyrazol-1-yl)acetate (Alinda Chemical Ltd, 275 mg, 1.638 mmol) in THF (8.4 mL) stirred under nitrogen at room temperature was added KHMDS 1M/THF (4.09 mL, 4.09 mmol) The reaction mixture was stirred at room temperature for 20 min before being quenched with MeOH, evaporated in vacuo and taken up in water (10 mL). The aqueous layer was acidified to pH=6-7 and filtered. The precipitate obtained was washed with acetonitrile, then with diisopropyl ether and filtered to give the title compound 7-chloro-6-(4-(dimethylamino)phenyl)-4-hydroxy-3-(3-methyl-1H-pyrazol-1-yl)quinolin-2(1H)-one (415 mg, 73.2% yield) as a light yellow powder. LCMS: (M+H)$^+$=395; Rt=2.68 min. HRMS: calculated for $C_{21}H_{20}ClN_4O_2$ (M+H)$^+$: 395.1275. found: 395.1283.

Examples 175 to 181 were prepared by methods analogous to that described for Example 174.

TABLE 20

| Example | Structure | From | Physical data |
|---|---|---|---|
| 175<br>7-Chloro-6-(4-(dimethylamino)phenyl)-4-hydroxy-3-((4-methoxypyridin-2-yl)oxy)quinolin-2(1H)-one | (structure) | methyl 4-amino-6-chloro-4'-(dimethylamino)-[1,1'-biphenyl]-3-carboxylate (Intermediate 47) and ethyl 2-((4-methoxypyridin-2-yl)oxy)acetate (Intermediate 19) | LCMS: (M + H)$^+$ = 438; Rt = 2.24 min. HRMS: calculated for $C_{23}H_{21}ClN_3O_4$ (M + H)$^+$: 438.1220; found: 438.1251. |
| 176<br>7-Chloro-4-hydroxy-3-(4-methoxyphenoxy)-6-(1-methyl-1H-indol-5-yl)quinolin-2(1H)-one | (structure) | methyl 2-amino-4-chloro-5-(1-methyl-1H-indol-5-yl)benzoate (Intermediate 45) and ethyl 2-(4-methoxyphenoxy)acetate (Anichem Inc.) | LCMS: (M + H)$^+$ = 447; Rt = 2.69 min. HRMS: calculated for $C_{25}H_{20}ClN_2O_4$ (M + H)$^+$: 447.1111; found: 447.1093. |
| 177<br>7-Chloro-6-(4-(dimethylamino)phenyl)-4-hydroxy-3-((5-methylpyridin-2-yl)oxy)quinolin-2(1H)-one | (structure) | methyl 4-amino-6-chloro-4'-(dimethylamino)-[1,1'-biphenyl]-3-carboxylate (Intermediate 47) and ethyl 2-((5-methylpyridin-2-yl)oxy)acetate (Intermediate 20) | LCMS: (M + H)$^+$ = 422; Rt = 2.27 min. HRMS; calculated for $C_{23}H_{21}ClN_3O_3$ (M + H)$^+$: 422.1271; found: 422.1266. |

TABLE 20-continued

| Example | Structure | From | Physical data |
|---|---|---|---|
| 178<br>7-Chloro-6-(2'-fluoro-[1,1'-biphenyl]-4-yl)-4-hydroxy-3-(1H-pyrazol-1-yl)quinolin-2(1H)-one | | methyl 4-amino-6-chloro-2''-fluoro-[1,1':4',1''-terphenyl]-3-carboxylate (Intermediate 53) and ethyl 2-(1H-pyrazol-1-yl)acetate (Apollo Scientific) | LCMS: $(M + H)^+ = 432$; Rt = 2.76 min. HRMS: calculated for $C_{24}H_{16}ClFN_3O_2$ $(M + H)^+$: 432.0915; found: 432.0933. |
| 179<br>7-Chloro-4-hydroxy-6-(4-(5-methylthiophen-2-yl)phenyl)-3-(1H-pyrazol-1-yl)quinolin-2(1H)-one | | methyl 4-amino-6-chloro-4'-(5-methylthiophen-2-yl)-[1,1'-biphenyl]-3-carboxylate (Intermediate 51) and ethyl 2-(1H-pyrazol-1-yl)acetate (Apollo Scientific) | LCMS: $(M + H)^+ = 434$; Rt = 2.87 min. HRMS: calculated for $C_{23}H_{17}ClN_3O_2S$ $(M + H)^+$: 434.0730; found: 434.0737. |
| 180<br>3-(4-Bromo-1H-pyrazol-1-yl)-7-chloro-6-(4-(dimethylamino)phenyl)-4-hydroxy quinolin-2(1H)-one | | methyl 4-amino-6-chloro-4'-(dimethylamino)-[1,1'-biphenyl]-3-carboxylate (Intermediate 47) and ethyl 2-(4-bromo-1H-pyrazol-1-yl)acetate (Intermediate 22) | LCMS: $(M + H)^+ = 459$-461; Rt = 2.46 min. HRMS: calculated for $C_{20}H_{17}BrClN_4O_2$ $(M + H)^+$: 459.0223; found: 459.0237. |
| 181<br>3-(4-Bromo-1H-pyrazol-1-yl)-7-chloro-4-hydroxy-6-(4-(piperidin-1-yl)phenyl)quinolin-2(1H)-one | | methyl 4-amino-6-chloro-4'-(piperidin-1-yl)-[1,1'-biphenyl]-3-carboxylate (Intermediate 48) and ethyl 2-(4-bromo-1H-pyrazol-1-yl)acetate (Intermediate 22) | LCMS: $(M + H)^+ = 499$-501; Rt = 2.76 min. HRMS: calculated for $C_{23}H_{21}BrClN_4O_2$ $(M + H)^+$: 499.0536; found: 499.0534. |

Example 182

6-[4-(2-Amino-1,3-thiazol-4-yl)phenyl]-7-chloro-4-hydroxy-3-phenylquinolin-2(1H)-one hydrochloride

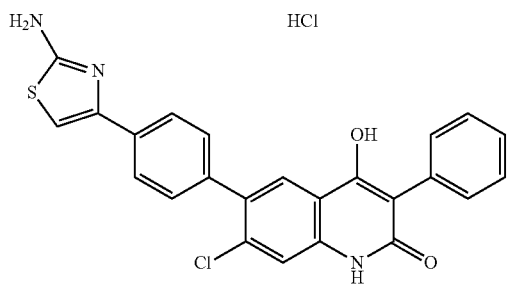 [SMILES: Nc1nc(-c2ccc(-c3cc4c(O)c(-c5ccccc5)c(=O)[nH]c4cc3Cl)cc2)cs1 ; Cl]

To a solution of N-{4-[4-(7-chloro-4-hydroxy-2-oxo-3-phenyl-1,2-dihydro-6-quinolinyl)phenyl]-1,3-thiazol-2-yl}acetamide (Example 9) (1.7 g, 3.81 mmol) in ethanol (20 mL) was added concentrated hydrochloric acid (5.72 mL, 57.2 mmol) and the reaction mixture was stirred at 100° C. for 4 h. After cooling, the reaction mixture was filtered. The solid was washed with water and dried under reduced pressure to give the title compound 6-[4-(2-amino-1,3-thiazol-4-yl)phenyl]-7-chloro-4-hydroxy-3-phenylquinolin-2(1H)-one hydrochloride (1.45 g, 3.01 mmol, 79% yield) as a grey powder. LCMS: $(M+H)^+=446$; Rt=2.44 min. HRMS calculated for $C_{24}H_{15}ClN_3O_2S$ $(M-H)^+$: 444.0574. found: 444.0532.

Examples 183 and 186 were prepared by methods analogous to that described for Example 182.

TABLE 21

| Example | Formula | From | Physical data |
|---|---|---|---|
| 183 6-[4-(2-Amino-1,3-thiazol-4-yl)phenyl]-7-chloro-4-hydroxy-3-[3-(methyloxy)phenyl]quinolin-2(1H)-one | | N-[4-(4-{7-Chloro-4-hydroxy-3-[3-(methyloxy)phenyl]-2-oxo-1,2-dihydro-6-quinolinyl}phenyl)-1,3-thiazol-2-yl]acetamide (Intermediate 97) | LCMS: $(M + H)^+$ = 476; Rt = 2.46 min. HRMS: calculated for $C_{25}H_{19}ClN_3O_3S$ $(M + H)^+$: 476.0836; found: 476.0831. |
| 184 6-(4-(2-Amino-1,3-thiazol-4-yl)phenyl)-7-chloro-4-hydroxy-3-(3-methylisoxazol-5-yl)quinolin-2(1H)-one | | N-(4-(4-(7-chloro-4-hydroxy-3-(3-methyl isoxazol-5-yl)-2-oxo-1,2-dihydroquinolin-6-yl)phenyl)thiazol-2-yl)acetamide (Intermediate 144) | LCMS: $(M + H)^+$ = 451; Rt = 2.21 min. HRMS: calculated For $C_{22}H_{16}ClN_4O_3S$ $(M + H)^+$: 451.0631; found: 451.0627. |
| 185 6-(4-(2-Amino-1,3-thiazol-4-yl)phenyl)-7-chloro-4-hydroxy-3-(3-methoxyphenyl)quinolin-2(1H)-one | | N-(4-(4-(7-chloro-4-hydroxy-2-oxo-3-phenoxy-1,2-dihydroquinolin-6-yl)phenyl)thiazol-2-yl)acetamide (Example 60) | LCMS: $(M + H)^+$ = 462; Rt = 2.39 min. HRMS: calculated for $C_{24}H_{17}ClN_3O_3S$ $(M + H)^+$: 462.0679; found: 462.0681. |
| 186 6-(4-(2-Amino-1,3-thiazol-4-yl)phenyl)-7-chloro-4-hydroxy-3-(pyridin-3-yl)quinolin-2(1H)-one | | N-(4-(4-(7-chloro-4-hydroxy-2-oxo-3-(pyridin-3-yl)-1,2-dihydroquinolin-6-yl)phenyl)thiazol-2-yl)acetamide (Intermediate 145) | LCMS: $(M + H)^+$ = 447; Rt = 2.15 min. HRMS: calculated for $C_{23}H_{16}ClN_4O_2S$ $(M + H)^+$: 447.0682; found: 447.0714. |

Example 187

6-[4-(2-Amino-1,3-thiazol-4-yl)phenyl]-7-chloro-4-hydroxy-3-(1H-pyrazol-1-yl)-2(1H)-quinolinone hydrochloride

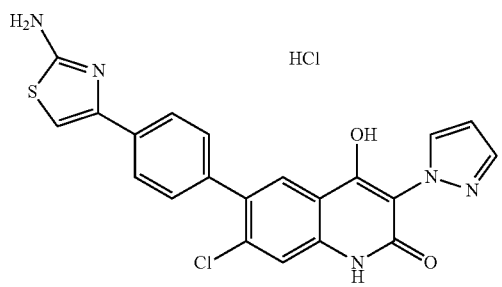 [SMILES: Nc1nc(-c2ccc(-c3cc4c(O)c(-n5cccn5)c(=O)[nH]c4cc3Cl)cc2)cs1 ; Cl]

7-Chloro-4-hydroxy-6-iodo-3-(1H-pyrazol-1-yl)quinolin-2(1H)-one (Intermediate 112) (300 mg, 0.774 mmol), N-(4-(4-(4,4,5,5-tetramethyl-1,3,2-dioxaborolan-2-yl)phenyl)thiazol-2-yl) acetamide (Intermediate 31) (264 mg, 1.0 mmol), Pd(Ph$_3$P)$_4$ (8.94 mg, 7.74 μmol), 1M Na$_2$CO$_3$ (2.32 mL, 2.32 mmol) were mixed in 1,4-dioxane (3 mL). The reaction mixture was stirred at 120° C. for 1 h under microwave irradiation then cooled to room temperature and filtered through celite. The filtrate was diluted with water and extracted twice with DCM. The organic layers were combined, dried over Na$_2$SO$_4$ and concentrated under reduced pressure. The crude product was then diluted with EtOH and concentrated hydrochloric acid and the resulting mixture was heated at 90° C. overnight. The reaction mixture was cooled to room temperature then filtered. The powder was washed successively with water, EtOH and Et$_2$O to afford the title compound 6-[4-(2-amino-1,3-thiazol-4-yl)phenyl]-7-chloro-4-hydroxy-3-(1H-pyrazol-1-yl)-2(1H)-quinolinone hydrochloride (70 mg, 19.1% yield) as a grey powder. LCMS: (M+H)$^+$=436; Rt=2.14 min. HRMS: calculated for C$_{21}$H$_{13}$ClN$_5$O$_2$S (M−H)$^+$: 434.0479. found: 434.0435.

Examples 188 to 190 were prepared by methods analogous to that described for Example 187.

TABLE 22

| Example | Structure | From | Physical data |
|---|---|---|---|
| 188<br>6-(4-(2-Amino-1,3-thiazol-4-yl)phenyl)-7-chloro-4-hydroxy-3-(pyridin-4-yl)quinolin-2(1H)-one | | 7-chloro-4-hydroxy-6-iodo-3-(pyridin-4-yl)quinolin-2(1H)-one (Intermediate 104) and N-(4-(4-(4,4,5,5-tetramethyl-1,3,2-dioxaborolan-2-yl) phenyl) thiazol-2-yl)acetamide (Intermediate 31) | LCMS: (M + H)$^+$ = 447; Rt = 2.23 min. HRMS: calculated for C$_{23}$H$_{16}$ClN$_4$O$_2$S (M + H)$^+$: 447.0682; found: 447.0678. |
| 189<br>6-(4-(2-Amino-1,3-thiazol-4-yl)phenyl)-7-chloro-4-hydroxy-3-(4-methyl-1H-pyrazol-1-yl)quinolin-2(1H)-one | | 7-chloro-4-hydroxy-6-iodo-3-(4-methyl-1H-pyrazol-1-yl)quinolin-2(1H)-one (Intermediate 121) and N-(4-(4-(4,4,5,5-tetramethyl-1,3,2-dioxaborolan-2-yl) phenyl)thiazol-2-yl) acetamide (Intermediate 31) | LCMS: (M + H)$^+$ = 450; Rt = 2.29 min. HRMS: calculated for C$_{22}$H$_{17}$ClN$_5$O$_2$S (M + H)$^+$: 450.0791; found: 450.0822. |
| 190<br>6-(4-(2-Amino-1,3-thiazol-4-yl)phenyl)-7-chloro-4-hydroxy-3-(1H-1,2,3-triazol-1-yl)quinolin-2(1H)-one | | 7-chloro-4-hydroxy-6-iodo-3-(1H-1,2,3-triazol-1-yl)quinolin-2(1H)-one (Intermediate 120) and N-(4-(4-(4,4,5,5-tetramethyl-1,3,2-dioxaborolan-2-yl) phenyl)thiazol-2-yl) acetamide (Intermediate 31) | LCMS: (M + H)$^+$ = 437; Rt = 2.11 min. HRMS: calculated for C$_{20}$H$_{14}$ClN$_6$O$_2$S (M + H)$^+$: 437.0587; found: 437.0604. |

Example 191

7-Chloro-4-hydroxy-6-(1-methyl-1H-indol-5-yl)quinolin-2(1H)-one

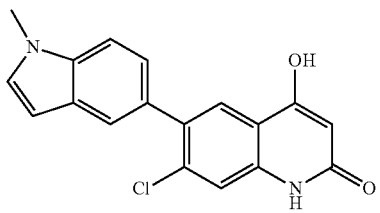 [SMILES: Cn1ccc2cc(-c3cc4c(O)cc(=O)[nH]c4cc3Cl)ccc21]

To a solution of ethyl 7-chloro-4-hydroxy-6-(1-methyl-1H-indol-5-yl)-2-oxo-1,2-dihydro-3-quinolinecarboxylate (Example 27) (50 mg, 0.126 mmol) in ethanol (5 mL) was added sodium hydroxide 1N (0.315 mL, 0.315 mmol). The reaction mixture was stirred at 80° C. for 2 h. Additional solution of 1N sodium hydroxide was added (1 mL) and the reaction mixture was stirred at 160° C. for another 30 nm under microwave irradiation. After cooling, the solvent was evaporated and the mixture was dissolved in water and acidified with 1N HCl. The resulting solid was filtered, dried then triturated in hot acetonitrile, filtered and dried to give the title compound 7-chloro-4-hydroxy-6-(1-methyl-1H-indol-5-yl)quinolin-2(1H)-one (16 mg, 0.049 mmol, 39.1% yield) as a cream solid. LCMS: (M+H)$^+$=325; Rt=2.66 min. HRMS: calculated for $C_{18}H_{14}ClN_2O_2$ (M+H)$^+$: 325.0744. found: 325.0739.

Example 192 was prepared by a method analogous to that described for Example 191.

quinolinecarboxylate (Example 28) (150 mg, 0.322 mmol) in THF (4 mL) and water (2 mL) was added lithium hydroxide (100 mg, 2.4 mmol). The reaction mixture was stirred 48 h at 50° C. and 24 h at room temperature before being cooled down. The mixture was then evaporated, acidified with 1N HCl, filtered and dried. The resulting solid was triturated in hot acetonitrile, filtered and dried to give the title compound 7-chloro-4-hydroxy-6-[2'-hydroxy-3'-(methyloxy)-4-biphenylyl]-2-oxo-1,2-dihydro-3-quinolinecarboxylic acid (25 mg, 0.057 mmol, 17.7% yield) as cream solid. LCMS: (M−H)$^+$=436; Rt=2.89 min. HRMS: calculated for $C_{23}H_{15}ClNO_6$ (M−H)$^+$: 436.0588. found: 436.0560.

Example 194

1-(4-(7-Chloro-3-(3-methylisoxazol-5-yl)-4-oxido-2-oxo-1,2-dihydroquinolin-6-yl)phenyl)cyclopropanecarboxylate, bis potassium salt

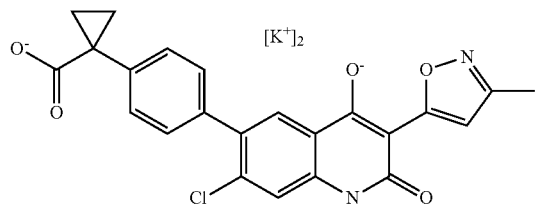

TABLE 23

| Example | Structure | From | Physical data |
|---|---|---|---|
| 192<br>7-Chloro-4-hydroxy-6-[4-(4-morpholinyl)phenyl]quinolin-2(1H)-one | 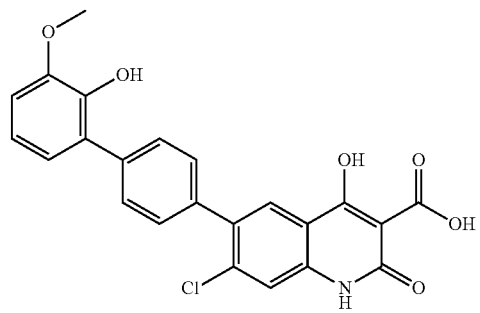 | ethyl 7-chloro-4-hydroxy-6-[4-(4-morpholinyl)phenyl]-2-oxo-1,2-dihydro-3-quinoline carboxylate (Example 30) | LCMS: (M + H)$^+$ = 357; Rt = 2.27 min. HRMS: calculated for $C_{19}H_{18}ClN_2O_3$ (M + H)$^+$: 357.1006; found: 357.1006. |

Example 193

7-chloro-4-hydroxy-6-[2'-hydroxy-3'-(methyloxy)-4-biphenylyl]-2-oxo-1,2-dihydro-3-quinolinecarboxylic acid To a suspension of ethyl 7-chloro-4-hydroxy-6-[2'-hydroxy-3'-(methyloxy)-4-biphenylyl]-2-oxo-1,2-dihydro-3-

To a suspension of methyl 1-(4-(7-chloro-4-hydroxy-3-(3-methylisoxazol-5-yl)-2-oxo-1,2-dihydroquinolin-6-yl)phenyl)cyclopropanecarboxylate (Example 165) (150 mg, 0.333 mmol) in tetrahydrofuran was added KHMDS 1M/THF (665 µl, 0.665 mmol), and the suspension was stirred at room temperature overnight. One additional equivalent of KHMDS 1M/THF was added and the reaction was stirred at room temperature for 2 h. The precipitate was filtered and washed with THF. The gummy solid was taken up in refluxing EtOH then filtered, washed with EtOH, IPr$_2$O and pentane to give the title compound 1-(4-(7-chloro-3-(3-methylisoxazol-5-yl)-4-oxido-2-oxo-1,2-dihydroquinolin-6-yl)phenyl)cyclopropanecarboxylate, 2 potassium salt (85 mg, 0.166 mmol, 49.6% yield) as off-white powder. LCMS: (M+H)$^+$=437; Rt=1.72 min. HRMS: calculated for $C_{23}H_{17}ClN_2O_5$ (M+H)$^+$: 437.0904. found: 437.0912.

Example 195

1-(7-Chloro-4-oxido-2-oxo-6-(4-(piperidin-1-yl)phenyl)-1,2-dihydroquinolin-3-yl)-1H-pyrazole-4-carboxylate, bis potassium salt

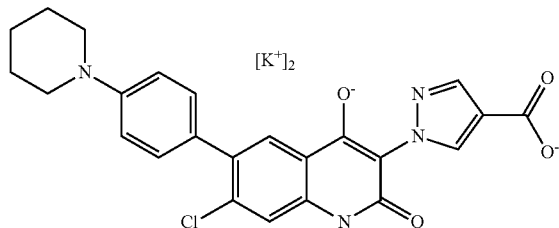

To a solution of methyl 1-(2-((2-chloro-5-(methoxycarbonyl)-4'-(piperidin-1-yl)-[1,1'-biphenyl]-4-yl)amino)acetyl)-1H-pyrazole-4-carboxylate (Intermediate 90) (400 mg, 0.783 mmol) in tetrahydrofuran (10 mL) stirred under nitrogen at room temperature was added a solution of KHMDS 1M/THF (2.348 mL, 2.348 mmol) in one charge. The reaction mixture was stirred at room temperature for 40 minutes. Solvent was removed under reduced pressure and the resulting material was taken up in water then acidified with HCl 1N. The solid was filtered. The solid was triturated with hot EtOH and hot MeCN. The solid was filtered and dried under reduced pressure to give the ester intermediate. To a suspension of this intermediate in water was added potassium hydroxide (176 mg, 3.13 mmol) and the reaction mixture was stirred at 50° C. overnight. The solvent was removed under reduced pressure. The resulting material was triturated in hot EtOH, filtered, washed with water and dried to give the title compound 1-(7-chloro-4-oxido-2-oxo-6-(4-(piperidin-1-yl)phenyl)-1,2-dihydroquinolin-3-yl)-1H-pyrazole-4-carboxylate, 2 potassium salt (61 mg, 0.101 mmol, 12.96% yield) as a yellow solid. LCMS: (M+H)$^+$=465; Rt=2.34 min. HRMS: calculated for $C_{24}H_{22}ClN_4O_4$ (M+H)$^+$: 465.1329. found: 465.1308.

Example 196

7-Chloro-3-(3-chlorophenyl)-4-hydroxy-6-(4-(piperidin-1-yl)phenyl) quinolin-2(1H)-one

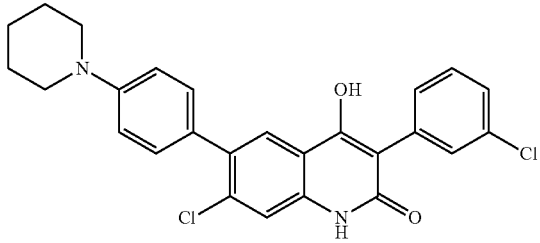 [SMILES: O=c1[nH]c2cc(Cl)c(-c3ccc(N4CCCCC4)cc3)cc2c(O)c1-c1cccc(Cl)c1]

To a solution of methyl 6-chloro-4-(2-(3-chlorophenyl)acetamido)-4'-(piperidin-1-yl)-[1',1'-biphenyl]-3-carboxylate (Intermediate 65) (532 mg, 1.070 mmol) in tetrahydrofuran (10 mL) stirred under nitrogen at room temperature was added KHMDS 1M/THF (3.21 mL, 3.21 mmol). The reaction mixture was stirred at room temperature for 20 minutes. The mixture was quenched with MeOH and evaporated in vacuo. The residue was taken in water and acidified to pH=5 then filtered. The resulting solid was triturated with acetonitrile then with diethyl ether, filtered and dried to give the title compound 7-chloro-3-(3-chlorophenyl)-4-hydroxy-6-(4-(piperidin-1-yl)phenyl)quinolin-2(1H)-one (451 mg, 0.921 mmol, 95% yield) as beige powder. LCMS: (M+H)$^+$=465; Rt=3.13 min. HRMS calculated for $C_{26}H_{23}Cl_2N_2O_2$ (M+H)$^+$: 465.1136. found: 465.1131.

Example 42b

7-Chloro-6-(4-(dimethylamino)phenyl)-3-(3-methylisoxazol-5-yl)-2-oxo-1,2-dihydroquinolin-4-olate, potassium salt

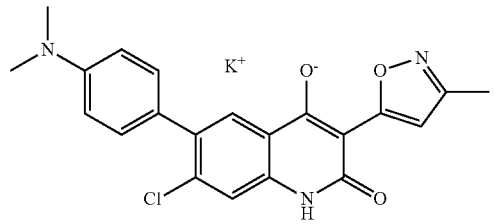

To a solution of methyl 6-chloro-4'-(dimethylamino)-4-(2-(3-methylisoxazol-5-yl)acetamido)-[1,1'-biphenyl]-3-carboxylate (Intermediate 146) (3 g, 7.01 mmol) in tetrahydrofuran (50 mL) at 60° C. was added dropwise KHMDS 1M/THF (18.23 mL, 18.23 mmol). The reaction mixture was stirred for 1 h at 60° C. After cooling, the precipitate was filtered, washed with THF and dried. The crude salt was recrystallized in EtOH/water mixture. The solid filtered and dried to give the title compound 7-chloro-6-(4-(dimethylamino)phenyl)-3-(3-methylisoxazol-5-yl)-2-oxo-1,2-dihydroquinolin-4-olate, potassium salt (1.9 g, 4.38 mmol, 62.4% yield) as white solid. LCMS: (M+H)$^+$=396; Rt=2.41 min. HRMS: calculated for $C_{21}H_{19}ClN_3O_3$ (M+H)$^+$: 396.1115. found: 396.1126.

Example 42c

7-Chloro-6-(4-(dimethylamino)phenyl)-3-(3-methylisoxazol-5-yl)-2-oxo-1,2-dihydroquinolin-4-olate, sodium salt

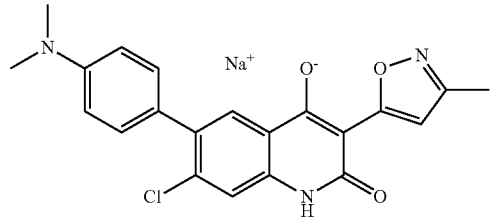

To a solution of methyl 6-chloro-4'-(dimethylamino)-4-(2-(3-methylisoxazol-5-yl)acetamido)-[1,1'-biphenyl]-3-carboxylate (Intermediate 146) (3 g, 7.01 mmol) in tetrahydrofuran (50 mL) at 60° C. was added dropwise NaHMDS 1M/THF (18.23 mL, 18.23 mmol). The reaction mixture was stirred for 2 h after the end of addition. After cooling, the precipitate was filtered, washed with THF and dried. The crude salt was recrystallized in EtOH/water mixture. The solid filtered and dried to give the title compound 7-chloro-6-(4-(dimethylamino)phenyl)-3-(3-methylisoxazol-5-yl)-2-oxo-1,2-dihydroquinolin-4-olate, sodium salt (2.25 g, 5.39 mmol, 77% yield) as off-white solid. LCMS: (M+H)$^+$=396; Rt=2.42 min. HRMS: calculated for $C_{21}H_{19}ClN_3O_3$ (M+H)$^+$: 396.1115. found: 396.1111.

Example 42d

7-Chloro-6-(4-(dimethylamino)phenyl)-3-(3-methyl-isoxazol-5-yl)-2-oxo-1,2-dihydroquinolin-4-olate, 2-amino-2-(hydroxymethyl)-1,3-propanediol salt

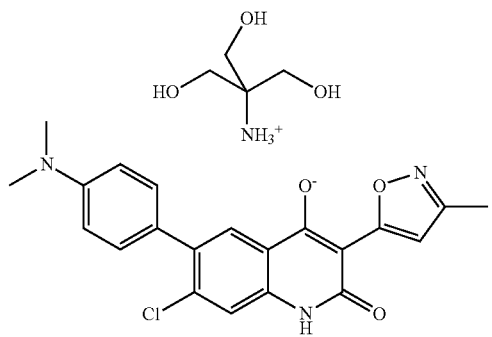

To a suspension of 7-chloro-6-(4-(dimethylamino)phenyl)-4-hydroxy-3-(3-methylisoxazol-5-yl) quinolin-2(1H)-one (Example 42) (2 g, 5.05 mmol) in methanol (20 mL) was added a solution of tris(hydroxymethyl)aminomethane (0.612 g, 5.05 mmol) in methanol (20 mL). The reaction mixture was stirred at room temperature overnight. The reaction mixture was filtered dried to give the title compound 7-chloro-6-(4-(dimethylamino)phenyl)-3-(3-methylisoxazol-5-yl)-2-oxo-1,2-dihydroquinolin-4-olate, 2-amino-2-(hydroxymethyl)-1,3-propanediol salt (2.2 g, 4.26 mmol, 84% yield) as white solid. LCMS: (M+H)$^+$=396; Rt=2.39 min. HRMS: calculated for $C_{21}H_{19}ClN_3O_3$ (M+H)$^+$: 396.1115. found: 396.1133.

Example 42e

7-Chloro-6-(4-(dimethylamino)phenyl)-3-(3-methyl-isoxazol-5-yl)-2-oxo-1,2-dihydroquinolin-4-olate, N-2-hydroxyethyl-N,N-dimethylmethanaminium salt

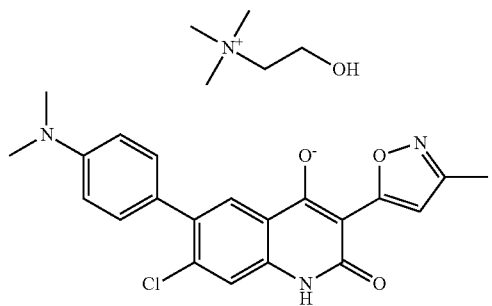

To a suspension of 7-chloro-6-(4-(dimethylamino)phenyl)-4-hydroxy-3-(3-methylisoxazol-5-yl) quinolin-2(1H)-one (Example 42) (1.5 g, 3.79 mmol) in methanol (8 mL) was added choline hydroxide 46% wt in water (1.997 g, 7.58 mmol). The reaction mixture was stirred at room temperature overnight. The reaction mixture was filtered, washed with methanol and dried. The resulting solid was recrystallized with acetonitrile to give the title compound 7-chloro-6-(4-(dimethylamino)phenyl)-3-(3-methylisoxazol-5-yl)-2-oxo-1,2-dihydroquinolin-4-olate, N-2-hydroxyethyl-N,N-dimethylmethanaminium salt (1.2 g, 2.40 mmol, 63.5% yield) as off-white solid. LCMS: (M+H)$^+$=396; Rt=2.39 min. HRMS: calculated for $C_{21}H_{19}ClN_3O_3$ (M+H)$^+$: 396.1115. found: 396.1092.

Example 42f

7-Chloro-6-(4-(dimethylamino)phenyl)-3-(3-methyl-isoxazol-5-yl)-2-oxo-1,2-dihydroquinolin-4-olate, hemi-1,2-ethanediamine salt

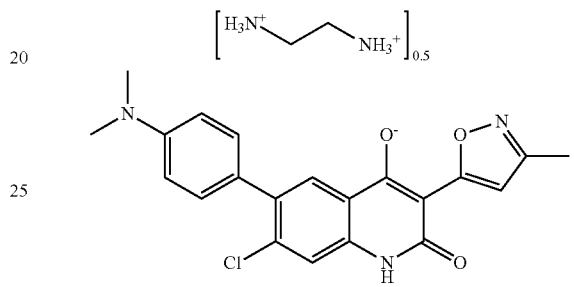

To a suspension of 7-chloro-6-(4-(dimethylamino)phenyl)-4-hydroxy-3-(3-methylisoxazol-5-yl) quinolin-2(1H)-one (Example 42) (300 mg, 0.758 mmol) in THF (8 mL) was added ethylenediamine (137 mg, 2.27 mmol). The reaction mixture was stirred at room temperature overnight. The reaction mixture was filtered, washed and dried. The resulting solid was recrystallized with ethanol/water mixture, filtered and dried to give the title compound 7-chloro-6-(4-(dimethylamino)phenyl)-3-(3-methylisoxazol-5-yl)-2-oxo-1,2-dihydroquinolin-4-olate, hemi-1,2-ethanediamine salt (230 mg, 0.541 mmol, 71.4% yield) as light yellow solid. LCMS: (M+H)$^+$=396; Rt=2.38 min. HRMS: calculated for $C_{21}H_{19}ClN_3O_3$ (M+H)$^+$: 396.1115. found: 396.1110.

Biological Assay

AMPK Enzymatic Assay

Human recombinant AMPK (Invitrogen #PV4673 & #PV4675) was used in a FRET assay format (Z'Lyte—Invitrogen). Assay conditions were as follow: ATP 100 μM, peptide (Invitrogen #PR8650) 2 μM, 1% final DMSO in Z'Lyte kinase buffer. Reaction was initiated by addition of 0.2-0.8 ng of AMPK and incubated for 1-hour @ 30° C. A further 1-hour incubation @ 30° C. with the development reagent (Invitrogen # PR5194) was performed. FRET signal was then measured and converted to "% peptide phosphorylation" according to Z'Lyte given calculation procedure. Evaluation of compounds was carried out using concentration-response curves. Final data were expressed in "% activation" calculating the ratio of "% peptide phosphorylation" between compound-condition and basal-condition. Alternatively pEC200 (−Log(compound concentration leading to a 2-fold AMPK activity increase)) was produced through fitting of the concentration-response curves. All data were means of at least 2 independent experiments.

The compounds of Examples 1-196 were tested essentially as described above and gave average pEC$_{50}$ values of greater than or equal to 5.5 or gave average pEC$_{200}$ values of greater than or equal to 5.0.

In a further aspect, some of the compounds of the invention give average pEC$_{50}$ values of ≥6.0 when tested in this assay. In a further aspect, some of the compounds of the invention give average pEC$_{50}$ values of ≥7.0 when tested in this assay. For instance, Example 42 was tested essentially as described above and gave an average pEC$_{50}$ value of 7.4.

Those of skill in the art will recognize that in vitro binding assays and cell-based assays for functional activity are subject to variability. Accordingly, it is to be understood that the pEC$_{50}$ and pEC$_{200}$ values for the Examples recited above are exemplary only.

The following compounds were also prepared and when tested by the above described in vitro assay for AMPK activity were found to exhibit an average pEC$_{50}$ value of less than 5.5 and pEC$_{200}$ values of less than 5.0:

7-chloro-4-hydroxy-3-(3-methyl-1H-pyrazol-1-yl)-6-(4-(pyrrolidin-1-yl)phenyl)quinolin-2(1H)-one;
7-chloro-4-hydroxy-3-(2-methylthiazol-4-yl)-6-(4-(piperidin-1-yl)phenyl)quinolin-2(1H)-one;
7-chloro-6-(4-(dimethylamino)phenyl)-4-hydroxy-3-(5-methylisoxazol-3-yl)quinolin-2(1H)-one;
7-chloro-6-(4-(dimethylamino)phenyl)-3-(2,5-dimethylthiazol-4-yl)-4-hydroxyquinolin-2(1H)-one; and
7-chloro-4-hydroxy-6-(3'-methoxy-[1,1'-biphenyl]-4-yl)-3-(1H-pyrazol-1-yl)quinolin-2(1H)-one.

The invention claimed is:

1. A compound of formula (I) or a salt thereof:

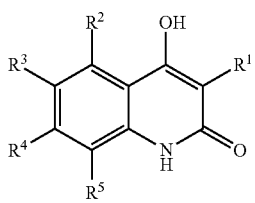

(I)

wherein:
R$^1$ is a) a 5-membered heteroaryl optionally substituted with 1, 2, or 3 groups independently selected from —CH$_3$, —OCH$_3$, —OH, —CH$_2$OH, —CF$_3$, —OCF$_3$, —CN, —CO$_2$H, —CH$_2$CO$_2$H, —CONH$_2$, —NH$_2$ and halogen;
b) O-phenyl optionally substituted with a group selected from methyl, methoxy, fluoro, and CO$_2$H;
c) selected from the group consisting of H, CO$_2$H, CO$_2$Et, and NO$_2$;
d) phenyl optionally substituted with a group selected from CO$_2$H, Cl, F, methyl, —CN, -NMe$_2$ and methoxy;
e) selected from the group consisting of 3-pyridinyl, 4-pyridinyl, and —S(O)$_n$-phenyl; or
f) selected from the group consisting of O-pyridin-2-yl, O-(4-methyl-pyridin-2-yl), O-(5-methoxy-pyridin-2-yl) and O-(5-methyl-pyridin-2-yl);
n=0 or 2;
R$^2$ is H;
R$^3$ is

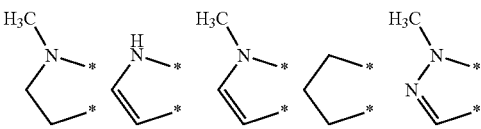

wherein * designates point of attachment;

R$^4$ is Cl;
R$^5$ is H; and

R$^7$ is H and R$^6$ is selected from a group consisting of, —NHMe, —NMe$_2$, —NHC(O)OMe, —OMe, —OEt, Et, iPr, —CH$_2$OH, and —CH$_2$CH$_2$OH or is a group selected from

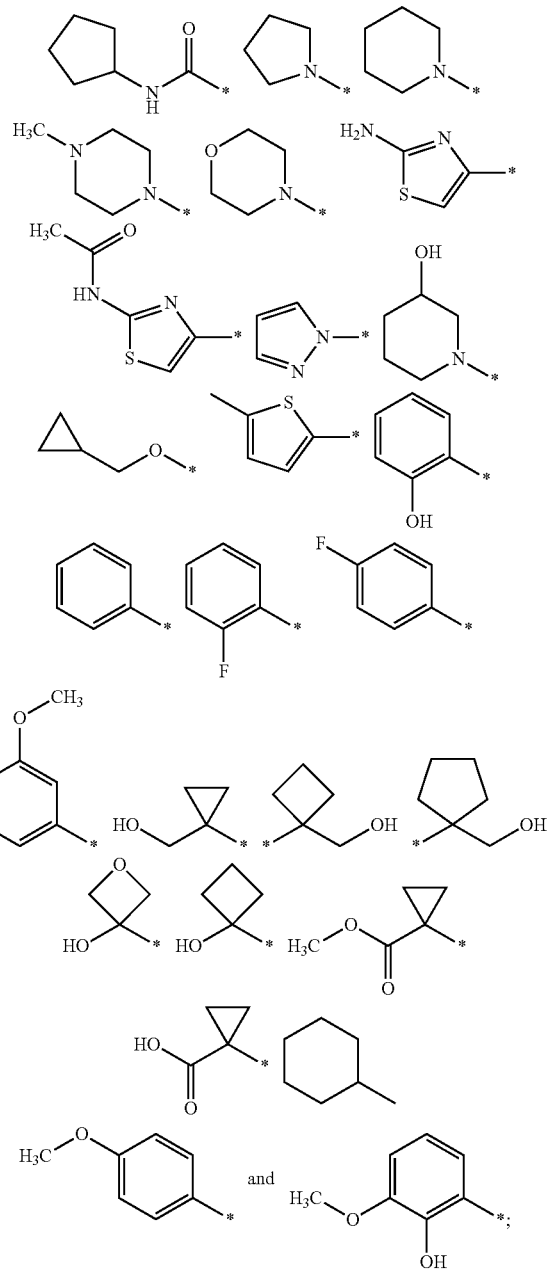

wherein *designates point of attachment;

or

R$^6$ and R$^7$ taken together form a group selected from

-continued

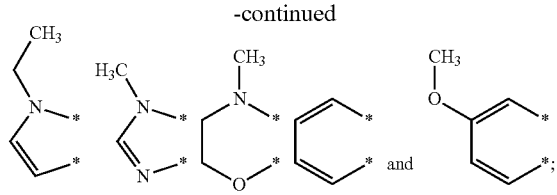

wherein *designates point of attachment;

or
wherein:
  i) R¹=3-methoxyphenyl, R⁴ is F and R³=4-(4-morpholino)phenyl;
  ii) R¹=3-methylisoxazol-5-yl, and R³=3-dimethylaminophenyl; or
  iii) R¹=3-methoxyphenyl, and R³=3-dimethylaminophenyl.

2. The compound or salt thereof according to claim 1 wherein R¹ represents 5-membered heteroaryl optionally substituted by a group selected from —CH₃, —OCH₃, —OH, —CH₂OH, —CF₃, —OCF₃, —CN, —CO₂H, —CH₂CO₂H, —CONH₂, —NH₂ and halogen.

3. The compound or salt thereof according to claim 1 wherein R¹ represents 5-membered heteroaryl optionally substituted with 1, 2, or 3 groups independently selected from methyl, chloro, bromo, CO₂H and methoxy.

4. The compound or salt thereof according to claim 1 wherein R³ represents

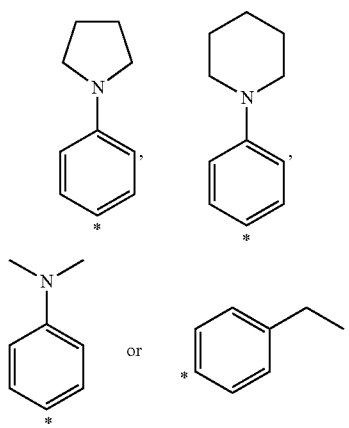

wherein * designates point of attachment.

5. The compound or salt thereof according to claim 1 wherein R³ represents

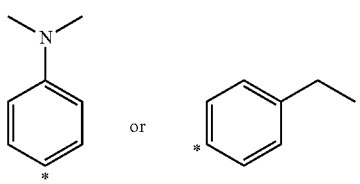

wherein * designates point of attachment.

6. A compound of formula (A) or a salt thereof:

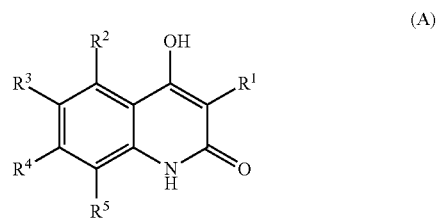

(A)

wherein
R¹ represents 5-membered heteroaryl optionally substituted by —CH₃, —OCH₃, —OH, —CH₂OH, —CF₃, —OCF₃, —CN, —CO₂H, —CH₂CO₂H, —CONH₂, —NH₂ or halogen;
R² represents H;
R³ is

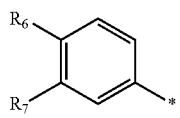

wherein * designates point of attachment;

R⁴ represents chloro;
R⁵ represents H; and
R⁷ is H and R⁶ is selected from a group consisting of —NHMe, —NMe₂, —NHC(O)OMe, Et, and iPr, or is a group selected from

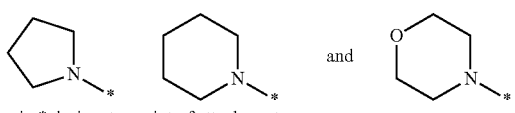

wherein * designates point of attachment.

7. The compound or salt thereof according to claim 1, selected from the group consisting of:
  7-Chloro-4-hydroxy-6-(2'-hydroxy-3'-methoxy-[1,1'-biphenyl]-4-yl)-3-phenylquinolin-2(1H)-one;
  3-{7-Chloro-4-hydroxy-6-[2'-hydroxy-3'-(methyloxy)-4-biphenylyl]-2-oxo-1,2-dihydro-3-quinolinyl}benzoic acid;
  7-chloro-4-hydroxy-3-(3-methoxyphenyl)-6-(4-morpholinophenyl)quinolin-2(1H)-one;
  7-Chloro-4-hydroxy-6-[4-(4-morpholinyl)phenyl]-3-phenylquinolin-2(1H)-one;
  4-{7-Chloro-4-hydroxy-3-[3-(methyloxy)phenyl]-2-oxo-1,2-dihydro-6-quinolinyl}-N-cyclopentylbenzamide;
  7-Fluoro-4-hydroxy-3-(3-methoxyphenyl)-6-(4-morpholinophenyl)quinolin-2(1H)-one;
  3-[7-Chloro-4-hydroxy-6-(1-methyl-1H-indol-5-yl)-2-oxo-1,2-dihydro-3-quinolinyl]benzoic acid;
  7-Chloro-4-hydroxy-6-(1-methyl-1H-indol-5-yl)-3-[3-(methyloxy)phenyl]quinolin-2(1H)-one;
  N-{4-[4-(7-Chloro-4-hydroxy-2-oxo-3-phenyl-1,2-dihydro-6-quinolinyl)phenyl]-1,3-thiazol-2-yl}acetamide;
  7-Chloro-4-hydroxy-6-(1-methyl-1H-indol-5-yl)-3-phenylquinolin-2(1H)-one;
  7-Chloro-4-hydroxy-3-(3-methylisoxazol-5-yl)-6-(4-(piperidin-1-yl)phenyl)quinolin-2(1H)-one;

7-Chloro-6-(4-(dimethylamino)phenyl)-4-hydroxyquinolin-2(1H)-one;
7-Chloro-4-hydroxy-3-(1-methyl-1H-pyrazol-4-yl)-6-(4-(piperidin-1-yl)phenyl)quinolin-2(1H)-one;
7-Chloro-6-(4'-fluoro-[1,1'-biphenyl]-4-yl)-4-hydroxy-3-(3-methylisoxazol-5-yl)quinolin-2(1H)-one;
7-Chloro-4-hydroxy-6-(3'-methoxy-[1,1'-biphenyl]-4-yl)-3-(3-methylisoxazol-5-yl)quinolin-2(1H)-one;
7-Chloro-4-hydroxy-3-(3-methylisoxazol-5-yl)-6-(4-(5-methylthiophen-2-yl)phenyl)quinolin-2(1H)-one;
7-Chloro-4-hydroxy-6-(4'-methoxy-[1,1'-biphenyl]-4-yl)-3-(3-methylisoxazol-5-yl)quinolin-2(1H)-one;
7-Chloro-6-(2'-fluoro-[1,1'-biphenyl]-4-yl)-4-hydroxy-3-(3-methylisoxazol-5-yl)quinolin-2(1H)-one;
3-(7-Chloro-6-(4-(dimethylamino)phenyl)-4-hydroxy-2-oxo-1,2-dihydroquinolin-3-yl)benzonitrile;
7-Chloro-6-(4-(dimethylamino)phenyl)-3-(3-methyl-1,2,4-oxadiazol-5-yl)-2-oxo-1,2-dihydroquinolin-4-olate;
7-Chloro-3,6-bis(4-(dimethylamino)phenyl)-2-oxo-1,2-dihydroquinolin-4-olate;
7-Chloro-3-(4-cyanophenyl)-6-(4-(dimethylamino)phenyl)-2-oxo-1,2-dihydroquinolin-4-olate;
7-Chloro-6-(4-(dimethylamino)phenyl)-3-(5-methyl-1,3,4-oxadiazol-2-yl)-2-oxo-1,2-dihydroquinolin-4-olate;
7-Chloro-6-(4-(dimethylamino)phenyl)-3-(2-methylthiazol-5-yl)-2-oxo-1,2-dihydroquinolin-4-olate;
7-Chloro-6-(4-(dimethylamino)phenyl)-3-(2,4-dimethylthiazol-5-yl)-2-oxo-1,2-dihydroquinolin-4-olate;
7-Chloro-3-(5-methyl-1,3,4-oxadiazol-2-yl)-2-oxo-6-(4-(piperidin-1-yl)phenyl)-1,2-dihydroquinolin-4-olate;
Ethyl 7-chloro-4-hydroxy-6-(1-methyl-1H-indol-5-yl)-2-oxo-1,2-dihydro-3-quinolinecarboxylate;
Ethyl 7-chloro-4-hydroxy-6-[2'-hydroxy-3'-(methyloxy)-4-biphenylyl]-2-oxo-1,2-dihydro-3-quinoline carboxylate;
7-Chloro-4-hydroxy-6-(1-methyl-1H-indol-5-yl)-3-nitroquinolin-2(1H)-one;
Ethyl 7-chloro-4-hydroxy-6-[4-(4-morpholinyl)phenyl]-2-oxo-1,2-dihydro-3-quinolinecarboxylate;
7-Chloro-4-hydroxy-3-(3-methylisoxazol-5-yl)-6-(4-morpholino phenyl)quinolin-2(1H)-one;
7-Chloro-4-hydroxy-3-(3-methoxyphenyl)-6-(4-(piperidin-1-yl)phenyl)quinolin-2(1H)-one;
7-Chloro-4-hydroxy-3-(3-methoxyphenyl)-6-(1-methyl-1H-benzo[d]imidazol-6-yl)quinolin-2(1H)-one;
7-Chloro-4-hydroxy-3-(3-methoxyphenyl)-6-(4-(pyrrolidin-1-yl)phenyl)quinolin-2(1H)-one;
Methyl (4-(7-chloro-4-hydroxy-3-(3-methoxyphenyl)-2-oxo-1,2-dihydroquinolin-6-yl)phenyl) carbamate;
7-Chloro-6-[4-(dimethylamino)phenyl]-4-hydroxy-3-[3-(methyloxy)phenyl]quinolin-2(1H)-one;
7-Chloro-6-(2,3-dihydro-1H-inden-5-yl)-4-hydroxy-3-(3-methoxyphenyl)quinolin-2(1H)-one;
7-Chloro-4-hydroxy-3-(3-methoxyphenyl)-6-(4-(4-methylpiperazin-1-yl)phenyl)quinolin-2(1H)-one;
7-Chloro-6-(4-ethylphenyl)-4-hydroxy-3-(3-methoxyphenyl)quinolin-2(1H)-one;
7-Chloro-6-[3-(dimethylamino) phenyl]-4-hydroxy-3-[3-(methyloxy)phenyl]-2(1H)-quinolinone;
7-Chloro-6-(3-(dimethylamino)phenyl)-4-hydroxy-3-(3-methylisoxazol-5-yl)quinolin-2(1H)-one;
7-Chloro-6-(4-ethylphenyl)-4-hydroxy-3-(3-methylisoxazol-5-yl)quinolin-2(1H)-one;
7-Chloro-4-hydroxy-6-(2'-hydroxy-3'-methoxy-[1,1'-biphenyl]-4-yl)-3-(3-methylisoxazol-5-yl) quinolin-2(1H)-one;
7-Chloro-4-hydroxy-6-(4-morpholinophenyl)-3-phenoxyquinolin-2(1H)-one;
7-Chloro-6-(4-(dimethylamino)phenyl)-4-hydroxy-3-phenylquinolin-2(1H)-one;
6-(4-(1H-Pyrazol-1-yl)phenyl)-7-chloro-4-hydroxy-3-phenylquinolin-2(1H)-one;
7-Chloro-4-hydroxy-6-(4-methoxyphenyl)-3-phenylquinolin-2(1H)-one;
7-Chloro-6-(4-(dimethylamino)phenyl)-4-hydroxy-3-(1H-pyrazol-1-yl)quinolin-2(1H)-one;
7-Chloro-4-hydroxy-6-(4-morpholinophenyl)-3-(1H-pyrazol-1-yl)quinolin-2(1H)-one;
7-Chloro-6-(4-(dimethylamino)phenyl)-4-hydroxy-3-phenoxyquinolin-2(1H)-one;
7-Chloro-4-hydroxy-3-phenyl-6-(4-(piperidin-1-yl)phenyl)quinolin-2(1H)-one;
7-Chloro-4-hydroxy-6-(4-(2-hydroxyethyl)phenyl)-3-phenylquinolin-2(1H)-one;
7-Chloro-4-hydroxy-6-(4-(3-hydroxypiperidin-1-yl)phenyl)-3-(3-methoxyphenyl)quinolin-2(1H)-one;
7-Chloro-4-hydroxy-6-(2'-hydroxy-3'-methoxy-[1,1'-biphenyl]-4-yl)-3-(1H-pyrazol-1-yl)quinolin-2(1H)-one;
7-Chloro-4-hydroxy-3-(3-methoxyphenyl)-6-(4-methyl-3,4-dihydro-2H-benzo[b][1,4]oxazin-7-yl)quinolin-2(1H)-one;
7-Chloro-4-hydroxy-3-phenyl-6-(4-(pyrrolidin-1-yl)phenyl)quinolin-2(1H)-one;
7-Chloro-4-hydroxy-6-(2'-hydroxy-3'-methoxy-[1,1'-biphenyl]-4-yl)-3-phenoxyquinolin-2(1H)-one;
7-Chloro-4-hydroxy-6-(2'-hydroxy-3'-methoxy-[1,1'-biphenyl]-4-yl)quinolin-2(1H)-one;
N-(4-(4-(7-Chloro-4-hydroxy-2-oxo-3-phenoxy-1,2-dihydroquinolin-6-yl)phenyl)thiazol-2-yl) acetamide;
7-Chloro-6-(4-(dimethylamino)phenyl)-4-hydroxy-3-(o-tolyloxy)quinolin-2(1H)-one;
7-Chloro-6-(4-(dimethylamino)phenyl)-4-hydroxy-3-(4-methoxyphenoxy)quinolin-2(1H)-one;
7-Chloro-4-hydroxy-6-(4-(hydroxymethyl)phenyl)-3-phenylquinolin-2(1H)-one;
7-Chloro-3-(3-fluorophenoxy)-4-hydroxy-6-(4-isopropylphenyl)quinolin-2(1H)-one;
7-Chloro-6-(4-(dimethylamino)phenyl)-3-(3-fluorophenoxy)-4-hydroxyquinolin-2(1H)-one;
7-Chloro-4-hydroxy-6-(4-(methylamino)phenyl)-3-phenylquinolin-2(1H)-one;
7-Chloro-4-hydroxy-3-(1H-pyrazol-1-yl)-6-(4-(pyrrolidin-1-yl)phenyl)quinolin-2(1H)-one;
7-Chloro-6-(4-ethoxyphenyl)-4-hydroxy-3-(1H-pyrazol-1-yl)quinolin-2(1H)-one;
7-Chloro-4-hydroxy-3-phenoxy-6-(4-(pyrrolidin-1-yl)phenyl)quinolin-2(1H)-one;
7-Chloro-6-(4-ethylphenyl)-4-hydroxy-3-phenoxyquinolin-2(1H)-one;
7-Chloro-4-hydroxy-6-(4-isopropylphenyl)-3-phenoxyquinolin-2(1H)-one;
7-Chloro-6-(4-(dimethylamino)phenyl)-4-hydroxy-3-(3-methoxyphenoxy)quinolin-2(1H)-one;
7-Chloro-4-hydroxy-3-(3-methoxyphenoxy)-6-(4-(pyrrolidin-1-yl)phenyl)quinolin-2(1H)-one;
7-Chloro-4-hydroxy-6-(4-isopropylphenyl)-3-(3-methoxyphenoxy)quinolin-2(1H)-one;
7-Chloro-4-hydroxy-6-(1-methyl-1H-indol-5-yl)-3-(1H-pyrazol-1-yl)quinolin-2(1H)-one;
7-Chloro-6-(4-(cyclopropylmethoxy)phenyl)-4-hydroxy-3-(1H-pyrazol-1-yl)quinolin-2(1H)-one;
7-Chloro-4-hydroxy-6-(4-methyl-3,4-dihydro-2H-benzo[b][1,4]oxazin-7-yl)-3-(1H-pyrazol-1-yl) quinolin-2(1H)-one;
7-Chloro-4-hydroxy-6-(1-methyl-1H-indazol-5-yl)-3-(1H-pyrazol-1-yl)quinolin-2(1H)-one;
7-Chloro-4-hydroxy-6-(4-isopropylphenyl)-3-(3-methylisoxazol-5-yl)quinolin-2(1H)-one;
7-Chloro-3-(3,5-dimethyl-1H-pyrazol-1-yl)-6-(4-(dimethylamino)phenyl)-4-hydroxyquinolin-2(1H)-one;

7-Chloro-6-(4-(dimethylamino)phenyl)-4-hydroxy-3-(p-tolyloxy)quinolin-2(1H)-one;
7-Chloro-6-(2,3-dihydro-1H-inden-5-yl)-4-hydroxy-3-(3-methylisoxazol-5-yl)quinolin-2(1H)-one;
7-Chloro-6-(4-(dimethylamino)phenyl)-4-hydroxy-3-(4-methyl-1,2,5-oxadiazol-3-yl)quinolin-2(1H)-one;
7-Chloro-6-(4-(dimethylamino)phenyl)-4-hydroxy-3-(pyridin-4-yl)quinolin-2(1H)-one;
7-Chloro-6-(4-(dimethylamino)phenyl)-4-hydroxy-3-(pyridin-2-yloxy)quinolin-2(1H)-one;
7-Chloro-6-(4-(dimethylamino)phenyl)-4-hydroxy-3-(1H-1,2,4-triazol-1-yl)quinolin-2(1H)-one;
7-Chloro-6-(4-(dimethylamino)phenyl)-4-hydroxy-3-(2-methoxyphenoxyl)quinolin-2 (1H)-one;
7-Chloro-6-(4-(dimethylamino)phenyl)-4-hydroxy-3-(1H-1,2,3-triazol-1-yl)quinolin-2(1H)-one;
7-Chloro-6-(4-(dimethylamino)phenyl)-4-hydroxy-3-(4-methyl-1H-pyrazol-1-yl)quinolin-2(1H)-one;
7-Chloro-6-(4-(dimethylamino)phenyl)-4-hydroxy-3-(m-tolyloxy)quinolin-2(1H)-one;
7-Chloro-6-(4-(dimethylamino)phenyl)-4-hydroxy-3-(pyridin-3-yl)quinolin-2(1H)-one;
3-((7-Chloro-6-(4-(dimethylamino)phenyl)-4-hydroxy-2-oxo-1,2-dihydroquinolin-3-yl)oxy) benzoic acid;
1-(7-Chloro-6-(4-(dimethylamino)phenyl)-4-hydroxy-2-oxo-1,2-dihydroquinolin-3-yl)-1H-pyrazole-4-carboxylic acid;
7-Chloro-6-(4-(dimethylamino)phenyl)-3-(4-fluorophenoxy)-4-hydroxyquinolin-2(1H)-one;
7-Chloro-4-hydroxy-6-(2'-hydroxy-[1, 1'-biphenyl]-4-yl)-3-(1H-pyrazol-1-yl)quinolin-2(1H)-one;
7-Chloro-3-(1,3-dimethyl-1H-pyrazol-5-yl)-6-(4-(dimethylamino)phenyl)-4-hydroxyquinolin-2(1H)-one;
7-Chloro-4-hydroxy-6-(4-(piperidin-1-yl)phenyl)-3-(1H-pyrazol-1-yl)quinolin-2(1H)-one;
7-Chloro-6-(4-(dimethylamino)phenyl)-4-hydroxy-3-((4-methylpyridin-2-yl)oxy)quinolin-2(1H)-one;
7-Chloro-4-hydroxy-6-(1-methyl-1H-indol-5-yl)-3-(3-methylisoxazol-5-yl)quinolin-2(1H)-one;
7-Chloro-4-hydroxy-3-(3-methylisoxazol-5-yl)-6-(4-(pyrrolidin-1-yl)phenyl)quinolin-2(1H)-one;
7-Chloro-4-hydroxy-6-(4-methoxyphenyl)-3-(3-methylisoxazol-5-yl)quinolin-2(1H)-one;
7-Chloro-4-hydroxy-6-(1-methyl-1H-indol-5-yl)-3-(pyridin-3-yl)quinolin-2(1H)-one;
1-(7-Chloro-4-hydroxy-2-oxo-6-(4-(pyrrolidin-1-yl)phenyl)-1,2-dihydroquinolin-3-yl)-1H-pyrazole-4-carboxylic acid;
7-Chloro-4-hydroxy-3-(pyridin-3-yl)-6-(4-(pyrrolidin-1-yl)phenyl)quinolin-2(1H)-one;
7-Chloro-4-hydroxy-3-(4-methyl-1,2,5-oxadiazol-3-yl)-6-(1-methyl-1H-indol-5-yl)quinolin-2(1H)-one;
7-Chloro-4-hydroxy-3-(4-methyl-1,2,5-oxadiazol-3-yl)-6-(4-(pyrrolidin-1-yl)phenyl)quinolin-2 (1H)-one;
7-Chloro-4-hydroxy-3-(pyridin-4-yl)-6-(4-(pyrrolidin-1-yl)phenyl)quinolin-2(1H)-one;
7-Chloro-4-hydroxy-6-(1-methyl-1H-indol-5-yl)-3-(4-methyl-1H-pyrazol-1-yl)quinolin-2(1H)-one;
7-Chloro-4-hydroxy-6-(1-methyl-1H-indol-5-yl)-3-(pyridin-4-yl)quinolin-2(1H)-one;
7-Chloro-4-hydroxy-6-(1-methyl-1H-indol-5-yl)-3-phenoxyquinolin-2(1H)-one;
7-Chloro-4-hydroxy-3-(2-methoxyphenoxy)-6-(1-methyl-1H-indol-5-yl)quinolin-2(1H)-one;
7-Chloro-4-hydroxy-6-(1-methyl-1H-indol-5-yl)-3-(p-tolyloxy)quinolin-2(1H)-one;
7-Chloro-3-(3-fluorophenoxy)-4-hydroxy-6-(1-methyl-1H-indol-5-yl)quinolin-2(1H)-one;
6-([1,1'-Biphenyl]-4-yl)-7-chloro-4-hydroxy-3-(3-methylisoxazol-5-yl)quinolin-2(1H)-one;
7-Chloro-6-(4-cyclohexylphenyl)-4-hydroxy-3-(3-methylisoxazol-5-yl)quinolin-2(1H)-one;
7-Chloro-6-(4-(dimethylamino)phenyl)-4-hydroxy-3-(5-methyl-1H-pyrazol-1-yl)quinolin-2(1H)-one;
7-Chloro-4-hydroxy-3-(5-methyl-1H-pyrazol-1-yl)-6-(4-(pyrrolidin-1-yl)phenyl)quinolin-2 (1H)-one;
7-Chloro-4-hydroxy-3-(3-methylisoxazol-5-yl)-6-(naphthalen-2-yl)quinolin-2(1H)-one;
7-Chloro-4-hydroxy-6-(4-(3-hydroxypiperidin-1-yl)phenyl)-3-(1H-pyrazol-1-yl)quinolin-2(1H)-one;
7-Chloro-6-(4-(dimethylamino)phenyl)-4-hydroxy-3-(phenylthio)quinolin-2(1H)-one;
7-Chloro-4-hydroxy-6-(4-morpholinophenyl)-3-(phenylthio)quinolin-2(1H)-one;
7-Chloro-4-hydroxy-6-(4-(hydroxymethyl)phenyl)-3-(phenylthio)quinolin-2(1H)-one;
7-Chloro-4-hydroxy-6-(6-methoxynaphthalen-2-yl)-3-(3-methylisoxazol-5-yl)quinolin-2(1H)-one;
7-Chloro-4-hydroxy-6-(4-methoxyphenyl)-3-phenoxyquinolin-2(1H)-one;
6-(4-(1H-Pyrazol-1-yl)phenyl)-7-chloro-4-hydroxy-3-(1H-pyrazol-1-yl)quinolin-2(1H)-one;
7-Chloro-4-hydroxy-6-(1H-indol-5-yl)-3-(1H-pyrazol-1-yl)quinolin-2(1H)-one;
7-Chloro-3-(1,3-dimethyl-1H-pyrazol-5-yl)-4-hydroxy-6-(1-methyl-1H-indol-5-yl)quinolin-2(1H)-one;
7-Chloro-3-(4-chloro-1H-pyrazol-1-yl)-6-(4-(dimethylamino)phenyl)-4-hydroxyquinolin-2(1H)-one;
7-Chloro-4-hydroxy-3-(3-methoxyphenoxy)-6-(1-methyl-1H-indol-5-yl)quinolin-2(1H)-one;
7-Chloro-3-(1,3-dimethyl-1H-pyrazol-5-yl)-4-hydroxy-6-(4-(pyrrolidin-1-yl)phenyl)quinolin-2(1H)-one;
7-Chloro-4-hydroxy-6-(1-methyl-1H-indol-5-yl)-3-(1H-1,2,4-triazol-1-yl)quinolin-2(1H)-one;
7-Chloro-4-hydroxy-6-(1-methyl-1H-indol-5-yl)-3-(1-methyl-1H-pyrazol-4-yl)quinolin-2(1H)-one;
7-Chloro-4-hydroxy-6-(1-methyl-1H-indol-5-yl)-3-((5-methylpyridin-2-yl)oxy)quinolin-2(1H)-one;
7-Chloro-3-(4-chloro-1H-pyrazol-1-yl)-4-hydroxy-6-(1-methyl-1H-indol-5-yl)quinolin-2(1H)-one;
7-Chloro-4-hydroxy-6-(4-(pyrrolidin-1-yl)phenyl)-3-(1H-1,2,4-triazol-1-yl)quinolin-2(1H)-one;
7-Chloro-4-hydroxy-6-(4-(piperidin-1-yl)phenyl)-3-(1H-1,2,4-triazol-1-yl)quinolin-2(1H)-one;
7-Chloro-6-(4-(dimethylamino)phenyl)-3-(3-fluorophenyl)-4-hydroxyquinolin-2(1H)-one;
7-Chloro-4-hydroxy-6-(4-(methylamino)phenyl)-3-(3-methylisoxazol-5-yl)quinolin-2(1H)-one;
7-Chloro-4-hydroxy-3-(4-methyl-1H-pyrazol-1-yl)-6-(4-(pyrrolidin-1-yl)phenyl)quinolin-2(1H)-one;
7-Chloro-4-hydroxy-3-(4-methyl-1H-pyrazol-1-yl)-6-(4-(piperidin-1-yl)phenyl)quinolin-2 (1H)-one;
7-Chloro-4-hydroxy-6-(4-(1-(hydroxymethyl)cyclopropyl)phenyl)-3-(1H-pyrazol-1-yl)quinolin-2(1H)-one;
7-Chloro-6-(1-ethyl-1H-indol-5-yl)-4-hydroxy-3-(1H-pyrazol-1-yl)quinolin-2(1H)-one;
7-Chloro-4-hydroxy-3-(4-methyl-1,2,5-oxadiazol-3-yl)-6-(4-(piperidin-1-yl)phenyl)quinolin-2 (1H)-one;
7-Chloro-4-hydroxy-6-(4-(piperidin-1-yl)phenyl)-3-(pyridin-3-yl)quinolin-2(1H)-one;
7-Chloro-4-hydroxy-6-(4-(1-(hydroxymethyl)cyclopropyl)phenyl)-3-(3-methylisoxazol-5-yl)quinolin-2(1H)-one;
7-Chloro-6-(4-(dimethylamino)phenyl)-4-hydroxy-3-nitroquinolin-2(1H)-one;
7-Chloro-6-(4-(dimethylamino)phenyl)-4-hydroxy-3-(phenylsulfonyl)quinolin-2(1H)-one;
7-Chloro-4-hydroxy-6-(1-methyl-1H-indol-5-yl)-3-(phenylsulfonyl)quinolin-2(1H)-one;

7-Chloro-6-(4-(dimethylamino)phenyl)-3-(4-fluorophenyl)-4-hydroxyquinolin-2(1H)-one;
7-Chloro-6-(4-(dimethylamino)phenyl)-4-hydroxy-3-(o-tolyl)quinolin-2(1H)-one;
7-Chloro-6-(4-(dimethylamino)phenyl)-4-hydroxy-3-(2-methoxyphenyl)quinolin-2(1H)-one;
7-Chloro-3-(4-chlorophenyl)-6-(4-(dimethylamino)phenyl)-4-hydroxyquinolin-2(1H)-one;
7-Chloro-3-(3-chlorophenyl)-6-(4-(dimethylamino)phenyl)-4-hydroxyquinolin-2(1H)-one;
7-Chloro-3-(2-chlorophenyl)-6-(4-(dimethylamino)phenyl)-4-hydroxyquinolin-2(1H)-one;
7-Chloro-6-(4-(dimethylamino)phenyl)-3-(2-fluoro phenyl)-4-hydroxyquinolin-2(1H)-one;
7-Chloro-4-hydroxy-6-(1-methyl-1H-indol-6-yl)-3-(3-methylisoxazol-5-yl)quinolin-2(1H)-one;
7-Chloro-4-hydroxy-6-(1-methylindolin-5-yl)-3-(3-methylisoxazol-5-yl)quinolin-2(1H)-one;
7-Chloro-4-hydroxy-3-(4-methoxy-1H-pyrazol-1-yl)-6-(4-(piperidin-1-yl)phenyl)quinolin-2 (1H)-one;
7-Chloro-6-(4-(dimethylamino)phenyl)-4-hydroxy-3-(m-tolyl)quinolin-2(1H)-one;
7-Chloro-6-(4-(dimethylamino)phenyl)-4-hydroxy-3-(p-tolyl)quinolin-2(1H)-one;
7-Chloro-4-hydroxy-6-(4-(1-(hydroxymethyl)cyclopropyl)phenyl)-3-(2-methoxyphenoxy) quinolin-2(1H)-one;
7-chloro-4-hydroxy-6-(4-(1-(hydroxymethyl)cyclopropyl)phenyl)-3-(4-methoxy-1H-pyrazol-1-yl)quinolin-2 (1H)-one;
7-Chloro-4-hydroxy-6-(4-(1-(hydroxymethyl)cyclopentyl)phenyl)-3-(3-methylisoxazol-5-yl) quinolin-2(1H)-one;
7-Chloro-6-(4-(dimethylamino)phenyl)-4-hydroxy-3-(4-methoxyphenyl) quinolin-2(1H)-one;
Methyl 1-(4-(7-chloro-4-hydroxy-3-(3-methylisoxazol-5-yl)-2-oxo-1,2-dihydroquinolin-6-yl)phenyl)cyclopropane carboxylate;
7-Chloro-3-(3-chlorophenyl)-4-hydroxy-6-(1-methyl-1H-indol-5-yl)quinolin-2(1H)-one;
7-Chloro-3-(3-chlorophenyl)-4-hydroxy-6-(4-(pyrrolidin-1-yl)phenyl)quinolin-2(1H)-one;
7-Chloro-6-(4-(dimethylamino)phenyl)-4-hydroxy-3-(4-methoxy-1H-pyrazol-1-yl)quinolin-2(1H)-one;
7-Chloro-4-hydroxy-6-(4-(1-(hydroxymethyl)cyclobutyl) phenyl)-3-(3-methylisoxazol-5-yl) quinolin-2(1H)-one;
7-Chloro-6-(4-(1-hydroxycyclobutyl)phenyl)-3-(3-methylisoxazol-5-yl)-2-oxo-1,2-dihydroquinolin-4-olate;
7-Chloro-6-(1-ethyl-1H-indol-5-yl)-3-(3-methylisoxazol-5-yl)-2-oxo-1,2-dihydroquinolin-4-olate;
7-Chloro-6-(4-ethoxyphenyl)-3-(3-methylisoxazol-5-yl)-2-oxo-1,2-dihydroquinolin-4-olate;
7-Chloro-6-(4-(3-hydroxyoxetan-3-yl)phenyl)-3-(3-methylisoxazol-5-yl)-2-oxo-1,2-dihydroquinolin-4-olate;
7-Chloro-6-(4-(dimethylamino)phenyl)-4-hydroxy-3-(3-methyl-1H-pyrazol-1-yl)quinolin-2(1H)-one;
7-Chloro-6-(4-(dimethylamino)phenyl)-4-hydroxy-3-((4-methoxypyridin-2-yl)oxy)quinolin-2(1H)-one;
7-Chloro-4-hydroxy-3-(4-methoxyphenoxy)-6-(1-methyl-1H-indol-5-yl)quinolin-2(1H)-one;
7-Chloro-6-(4-(dimethylamino)phenyl)-4-hydroxy-3-((5-methylpyridin-2-yl)oxy)quinolin-2(1H)-one;
7-Chloro-6-(2'-fluoro-[1,1'-biphenyl]-4-yl)-4-hydroxy-3-(1H-pyrazol-1-yl)quinolin-2(1H)-one;
7-Chloro-4-hydroxy-6-(4-(5-methylthiophen-2-yl)phenyl)-3-(1H-pyrazol-1-yl)quinolin-2(1H)-one;

3-(4-Bromo-1H-pyrazol-1-yl)-7-chloro-6-(4-(dimethylamino)phenyl)-4-hydroxyquinolin-2(1H)-one;
3-(4-Bromo-1H-pyrazol-1-yl)-7-chloro-4-hydroxy-6-(4-(piperidin-1-yl)phenyl)quinolin-2 (1H)-one;
6-[4-(2-Amino-1,3-thiazol-4-yl)phenyl]-7-chloro-4-hydroxy-3-phenylquinolin-2(1H)-one;
6-[4-(2-Amino-1,3-thiazol-4-yl)phenyl]-7-chloro-4-hydroxy-3-[3-(methyloxy)phenyl]quinolin-2(1H)-one;
6-(4-(2-Amino-1,3-thiazol-4-yl)phenyl)-7-chloro-4-hydroxy-3-(3-methylisoxazol-5-yl)quinolin-2(1H)-one;
6-(4-(2-Amino-1,3-thiazol-4-yl)phenyl)-7-chloro-4-hydroxy-3-(3-methoxyphenyl)quinolin-2(1H)-one;
6-(4-(2-Amino-1,3-thiazol-4-yl)phenyl)-7-chloro-4-hydroxy-3-(pyridin-3-yl)quinolin-2(1H)-one;
6-[4-(2-Amino-1,3-thiazol-4-yl)phenyl]-7-chloro-4-hydroxy-3-(1H-pyrazol-1-yl)-2(1H)-quinolinone;
6-(4-(2-Amino-1,3-thiazol-4-yl)phenyl)-7-chloro-4-hydroxy-3-(pyridin-4-yl)quinolin-2(1H)-one;
6-(4-(2-Amino-1,3-thiazol-4-yl)phenyl)-7-chloro-4-hydroxy-3-(4-methyl-1H-pyrazol-1-yl) quinolin-2(1H)-one;
6-(4-(2-Amino-1,3-thiazol-4-yl)phenyl)-7-chloro-4-hydroxy-3-(1H-1,2,3-triazol-1-yl)quinolin-2(1H)-one;
7-Chloro-4-hydroxy-6-(1-methyl-1H-indol-5-yl)quinolin-2(1H)-one;
7-Chloro-4-hydroxy-6-[4-(4-morpholinyl)phenyl]quinolin-2(1H)-one;
7-Chloro-4-hydroxy-6-[2'-hydroxy-3'-(methyloxy)-4-biphenylyl]-2-oxo-1,2-dihydro-3-quinolinecarboxylic acid;
1-(4-(7-Chloro-3-(3-methylisoxazol-5-yl)-4-oxido-2-oxo-1,2-dihydroquinolin-6-yl)phenyl)cyclopropanecarboxylate;
1-(7-Chloro-4-oxido-2-oxo-6-(4-(piperidin-1-yl)phenyl)-1,2-dihydroquinolin-3-yl)-1H-pyrazole-4-carboxylate; and
7-Chloro-3-(3-chlorophenyl)-4-hydroxy-6-(4-(piperidin-1-yl)phenyl) quinolin-2(1H)-one;
or a pharmaceutically acceptable salt thereof.

8. The compound or salt thereof according to claim 1 wherein the salt is a pharmaceutically acceptable salt.

9. A compound which is 7-chloro-6-(4-(dimethylamino) phenyl)-4-hydroxy-3-(3-methylisoxazol-5-yl)quinolin-2 (1H)-one, represented by the formula:

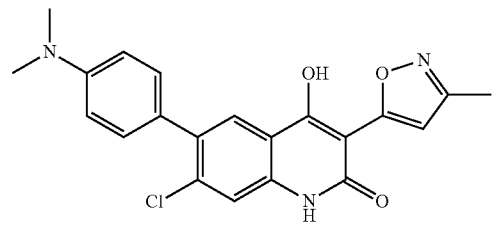

or a pharmaceutically acceptable salt thereof.

10. The compound according to claim 9 which is 7-chloro-6-(4-(dimethylamino)phenyl)-4-hydroxy-3-(3-methylisoxazol-5-yl)quinolin-2(1H)-one, represented by the formula:

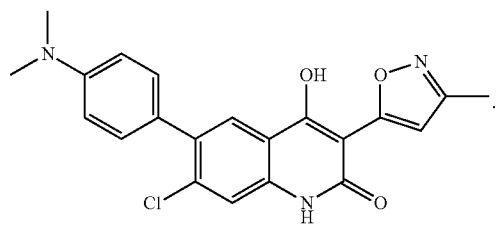

11. A pharmaceutical composition comprising the compound or pharmaceutically acceptable salt thereof according to claim 8 and a pharmaceutically acceptable carrier.

12. A pharmaceutical composition comprising the compound or pharmaceutically acceptable salt thereof according to claim 9 and a pharmaceutically acceptable carrier.

13. A pharmaceutical composition comprising the compound according to claim 10 and a pharmaceutically acceptable carrier.

* * * * *